United States Patent [19]

Aoki et al.

[11] Patent Number: 5,728,835
[45] Date of Patent: Mar. 17, 1998

[54] SUBSTITUTED CYCLIC AMINE COMPOUND, PRODUCTION PROCESS THEREOF AND PHARMACEUTICAL COMPOSITION FOR CIRCULATORY ORGAN USE CONTAINING THE SAME

[75] Inventors: Tsuyoshi Aoki; Atsuo Takahashi; Hiroyasu Sato; Eiji Shimanuki; Kaoru Gengyou; Toyoki Nishimata; Sachiko Ishigami; Shin-ichi Yamada; Takahiro Yamaguchi; Yoichi Manome; Isamu Sato, all of Fukushima; Kentaro Kogi, Miyagi; Sen-ichi Narita, Saitama, all of Japan

[73] Assignee: Toa Eiyo, Ltd., Tokyo, Japan

[21] Appl. No.: 575,062

[22] Filed: Dec. 19, 1995

Related U.S. Application Data

[63] Continuation-in-part of Ser. No. 363,223, Dec. 23, 1994, abandoned.

[30] Foreign Application Priority Data

Dec. 27, 1993 [JP] Japan ................... 5-346805

[51] Int. Cl.$^6$ ................... C07D 211/32; A61K 31/445
[52] U.S. Cl. ................... 546/194; 514/318; 514/330; 546/225
[58] Field of Search ................... 546/194, 225; 514/318, 330

[56] References Cited

U.S. PATENT DOCUMENTS

| | | | |
|---|---|---|---|
| 5,130,313 | 7/1992 | Comte et al. | 514/253 |
| 5,229,400 | 7/1993 | Hirosawa et al. | 514/325 |
| 5,231,105 | 7/1993 | Shoji et al. | 514/325 |

FOREIGN PATENT DOCUMENTS 0124476  3/1984  European Pat. Off. .

*Primary Examiner*—Mukund J. Shah
*Assistant Examiner*—King Lit Wong
*Attorney, Agent, or Firm*—Nikaido Marmelstein Murray & Oram LLP

[57] ABSTRACT

A substituted cyclic amine compound represented by the following general formula (1)

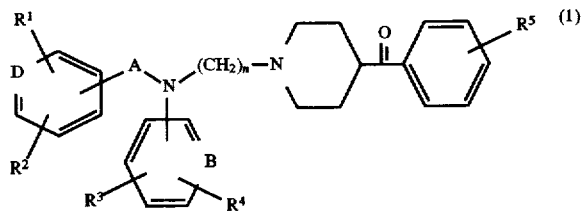

wherein each of $R^1$ to $R^5$ represents a hydrogen atom, a halogen atom, a lower alkyl group, a lower alkoxy group or the like, A represents a carbonyl group or a sulfonyl group, B represents a methine moiety or a nitrogen atom, D represents a methine moiety, a nitrogen atom or =N(→O)— and n is an integer of 2 to 3; and synthetic methods thereof. The inventive compound is useful in preventing and treating circulatory organ-related diseases such as hypertension, ischemic heart disease, cerebrovascular disease, peripheral circulatory disease and the like.

7 Claims, No Drawings

SUBSTITUTED CYCLIC AMINE COMPOUND, PRODUCTION PROCESS THEREOF AND PHARMACEUTICAL COMPOSITION FOR CIRCULATORY ORGAN USE CONTAINING THE SAME

This is a continuation-in-part application of Ser. No. 08/363,223, filed Dec. 23, 1994, now abandoned.

FIELD OF THE INVENTION

This invention relates to a novel substituted cyclic amine compound and a pharmaceutical composition which contains the novel compound.

The substituted cyclic amine compound and salts thereof of the present invention show a strong serotonin 2 receptor antagonism with no central nervous action and are useful as pharmaceutical drugs for the prevention and treatment of circulatory organ-related diseases such as hypertension, ischemic heart disease and other diseases caused by the cerebrovascular and peripheral circulatory disturbances.

BACKGROUND OF THE INVENTION

In recent years, attention has been paid to the participation of serotonin in the generation mechanism of unstable angina and myocardial infarction caused by coronary arteriosclerosis and hypertension.

That is, platelet aggregation is apt to occur in blood vessels where arteriosclerosis or endothelial disorder is generated, and platelets in the aggregation-caused vessel region release a high concentration of serotonin which subsequently increases the platelet aggregation to form thrombi and induces strong angiospasm mediated by the serotonin 2 receptor. Since peripheral-selective serotonin 2 receptor antagonists seem to be effective in inhibiting such phenomena, studies have been made on such antagonists. For example, a quinazoline derivative, ketanserin, has been disclosed in U.S. Pat. No. 4,335,127 and JP-A-55-105679 (the term "JP-A" as used herein means an "unexamined published Japanese patent application). However, since most of the prior art serotonin 2 receptor antagonists show not only peripheral serotonin 2 antagonism but also central nervous actions, these compounds are problematic as pharmaceutical drugs for circulatory organ use.

SUMMARY OF THE INVENTION

As a result of extensive investigation to develop a novel serotonin 2 receptor antagonist which shows strong serotonin 2 receptor antagonism and from which the central nervous action is separated, the present invention has been completed.

According to the present invention, there is provided a substituted cyclic amine compound represented by the following general formula (1)

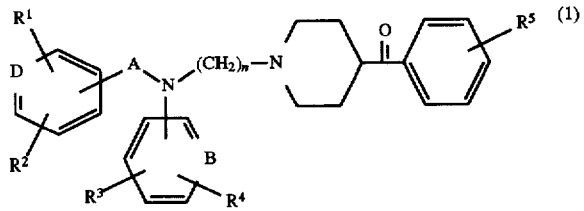

wherein $R^1$ and $R^2$ may be the same or different from each other and each represents a hydrogen atom, a halogen atom, lower straight or branched-chain alkyl group which may be substituted with halogen atom(s), a hydroxy group, a lower alkoxy group, a five- or six-membered cycloalkyl group including an oxygen atom, a amino group, a lower mono or dialkylamino group, a five- or six-membered cyclic amine group, a lower acylamino group, a substituted or unsubstituted benzyloxymethylcarbonylamino group or a phthalimide group, a lower alkoxy group, a cyano group, a formyl group, an oxyme group, a carboxyl group, a lower alkoxycarbonyl group, a carbamoyl group, a nitro group, an amino group which may be substituted with a lower mono or dialkyl group, a lower acyl group, a lower halogenated acyl group, a lower aminoacyl group, a lower alkoxycarbonyl group or a lower alkylsulfonyl group, an amidino group which may be substituted with a lower acyl group, a lower alkoxycarbonyl group or a lower alkylsulfonyl group, an ureido group which may be substituted with a lower alkyl group, a thioureido group which may be substituted with a lower alkyl group or pyrrole ring, $R^3$ and $R^4$ may be the same or different from each other and each represents a hydrogen atom, a halogen atom, a lower alkyl group, a lower halogenated alkyl group, a hydroxy group, a lower alkoxy group, methylenedioxy group combined together $R^3$ and $R^4$, a lower alkylthio group, a cyano group, a lower alkoxycarbonyl group, a nitro group or an amino group which may be substituted with a lower acyl group, $R^5$ represents a hydrogen atom, a halogen atom or an amino group which may be substituted with a lower mono or dialkyl group, A represents a carbonyl group or a sulfonyl group, B represents a methine moiety or a nitrogen atom, D represents a methine moiety, a nitrogen atom or =N(→O)—, and n is an integer of 2 to 3; or a pharmaceutically acceptable salt thereof.

The present invention also relates to a process for the production of the compound of general formula (1), and to its use as a pharmaceutical composition for circulatory organ use.

DETAILED DESCRIPTION OF THE INVENTION

Illustrative examples of halogen atoms of $R^1$ and $R^2$ include fluorine, chlorine, bromine and iodine. Lower alkyl groups of the substituents $R^1$ and $R^2$ may be either in the straight or branched form, and their illustrative examples include those having 1 to 4 carbon atoms, such as methyl, ethyl, n-propyl, isopropyl, n-butyl, isobutyl and tert-butyl. Illustrative examples of substituted lower alkyl groups of $R^1$ and $R^2$ with halogen atoms include those having 1 to 4 carbon atoms, such as difluoromethyl, trifluoromethyl, chloromethyl, trichloromethyl, difluoroethyl, trifluoroethyl, chloroethyl, dichloroethyl, trichloroethyl, trifluoropropyl, tetrafluoropropyl, pentafluoropropyl, dichloropropyl, trichloropropyl, trifluorobutyl, pentafluorobutyl and the like. Illustrative examples of substituted lower alkyl groups of $R^1$ and $R^2$ with hydroxy group include those having 1 to 4 carbon atoms, such as hydroxymethyl, 2-hydroxyethyl, 1-hydroxyethyl, 3-hydroxypropyl, 2-hydroxypropyl, 4-hydroxybutyl, 3-hydroxybutyl and the like, which may be protected by protecting groups such as methyl, ethyl, phenyl, acetyl, pivaloyl, benzyl, tetrahydrofuranyl, tetrahydropyranyl and the like. Illustrative examples of substituted lower alkyl groups of $R^1$ and $R^2$ with amino group include those having 1 to 4 carbon atoms, such as aminomethyl, 2-aminoethyl, 1-aminoethyl, 3-aminopropyl, 2-aminopropyl, 4-aminobutyl, 3-aminobutyl and the like, and the amino group of these aminoalkyl groups may be unsubstituted, monosubstituted or disubstituted amino group, with illustrative examples of the substituents including lower alkyl groups such as methyl, ethyl, propyl, butyl and the like, acyl groups such as acetyl, trifluoroacetyl, propionyl, butylyl, benzoyl, benzyloxycarbonyl and the like, amino acid residues such as glycyl, alanyl, phenylalanyl and the like, sulfonyl groups such as methanesulfonyl, benzenesulfonyl, p-toluenesulfonyl and the like and alkoxycarbonyl groups such as methoxycarbonyl, ethoxycarbonyl, tert-butylcarbonyl and the like. In this instance, two of such substituents may be linked to each other to form a ring such as pyrrolidinyl, piperidino, morpholino, piperazinyl, succinimide, phthalimide or the like.

Illustrative examples of lower alkoxy groups of $R^1$ and $R^2$ include those either in the straight or branched form and having 1 to 4 carbon atoms, such as methoxy, ethoxy, n-propoxy, isopropoxy, n-butoxy, tert-butoxy and the like. Illustrative examples of lower alkoxycarbonyl groups of $R^1$ and $R^2$ include those either in the straight or branched form and having 1 to 5 carbon atoms, such as methoxycarbonyl, ethoxycarbonyl, n-propoxycarbonyl, isopropoxycarbonyl, n-butoxycarbonyl, tert-butoxycarbonyl and the like. Amino groups of $R^1$ and $R^2$ may be unsubstituted, monosubstituted or disubstituted amino groups, and illustrative examples of the substituents include lower alkyl groups such as methyl, ethyl, propyl, butyl and the like, acyl groups such as acetyl, trifluoroacetyl, propionyl, butylyl, benzoyl and the like, amino acid residues such as glycyl, alanyl, phenylalanyl and the like, sulfonyl groups such as methanesulfonyl, ethanesulfonyl, benzenesulfonyl, p-toluenesulfonyl and the like and alkoxycarbonyl groups such as methoxycarbonyl, ethoxycarbonyl, tert-butylcarbonyl and the like. In this instance, two of such substituents may be linked to each other to form a ring such as, pyrrolidinyl, piperidino, morpholino, piperazinyl, succinimide, phthalimide or the like.

One or two nitrogen atoms of the amidino group of $R^1$ and $R^2$ may be substituted, and illustrative examples of such substituents include methyl, ethyl, benzyl, acetyl, trifluoroacetyl, propionyl, alkoxycarbonyl such as methoxy carbonyl, ethoxycarbonyl and the like, cyano, nitro, methanesulfonyl, p-toluenesulfonyl and the like.

One or two nitrogen atoms of the ureido group of $R^1$ and $R^2$ may be substituted, and illustrative examples of such substituents include methyl, ethyl, propyl, tert-butyl and the like. One or two nitrogen atoms of the thioureido group of $R^1$ and $R^2$ may be substituted, and illustrative examples of such substituents include methyl, ethyl, propyl, tert-butyl and the like.

Illustrative examples of halogen atoms of $R^3$ and $R^4$ include fluorine, chlorine, bromine and iodine. Lower alkyl groups of the substituents $R^3$ and $R^4$ may be either in the straight or branched form, and their illustrative examples include those having 1 to 4 carbon atoms, such as methyl, ethyl, n-propyl, isopropyl, n-butyl, isobutyl, tert-butyl. Illustrative examples of lower halogenated alkyl groups of $R^3$ and $R^4$ include those having 1 to 4 carbon atoms, such as difluoromethyl, trifluoromethyl, chloromethyl, trichloromethyl, difluoroethyl, trifluoroethyl, chloroethyl, dichloroethyl, trichloroethyl, trifluoropropyl, tetrafluoropropyl, pentafluoropropyl, dichloropropyl, trichloropropyl, trifluorobutyl, pentafluorobutyl and the like. Illustrative examples of lower alkoxy groups of $R^3$ and $R^4$ include those either in the straight or branched form and having 1 to 4 carbon atoms, such as methoxy, ethoxy, n-propoxy, isopropoxy, n-butoxy, tert-butoxy and the like.

Illustrative examples of lower alkylthio groups of $R^3$ and $R^4$ include those either in the straight or branched form and having 1 to 4 carbon atoms, such as methylthio, ethylthio, n-propylthio, isopropylthio, n-butylthio, tert-butylthio and the like.

Illustrative examples of lower alkoxycarbonyl groups of $R^3$ and $R^4$ include those either in the straight or branched form and having 1 to 5 carbon atoms, such as methoxycarbonyl, ethoxycarbonyl, n-propoxycarbonyl, isopropoxycarbonyl, n-butoxycarbonyl, tert-butoxycarbonyl and the like. Amino groups of $R^3$ and $R^4$ may be unsubstituted or substituted amino groups, and illustrative examples of the substituents include acyl groups such as acetyl, trifluoroacetyl, propionyl, butylyl, benzoyl and the like.

Illustrative examples of halogen atoms of $R^5$ include fluorine, chlorine and bromine. Amino group of $R^5$ may be unsubstituted, monosubstituted or disubstituted amino groups, and illustrative examples of the substituents include lower alkyl groups such as methyl, ethyl, propyl, butyl and the like.

Illustrative examples of salts of the compound (1) include acid addition salts such as of hydrochloric acid, sulfuric acid, nitric acid, phosphoric acid and the like mineral acids, methanesulfonic acid, ethanesulfonic acid, benzenesulfonic acid, toluenesulfonic acid and the like organic sulfonic acids and acetic acid, tartaric acid, maleic acid, fumaric acid, oxalic acid, lactic acid, citric acid and the like organic carboxylic acids.

Among the novel substituted cyclic amine compound of the present invention represented by the aforementioned general formula (1), there is provided a preferable compound wherein $R^1$ and $R^2$ may be the same or different from each other and each represents a hydrogen atom, a halogen atom, lower straight or branched-chain alkyl group which may be substituted with a halogen atom, a hydroxy group, a lower alkoxy group, a amino group, a lower mono or dialkylamino group, a five- or six-membered cyclic amine group or a lower acylamino group, a lower alkoxy group or an amino group which may be substituted with a lower mono or dialkyl group, a lower acyl group, a lower halogenated acyl group, a lower alkoxycarbonyl group or a lower alkylsulfonyl group, $R^3$ and $R^4$ may be the same or different from each other and each represents a hydrogen atom, a halogen atom, a lower alkyl group, a lower halogenated alkyl group, a hydroxy group, a lower alkoxy group, methylenedioxy group combined together $R^3$ and $R^4$, a lower alkylthio group or an amino group which may be substituted with a lower acyl group. $R^5$ represents a hydrogen atom or a halogen atom, A represents a carbonyl group, B represents a methine moiety or a nitrogen atom, D represents a methine moiety, a nitrogen atom or =N(→O)—, especially nitrogen atom is preferable and n is an integer of 2 to 3.

Illustrative examples of halogen atoms of $R^1$ and $R^2$ in the preferable compound include fluorine and chlorine. Lower alkyl groups of the substituents $R^1$ and $R^2$ in the preferable compound may be either in the straight or branched form, and their illustrative examples include those having 1 to 4 carbon atoms, such as methyl, ethyl, n-propyl, isopropyl, n-butyl, isobutyl and tert-butyl.

Illustrative examples of substituted lower alkyl groups of $R^1$ and $R^2$ with hydroxy group include those having 1 to 4 carbon atoms, such as hydroxymethyl, 2-hydroxyethyl, 1-hydroxyethyl, 3-hydroxypropyl, 2-hydroxypropyl, 4-hydroxybutyl, 3-hydroxybutyl and the like, which may be protected by protecting groups such as methyl, ethyl, phenyl, acetyl, pivaloyl, benzyl, tetrahydrofuranyl, tetrahydropyranyl and the like. Illustrative examples of substituted lower alkyl groups of $R^1$ and $R^2$ with amino group include those having 1 to 4 carbon atoms, such as aminomethyl, 2-aminoethyl, 1-aminoethyl, 3-aminopropyl, 2-aminopropyl, 4-aminobutyl, 3-aminobutyl and the like, and the amino group of these aminoalkyl groups may be unsubstituted, monosubstituted or disubstituted amino group with lower alkyl or acyl group such as methyl, ethyl, propyl, butyl, acetyl, trifluoroacetyl, propionyl, butylyl, benzoyl, benzyloxycarbonyl and the like, and illustrative example of a five- or six-membered cyclic amine group include pyrrolidine, piperidine, morpholine.

Illustrative examples of lower alkoxy groups of $R^1$ and $R^2$ include those either in the straight or branched form and having 1 to 4 carbon atoms, such as methoxy, ethoxy, n-propoxy, isopropoxy, n-butoxy, tert-butoxy and the like.

Amino groups of $R^1$ and $R^2$ of the preferable compound may be unsubstituted, monosubstituted or disubstituted amino groups, and illustrative examples of the substituents include lower alkyl groups such as methyl, ethyl, propyl, butyl, benzyl and the like, acyl groups such as acetyl, trifluoroacetyl, propionyl, butylyl, benzoyl and the like, sulfonyl groups such as methanesulfonyl, ethanesulfonyl, benzenesulfonyl, p-toluenesulfonyl and the like and alkoxycarbonyl groups such as methoxycarbonyl, ethoxycarbonyl, tert-butylcarbonyl and the like.

Illustrative examples of halogen atoms of $R^3$ and $R^4$ in the preferable compound include fluorine, chlorine and bromine. Lower alkyl groups of the substituents $R^3$ and $R^4$ may be either in the straight or branched form, and their illustrative examples include those having 1 to 4 carbon atoms, such as methyl, ethyl, n-propyl, isopropyl, n-butyl, isobutyl, tert-butyl. Illustrative examples of lower halogenated alkyl groups of $R^3$ and $R^4$ include those having 1 to 4 carbon atoms, such as difluoromethyl, trifluoromethyl, chloromethyl, trichloromethyl, difluoroethyl, trifluoroethyl, chloroethyl, dichloroethyl, trichloroethyl, trifluoropropyl, tetrafluoropropyl, pentafluoropropyl, dichloropropyl, trichloropropyl, trifluorobutyl, pentafluorobutyl and the like.

Illustrative examples of lower alkoxy groups of $R^3$ and $R^4$ include those either in the straight or branched form and having 1 to 4 carbon atoms, such as methoxy, ethoxy, n-propoxy, isopropoxy, n-butoxy, tert-butoxy and the like.

Illustrative examples of lower alkylthio groups of $R^3$ and $R^4$ include those either in the straight or branched form and having 1 to 4 carbon atoms, such as methylthio, ethylthio, n-propylthio, isopropylthio, n-butylthio, tert-butylthio and the like.

Amino groups of $R^3$ and $R^4$ may be unsubstituted or substituted amino groups, and illustrative examples of the substituents include acyl groups such as acetyl, trifluoroacetyl, propionyl, butylyl, benzoyl and the like.

Illustrative examples of halogen atoms of $R^5$ in the preferable compound include fluorine, chlorine and bromine.

Illustrative examples of salts of the preferable compound include acid addition sales such as of hydrochloric acid, sulfuric acid, nitric acid, phosphoric acid and the like mineral acids, methanesulfonic acid, ethanesulfonic acid, benzenesulfonic acid, toluenesulfonic acid and the like organic sulfonic acids and acetic acid, tartaric acid, maleic acid, fumaric acid, oxalic acid, lactic acid, citric acid and the like organic carboxylic acids.

Processes for the production of the intended compound (1) of the present invention are described in detail in the following.

The novel substituted cyclic amine compound of the present invention represented by the aforementioned general formula (1) and its salts can be produced in accordance with the following reaction formulae.

[Production process 1]

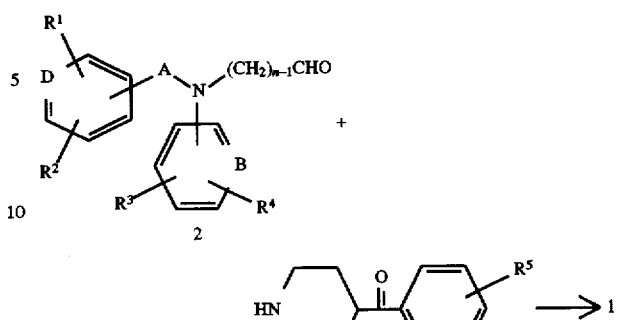

In this formula, $R^1$, $R^2$, $R^3$, $R^4$, $R^5$, A, B, D and n are as defined in the foregoing.

[Production process 2]

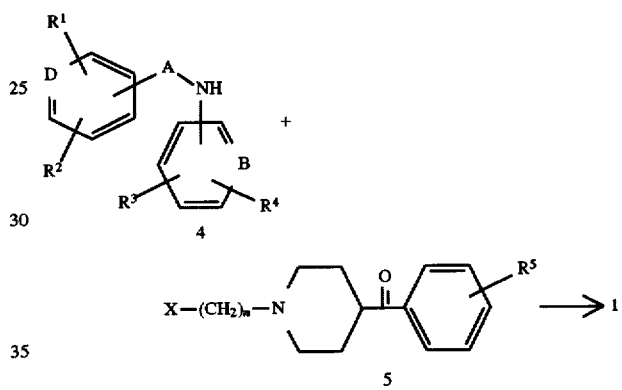

In this formula, X represents a halogen atom, a p-toluenesulfonyloxy group, a methanesulfonyloxy group or a trifluoromethanesulfonyloxy group, and $R^1$, $R^2$, $R^3$, $R^4$, $R^5$, A, B, D and n are as defined in the foregoing.

[Production process 3]

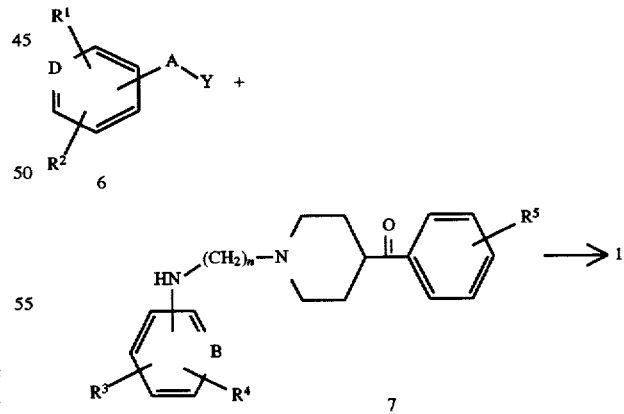

In this formula, Y represents a halogen atom and $R^1$, $R^2$, $R^3$, $R^4$, $R^5$, A, B, D and n are as defined in the foregoing.

[Production process 1]

The compound (1) can be produced by allowing the compound (2) to react with the compound (3). The reaction is carried out in an alcohol such as methanol, ethanol or the like or in a solvent such as ethylene chloride, chloroform, THF or the like, in the presence of a boron base reducing agent such as sodium cyanoborohydride or the like alkali metal cyanoborohydride, sodium borohydride or the like alkali metal borohydride or diborane, or in an atmosphere of hydrogen in the presence of a transition metal catalyst such as palladium carbon, palladium black, rhodium carbon or the like. The reaction temperature can be selected within the range of from 0 to room temperature. If necessary, a catalytically effective amount of an organic acid such as acetic acid, p-toluenesulfonic acid or the like, or a dehydrating agent such as molecular sieves, magnesium sulfate or the like, may be added to the reaction system. The reaction is completed within 1 to 4 hours. It is desirable to carry out this reaction in an atmosphere of an inert gas such as argon or nitrogen.

[Production process 2]

The compound (1) can be produced by allowing the compound (4) to react with the compound (5). Examples of the base to be used in the reaction include organic bases such as triethylamine and the like, alkali metal amide bases such as lithium diisopropylamide (LDA), sodium amide and the like, alkali metal salts such as sodium hydride, n-butyl lithium, sec-butyl lithium, tert-butyl lithium, tert-butoxy potassium and the like and alkali metal carbonates such as potassium carbonate. Examples of the solvent to be used in the reaction include THF, DMF, DMSO, methylene chloride, benzene, toluene, acetone, methyl ethyl ketone and the like. The reaction temperature can be selected within the range of from 0 to 100° C., and the reaction is completed within 2 to 24 hours. It is desirable to carry out this reaction in an atmosphere of an inert gas such as argon or nitrogen. As occasion demands, an alkali metal halide such as sodium iodide, potassium iodide or the like may be added to the reaction system.

[Production process 3]

The compound (1) can be produced by allowing the compound (6) to react with the compound (7). Examples of the base to be used in the reaction include organic bases such as triethylamine and the like, alkali metal amide bases such as LDA, sodium amide and the like, alkali metal salts such as sodium hydride, n-butyl lithium, sec-butyl lithium, tert-butyl lithium, tert-butoxy potassium and the like and alkali metal carbonates such as potassium carbonate. Examples of the solvent to be used in the reaction include diethyl ether, THF, DMF, DMSO, methylene chloride, benzene, toluene, acetone, methyl ethyl ketone and the like. The reaction temperature can be selected within the range of from 0° to 100° C., and the reaction is completed within 2 to 24 hours. It is desirable to carry out this reaction in an atmosphere of an inert gas such as argon or nitrogen.

[Production process 4]

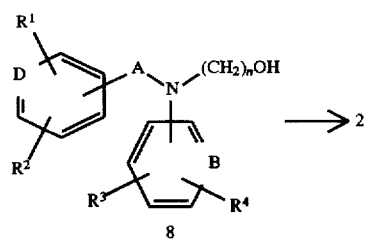

8

In this formula, $R^1$, $R^2$, A, B, D and n are as defined in the foregoing.

[Production process 5]

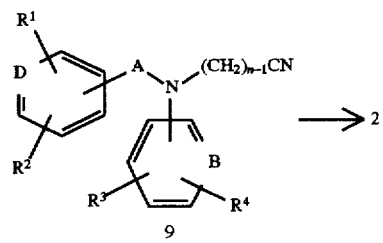

In this formula, $R^1$, $R^2$, A, B, D and n are as defined in the foregoing.

[Production process 6]

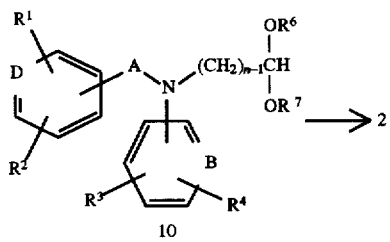

In this formula, $R^6$ and $R^7$ may be the same or different from each other and each represents a straight or branched-chain lower alkyl group such as methyl, ethyl, isobutyl or the like, $R^6$ and $R^7$ may be linked to each other to form a lower alkyl chain such as —$C_2H_5$— or the like, and $R^1$, $R^2$, A, B, D and n are as defined in the foregoing.

[Production process 4]

The compound (2) can be produced by subjecting the compound (8) to oxidation reaction. The oxidation reaction may be carried out in a hydrocarbon halide solvent such as methylene chloride or the like in the presence of Collins reagent or a chromic acid base oxidizing agent such as pyridinium chlorochromate or the like, or Swern oxidation or the like oxidation agent or a sulfur trioxide-pyridine complex in DMSO solvent. The reaction temperature can be selected within the range of from −78° C. to room temperature, and the reaction is completed within 1 to 12 hours. It is desirable to carry out this reaction in an atmosphere of an inert gas such as argon or nitrogen.

[Production process 5]

The compound (2) can be produced by reducing the compound (9) into iminium salt which is then subjected to hydrolysis. The reduction reaction may be carried out in a hydrocarbon solvent such as hexane, toluene or the like in the presence of an aluminum hydride base reducing agent such as lithium aluminum hydride, DIBAH or the like, and the subsequent hydrolysis may be carried out using a mineral acid such as sulfuric acid, hydrochloric acid or the like. The reaction temperature can be selected within the range of from −78° C. to room temperature, and the reaction is completed within 1 to 12 hours. It is desirable to carry out this reaction in an atmosphere of an inert gas such as argon or nitrogen.

[Production process 6]

The compound (2) can be produced by deprotecting the acetal moiety of the compound (10). The reaction may be carried out in a polar solvent such as THF, acetone or the like using a mineral acid such as hydrochloric acid, sulfuric acid or the like, an organic acid such as acetic acid, trifluoroacetic acid or the like or a Lewis acid such as aluminium chloride, silica gel, trimethylsilane iodide. The reaction temperature can be selected within the range of from $-20°$ C. to boiling point, and the reaction is completed within 30 minutes to 24 hours.

The serotonin 2 receptor antagonism, platelet aggregation inhibition activity and serotonin-induced head-twitch inhibition activity of representative compounds of the general formula (1) in the present invention are described in the following in detail.

N-{2-[4-(4-Fluorobenzoyl)piperidino]ethyl}-4-hydroxymethyl-N-(2-methoxyphenyl) benzenesulfonamide oxalate (compound A: Inventive Example 188)

4-Aminomethyl-N-{2-[4-(4-fluorobenzoyl)piperidino]ethyl}-N-(2-methoxyphenyl)benzamide oxalate (compound B: Inventive Example 196)

4-Acetylamino-N-{2-[4-(4-Fluorobenzoyl)piperidino]ethyl}-N-(2-methoxyphenyl)benzamide oxalate (compound C: Inventive Example 209)

4-Acetylamino-N-{2-[4-(4-fluorobenzoyl)piperidino]ethyl}-N-(3-methoxyphenyl)benzamide fumarate (compound D: Inventive Example 211)

4-Acetylamino-N-{2-[4-(4-fluorobenzoyl)piperidino]ethyl}-N-(4-methoxyphenyl)benzamide fumarate (compound E: Inventive Example 220)

4-Acetylamino-N-{2-[4-(4-fluorobenzoyl)piperidino]ethyl}-N-(3-methylphenyl)benzamide fumarate (compound F: Inventive Example 230)

4-Acetylamino-N-{2-[4-(4-fluorobenzoyl)piperidino]ethyl}-N-(phenyl)benzamide fumarate (compound G: Inventive Example 231)

4-Benzoylamino-N-{2-[4-(4-fluorobenzoyl)piperidino]ethyl}-N-(3-pyridyl)benzamide fumarate (compound H: Inventive Example 266)

4-Valerylamino-N-{2-[4-(4-fluorobenzoyl)piperidino]ethyl}-N-(3-pyridyl)benzamide hemifumarate (compound I: Inventive Example 273).

4-Ethyamino-N-{2-[4-(4-fluorobenzoyl)piperidino]ethyl}-N-(3-pyridyl)benzamide hemifumarate (compound J: Inventive Example 277)

Ketanserin (comparative compound)

[Measurement of serotonin 2 receptor antagonistic activity]

Male rats of Wistar-KY line (body weight, approximately 220 to 370 g) were sacrificed and subjected to bloodletting to excise abdominal side tail arteries. A piece of wire was inserted into each of the thus excised blood vessels to prepare a spiral specimen (approximately 1.5×30 mm). The specimen was suspended in a Magnus tube (10 ml; Krebs-Hensereit solution) with a load of 500 mg at 37° C., and a gas mixture of 95% $O_2+CO_2$ was passed through the tube. Tensile force was measured using a tension transducer (TB-621T, manufactured by Nippon Koden) and writing the data on an ink recorder (FBR-253A, manufactured by Toa Denpa) via a pressure amplifier (AP-621G, manufactured by Nippon Koden). After 1 hour of equilibration time, the specimen was contracted with $10^{-5}M$ of serotonin, washed and then subjected to cumulative administration of $10^{-8}$ to $3\times10^{-5}M$ serotonin at intervals of 45 minutes to record the resulting contraction twice. The second recording was used as a control. Thereafter, each of the drugs to be tested was administered 10 minutes before the commencement of the cumulative administration to evaluate its serotonin antagonism. The serotonin antagonism of these test drugs on the serotonin contraction was expressed by $IC_{50}$ values against the contraction of $3\times10^{-6}$ serotonin, with the results shown in Table 1. In the table, each result was indicated by "+" when the $IC_{50}$ value was $1.0\times10^{-7}M$ or more, "++" when the value was $9.9\times10^{-8}$ to $1.0\times10^{-8}M$ and "+++" when the value was $9.9\times10^{-9}M$ or smaller.

TABLE 1

| Serotonin 2 receptor antagonism | |
|---|---|
| Compound | $IC_{50}$ value |
| A | +++ |
| B | ++ |
| C | ++ |
| D | ++ |
| E | +++ |
| F | ++ |
| G | ++ |
| H | +++ |
| I | +++ |
| J | +++ |
| ketanserin | ++ |

[Measurement of platelet aggregation inhibition activity]

Measurement of platelet aggregation was carried out using a platelet aggregation measuring apparatus NSB Hematracer 601.

Blood samples were collected from auricular arteries of male Japanese white rabbits (2 to 3 kg) using a syringe containing 1 volume of 3.8% sodium citrate per 9 volumes of blood and centrifuged at 900 rpm for 10 minutes. After collecting the resulting supernatant fluid as platelet rich plasma (PRP), the remaining lower layer was centrifuged at 3,000 rpm for 10 minutes to obtain platelet poor plasma (PPP). Platelets in the thus obtained PRP were counted using a microcell counter (Sysmex F-800, manufactured by Toa Iyo Denshi) and diluted with the PPP to a density of $30\times10^4/\mu l$. Firstly, aggregation of the diluted PRP by collagen alone was examined to find a collagen concentration which does not cause aggregation.

A 220 µl portion of PRP was mixed with 5 µl of 104 mM $CaCl_2$, incubated at 37° C. for 1 minute and then mixed with 5 µl of a drug to be tested or physiological saline as a control. To this were added 5 µl of serotonin (final concentration, 3 µM) 2 minutes thereafter and collagen 1 minute further thereafter in a concentration which alone does not cause aggregation, thereby inducing platelet aggregation reaction. Activities to inhibit the aggregation reaction were measured to calculate 50% inhibition concentration ($IC_{50}$) by probit analysis, with the results shown in Table 2. In the table, each result was indicated by "+" when the $IC_{50}$ value was $1.0\times10^{-6}M$ or more, "++" when the value was $9.9\times10^{-7}$ to $1.0\times10^{-7}M$ and "+++" when the value was $9.9\times10^{-8}M$ or smaller.

TABLE 2

| Platelet aggregation inhibition activity | |
|---|---|
| Compound | $IC_{50}$ value |
| B | ++ |
| C | +++ |
| D | +++ |
| E | +++ |
| F | +++ |
| ketanserin | ++ |

[Measurement of activity to inhibit serotonin-induced head-twitch]

To each ICR male mouse of 4 weeks of age were administered 300 mg/kg of serotonin by intraperitoneal injection (i.p.) and then 0.03 to 3 mg/kg of each test drug 25 minutes thereafter by intravenous injection, thereby counting the number of head-twitch induced after 5 minutes of the administration (for 20 minutes) and calculating the $IC_{50}$ value. The results shown in Table 3. In the table, each result was indicated by "+" when the $IC_{50}$ value was 1,000 mg/kg or more, "++" when the value was 100 to 999 mg/kg and "+++" when the value was 99 mg/kg or less.

TABLE 3

| Activity to inhibit serotonin-induced head-twitch | |
|---|---|
| Compound | $IC_{50}$ value |
| B | + |
| C | + |
| D | ++ |
| H | ++ |
| I | ++ |
| J | ++ |
| ketanserin | +++ |

As is evident from the results of the above pharmacological tests, the substituted cyclic amine compound represented by the general formula (1) and salts thereof have a strong serotonin 2 receptor antagonism, because they showed activities similar to or higher than those of the control drug ketanserin in the serotonin 2 antagonism test in which excised rat blood vessels were used and in the inhibition test of rabbit platelet aggregation induced by serotonin. On the other hand, since the activity to inhibit serotonin-induced head-twitch in mice is weaker than that of ketanserin, it is evident that the central action of the inventive compound is separated.

Since the substituted cyclic amine compound represented by the general formula (1) and salts thereof show strong serotonin 2 receptor antagonism and excellent reaction selectivity, they are useful as pharmaceutical drugs for the prevention and treatment of circulatory organ-related diseases such as hypertension, ischemic heart disease and other diseases caused by the cerebrovascular and peripheral circulatory disturbances. The compound (1) or a salt thereof can be used in oral or parenteral administration as it is or in various dosage forms such as powders, granules, tablets, capsules, injections and the like by mixing it with optionally selected pharmaceutically acceptable carriers, fillers, diluents and the like. Its dose varies depending on the diseases to be treated, conditions of the symptoms and patients, administration methods and the like. In general, when administered to adults, it may be used in an amount of from 1 to 200 mg per day in the case of oral administration or from 0.5 to 50 mg per day in the case of intravenous injection, and the daily dose recited above may preferably be divided into 1 to 3 doses per day.

The following examples are provided to further illustrate the present invention. It is to be understood, however, that the examples are for purpose of illustration only and are not intended as a definition of the limits of the present invention. All the percents and ratios are by weight unless otherwise indicated.

REFERENCE EXAMPLE 1

N-(2-Methoxyphenyl)-3-pyridinesulfonamide o-Anisidine (377 mg, 3.0 mmol) was dissolved in toluene (10 ml) to which were subsequently added pyridine (0.48 ml, 6.0 mmol) and 3-pyridinesulfonylchloride hydrochloride (642 mg, 3.0 mmol) at room temperature. After 1.5 hours of stirring at 100° C., the resulting reaction solution was mixed with water (20 ml), adjusted to pH 7 to 8 with anhydrous sodium carbonate, extracted with ethyl acetate and then washed with water and saturated brine. After drying on anhydrous sodium carbonate and removing the solvent by evaporation, the resulting orange solid was purified by a silica gel column chromatography (ether:hexane=3:1) to obtain a light orange solid which was subsequently washed with an ether-hexane (1:3) mixture solution to obtain 662 mg (83.5%) of the title compound in the form of colorless prism crystals.

Melting point: 101.5°–103° C.

IR (KBr): 3008, 2712, 1586, 1498, 1420, 1336, 1320, 1280, 1256, 1194, 1110, 1020, 762, 744, 600, 578, 544 cm$^{-1}$

NMR (CDCl$_3$) δ: 3.58 (3H, s), 6.71 (1H, dd, J=7.5 Hz, 2 Hz), 6.80–7.14 (3H, m) 7.31 (1H, dd, J=8 Hz, 5 Hz), 7.54 (1H, dd, J=7.5 Hz, 2 Hz), 7.96 (1H, dd, J=8 Hz, 2 Hz), 8.70 (1H, dd, J=5 Hz, 2 Hz), 8.93 (1H, d, J=2 Hz)

REFERENCE EXAMPLE 2

N-(2-Methoxyphenyl)-p-toluenesulfonamide o-Anisidine (2.34 ml, 20 mmol) was dissolved in toluene (60 ml) to which were subsequently added, with cooling in an ice bath, pyridine (4.58 ml, 60 mmol), p-toluenesulfonyl chloride (3.89 g, 20 mmol) and a catalytically effective amount of 4-dimethylaminopyridine. After 2.5 hours of stirring at room temperature, the resulting reaction solution was mixed-with water (50 ml), extracted with ethyl acetate and then washed with water, 10% sodium hydroxide aqueous solution, 1N hydrochloric acid, water and saturated brine in that order. After drying on anhydrous magnesium sulfate and removing the solvent by evaporation, the resulting orange solid was dissolved in ethyl acetate (50 ml), adsorbed to anhydrous magnesium sulfate (20 g), eluted with ether and then subjected to evaporation to remove the solvent. The resulting colorless solid which was then washed with an ether-hexane (1:1) mixture solution to obtain 3.44 g (62.0%) of the title compound in the form of colorless prism crystals.

Melting point: 126.5°–128.5° C.

IR (KBr): 3336, 1594, 1498, 1440, 1286, 1256, 1158, 1112, 1088, 1024, 822, 752, 660, 554, 534 cm$^{-1}$

NMR (CDCl$_3$) δ: 2.35 (3H, s), 3.63 (3H, s), 6.58–7.34 (7H, m), 7.35–7.75 (2H, m)

REFERENCE EXAMPLE 3

4-Methoxy-N-(2-methoxyphenyl) benzenesulfonamide

Using o-anisidine (1.0 ml, 8.55 mmol) and 4-methoxybenzenesulfonyl chloride (1.78 g, 8.55 mmol), the procedure of Reference Example 2 was repeated to obtain 2.26 g (90.1%) of the title compound in the form of colorless powder.

Melting point: 85.5°–87° C.

IR (KBr): 3620, 3540, 3248, 1594, 1500, 1448, 1342, 1286, 1246, 1156, 1114, 1094, 1024, 910, 836, 754, 678, 582, 568, 546 cm$^{-1}$

NMR (CDCl$_3$) δ: 3.63, 3.77 (each, 3H, s), 6.55–7.15 (6H, m), 7.35–7.90 (3H, m)

REFERENCE EXAMPLE 4

4-Fluoro-N-(2-methoxyphenyl)benzenesulfonamide

Using o-anisidine (1.0 ml, 8.55 mmol) and 4-fluorobenzenesulfonyl chloride (1.7 g, 8.55 mmol), the procedure of Reference Example 2 was repeated to obtain 2.24 g (93.1%) of the title compound in the form of colorless prism crystals.

Melting point: 101°–102.5° C.

IR (KBr): 3272, 1598, 1494, 1396, 1342, 1254, 1222, 1178, 1154, 1112, 1088, 840, 754, 690, 552, 538 cm$^{-1}$

NMR (CDCl$_3$) δ: 3.60 (3H, s), 6.60–7.25 (6H, m), 7.37–7.94 (3H, m)

REFERENCE EXAMPLE 5

N-(2-Methoxyphenyl)-3-nitrobenzenesulfonamide

Using o-anisidine (1.0 ml, 8.55 mmol) and 3-nitrobenzenesulfonyl chloride (1.95 g, 8.55 mmol), the procedure of Reference Example 2 was repeated to obtain 2.36 g (89.5%) of the title compound in the form of light yellow needle crystals.

Melting point: 130°–131.5° C.

IR (KBr): 3252, 1608, 1532, 1496, 1406, 1354, 1258, 1154, 1112, 746, 684, 668 cm$^{-1}$

NMR (CDCl$_3$) δ: 3.63 (3H, s), 6.65–7.15 (4H, m), 7.56 (1H, d, J=7.5 Hz), 7.63 (1H, d, J=7.5 Hz), 8.05 (1H, d, J=7.5 Hz), 8.33 (1H, d, J=7.5 Hz), 8.60 (1H, br-s)

REFERENCE EXAMPLE 6

4-Methoxy-N-(3-methoxyphenyl)benzenesulfonamide

Using m-anisidine (0.99 ml, 8.55 mmol) and 4-methoxybenzenesulfonyl chloride (1.78 g, 8.55 mmol), the procedure of Reference Example 2 was repeated to obtain 2.50 g (99.7%) of the title compound in the form of light yellow oil.

IR (neat): 3268, 1596, 1500, 1328, 1262, 1152, 1094, 834, 692, 570, 550 cm$^{-1}$ NMR (CDCl$_3$) δ: 3.72, 3.81 (each 3H, s), 6.45–7.40 (7H, m), 7.74 (2H, d, J=9 Hz)

REFERENCE EXAMPLE 7

N-(2-Cyanophenyl)-4-methoxybenzenesulfonamide

Using 2-aminobenzonitrile (1.03 g, 8.55 mmol) and 4-methoxybenzenesulfonyl chloride (1.78 g, 8.55 mmol), the procedure of Reference Example 2 was repeated to obtain 1.57 g (63.7%) of the title compound in the form of colorless solid.

Melting point: 102°–103° C.

IR (KBr): 3252, 2228, 1596, 1578, 1496, 1456, 1416, 1340, 1310, 1180, 1162, 1092, 1024, 908, 834, 762, 670, 592 cm$^{-1}$

NMR (CDCl$_3$) δ: 3.83 (3H, s), 6.92 (2H, d, J=9 Hz), 7.50–7.29 (2H, m), 7.35–7.90 (5H, m)

REFERENCE EXAMPLE 8

N-(2-Trifluoromethylphenyl)-4-methoxybenzenesulfonamide

Using 2-trifluoromethylaniline (1.39 g, 8.55 mmol) and 4-methoxybenzenesulfonyl chloride (1.78 g, 8.55 mmol), the procedure of Reference Example 2 was repeated to obtain 2.14 g (75.5%) of the title compound in the form of colorless solid.

Melting point: 92°–93° C.

IR (KBr): 3292, 1596, 1494, 1416, 1346, 1318, 1270, 1254, 1164, 1112, 1094, 1026, 834, 758, 670, 556 cm$^{-1}$

NMR (CDCl$_3$) δ: 3.82 (3H, s), 6.65–7.00 (3H, m), 7.03–7.30 (1H, m), 7.35–7.90 (5H, m)

REFERENCE EXAMPLE 9

4-[(2-Methoxyanilino)sulfonyl]benzoic acid

Using o-anisidine (0.585 ml, 5.0 mmol) and 4-(chlorosulfonyl)benzoic acid (1.15 g, 5.0 mmol), the procedure of Reference Example 2 was repeated to obtain 1.47 g (95.5%) of the title compound in the form of pink powder.

Melting point: 202°–205° C.

IR (KBr): 3268, 1688, 1502, 1406, 1346, 1314, 1286, 1258, 1166, 744, 724 cm$^{-1}$

NMR (CDCl$_3$) δ: 3.57 (3H, s), 6.55–7.20 (3H, m), 7.25–7.60 (2H, m), 7.76 (2H, m, J=8.5 Hz), 8.07 (2H, m, J=8.5 Hz), 8.35 (1H, br-s)

REFERENCE EXAMPLE 10

3-Methoxy-N-(2-methoxyphenyl)benzamide

Using o-anisidine (1.0 ml, 8.55 mmol) and m-anisoyl chloride (1.2 ml, 8.55 mmol), the procedure of Reference Example 2 was repeated to obtain 2.2 g (100%) of the title compound in the form of brown oil.

IR (neat): 3436, 2940, 1674, 1600, 1526, 1482, 1460, 1434, 1336, 1288, 1274, 1250, 1220, 1120, 1046, 1028, 748 cm$^{-1}$ NMR (CDCl$_3$) δ: 3.88, 4.02 (each 3H, s), 6.80–7.20 (5H, m), 7.30–7.55 (3H, m), 8.50 (1H, br-s)

REFERENCE EXAMPLE 11

4-Cyano-N-(2-methoxyphenyl)benzamide

In an atmosphere of dry air, 4-cyanobenzoic acid (1.5 g, 10 mmol) was dissolved in benzene (5 ml), and DMF (0.1 ml) and thionyl chloride (2.2 ml, 30 mmol) were added dropwise to the resulting solution at room temperature, followed by 30 minutes of heating under reflux. After removing the solvent by evaporation, the resulting residue was subjected to azeotropy using benzene (10 ml×2) to obtain a yellow solid which was subsequently dissolved in methylene chloride (10 ml) and mixed with o-anisidine (1.16 ml, 10 mmol) and 20% sodium hydroxide aqueous solution (4 ml) with cooling in an ice bath. After 20 minutes of stirring at the same temperature, the resulting mixture was extracted with methylene chloride and then washed with 1N hydrochloric acid, water and saturated brine in that order. After drying on anhydrous magnesium sulfate, the solvent was removed by evaporation, and the resulting light yellow solid was purified by recrystallization (methylene chloride-ether) to obtain 2.36 g (93.6%) of the title compound in the form of creamy-colored crystals.

Melting point: 157.5°–160° C.

IR (KBr): 3312, 2228, 1666, 1644, 1600, 1534, 1486, 1460, 1434, 1334, 1288, 1256, 1218, 1022, 742 cm$^{-1}$

NMR (CDCl$_3$) δ: 3.93 (3H, s), 6.81–7.20 (3H, m), 7.77 (2H, d, J=8.5 Hz), 7.98 (2H, d, J=8.5 Hz), 8.32–8.58 (2H, m)

REFERENCE EXAMPLE 12

4-[(2-Methoxyanilino)carbonyl]pyridine

Using o-anisidine (2.34 g, 19.0 mmol) and 4-carboxypyridine (2.29 g, 19.0 mmol), the procedure of Reference Example 11 was repeated to obtain 4.22 g (97.2%) of the title compound in the form of colorless powder.

Melting point: 79°–80° C.

IR (KBr): 3316, 1665, 1596, 1533, 1485, 1464, 1440, 747 cm$^{-1}$

NMR (CDCl$_3$) δ: 3.92 (3H, s), 6.85–7.16 (3H, m), 7.72 (2H, d, J=6.0 Hz), 8.36–8.60 (2H, m), 8.78 (2H, d, J=6.0 Hz)

REFERENCE EXAMPLE 13

4-Chloromethyl-N-(2-methoxyphenyl)benzamide o-Anisidine (0.69 ml, 6.0 mmol) was dissolved in methylene chloride (10 ml) and, with cooling in an ice bath, mixed with 20% sodium hydroxide (5 ml) and 4-chloromethylbenzoyl chloride (1.17 g, 6.0 mmol). After 30 minutes of stirring at the same temperature, the reaction mixture was extracted with methylene chloride and then washed with 1N hydrochloric acid, water and saturated brine in that order. After drying on anhydrous magnesium sulfate, the solvent was removed by evaporation, and the resulting light beige solid was purified by recrystallization (etherhexane) to obtain 1.56 g (94.2%) of the title compound in the form of colorless needle crystals.

Melting point: 101°–103° C.

IR (KBr):.3448, 1668, 1600, 1536, 1510, 1484, 1460, 1438, 1344, 1290, 1248, 1220, 1022, 750, 702, 592, 556 cm$^{-1}$

NMR (CDCl$_3$) δ: 3.93 (3H, s), 4.64 (2H, s), 6.80–7.16 (3H, m), 7.51 (2H, d, J=8.5 Hz), 7.98 (2H, d, J=8.5 Hz), 8.33–8.66 (2H, m)

REFERENCE EXAMPLE 14

3-Methoxy-N-(2-pyridyl)benzamide

Using 2-aminopyridine (670 mg, 7.12 mmol) and m-anisoyl chloride (1.2 ml, 8.55 mmol), the procedure of Reference Example 13 was repeated to obtain 341 mg (21.0%) of the title compound in the form of light yellow oil.

IR (neat): 3250, 1676, 1580, 1526, 1488, 1464, 1432, 1306, 1272, 1226, 1042, 778 cm$^{-1}$ NMR (CDCl$_3$) δ: 3.80 (3H, s), 6.85–7.17 (2H, m), 7.20–7.57 (3H, m), 7.72 (1H, dd, J=7.5 Hz, 7.5 Hz), 8.11 (1H, br-s), 8.40 (1H, d, J=8 Hz), 9.37 (1H, br-s)

REFERENCE EXAMPLE 15

4-Chloromethyl-N-(3-methoxybenzyl)benzamide

Using 3-methoxybenzylamine (754 mg, 5.39 mmol) and 4-chloromethylbenzoyl chloride (1.17 g, 6.0 mmol), the procedure of Reference Example 13 was repeated to obtain 1.31 g (83.9%) of the title compound in the form of colorless crystals.

Melting point: 108°–109.5° C.

IR (KBr): 3292, 1634, 1612, 1584, 1572, 1552, 1438, 1304, 1266, 1234, 1052, 784, 740, 700, 678 cm$^{-1}$

NMR (CDCl$_3$) δ: 3.78 (3H, s), 4.57 (2H, s), 4.62 (2H, d, J=5 Hz), 6.16–6.55 (1H, m), 6.66–7.03 (3H, m), 7.10–7.31 (1H, m), 7.43 (2H, d, J=8 Hz), 7.78 (2H, d, J=8 Hz)

REFERENCE EXAMPLE 16

4-Nitro-N-(2-methoxyphenyl)benzamide

With cooling in an ice bath, 1-(3-dimethylaminopropyl)-3-ethylcarbodiimide hydrochloride (EDC.HCl) (630 mg, 3.29 mmol) was added to 15 ml of methylene chloride solution containing o-anisidine (368 mg, 2.99 mmol) and 4-nitrobenzoic acid (500 mg, 2.99 mmol). After 1 hour of stirring at the same temperature, the reaction mixture was roughly adjusted to pH 8 with saturated sodium bicarbonate aqueous solution, extracted with methylene chloride and then washed with water and saturated brine in that order. After drying on anhydrous magnesium sulfate, the solvent was removed by evaporation, and the resulting solid material was purified by silica gel column chromatography (methylene chloride) to obtain 712 mg (87.4%) of the title compound in the form of yellow powder.

Melting point: 146°–147° C.

IR (KBr): 3322, 1647, 1599, 1545, 1521, 1461, 1338, 1266, 741 cm$^{-1}$

NMR (CDCl$_3$) δ: 3.93 (3H, s), 6.81–7.18 (3H, m), 8.03 (2H, d, J=10.0 Hz), 8.34 (2H, d, J=10.0 Hz), 8.40 (1H, m)

REFERENCE EXAMPLE 17

4-Nitro-N-(3-methoxyphenyl)benzamide

Using m-anisidine (2.50 g, 15.0 mmol) and 4-nitrobenzoic acid (2.03 g, 16.5 mmol), the procedure of Reference Example 16 was repeated to obtain 3.80 g (93.2%) of the title compound in the form of light yellow needle crystals.

Melting point: 189°–191° C.

IR (KBr): 3316, 1642, 1598, 1536, 1522, 1434, 1320, 1296, 1162, 1046, 970 cm$^{-1}$

NMR (CDCl$_3$) δ: 3.83 (3H, s), 6.60–6.80 (1H, m), 7.10–7.43 (4H, m), 8.05 (2H, d, J=9.0 Hz), 8.33 (2H, d, J=9.0 Hz)

REFERENCE EXAMPLE 18

4-Nitro-N-14-methoxyphenyl)benzamide

Using p-anisidine (492.6 mg, 4.0 mmol) and 4-nitrobenzoic acid (668.5 mg, 4.0 mmol), the procedure of Reference Example 16 was repeated to obtain 904.9 mg (83.2%) of the title compound in the form of light yellow powder.

Melting point: 199°–200° C.

IR (KBr): 3296, 1644, 1600, 1530, 1516, 1462, 1348, 1322, 1302, 1248, 1104, 1028, 872, 828, 704, 690 cm$^{-1}$

NMR (CDCl$_3$) δ: 3.82 (3H, s), 6.62 (2H, d, J=9.0 Hz), 7.53 (2H, d, J=9.0 Hz), 8.01 (2H, d, J=8.7 Hz), 8.33 (2H, d, J=8.7 Hz)

REFERENCE EXAMPLE 19

4-Nitro-N-(2,5-dimethoxyphenyl)benzamide

Using 2,5-dimethoxyaniline (2.53 g, 16.5 mmol) and 4-nitrobenzoic acid (2.51 g, 15.0 mmol), the procedure of Reference Example 16 was repeated to obtain 3.50 g (77.2%) of the title compound in the form of orange needle crystals.

Melting point: 184°–186° C.

IR (KBr): 3424, 1686, 1604, 1536, 1346, 1220, 1042, 850, 614 cm$^{-1}$

NMR (CDCl$_3$) δ: 3.83 (3H, s), 3.91 (3H, s), 6.65 (1H, dd, J=2.9 Hz, 9.0 Hz), 6.85 (1H, d, J=9.0 Hz), 8.06 (2H, dd, J=7.0 Hz, 2.0 Hz), 8.21–8.65 (3H, m)

REFERENCE EXAMPLE 20

3-Nitro-N-(3-methoxyphenyl)benzamide

Using m-anisidine (2.03 g, 16.5 mmol) and 3-nitrobenzoic acid (2.51 g, 15.0 mmol), the procedure of Reference Example 16 was repeated to obtain 3.72 g (91.3%) of the title compound in the form of colorless powder.

Melting point: 120°–121.5° C.

IR (KBr): 3300, 1648, 1608, 1600, 1534, 1452, 1432, 1358, 1272, 1156 cm$^{-1}$

NMR (CDCl$_3$) δ: 3.83 (3H, s), 6.66–6.83 (1H, m), 7.06–7.33 (3H, m), 7.33–7.45 (1H, m), 7.68 (1H, dd, each J=9.0 Hz), 8.20–8.46 (2H, m), 8.70–8.88 (1H, m)

REFERENCE EXAMPLE 21

4-Nitro-N-(2,4-dimethoxyphenyl)benzamide

Using 2,4-dimethoxyaniline (2.53 g, 16.0 mmol) and 4-nitrobenzoic acid (2.50 g, 14.8 mmol), the procedure of Reference Example 16 was repeated to obtain 3.72 g (91.3%) of the title compound in the form of yellow needle crystals.

Melting point: 172°–174° C.

IR (KBr): 1680, 1522, 1502, 1422, 1342, 1286, 1252, 1212, 1156, 1136, 1032, 852, 836, 708, 550 cm$^{-1}$

NMR (CDCl$_3$) δ: 3.82 (3H, s), 3.91 (3H, s), 6.51–6.85 (2H, m), 7.76–8.29 (1H, m), 8.03 (2H, dd, each J=8.8 Hz), 8.34 (2H, d, J=8.8 Hz), 8.39 (1H, d, J=4.2 Hz)

REFERENCE EXAMPLE 22

4-Nitro-N-13-methylphenyl)benzamide

Using m-toluidine (1.61 g, 15.0 mmol) and 4-nitrobenzoic acid (2.76 g, 16.5 mmol), the procedure of Reference Example 16 was repeated to obtain 3.34 g (84.3%) of the title compound in the form of colorless needle crystals.

Melting point: 140.5°–146.5° C.

IR (KBr): 3298, 1641, 1599, 1533, 1515, 1449, 1347, 1320, 1302, 1260, 867, 708 cm$^{-1}$

NMR (CDCl$_3$) δ: 2.37 (3H, s), 6.87–7.53 (4H, m), 7.64–8.10 (1H, m), 7.99 (2H, dd, each J=9.0 Hz), 8.32 (2H, d, J=9.0 Hz)

REFERENCE EXAMPLE 23

4-Nitro-N-(phenyl)benzamide

Using aniline (1.50 ml, 16.5 mmol) and 4-nitrobenzoic acid (1.77 g, 10.5 mmol), the procedure of Reference Example 16 was repeated to obtain 2.48 g (97.5%) of the title compound in the form of colorless powder.

Melting point: 90°–93° C.

IR (KBr): 3324, 1652, 1598, 1530, 1494, 1440, 1348, 1324, 1300, 1264, 852, 758 722, 694 cm$^{-1}$

NMR (CDCl$_3$) δ: 7.25 (1H, t, J=5.7 Hz), 7.41 (2H, dd, J=5.7 Hz), 7.64 (2H, d, J=7.9 Hz), 7.68–7.99 (1H, s), 8.03 (2H, d, J=8.8 Hz), 8.35 (2H, d, J=8.8 Hz)

REFERENCE EXAMPLE 24

4-Nitro-N-(3-methylthiophenyl)benzamide

Using 3-methylthioaniline (1.40 ml, 11.0 mmol) and 4-nitrobenzoic acid (1.67 g, 10.0 mmol), the procedure of Reference Example 16 was repeated to obtain 2.46 g (85.2%) of the title compound in the form of yellow powder.

Melting point: 158°–161° C.

IR (KBr): 3280, 1648, 1598, 1540, 1518, 1476, 1344, 1326, 1310, 1300, 1264, 868, 848, 716, 684 cm$^{-1}$

NMR (CDCl$_3$) δ: 2.51 (3H, s), 7.08–7.35 (3H, m), 7.63 (1H, s), 7.81 (1H, s), 8.02 (2H, d, J=8.8 Hz), 8.35 (2H, d, J=8.8 Hz)

REFERENCE EXAMPLE 25

4-Nitro-N-(2-trifluoromethylphenyl)benzamide

Using 2-trifluoromethylaniline (1.77 g, 11.0 mmol) and 4-nitrobenzoic acid (1.67 g, 10.0 mmol), the procedure of Reference Example 16 was repeated to obtain 474 mg (15.3%) the title compound in the form of colorless powder.

Melting point: 125.6°–126.1° C.

IR (KBr): 3308, 1660 1524, 1348, 1318, 1294, 1164, 1114, 762 cm$^{-1}$

NMR (CDCl$_3$) δ: 7.53 (1H, d, J=7.7 Hz), 7.66 (2H, t, J=7.7 Hz), 7.98–8.43 (5H, m)

REFERENCE EXAMPLE 26

4-Nitro-N-(3-trifluoromethylphenyl)benzamide

Using 3-trifluoromethylaniline (1.77 g, 11.0 mmol) and 4-nitrobenzoic acid (1.67 g, 10.0 mmol), the procedure of Reference Example 16 was repeated to obtain 2.48 g (80.0%) of the title compound in the form of colorless powder.

Melting point: 209.6°–210.3° C.

IR (KBr): 3304, 1658, 1652, 1350, 1332, 714, 698 cm$^{-1}$

NMR (CDCl$_3$) δ: 7.50 (1H, dd, J=2.0 Hz, 6.8 Hz), 7.83–8.09 (4H, m), 8.36 (2H, m, J=2.0 Hz, 6.8 Hz)

REFERENCE EXAMPLE 27

4-Nitro-N-(3-pyridyl)benzamide

Using 3-aminopyridine (1.55 g, 16.5 mmol) and 4-nitrobenzoic acid (2.5 g, 15.0 mmol), the procedure of Reference Example 16 was repeated to obtain 1.81 g (49.6%) of the title compound in the form of colorless powder.

Melting point: 191°–194.5° C.

IR (KBr): 3305, 3025, 1605, 1602, 1539, 1521, 1422, 1353, 1305, 1281, 1236, 711 cm$^{-1}$

NMR (CDCl$_3$—CD$_3$OD) δ: 7.15–7.47 (2H, m), 8.08 (2H, d, J=9.0 Hz), 8.36 (2H, d, J=9.0 Hz), 8.19–8.54 (2H, m), 8.58–8.82 (1H, m)

REFERENCE EXAMPLE 28

2-Nitro-N-(3-methoxyphenyl)benzamide

Using m-anisidine (2.03 g, 16.5 mmol) and 2-nitrobenzoic acid (2.51 g, 15.0 mmol), the procedure of Reference Example 16 was repeated to obtain 3.47 g (84.9%) of the title compound in the form of light yellow needle crystals.

Melting point: 156°–158° C.

IR (KBr): 3252, 1656, 1612, 1598, 1488, 1470, 1350, 1266, 1202, 1030 cm$^{-1}$

NMR (CDCl$_3$—CD$_3$OD) δ: 3.80 (3H, s), 6.58–6.80 (1H, m), 7.00–7.40 (3H, m), 7.43–7.75 (4H, m), 7.96–8.18 (1H, m)

REFERENCE EXAMPLE 29

4-Nitro-N-(3-nitrophenyl)benzamide

Using 3-nitroaniline (2.76 g, 16.5 mmol) and 4-nitrobenzoic acid (2.51 g, 15.0 mmol), the procedure of Reference Example 16 was repeated to obtain 3.58 g (83.2%) of the title compound in the form of light yellow crystals.

Melting point: 229.2°–232° C.

IR (KBr): 3394, 3106, 3076, 1680, 1602, 1548, 1518, 1428, 1344, 1281, 1086, 870 cm$^{-1}$

NMR (CDCl$_3$—CD$_3$OD) δ: 7.40–7.83 (3H, m), 8.11 (2H, d, J=9.0 Hz), 8.36 (2H, d, J=9.0 Hz), 7.92–8.60 (2H, m)

REFERENCE EXAMPLE 30

4-Nitro-N-(2-methoxycarbonylphenyl)benzamide

Using methyl anthranilate (3.02 g, 20.0 mmol) and 4-nitrobenzoic acid (3.67 g, 22.0 mmol), the procedure of Reference Example 16 was repeated to obtain 4.20 g (72.9%) of the title compound in the form of light yellow prism crystals.

Melting point: 196°–199° C.

IR (KBr): 3368, 1676, 1606, 1520, 1346, 1276, 758, 697 cm$^{-1}$

NMR (CDCl$_3$) δ: 3.99 (3H, s), 7.18 (1H, t, J=7.3 Hz), 7.64 (1H, t, J=7.3 Hz), 8.06–8.44 (5H, m), 8.89 (1H, d, J=8.4 Hz)

REFERENCE EXAMPLE 31

4-Cyano-N-(4-methoxyphenyl)benzamide

Using p-anisidine (1.35 g, 11.0 mmol) and 4-cyanobenzoic acid (1.47 g, 10.0 mmol), the procedure of Reference Example 16 was repeated to obtain 2.31 g (91.7%) of the title compound in the form of colorless needle crystals.

Melting point: 154.6°–157.3° C.

IR (KBr): 3440, 2945, 1646, 1348, 1258, 973, 850, 715, 601 cm$^{-1}$

NMR (CDCl$_3$) δ: 3.82 (3H, s), 6.91 (2H, t, J=9.0 Hz), 7.51 (2H, d, J=9.0 Hz), 7.77 (2H, d, J=8.6 Hz), 7.94 (2H, d, J=8.6 Hz)

REFERENCE EXAMPLE 32

3-Methyl-4-nitro-N-(4-methoxyphenyl)benzamide

Using p-anisidine (738 mg, 6.0 mmol) and 3-methyl-4-nitrobenzoic acid (906 mg, 5.0 mmol), the procedure of Reference Example 16 was repeated to obtain 1.33 g (93.0%) of the title compound in the form of yellow powder.

Melting point: 167.8°–169.1° C.

IR (KBr): 3276, 1642, 1534, 1514, 1356, 1248, 1031, 826, 713, 522 cm$^{-1}$

NMR (CDCl$_3$) δ: 2.63 (3H, s), 3.81 (3H, s), 6.90 (2H, dd, J=2.2 Hz, 6.8 Hz), 7.42 (2H, dd, J=2.2 Hz, 6.8 Hz), 7.71–8.04 (3H, m)

REFERENCE EXAMPLE 33

3-Methoxy-4-nitro-N-(4-methoxyphenyl)benzamide

Using p-anisidine (738 mg, 6.0 mmol) and 3-methoxy-4-nitrobenzoic acid (986 mg, 5.0 mmol), the procedure of Reference Example 16 was repeated to obtain 1.40 g (92.7%) of the title compound in the form of colorless powder.

Melting point: 168°–169.3° C.

IR (KBr): 3312, 1650, 1526, 1514, 1238, 1028, 803,680 cm$^{-1}$

NMR (CDCl$_3$) δ: 3.82 (3H, s), 4.01 (3H, s), 6.92 (2H, d, J=9.0 Hz), 7.31–7.65 (3H, m), 7.84 (2H, d, J=8.1 Hz)

REFERENCE EXAMPLE 34

4-Nitro-N-(4-methylphenyl)benzamide

Using p-toluidine (1.19 g, 11.0 mmol) and 4-nitrobenzoic acid (1.77 g, 10.5 mmol), the procedure of Reference Example 16 was repeated to obtain 2.68 g (99.6%) of the title compound in the form of light yellow needle crystals.

Melting point: 140.5°–146.5° C.

IR (KBr): 3298, 1641, 1599 1533, 1515, 1449, 1347, 1320, 1302, 1260, 867, 708 cm$^{-1}$

NMR (CDCl$_3$) δ: 2.37 (3H, s), 6.87–7.53 (4H, m), 7.64–8.10 (1H, m), 7.99 (2H, d, J=9.0 Hz), 8.32 (2H, d, J=9.0 Hz)

REFERENCE EXAMPLE 35

4-Nitro-N-(4-fluorophenyl)benzamide

Using 4-fluoroaniline (1.0 ml, 9.93 mmol) and 4-nitrobenzoic acid (1.58 g, 9.36 mmol), the procedure of Reference Example 16 was repeated to obtain 1.60 g (65.8%) of the title compound in the form of light yellow needle crystals.

Melting point: 143°–146° C.

IR (KBr): 3280, 1648, 1598, 1554, 1524, 1504, 1348, 1322, 1244, 1212, 838, 824 cm$^{-1}$

NMR (CDCl$_3$) δ: 7.09 (2H, t, J=8.8 Hz), 7.63 (2H, dd, J=4.6 Hz, 8.8 Hz), 8.05 (2H, d, J=8.6 Hz), 8.10 (1H, s), 8.34 (2H, d, J=8.6Hz)

REFERENCE EXAMPLE 36

3-Nitro-N-(phenyl)benzamide

Using aniline (1.50 ml, 16.5 mmol) and 3-nitrobenzoic acid (2.64 g, 15.0 mmol), the procedure of Reference Example 16 was repeated to obtain 2.84 g (78.2%) of the title compound in the form of light yellow needle crystals.

Melting point: 153°–154° C.

IR (KBr): 1654, 1600, 1528, 1494, 1444, 1348, 1326, 1304, 1260, 756, 714 cm$^{-1}$

NMR (CDCl$_3$) δ: 7.19–7.48 (2H, m), 7.60–7.79 (4H, m), 7.86 (1H, br-s), 8.25 (1H, d, J=7.7 Hz), 8.40 (1H, d, J=7.7 Hz), 8.69 (1H, s)

REFERENCE EXAMPLE 37

3-Nitro-N-(4-methylphenyl)benzamide

Using p-toluidine (1.19 g, 11.0 mmol) and 3-nitrobenzoic acid (1.76 g, 10.0 mmol), the procedure of Reference Example 16 was repeated to obtain 2.27 g (88.3%) of the title compound in the form of colorless needle crystals.

Melting point: 160°–162° C.

IR (KBr): 3304, 1648, 1522, 1350, 1322, 814 cm$^{-1}$

NMR (CDCl$_3$) δ: 2.37 (3H, s), 7.18–7.28 (3H, m), 7.51–7.81 (4H, m), 8.28 (1H, d, J=8.6 Hz), 8.43 (1H, d, J=8.6 Hz), 8.72 (1H, s)

REFERENCE EXAMPLE 38

3-Nitro-N-(4-fluorophenyl)benzamide

Using 4-fluoroaniline (1.1 ml, 10.9 mmol) and 3-nitrobenzoic acid (1.76 g, 10.0 mmol), the procedure of Reference Example 16 was repeated to obtain 1.98 g (76.0%) of the title compound in the form of light yellow needle crystals.

Melting point: 167°–168° C.

IR (KBr): 3312, 1650, 1614, 1528, 1504, 1408, 1350, 1322, 1264, 1240, 1210, 1098, 832, 712, 518 cm$^{-1}$

NMR (CDCl$_3$) δ: 6.98–7.18 (3H, m), 7.53–7.79 (3H, m), 7.79–7.98 (1H, m), 8.24 (1H, d, J=7.8 Hz), 8.40 (1H, d, J=7.8 Hz), 8.68 (1H, s)

REFERENCE EXAMPLE 39

3-Nitro-N-(3-methylthiophenyl)benzamide

Using 3-methylthioaniline (2.1 ml, 16.5 mmol) and 3-nitrobenzoic acid (2.64 g, 15.0 mmol), the procedure of Reference Example 16 was repeated to obtain 4.09 g (94.6%) of the title compound in the form of light yellow needle crystals.

Melting point: 145° C.

IR (KBr): 3300, 1658, 1596, 1528, 1476, 1432, 1404, 1350, 1316, 1304, 832 cm$^{-1}$

NMR (CDCl$_3$) δ: 2.51 (3H, s), 7.04–7.35 (3H, m), 7.62 (1H, s), 7.73 (1H, d, J=8.7 Hz), 7.70–7.98 (1H, m), 8.24 (1H, d, J=7.8 Hz), 8.40 (1H, d, J=7.8 Hz), 8.68 (1H, s)

REFERENCE EXAMPLE 40

4-Nitro-N-(3,4-dimethylphenyl)benzamide

Using 3,4-xylidine (1.35 g, 11.0 mmol) and 4-nitrobenzoic acid (1.69 g, 10.0 mmol), the procedure of Reference Example 16 was repeated to obtain 2.70 g (quantitative) of the title compound in the form of light yellow crystals.

Melting point: 221°–223° C.

IR (KBr): 3292, 1650, 1600, 1540, 1514, 1500, 1414, 1342, 1326, 1312, 1300, 1288, 1262, 848, 812, 706 cm$^{-1}$

NMR (CDCl$_3$) δ: 2.27 (6H, s), 7.09–7.41 (3H, m), 7.80–7.81 (1H, m), 8.02 (2H, d, J=8.6 Hz), 8.33 (2H, d, J=8.6 Hz)

REFERENCE EXAMPLE 41

4-Nitro-N-(3,5-dimethylphenyl)benzamide

Using 3,5-xylidine (1.42 ml, 11.0 mmol) and 4-nitrobenzoic acid (1.76 g, 10.4 mmol), the procedure of Reference Example 16 was repeated to obtain 2.72 g (quantitative) of the title compound in the form of light yellow crystals.

Melting point: 206°–210° C.

IR (KBr): 3296, 1648, 1618, 1600, 1562, 1522, 1462, 1344, 1326, 1290, 1254, 864, 850, 838, 704, 682 cm$^{-1}$

NMR (CDCl$_3$) δ: 2.33 (6H, s), 6.84 (1H, s), 7.26 (2H, s), 8.00 (2H, d, J=8.8 Hz), 8.33 (2H, d, J=8.8 Hz)

REFERENCE EXAMPLE 42

4-Nitro-N-(4-chlorophenyl)benzamide

Using 4-chloroaniline (1.42 g, 11.0 mmol) and 4-nitrobenzoic acid (1.76 g, 10.4 mmol), the procedure of Reference Example 16 was repeated to obtain 2.84 g (98.5%) of the title compound in the form of yellow crystals.

Melting point: 233°–235° C.

IR (KBr): 3424, 1680, 1604, 1532, 1512, 1492, 1394, 1346, 1328, 1310, 1300, 1248 cm$^{-1}$

NMR (CDCl$_3$) δ: 7.36 (2H, d, J=9.0 Hz), 7.67 (2H, d, J=9.0 Hz), 7.84–7.88 (1H, m), 8.04 (2H, d, J=8.8 Hz), 8.35 (2H, d, J=8.8 Hz)

REFERENCE EXAMPLE 43

4-Nitro-N-(3,4-methylenedioxyphenyl)benzamide

Using 3,4-methylenedioxyaniline (1.44 g, 10.5 mmol) and 4-nitrobenzoyl chloride (1.86 g, 10.0 mmol), the procedure of Reference Example 11 was repeated to obtain 2.49 g (87.2%) of the title compound in the form of yellow crystals.

Melting point: 231°–234° C.

IR (KBr): 3316, 1650, 1599, 1533, 1512, 1494, 1452, 1344, 1320, 1278, 1245, 1200, 1035, 924, 864, 852 cm$^{-1}$

NMR (CDCl$_3$) δ: 5.98 (2H, s), 6.80 (2H, d, J=8.1 Hz), 7.06 (1H, dd, J=8.1 Hz, 1.9 Hz), 8.07 (2H, d, J=8.7 Hz), 8.32 (2H, d, J=8.7 Hz)

REFERENCE EXAMPLE 44

4-Hydroxymethyl-N-(2-methoxyphenyl)benzenesulfonamide

In an atmosphere of argon and with cooling in an ice bath, 4-[(2-methoxyanilino)sulfonyl]benzoic acid (150 mg, 0.488 mmol) was dissolved in THF (5 ml), to which were subsequently added dropwise triethylamine (0.14 ml, 1.0 mmol) and ethyl chloroformate (50 μl, 0.509 mmol). After 30 minutes of stirring at the same temperature, the thus formed precipitate was removed by filtration, and the resulting filtrate was concentrated. The thus obtained residue was dissolved in 5 ml of THF, and, with cooling in an ice bath, sodium borohydride (46.5 mg, 1.22 mmol) and water (1 ml) were added to the resulting solution. After 40 minutes of stirring at the same temperature, the reaction mixture was adjusted to pH 4 to 5 with 2N hydrochloric acid and extracted with ether. The organic layer was washed with saturated brine and dried on anhydrous magnesium sulfate. After removing the solvent by evaporation, the resulting colorless oily material was purified by silica gel column chromatography (ether) to obtain 99.6 mg (69.6%) of the title compound in the form of colorless solid.

Melting point: 101°–104° C.

IR (KBr): 3528, 3180, 1598, 1502, 1448, 1412, 1332, 1254, 1182, 1154, 1114, 1088, 1052, 922, 754, 590, 544 cm$^{-1}$

NMR (CDCl$_3$) δ: 1.79 (1H, t, J=6 Hz), 3.63 (3H, s), 4.72 (2H, d, J=6 Hz), 6.72 (1H, dd, J=8 Hz, 2 Hz), 6.83–7.16 (3H, m), 7.38 (2H, d, J=9 Hz), 7.51 (1H, dd, J=8 Hz, 2 Hz), 7.74 (2H, d, J=9 Hz)

REFERENCE EXAMPLE 45

4-Methoxymethyl-N-(2-methoxyphenyl)benzamide

4-Chloromethyl-N-(2-methoxyphenyl)benzamide (138 mg, 0.50 mmol) was dissolved in a methanol-THF (1:1) mixture solution (6 ml) to which was subsequently added 10% sodium hydroxide aqueous solution (3 ml) at room temperature. After 14 hours of stirring at the same temperature, the reaction solution was subjected to 3 hours of ultrasonic treatment. After removing the organic solvent by evaporation, the resulting residue was extracted with methylene chloride and dried on anhydrous magnesium sulfate. After removing the solvent by evaporation, the resulting colorless oily material was purified by silica gel column chromatography (ether:hexane=1:2) to obtain 126 mg (92.9%) of the title compound in the form of colorless oil.

IR (neat): 3440, 2930, 1674, 1602, 1530, 1510, 1482, 1460, 1434, 1252, 1102, 748 cm$^{-1}$ NMR (CDCl$_3$) δ: 3.41 (3H, s), 3.92 (3H, s), 4.52 (2H, s), 6.80–7.14 (3H, m), 7.45 (2H, d, J=8.5 Hz), 7.88 (2H, d, J=8.5 Hz), 8.35–8.68 (2H, m)

REFERENCE EXAMPLE 46

3-Hydroxymethyl-N-(2-methoxyphenyl)benzamide

N-Bromosuccinimide (1.29 g, 7.2 mmol) and AIBN (50 mg, 0.30 mmol) were suspended in carbon tetrachloride (80 ml), mixed with m-toluyl chloride (0.8 ml, 6.0 mmol) and then heated under reflux for 4 hours while exposing to light. After concentrating the reaction solution to ⅓ volume, insoluble materials were removed by filtration. To the resulting filtrate cooled in an ice bath were added dropwise o-anisidine (0.69 ml, 6 mmol) and 20% sodium hydroxide aqueous solution (5 ml) in that order. The resulting reaction mixture was stirred for 20 minutes at room temperature, extracted with methylene chloride and then washed with 10% citric acid aqueous solution, water and saturated brine in that order. After drying on anhydrous magnesium sulfate and removing the solvent by evaporation, the resulting light beige solid material was subjected to silica gel column chromatography (ether:hexane=1:1) to obtain creamy-colored powder. To this were added precipitated calcium carbonate (2.34 g, 23.4 mmol) and a dioxane-water (1:1) mixture solution (20 ml), followed by 6 hours of heating under reflux. After adding THF (50 ml) and filtering off the formed insoluble materials, the organic solvent was removed by evaporation. The resulting residue was extracted with ethyl acetate, and the organic layer was washed with saturated brine and dried on anhydrous magnesium sulfate, followed by the removal of the solvent by evaporation to obtain an orange oily material. This was dissolved in methanol (15 ml), and sodium borohydride (90 mg, 2.34 mmol) was added to the solution in one portion at −15° C. After 1 hour of stirring at the same temperature, the reaction mixture was mixed with acetone (1 ml), warmed to room temperature and then mixed with saturated ammonium chloride aqueous solution (10 ml). After removing methanol by evaporation, ethyl acetate extraction was carried out, and the resulting organic layer was washed with saturated brine, dried on anhydrous magnesium sulfate and then subjected to evaporation to remove the solvent. The thus obtained residue was subjected to silica gel column chromatography (ether:hexane=3:1), and the resulting colorless solid material was washed with an ether-hexane (2:1) mixture solution to obtain 1.02 g (66.1%) of the title compound in the form of colorless powder.

Melting point: 101.5°–102.5° C.

IR (KBr): 3312, 1650, 1594, 1534, 1494, 1462, 1434, 1332, 1288, 1256, 1224, 1030 cm$^{-1}$

NMR (CDCl$_3$) δ: 1.95 (1H, t, J=5 Hz), 3.93 (3H, s), 4.79 (2H, d, J=5 Hz), 6.76–7.18 (3H, m), 7.35–7.65 (2H, m), 7.67–8.00 (2H, m), 8.35–8.70 (2H, m)

REFERENCE EXAMPLE 47

4-Hydroxymethyl-N-(2-methoxyphenyl)benzamide

4-Chloromethyl-N-(2-methoxyphenyl)benzamide (500 mg, 1.81 mmol) and precipitated calcium carbonate (970 mg, 9.7 mmol) were suspended in a dioxane-water (1:1) mixture solution (9 ml) and subjected to 25 hours of heating under reflux. After adding THF (25 ml) and filtering off the formed insoluble materials, the organic solvent was removed by evaporation. The thus obtained residue was extracted with ethyl acetate, and the resulting organic layer was washed with saturated brine and dried on anhydrous magnesium sulfate. After removing the solvent by evaporation, the resulting colorless solid material was purified by subjecting it to a silica gel column chromatography (ether:hexane=3:1), thereby obtaining 411 mg (88.3%) of the title compound in the form of colorless crystals.

Melting point: 104°–105.5° C.

IR (KBr): 3428, 1648, 1604, 1536, 1510, 1488, 1456, 1438, 1346, 1292, 1254, 1038, 744, 614 cm$^{-1}$

NMR (CDCl$_3$) δ: 1.88 (1H, t, J=5 Hz), 3.93 (3H, s), 4.80 (2H, d, J=5 Hz), 6.76–7.16 (3H, m), 7.49 (2H, d, J=8 Hz), 7.89 (2H, d, J=8 Hz), 8.30–8.70 (2H, m)

REFERENCE EXAMPLE 48

4-Tetrahydropyranyloxymethyl-N-(2-methoxyphenyl)benzenesulfonamide

4-Hydroxymethyl-N-(2-methoxyphenyl)benzenesulfonamide (99.6 mg, 0.34 mmol) was dissolved in methylene chloride (3 ml) to which, with cooling in an ice bath, were subsequently added 3,4-dihydro-2H-pyrane (48 μl, 0.51 mmol) and a catalytically effective amount of p-toluenesulfonic acid monohydrate. After 90 minutes of stirring at the same temperature, the reaction solution was mixed with saturated sodium bicarbonate aqueous solution (5 ml) and extracted with ether. The resulting organic layer was washed with saturated brine and dried on anhydrous magnesium sulfate, and the solvent was removed by evaporation. Thereafter, the thus obtained light yellow oily material was purified by a silica gel column chromatography (ether:hexane=1:1) to obtain 117 mg (91.2%) of the title compound in the form of colorless solid.

Melting point: 67°–70° C.

IR (KBr): 3272, 2932, 1598, 1502, 1398, 1342, 1256, 1168, 1114, 1090, 1028, 972,908, 752,696, 548 cm$^{-1}$

NMR (CDCl$_3$) δ: 1.34–2.10 (6H, m), 3.30–4.10 (2H, m), 3.63 (3H, s), 4.46 (1H, d, J=13.2 Hz), 4.65 (1H, br-s), 4.78 (1H, d, J=13.2 Hz), 6.56–7.14 (4H, m), 7.19–7.60 (1H, m), 7.36 (2H, d, J=8 Hz), 7.74 (2H, d, J=8 Hz)

REFERENCE EXAMPLE 49

4-Tetrahydropyranyloxymethyl-N-(2-methoxyphenyl)benzamide

Using 4-hydroxymethyl-N-(2-methoxyphenyl)benzamide (129 mg, 0.5 mmol), the procedure of Reference Example 48 was repeated to obtain 166 mg (97.2%) of the title compound in the form of colorless solid.

Melting point: 67°–70° C.

IR (KBr): 3445, 2944, 1676, 1602, 1528, 1510, 1482, 1460, 1434, 1340, 1288, 1124, 1032, 748 cm$^{-1}$

NMR (CDCl$_3$) δ: 1.60–2.10 (6H, m), 3.40–3.72 (1H, m), 3.73–4.15 (1H, m), 3.92 (3H, s), 4.57 (1H, d, J=12.5 Hz), 4.73 (1H, br-s), 4.85 (1H, d, J=12.5 Hz), 6.80–7.15 (3H, m), 7.49 (2H, d, J=8 Hz), 7.87 (2H, d, J=8 Hz), 8.35–8.67 (2H, m)

REFERENCE EXAMPLE 50

4-Tetrahydropyranyloxymethyl-N-(2-methoxyphenyl)benzamide

Using 3-hydroxymethyl-N-(2-methoxyphenyl)benzamide (129 mg, 0.5 mmol), the procedure of Reference Example 48 was repeated to obtain 159 mg (93.1%) of the title compound in the form of colorless oil.

IR (neat): 3435, 2944, 1676, 1602, 1526, 1460, 1432, 1338, 1288, 1250, 1120, 1030, 746 cm$^{-1}$ NMR (CDCl$_3$) δ: 1.40–2.00 (6H, m), 3.40–3.70 (1H, m), 3.78–4.11 (1H, m), 3.92 (3H, s), 4.57 (1H, d, J=12.5 Hz), 4.75 (1H, br-s), 4.89 (1H, d, J=12.5 Hz), 6.80–7.15 (3H, m), 7.40–7.64 (2H, m), 7.67–7.98 (2H, m), 8.35–8.66 (2H, m)

REFERENCE EXAMPLE 51

4-Tetrahydropyranyloxymethyl-N-(3-methoxybenzyl)benzamide

Using 4-hydroxymethyl-N-(3-methoxybenzyl)benzamide (136 mg, 0.5 mmol), the procedure of Reference Example 48 was repeated to obtain 178 mg (100%) of the title compound in the form of colorless solid.

Melting point: 66°–68.5° C.

IR (KBr): 3308, 2944, 1640, 1552, 1492, 1352, 1320, 1260, 1140, 1116, 1032, 980, 770, 674 cm$^{-1}$

NMR (CDCl$_3$) δ: 1.35–2.23 (6H, m), 3.37–4.13 (2H, m), 3.79 (3H, s), 4.35–4.97 (5H, m), 6.15–6.55 (1H, m), 6.67–7.06 (3H, m), 7.12–7.33 (1H, m), 7.42 (2H, d, J=8 Hz), 7.77 (2H, d, J=8 Hz)

REFERENCE EXAMPLE 52

N-(2-Methoxyphenyl)-4-phthalimidomethylbenzamide

In an atmosphere of argon, phthalimide (150 mg, 1.0 mmol) was dissolved in THF (10 ml) to which was subsequently added sodium hydride (44 mg, 60%, 1.1 mmol) at room temperature. After 40 minutes of stirring at the same temperature, to this was added a DMF solution (5 ml) containing 4-chloromethyl-N-(2-methoxyphenyl)benzamide (276 mg, 1.0 mmol) and a catalytically effective amount of sodium iodide. After 2 hours of stirring at 80° C. and subsequent removal of the solvent by evaporation, the resulting residue was mixed with water (10 ml) and extracted with an ethyl acetate-methylene chloride (1:2) mixture solution. The resulting organic layer was washed with water and saturated brine and dried on anhydrous magnesium sulfate. Thereafter, the solvent was removed by evaporation, and the resulting residue was subjected to a silica gel column chromatography (methylene chloride-ether:hexane=2:1) and then washed with ether to obtain 300 mg (77.6%) of the title compound in the form of colorless solid.

Melting point: 176.5°–179.5° C.

IR (KBr): 3350, 1710, 1658, 1522, 1462, 1432, 1394, 1288, 938, 748, 724 cm$^{-1}$

NMR (CDCl$_3$) δ: 3.90 (3H, s), 4.91 (2H, s), 6.80–7.14 (3H, m), 7.54 (2H, d, J=8.5 Hz), 7.65–8.10 (6H, m), 8.30–8.67 (2H, m)

REFERENCE EXAMPLE 53

N-(2-Methoxyphenyl)-4-morpholinomethylbenzamide

In an atmosphere of argon, morpholine (192 mg, 2.2 mmol) was dissolved in ether (5 ml) to which, with cooling in an ice bath, was subsequently added n-butyl lithium (1.45 ml, 1.52M, 2.2 mmol). After 5 minutes of stirring at room temperature, to this was added 4-chloromethyl-N-(2-methoxyphenyl)benzamide (276 mg, 1.0 mmol) at the same temperature. After adding THF (5 ml) and stirring for 2.5 hours at 60° C., the reaction solution was mixed with water (20 ml) and extracted with ethyl acetate. After removing insoluble materials by filtration, the organic layer was washed with water and saturated brine and then dried on anhydrous sodium carbonate. Thereafter, the solvent was removed by evaporation, and the resulting residue was purified by subjecting it to a silica gel column chromatography (ether) to obtain 128 mg (39.2%) of the title compound in the form of light yellow solid.

Melting point: 90°–93.5° C.

IR (KBr): 3440, 1666, 1600, 1530, 1510, 1486, 1460, 1440, 1340, 1292, 1252, 1112, 1020, 866, 754 cm$^{-1}$

NMR (CDCl$_3$) δ: 2.46 (4H, t, J=5 Hz), 3.56 (2H, s), 3.72 (4H, t, J=5 Hz), 3.92 (3H, s), 6.70–7.14 (3H, m), 7.45 (2H, d, J=8.5 Hz), 7.85 (2H, d, J=8.5 Hz), 8.33–8.70 (2H, m)

REFERENCE EXAMPLE 54

N-(2-Methoxyphenyl)-4-dimethylaminomethylbenzamide

In an atmosphere of argon, 4-chloromethyl-N-(2-methoxyphenyl)benzamide (276 mg, 1.0 mmol) was put into a 25 ml capacity eggplant type flask equipped with a cold finger and dissolved in dioxane (3 ml), followed by the addition of 50% dimethylamine aqueous solution (3 ml) at room temperature. After 2.5 hours of stirring at 80° C. and subsequent removal of dioxane by evaporation, the resulting residue was diluted with ethyl acetate (30 ml). The thus diluted solution was dried on anhydrous sodium carbonate, and the resulting residue was purified by subjecting it to a silica gel column chromatography (ether-ethyl acetate-ethyl acetate:methanol=10:1) to obtain 284 mg (100%) of the title compound in the form of colorless oil.

IR (neat): 3440, 2944, 2816, 2772, 1676, 1602, 1530, 1482, 1460, 1434, 1338, 1290, 1250, 1028, 748 cm$^{-1}$ NMR (CDCl$_3$) δ: 2.25 (6H, s), 3.48 (2H, s), 3.93 (3H, s), 6.80–7.13 (3H, m), 7.42 (2H, d, J=8.5 Hz), 7.84 (2H, d, J=8.5 Hz), 8.35–8.66 (2H, m)

REFERENCE EXAMPLE 55

N-(2-Methoxyphenyl)-4-(methylamino)methylbenzamide

4-Chloromethyl-N-(2-methoxyphenyl)benzamide (400 mg, 1.45 mmol) was dissolved in dioxane (4 ml) and then mixed with 50% methylamine aqueous solution (4 ml) at room temperature. After 1 hour of stirring at the same temperature, dioxane was removed by evaporation, and the resulting residue was diluted with methylene chloride (10 ml). After drying on anhydrous sodium carbonate, the solvent was removed by evaporation to obtain 500 mg (100%) of the title compound in the form of colorless oil.

IR (neat): 3436, 2956, 2848, 1674, 1602, 1527, 1485, 1461, 1251, 1122, 747 cm$^{-1}$ NMR (CDCl$_3$) δ: 1.51 (1H, s), 2.47 (3H, s), 3.84 (2H, s), 3.92 (3H, s), 6.81–7.10 (3H, m), 7.42 (2H, d, J=8.5 Hz), 7.83 (2H, d, J=8.5 Hz), 8.42–8.58 (2H, m)

REFERENCE EXAMPLE 56

4-(N-tert-Butoxycarbonyl-N-methylamino)methyl-N-(2-methoxyphenyl)benzamide

N-(2-Methoxyphenyl)-4-(methylamino)methylbenzamide (500 mg, 1.45 mmol) was dissolved in a dioxane-water (2:1) mixture solution (5 ml) to which, with cooling in an ice bath, were subsequently added 1N sodium hydroxide aqueous solution (2 ml) and di-tert-butyl dicarbonate (380 mg, 1.74 mmol). After 14 hours of stirring at room temperature, the resulting solution was extracted with methylene chloride, and thus obtained organic layer was washed with saturated brine and then dried on anhydrous sodium carbonate. Thereafter, the solvent was removed by evaporation, and the resulting residue was purified by subjecting it to a silica gel column chromatography (ethyl acetate:hexane=1:2) to obtain 537 mg (100%) of the title compound in the form of colorless oil.

IR (neat): 2974, 2932, 1689, 1605, 1527, 1485, 1461, 1395, 1248, 1146 cm$^{-1}$

NMR (CDCl$_3$) δ: 1.57 (9H, s), 2.85 (3H, s), 3.93 (3H, s), 4.49 (2H, s), 6.89–7.12 (3H, m), 7.33 (2H, d, J=8.5 Hz), 7.85 (2H, d, J=8.5 Hz), 8.42–8.55 (2H, m)

REFERENCE EXAMPLE 57

4-Chloromethyl-N-(2-methoxyphenyl)-N-(1,3-dioxolan-2-yl)methylbenzamide

In an atmosphere of argon, a mixture consisting of o-anisidine (500 mg, 4.06 mmol), triethylamine (1.6 ml, 11.5 mmol) and 2-bromomethyl-1,3-dioxolan (0.96 ml, 8.18 mmol) was stirred at 80° C. for 4 days, dissolved in methylene chloride (8 ml) and then, with cooling in an ice bath, mixed with 20% sodium hydroxide aqueous solution (4 ml) and 4-chloromethylbenzoyl chloride (768 mg, 4.06 mmol). After 1 hour of stirring at the same temperature, the resulting mixture was extracted with methylene chloride, washed with 10% citric acid aqueous solution and saturated brine and then dried on anhydrous sodium sulfate. Thereafter, the solvent was removed by evaporation, and the resulting residue was purified by subjecting it to a silica gel column chromatography (ethyl acetate:hexane=2:5) to obtain 704 mg (47.9%) of the title compound in the form of colorless solid.

Melting point: 126°–129° C.

IR (KBr): 1644, 1500, 1418, 1384, 1306, 1276, 1162, 1134, 1074, 1030, 746 cm$^{-1}$

NMR (CDCl$_3$) δ: 3.68 (3H, s), 3.80–4.02 (1H, m), 3.91 (4H, d, J=3 Hz), 4.20–4.65 (1H, m), 4.45 (2H, s), 5.25 (1H, t, J=5 Hz), 6.74 (1H, d, J=8.5 Hz), 6.85 (1H, d, J=7.5 Hz), 6.96–7.43 (6H, m)

REFERENCE EXAMPLE 58

N-(2-Methoxyphenyl)-N-(1,3-dioxolan-2-yl)-methyl-4-phthalimidomethylbenzamide

Using 4-chloromethyl-N-(2-methoxyphenyl)-N-(1,3-dioxoian-2-yl)methylbenzamide (556 mg, 1.54 mmol), the procedure of Reference Example 52 was repeated to obtain 546 mg (75.1%) of the title compound in the form of colorless solid.

Melting point: 150°–152° C.

IR (KBr): 1716, 1641, 1503, 1422, 1392, 1347, 1308, 1278, 1251, 1134, 1122, 1086, 1035, 1014, 942, 744, 720 cm$^{-1}$

NMR (CDCl$_3$) δ: 3.47–4.02 (1H, m), 3.66 (3H, s), 3.88 (4H, d, J=3 Hz), 4.20–4.55 (1H, m), 4.72 (2H, s), 5.23 (1H, t, J=5 Hz), 6.71 (1H, d, J=8 Hz), 6.81 (1H, d, J=7.5 Hz), 6.96–7.38 (6H, m), 7.55–7.93 (4H, m)

REFERENCE EXAMPLE 59

4-(4-Fluorobenzoyl)-1-(2-hydroxyethyl)piperidine

In an atmosphere of argon, 4-(4-fluorobenzoyl)piperidine (2.07 g, 10 mmol) was dissolved in triethylamine (30 ml) to which was subsequently added dropwise 2-bromoethanol (1.1 ml, 14.7 mmol) at room temperature. After 1 hour of heating under reflux, triethylamine was removed by evaporation, and the resulting residue was mixed with saturated sodium carbonate aqueous solution (40 ml) and extracted with ethyl acetate. The resulting organic layer was dried on anhydrous sodium carbonate, the solvent was removed by evaporation and then the resulting residue was purified by subjecting it to a silica gel column chromatography (ethyl acetate-methylene chloride:methanol=10:1) to obtain 1.96 g (78.0%) of the title compound in the form of light yellow solid.

Melting point: 45°–47° C.

IR (KBr): 3428, 2944, 1680, 1596, 1278, 1238, 1204 cm$^{-1}$

NMR (CDCl$_3$) δ: 1.71–1.95 (4H, m), 2.01–2.43 (3H, m), 2.54 (2H, t, J=6 Hz), 2.83–3.38 (3H, m), 3.60 (2H, t, J=6 Hz), 7.12 (2H, dd, J=9 Hz, 9 Hz), 7.93 (2H, dd, J=9 Hz, 6 Hz)

REFERENCE EXAMPLE 60

1-(2-Chloroethyl)-4-(4-fluorobenzoyl)piperidine hydrochloride

In an atmosphere of dry air, 4-(4-fluorobenzoyl)-1-(2-hydroxyethyl)piperidine (1.96 g, 7.8 mmol) was dissolved in methylene chloride (10 ml) to which, with cooling in an ice bath, were subsequently added dropwise DMF (0.1 ml) and thionyl chloride (2.5 ml, 34.2 mmol). After 7 hours of stirring at room temperature, the solvent was removed by evaporation, and the resulting residue was subjected to azeotropic distillation using benzene (15 ml×2). Thereafter, the thus obtained residue was washed with an ether-methylene chloride (4:1) mixture solution (30 ml) to obtain 2.3 g (96.3%) of the title compound in the form of light beige powder.

IR (KBr): 2620, 2520, 1678, 1598, 1506, 1446, 1408, 1278, 1224, 1158, 950, 840, 606 cm$^{-1}$

NMR (CDCl$_3$) δ: 1.75–2.90 (4H, m), 2.90–4.50 (9H, m), 6.90–7.40 (2H, m), 7.65–8.30 (2H, m)

REFERENCE EXAMPLE 61

1-(2-Chloroethyl)-4-(4-fluorobenzoyl)piperidine 1-(2-Chloroethyl)-4-(4-fluorobenzoyl)piperidine hydrochloride (800 mg, 2.61 mmol) was suspended in ether (20 ml). With cooling in an ice bath, saturated sodium carbonate aqueous solution (5 ml) was added dropwise to the suspension. The reaction solution was extracted with ether and washed with saturated brine, and the resulting organic layer was dried on anhydrous sodium carbonate. Thereafter, the organic layer was filtered through silica gel (5 g), the solvent was removed by evaporation and then the resulting residue was purified by subjecting it to a silica gel column chromatography (ether) to obtain 650 mg (92.3%) of the title compound in the form of light yellow solid.

Melting point: 33°–37° C.

IR (KBr): 2944, 2812, 1666, 1598, 1446, 1412, 1376, 1298, 1264, 1230, 1208, 1164, 1132, 1104, 976, 852 cm$^{-1}$

NMR (CDCl$_3$) δ: 1.67–1.96 (4H, m), 2.07–2.43 (2H, m), 2.75 (2H, t, J=7.5 Hz), 2.86–3.30 (3H,m), 3.60 (2H, d, J=7.5 Hz), 7.12 (2H, dd, J=9 Hz, 9 Hz), 7.93 (2H, dd, J=9 Hz, 6 Hz)

REFERENCE EXAMPLE 62

1-(2,2-Diethoxyethyl)-4-(4-fluorobenzoyl)piperidine 4-(4-Fluorobenzoyl)piperidine (207 mg, 1.0 mmol) was dissolved in methylene chloride (5 ml) to which were subsequently added bromoacetoaldehyde diethylacetal (305 mg, 1.5 mmol) and triethylamine (0.5 ml). After 12 hours of heating under reflux, the solvent was removed by evaporation, and the resulting residue was purified by subjecting it to a silica gel column chromatography (ether) to obtain 81 mg (25.0%) of the title compound in the form of orange oil.

IR (neat): 2976, 2944, 1682, 1598, 1278, 1230, 1206 1156, 1120, 1062, 976, 852 cm$^{-1}$ NMR (CDCl$_3$) δ: 1.21 (6H, t, J=7 Hz), 1.50–1.98 (4H, m), 2.02–2.44 (2H, m), 2.56 (2H, d, J=5.6 Hz), 2.85–3.30 (3H, m), 3.58, 3.66 (each 2H, q, J=7 Hz), 4.65 (1H, t, J=5.6 Hz), 7.12 (2H, dd, J=9 Hz, 9 Hz), 7.95 (2H, dd, J=9 Hz, 6 Hz)

REFERENCE EXAMPLE 63

4-(4-Fluorobenzoyl)-1-[2-(2-methoxyanilino)ethyl] piperidine 1-(2,2-Diethoxyethyl)-4-(4-fluorobenzoyl)piperidine (81 mg, 0.25 mmol) was dissolved in THF (3 ml) to which was subsequently added 10% hydrochloric acid (2 ml) at room temperature. After 1 hour of stirring at the same temperature, the solvent was removed by evaporation, and the resulting residue was subjected to azeotropic distillation using benzene (5 ml×4) to obtain an orange glutinous material. The thus obtained residue was dissolved in methanol (2 ml) to which were subsequently added o-anisidine (29 µl, 0.25 mmol) and sodium cyanoborohydride (11 mg, 0.166 mmol) at room temperature. After 2 hours of stirring at the same temperature, the reaction solution was mixed with saturated sodium carbonate aqueous solution (10 ml), extracted with ethyl acetate and then washed with water and saturated brine. The resulting organic layer was dried on anhydrous sodium carbonate, the solvent was removed by evaporation and then the resulting residue was purified by subjecting it to a silica gel column chromatography (ether:hexane=2:1-ether) to obtain 59 mg (66.2%) of the title compound in the form of colorless solid.

Melting point: 116°–120° C.

IR (KBr): 3410, 2956, 2810, 1678, 1600, 1510, 1450, 1288, 1268, 1234, 1224, 1204, 1154, 1022, 728 cm$^{-1}$

NMR (CDCl$_3$) δ: 1.60–2.38 (7H, m), 2.70 (2H, t, J=6 Hz), 2.83–3.45 (5H, m), 3.85 (3H, s), 6.47–6.92 (4H, m), 7.13 (2H, dd, J=9 Hz, 9 Hz), 7.96 (2H, dd, J=9 Hz, 6 Hz)

REFERENCE EXAMPLE 64

N-(2-Tetrahydropyranyloxyethyl)-3-methoxy-N-(2-methoxyphenyl)benzamide

In an atmosphere of argon, 3-methoxy-N-(2-methoxyphenyl) benzamide (500 mg, 1.94 mmol) was dissolved in DMF (10 ml) to which was subsequently added sodium hydride (85 mg, 60%, 2.13 mmol) at room temperature, followed by 20 minutes of stirring. After additional 5 minutes of stirring under an ultrasonic irradiation condition at the same temperature, to this was added 2-tetrahydropyranyloxyethyl bromide (446 mg, 2.13 mmol) at room temperature. After 1 hour of stirring at room temperature and subsequent stirring at 70° C. for 6 hours, DMF was removed by evaporation, and the resulting residue was mixed with water (20 ml), extracted with ether and then washed with water and saturated brine. The resulting organic layer was dried on anhydrous magnesium sulfate, the solvent was removed by evaporation and then the resulting orange oily residue was purified by subjecting it to a silica gel column chromatography (ether:hexane=2:1) to obtain 501 mg (67.0%) of the title compound in the form of yellow oil.

IR (neat): 2944, 1650, 1586, 1502, 1456, 1434, 1384, 1318, 1286, 1252, 1122, 1074, 1034, 750 cm$^{-1}$ NMR (CDCl$_3$) δ: 1.20–2.00 (6H, m), 3.25–4.40 (6H, m), 3.63, 3.66 (each 3H, s), 4.57 (1H, br-s), 6.58–7.30 (8H, m)

REFERENCE EXAMPLE 65

4-Methoxy-N-(hydroxyethyl)-N-(2-methoxyphenyl) benzenesulfonamine

In an atmosphere of argon, 4-methoxy-N-(2-methoxyphenyl) benzene sulfonamide (300 mg, 1.02 mmol) was dissolved in DMF (6 ml) to which was subsequently added sodium hydride (49 mg, 60%, 1.23 mmol) at room temperature. After 1 hour of stirring, to this was added 2-tetrahydropyranyloxyethyl bromide (258 mg, 1.23 mmol) at room temperature. After 4 hours of stirring at 70° C., DMF was removed by evaporation, and the resulting residue was mixed with saturated ammonium chloride aqueous solution (10 ml), extracted with ethyl acetate and then washed with water and saturated brine, followed by drying on anhydrous magnesium sulfate and distillation removal of the solvent to obtain a light yellow oily material. The thus obtained residue was dissolved in methanol (5 ml) and stirred for 3 hours at room temperature in the presence of a catalytically effective amount of p-toluenesulfonic acid monohydrate. After removing methanol by evaporation, the reaction solution was mixed with saturated sodium bicarbonate aqueous solution (10 ml), extracted with ethyl acetate and then washed with saturated brine. The resulting organic layer was dried on anhydrous magnesium sulfate, the solvent was removed by evaporation and then the resulting light yellow oily residue was purified by subjecting it to a silica gel column chromatography (ether:hexane=4:1) to obtain 235 mg (68.3%) of the title compound in the form of colorless oil.

IR (neat): 3532, 2944, 1596, 1498, 1462, 1342, 1302, 1260, 1156, 1116, 1072, 1042, 1024, 586, 562 cm$^{-1}$ NMR (CDCl$_3$) δ: 2.65–2.97 (1H, m), 3.38–3.85 (4H, m), 3.63, 3.87 (each 3H, s), 6.70–7.45 (6H, m), 7.67 (2H, d, J=9 Hz)

REFERENCE EXAMPLE 66

4-Fluoro-N-(2-hydroxyethyl)-N-(2-methoxyphenyl) benzenesulfonamine

Using 4-fluoro-N-(2-methoxyphenyl)benzene sulfonamide (282 mg, 1.0 mmol), the procedure of Reference Example 65 was repeated to obtain 302 mg (92.8%) of the title compound in the form of colorless oil.

IR (neat): 3536, 2940, 1592, 1494, 1344, 1290, 1234, 1166, 1118, 1088, 1072, 1042, 1024, 838, 756, 586, 554 cm$^{-1}$ NMR (CDCl$_3$) δ: 2.44–2.73 (1H, m), 3.30–3.83 (4H, m), 3.56 (3H, s), 6.65–7.43 (6H, m), 7.73 (2H, dd, J=9 Hz, 6 Hz)

REFERENCE EXAMPLE 67

N-(2-Hydroxyethyl)-3-methoxy-N-(2-methoxyphenyl)benzamide

3-Methoxy-N-(2-methoxyphenyl)-N-(2-tetrahydropyranyloxyethyl)benzamide (501 mg, 1.30 mmol) was dissolved in methanol (4 ml) to which was subsequently added a catalytically effective amount of p-toluenesulfonic acid monohydrate and stirred for 3 hours at room temperature. The reaction solution was mixed with saturated sodium bicarbonate aqueous solution (10 ml) and extracted with ether, and then washed with water and saturated brine. The resulting organic layer was dried on anhydrous magnesium sulfate, the solvent was removed by evaporation and then the resulting colorless oily residue was purified by subjecting it to a silica gel column chromatography (ether:hexane=3:1) to obtain 340 mg (86.8%) of the title compound in the form of light yellow oil.

IR (neat): 3432, 1638, 1580, 1502, 1458, 1434, 1396, 1320, 1288, 1250, 1046, 1026, 750 cm$^{-1}$ NMR (CDCl$_3$) δ: 3.30–4.13 (5H, m), 3.63, 3.73 (each 3H, s), 6.60–7.30 (8H, m)

REFERENCE EXAMPLE 68

N-Formylmethyl-3-methoxy-N-(2-methoxyphenyl) benzamide

In an atmosphere of argon, N-(2-hydroxyethyl)-3-methoxy-N-(2-methoxyphenyl)benzamide (339 mg, 1.12 mmol) was dissolved in DMSO (4 ml) to which were subsequently added dropwise triethylamine (0.724 ml, 5.20 mmol) and a DMSO solution (8 ml) of a sulfur trioxide-pyridine complex (844 mg, 5.20 mmol) at room temperature. After 20 minutes of stirring at the same temperature, this was mixed with ice water (40 ml) and extracted with ethyl acetate, and then washed with water and saturated brine. The resulting organic layer was dried on anhydrous magnesium sulfate, and the solvent was removed by evaporation to obtain 220 mg (65.6%) of the title compound the form of light yellow solid.

Melting point: 77°–81° C.

IR (KBr): 1732, 1648, 1588, 1502, 1462, 1432, 1372, 1322, 1280, 1252, 1044, 1026 cm$^{-1}$

NMR (CDCl$_3$) δ: 3.64, 3.77 (each 3H, s), 4.40 (2H, s), 6.55–7.30 (8H, m), 9.76 (1H, s)

REFERENCE EXAMPLE 69

N-Formylmethyl-N-(2-methoxyphenyl)-4-phthalimidomethylbenzamide

N-(2-Methoxyphenyl)-N-(1,3-dioxolan-2-yl)methyl-4-phthalimidomethylbenzamide (450 mg, 0.953 mmol) was dissolved in THF (6 ml) to which was subsequently added 10% hydrochloric acid (4 ml) at room temperature. After 2 hours of stirring at 60° C., the resulting reaction solution was extracted with chloroform and washed with saturated brine. The resulting organic layer was dried on anhydrous magnesium sulfate, the solvent was removed by evaporation and then the resulting residue was mixed with 5 ml of chloroform to remove insoluble materials by filtration, thereby obtaining 300 mg (73.5%) of the title compound in the form of yellow oil which was used in the subsequent reaction without further purification.

IR (neat): 1716, 1644, 1500, 1428, 1392, 1248, 747, 717 cm$^{-1}$

NMR (CDCl$_3$) δ: 3.73 (3H, s), 4.35 (2H, s), 4.72 (2H, s), 6.63– 7.35, (8H, m), 7.60–7.88 (4H, m), 9.61 (1H, s)

INVENTIVE EXAMPLE 1

N-{2-[4-(4-Fluorobenzoyl)piperidino]ethyl}-3-methoxy-N-(2-methoxyphenyl)benzamide N-Formylmethyl-3-methoxy-N-(2-methoxyphenyl)-benzamide (141 mg, 0.473 mmol), and 4-(4-fluorobenzoyl) piperidine (125 mg, 0.60 mmol) were dissolved in methanol (4.5 ml) to which was subsequently added molecular sieve 4A (300 mg) at room temperature. After 1 hour of stirring at the same temperature, sodium cyanoborohydride (12 mg, 0.191 mmol) was added to the above mixture, followed by 45 minutes of stirring and subsequent addition of acetone (2 ml). The reaction solution was diluted with ether (15 ml) and filtered through cerite, and the solvent was removed by evaporation. The thus obtained colorless oily residue was dissolved in ether (7 ml), mixed with saturated hydrogen chloride/ether solution (7 ml) and stirred for 5 minutes. After removing the ether layer, the reaction solution was mixed with water (7 ml) and potassium carbonate (1.5 g) and extracted with ether and dried on potassium carbonate, and then the solvent was removed by evaporation. Thereafter, the resulting colorless oily residue was purified by subjecting it to a silica gel column chromatography (ether:hexane= 3:2) to obtain 107 mg (46.1%) of the title compound in the form of light yellow oil.

IR (neat): 2944, 1678, 1638, 1596, 1500, 1458, 1390, 1278, 1248, 1156, 1046, 748 cm$^{-1}$ NMR (CDCl$_3$) δ: 1.58–1.93 (4H, m), 2.00–2.36 (2H, m), 2.63 (2H, t, J=7.5 Hz), 2.80–3.30 (3H, m), 3.64, 3.70 (each 3H, s), 3.90–4.40 (2H, m), 6.55–7.30 (10H, m), 7.95 (2H, dd, J=9 Hz, 6 Hz)

INVENTIVE EXAMPLE 2

N-{2-[4-(4-Fluorobenzoyl)piperidino]ethyl}-4-methoxy-N-(2-methoxyphenyl)benzene sulfonamide In an atmosphere of argon at room temperature, N-hydroxyethyl-4-methoxy-N-(2-methoxyphenyl)benzene sulfonamide (235 mg, 0.697 mmol) was dissolved in DMSO (3 ml) to which were subsequently added dropwise triethylamine (0.48 ml, 3.44 mmol) and sulfur trioxide-pyridine complex (558 mg, 3.44 mmol) which has been dissolved in DMSO (3 ml). After 20 minutes of stirring at the same temperature, ice water (10 ml) was added to the reaction solution, and the mixture was extracted with ethyl acetate and then washed with water and saturated brine. The resulting organic layer was dried on anhydrous magnesium sulfate, and the solvent was removed by evaporation to obtain a light yellow oily material. The thus obtained residue was dissolved in methanol (5 ml) to which were subsequently added 4-(4-fluorobenzoyl)piperidine (108 mg, 0.52 mmol) and molecular sieve 4A (200 mg) at room temperature. After 45 minutes of stirring at the same temperature, sodium cyanoborohydride (11 mg, 0.166 mmol) was added to the reaction mixture which was stirred for additional 30 minutes, followed by the addition of acetone (1 ml). The resulting reaction solution was diluted with ether (10 ml) and filtered through cerite, followed by the removal of the solvent by evaporation. The thus obtained colorless oily residue was dissolved in ether (10 ml) and extracted with 2N hydrochloric acid (10 ml). After removing the ether layer, the resulting reaction solution was adjusted to pH 9 to 10 with 10% sodium hydroxide aqueous solution and extracted with methylene chloride, the resulting organic layer was dried on potassium carbonate and then the solvent was removed by evaporation. Thereafter, the resulting yellow oily residue was purified by subjecting it to a silica gel column chromatography and PTLC (ether:hexane=7:1) to obtain 56.7 mg (15.4%) of the title compound in the form of colorless oil.

IR (neat): 2944, 1680, 1598, 1498, 1342, 1258, 1158, 732, 588, 562 cm$^{-1}$

NMR (CDCl$_3$) δ: 1.53–2.30 (6H, m), 2.52 (2H, t, J=7.5 Hz), 2.73–3.30 (3H, m), 3.43 (3H, s), 3.72 (2H, t, J=7.5 Hz), 3.84 (3H, s), 6.67–7.40 (8H, m), 7.62 (2H, d, J=9 Hz), 7.93 (2H, dd, J=9 Hz, 6 Hz)

INVENTIVE EXAMPLE 3

4-Fluoro-N-{2-[4-(4-fluorobenzoyl)piperidino]ethyl}-N-(2-methoxyphenyl)benzene sulfonamide Using 4-fluoro-N-hydroxymethyl-N-(2-methoxyphenyl)benzene sulfonamide (302 mg, 0.928 mmol), the procedure of Inventive Example 2 was repeated to obtain 81 mg (16.9%) of the title compound in the form of yellow oil.

IR (neat): 2948, 1680, 1596, 1494, 1344, 1234, 1156, 1094, 838, 732, 586, 554 cm$^{-1}$ NMR (CDCl$_3$) δ: 1.50–2.31 (6H, m), 2.51 (2H, t, J=7.5 Hz), 2.72–3.30 (3H, m), 3.39 (3H, s), 3.66–3.90 (2H, m), 6.60–7.50 (8H, m), 7.69, 7.93 (each 2H, dd, J=9 Hz, 6 Hz)

INVENTIVE EXAMPLE 4

4-Chloromethyl-N-{2-[4-(4-fluorobenzoyl)piperidino]ethyl}-N-2-methoxyphenyl)benzamide In an atmosphere of argon, 4-(4-fluorobenzoyl)-1-[2-(2-methoxyanilino)ethyl]piperidine (264 mg, 0.741 mmol) was dissolved in methylene chloride (7.5 ml) to which were subsequently added triethylamine (0.42 ml, 3.0 mmol), p-toluenesulfonyl chloride (158 mg, 0.83 mmol) and a catalytically effective amount of 4-dimethylaminopyridine at room temperature. After 15 hours of stirring at the same temperature, 4-chloromethylbenzoyl chloride (145 mg, 0.741 mmol) was added to the reaction mixture which was subject to heat under reflux for 2.5 days. The resulting residue was diluted with water (10 ml) and added with 2N hydrochloric acid (5 ml) and extracted with methylene chloride, and then washed with 5% sodium hydroxide aqueous solution and water. After drying on anhydrous magnesium sulfate, the solvent was removed by evaporation, and the resulting orange oily residue was purified by subjecting it to a silica gel column chromatography (methylene chloride:ether=1:1) to obtain 314 mg (83.2%) of the title compound in a light yellow amorphous form.

IR (KBr): 2944, 1680, 1644, 1596, 1502, 1440, 1392, 1278, 1238, 1156, 750 cm$^{-1}$

NMR (CDCl$_3$) δ: 1.57–2.00 (4H, m), 2.00–2.45 (2H, m), 2.48–2.80 (2H, m), 2.80–3.38 (3H, m), 3.48–3.94 (1H, m), 3.66 (3H, s), 3.96–4.32 (1H, m), 4.44 (2H, s), 6.73 (1H, d, J=7.5 Hz), 6.84 (1H, d, J=8 Hz), 6.92–7.43 (8H, m), 7.94 (2H, dd, J=9 Hz, 6 Hz)

INVENTIVE EXAMPLE 5

N-{2-[4-(4-fluorobenzoyl)piperidino]ethyl}-4-methoxymethyl-N-(2-methoxyphenyl)benzamide In an atmosphere of argon, 4-methoxymethyl-N-(2-methoxyphenyl)benzamide (126 mg, 0.464 mmol), 1-(2-chloroethyl)-4-(4-fluorobenzoyl)piperidine hydrochloride (157 mg, 0.511 mmol) and sodium iodide (154 mg, 1.02 mmol) were dissolved in DMF (3 ml) to which was subsequently added sodium hydride (40 mg, 60%, 1.0 mmol) at room temperature. After stirring at room temperature for 10 minutes and then at 60° C. for 3.5 hours, DMF was removed by evaporation. The resulting residue was diluted with water (10 ml) and extracted with ethyl acetate, and the organic layer was washed with water and saturated brine and then dried on anhydrous sodium carbonate. Thereafter, the solvent was removed by evaporation, and the resulting residue was purified by subjecting it to a silica gel column chromatography (methylene chloride:methanol=80:1-ethyl acetate) to obtain 128 mg (54.7%) of the title compound in the form of colorless oil.

IR (neat): 2940, 1680, 1644, 1598, 1410, 1378, 1308, 1278, 1262, 1240, 1158, 1112, 752, 604 cm$^{-1}$ NMR (CDCl$_3$) δ: 1.55–1.95 (4H, m), 1.98–2.36 (2H, m), 2.63 (2H, t, J=7.5 Hz), 2.80–3.46 (3H, m), 3.29 (3H, s), 3.48–3.92 (1H, m), 3.67(3H, s), 3.94–4.50 (1H, m), 4.33 (2H, s), 6.73 (1H, d, J=8 Hz), 6.83 (1H, d, J=8 Hz), 6.93–7.43 (8H, m), 7.95 (2H, dd, J=9 Hz, 6 Hz)

INVENTIVE EXAMPLE 6

N-{2-[4-(4-fluorobenzoyl)piperidino]-ethyl}-3-methoxy-N-(2-pyridyl)benzamide

Using 3-methoxy-N-(2-pyridyl)benzamide (41 mg, 0.18 mmol), the procedure of Inventive Example 5 was repeated to obtain 19 mg (25.9%) of the title compound in the form of yellow oil.

IR (neat): 2928, 1680, 1634, 1598, 1572, 1544, 1502, 1452, 1388, 1350, 1286, 1228, 1156, 766, 730 cm$^{-1}$ NMR (CDCl$_3$) δ: 1.40–2.06 (4H, m), 2.06–2.47 (2H, m), 2.57–3.40 (5H, m), 3.85 (3H, s), 4.43 (2H, t, J=6 Hz), 6.35–6.62 (1H, m), 6.70–7.70 (7H, m), 7.70–8.07 (3H, m), 8.35 (1H, d, J=9 Hz)

INVENTIVE EXAMPLE 7

N-{2-[4-(4-fluorobenzoyl)piperidino]ethyl}-4-tetrahydropyranyloxymethyl-N-(2-methoxyphenyl)benzamide Using 4-tetrahydropyranyloxymethyl-N-(2-methoxyphenyl)-benzamide (166 mg, 0.486 mmol), the procedure of Inventive Example 5 was repeated to obtain 163 mg (58.4%) of the title compound in the form of light yellow oil.

IR (neat): 2944, 1680, 1644, 1598, 1502, 1390, 1278, 1240, 1202, 1156, 1118, 1032, 974, 752, 604 cm$^{-1}$ NMR (CDCl$_3$) δ: 1.36–2.00 (10H, m), 2.00–2.40 (2H, m), 2.63 (2H, t, J=7.5 Hz), 2.80–3.30 (3H, m), 3.30–4.30 (4H, m), 3.78 (3H, s), 4.36 (1H, d, J=12.5 Hz), 4.60 (1H, br-s), 4.66 (1H, d, J=12.5 Hz), 6.72 (1H, d, J=8 Hz), 6.82 (1H, d, J=7.5 Hz), 6.93–7.40 (8H, m), 7.93 (2H, dd, J=9 Hz, 6 Hz)

INVENTIVE EXAMPLE 8

N-{2-[4-(4-fluorobenzoyl)piperidino]ethyl}-3-tetrahydropyranyloxymethyl-N-(2-methoxymhenyl)benzamide Using 3-tetrahydropyranyloxymethyl-N-(2-methoxyphenyl)-benzamide (159 mg, 0.466 mmol), the procedure of Inventive Example 5 was repeated to obtain 191 mg (71.3%) of the title compound in the form of light yellow oil.

IR (neat): 2944, 1680, 1646, 1598, 1502, 1386, 1278, 1118, 1026 cm$^{-1}$

NMR (CDCl$_3$) δ: 1.38–2.00 (10H, m), 2.00–2.36 (2H, m), 2.63 (2H, t, J=6.5 Hz), 2.80–3.30 (3H, m), 3.35–4.30 (4H, m), 3.68 (3H, s), 4.33 (1H, d, J=12.5 Hz), 4.54 (1H, br-s), 4.61 (1H, d, J=12.5 Hz), 6.72 (1H, d, J=8 Hz), 6.82 (1H, d, J=8 Hz), 6.91–7.40 (8H, m), 7.95 (2H, dd, J=9 Hz, 6 Hz)

INVENTIVE EXAMPLE 9

4-Nitro-N-{2-[4-(4-fluorobenzoyl)piperidino]ethyl}-N-(2-methoxyphenyl)benzamide

Using 4-nitro-N-(2-methoxyphenyl)benzamide (272 mg, 1 mmol), the procedure of Inventive Example 5 was repeated to obtain 348 mg (68.8%) of the title compound in the form of light yellow powder.

Melting point: 166°–168° C.

IR (KBr): 2938, 2818, 1680, 1644, 1596, 1518, 1503, 1380, 1344, 1302, 1275 cm$^{-1}$

NMR (CDCl$_3$) δ: 1.60–1.95 (4H, m), 2.00–2.34 (2H, m), 2.45–2.76 (2H, m), 2.80–3.30 (3H, m), 3.68 (3H, s), 3.60–3.85 (1H, m), 4.02–4.34 (1H, m), 6.62–6.90 (2H, m), 6.98–7.26 (4H, m), 7.40 (2H, d, J=8.0 Hz), 7.80–8.03 (4H, m)

INVENTIVE EXAMPLE 10

4-{[N-[2-[4-(4-Fluorobenzoyl)piperidino]ethyl]-2-methoxyanilino]carbonyl}pyridine Using 4-[(2-methoxyanilino)carbonyl]pyridine (200 mg, 0.87 mmol, the procedure of Inventive Example 5 was repeated to obtain 215 mg (53.2%) of the title compound in a colorless amorphous form.

IR (KBr): 2944, 2818, 1674, 1647, 1598, 1503, 1413, 1230, 1206, 747 cm$^{-1}$

NMR (CDCl$_3$) δ: 1.65–2.35 (6H, m), 2.50–2.76 (2H, m), 2.80–3.28 (3H, m), 3.70 (3H, s), 3.55–3.82 (1H, m), 4.05–4.33 (1H, m), 6.64–6.92 (2H, m), 7.00–7.24 (6H, m), 7.80–8.07 (2H, m), 8.40 (2H, d, J=6.0 Hz)

INVENTIVE EXAMPLE 11

4-{N-[2-[4-(4-Fluorobenzoyl)piperidino]ethyl]-2-methoxyanilino]-carbonyl}pyridine N-oxide Using 4-[(2-methoxyanilino)carbonyl]pyridine N-oxide (200 mg, 0.82 mmol), the procedure of Inventive Example 5 was repeated to obtain 302 mg (77.2%) of the title compound in the form of light yellow powder amorphous.

IR (KBr): 2944, 1680, 1647, 1596, 1503, 1443, 1398, 1260, 1167 cm$^{-1}$

NMR (CDCl$_3$) δ: 1.60–2.40 (6H, m), 2.49–2.72 (2H, m), 2.78–3.29 (3H, m), 3.69 (3H, s), 3.66–3.87 (1H, m), 3.97–4.25 (1H, m), 6.70–7.34 (8H, m), 7.80–8.06 (4H, m)

INVENTIVE EXAMPLE 12

N-{2-[4-(4-Fluorobenzoyl)piperidino]ethyl}-N-(2-methoxyphenyl)-3-nitrobenzene sulfonamide Using N-(2-methoxyphenyl)-3-nitrobenzenesulfonamide (190 mg, 0.616 mmol), the procedure of Inventive Example 5 was repeated to obtain 70 mg (21.0%) of the title compound in the form of yellow oil.

IR (neat): 2950, 1678, 1596, 1530, 1496, 1350, 1280, 1260, 1160, 1123, 974, 910, 754, 732, 592, 576 cm$^{-1}$ NMR (CDCl$_3$) δ: 1.54–2.32 (6H, m), 2.53 (2H, t, J=7.5 Hz), 2.70–3.30 (3H, m), 3.38 (3H, s), 3.57–4.00 (2H, m), 6.67–7.77 (7H, m), 7.77–8.14 (3H, m), 8.37 (1H, d, J=7.5 Hz), 8.57 (1H, br-s)

INVENTIVE EXAMPLE 13

N-{2-[4-(4-Fluorobenzoyl)piperidino]ethyl}-4-methoxy-N-(3-methoxyphenyl)benzenesulfonamide Using 4-methoxy-N-(3-methoxyphenyl)benzenesulfonamide (174 mg, 0.593 mmol), the procedure of Inventive Example 5 was repeated to obtain 87.4 mg (28.0%) of the title compound in the form of colorless flocculent crystals.

Melting point: 129°–132° C.

IR (KBr): 1674, 1598, 1496, 1344, 1258, 1238, 1210, 1160, 1098 1030, 690, 586, 562 cm$^{-1}$

NMR (CDCl$_3$) δ: 1.44–1.90 (4H, m), 1.97–2.32 (2H, m), 2.49 (2H, t, J=7.5 Hz), 2.68–3.33 (3H, m), 3.67 (2H, t, J=7.5 Hz), 3.74, 3.85 (each 3H, s), 6.47–7.33 (8H, m), 7.54 (2H, d, J=9 Hz), 7.93 (2H, dd, J=9 Hz, 6 Hz)

INVENTIVE EXAMPLE 14

N-(2-Cyanophenyl)-N-{2-[4-(4-fluorobenzoyl)piperidino]ethyl}-4-methoxybenzenesulfonamide Using N-(2-cyanophenyl)-4-methoxybenzenesulfonamide (234 mg, 0.812 mmol), the procedure of Inventive Example 5 was repeated to obtain 107 mg (25.3%) of the title compound in a light yellow amorphous form.

IR (KBr): 2950, 2228, 1680, 1596, 1496, 1350, 1262, 1158, 1092, 834, 688, 576, 552 cm$^{-1}$

NMR (CDCl$_3$) δ: 1.35–2.22 (6H, m), 2.54 (2H, t, J=6.5 Hz), 2.65–3.28 (3H, m), 3.73 (2H, t, J=6.5 Hz), 3.87 (3H, s), 6.77–7.35 (5H, m), 7.35–7.77 (5H, m), 7.91 (2H, dd, J=9 Hz, 6 Hz)

INVENTIVE EXAMPLE 15

N-{2-[4-(4-Fluorobenzoyl)piperidino]ethyl-N-(2-trifluoromethyl-phenyl)-4-methoxybenzenesulfonamide Using N-(2-trifluoromethylphenyl)-4-methoxybenzenesulfonamide (225 mg, 0.679 mmol), the procedure of Inventive Example 5 was repeated to obtain 46.7 mg (12.2%) of the title compound in the form of colorless oil.

IR (neat): 2948, 1680, 1598, 1498, 1450, 1352, 1316, 1262, 1228, 1206, 1158, 1112, 1092, 1036, 836, 730, 664, 604, 580, 556 cm$^{-1}$ NMR (CDCl$_3$) δ: 1.40–2.20 (6H, m), 2.30–3.30 (5H, m), 3.40–3.78 (2H, m), 3.88 (3H, s), 6.83–7.27 (5H, m), 7.35–7.55 (2H, m), 7.56–7.80 (3H, m), 7.90 (2H, dd, J=9 Hz, 6 Hz)

INVENTIVE EXAMPLE 16

N-{2-[4-(4-Fluorobenzoyl)piperidino]ethyl}-N-(2-methoxyphenyl)-3-pyridinesulfonamide Using N-(2-methoxyphenyl)-3-pyridinesulfonamide (132 mg, 0.50 mmol), the procedure of Inventive Example 5 was repeated to obtain 55 mg (22.1%) of the title compound in the form of colorless solid.

Melting point: 126.5°–128.5° C.

IR (KBr): 2924, 1676, 1594, 1500, 1364, 1284, 1204, 1164, 1116, 982, 744, 608, 600 cm$^{-1}$

NMR (CDCl$_3$) δ: 1.40–1.90 (4H, m), 1.94–2.31 (2H, m), 2.52 (2H, t, J=7.5 Hz), 2.68–3.45 (3H, m), 3.33 (3H, s), 3.50–3.90 (2H, m), 6.76 (1H, d, J=8 Hz), 6.85–7.60 (6H, m), 7.73–8.20 (2H, m), 8.60–9.00 (2H, m)

INVENTIVE EXAMPLE 17

3-{[N-[2-[4-(4-Fluorobenzoyl)piperidino]ethyl]-2-methoxyanilino]-sulfonyl}pyridine N-oxide Using 3-[(2-methoxyanilino)sulfonyl]pyridine N-oxide (120 mg, 0.428 mmol), the procedure of inventive Example 5 was repeated to obtain 101 mg (45.9%) of the title compound in the form of yellow oil.

IR (neat): 3430, 3110, 2944, 2805, 1678, 1596, 1498, 1466, 1430, 1358, 1258, 1160, 1010, 976, 912, 854, 786, 720, 670, 588 cm$^{-1}$ NMR (CDCl$_3$) δ: 1.55–1.95 (4H, m), 1.96–2.31 (2H, m), 2.50 (2H, t, J=7.5 Hz), 2.70–3.24 (3H, m), 3.51 (3H, s), 3.60–3.91 (2H, m), 6.83 (1H, d, J=8 Hz), 7.00 (1H, d, J=7.5 Hz), 7.13 (2H, dd, J=9 Hz, 9 Hz), 7.20–7.58 (4H, m), 7.95 (2H, dd, J=9 Hz, 6 Hz), 8.27 (1H, d, J=6 Hz), 8.50 (1H, br-s)

INVENTIVE EXAMPLE 18

4-{[2-[4-(4-Fluorobenzoyl)piperidino]ethyl]-2-methoxyanilino]-sulfonyl}benzoic acid In an atmosphere of argon, 4-[(2-methoxyanilino)sulfonyl]-benzoic acid (261 mg, 0.85 mmol), 1-(2-chloroethyl)-4-(4-fluorobenzoyl)piperidine hydrochloride (286 mg, 0.935 mmol) and sodium iodide (281 mg, 1.87 mmol) were dissolved in DMF (8 ml) to which was subsequently added sodium hydride (136 mg, 60%, 3.4 mmol) at room temperature. After 8 hours of stirring at 60° C., DMF was removed by evaporation. The thus obtained residue was diluted with water (10 ml), adjusted to pH 6 to 7 with 2N hydrochloric acid and extracted with ethyl acetate (salting out). The resulting organic layer was washed with water and saturated brine and dried on anhydrous sodium sulfate. Thereafter, the solvent was removed by evaporation, and the resulting residue was purified by a silica gel column chromatography (methylene chloride:methanol=50:1-40:1-30:1) to obtain 135 mg (29.4%) of the title compound in the form of beige amorphous powder.

IR (KBr): 1680, 1596, 1504, 1384, 1344, 1226, 1160 cm$^{-1}$

NMR (CDCl$_3$) δ: 1.75–2.50 (4H, m), 2.65–4.30 (12H, m), 6.50–8.20 (13H, m)

MS (FAB, m/z): 321, 357, 467, 499, 541 (M$^+$+1)

INVENTIVE EXAMPLE 19

N-{2-[4-(4-Fluorobenzoyl)piperidino]ethyl}-N-(2-methoxyphenyl)-p-toluenesulfonamide In an atmosphere of argon, N-(2-methoxyphenyl)-p-toluenesulfonamide (277 mg, 1.0 mmol) and a catalytically effective amount of sodium iodide were dissolved in DMF (3 ml) to which was subsequently added sodium hydride (44 mg, 60%, 1.1 mmol) at room temperature. After stirring at the same temperature for 30 minutes and then at 60° C. for 10 minutes, 1-(2-chloroethyl)-4-(4-fluorobenzoyl)piperidine (324 mg, 1.2 mmol) which has been divided into 3 portions, each being dissolved in DMF (1 ml), was added to the reaction solution at 1 hour intervals at 60° C. After 1.5 hours of additional stirring at the same temperature, DMF was removed by evaporation. The thus obtained residue was diluted with water (10 ml) and extracted with ether. The resulting organic layer was washed with water and saturated brine, and dried on anhydrous sodium carbonate. Thereafter, the solvent was removed by evaporation, and the resulting residue was purified by a silica gel column chromatography (ether:hexane=2:1) to obtain 467 mg (91.5%) of the title compound in the form of colorless oil.

IR (neat): 2944, 1680, 1598, 1496, 1342, 1280, 1262, 1158, 1094, 656 cm$^{-1}$

NMR (CDCl$_3$) δ: 1.54–1.94 (4H, m), 1.95–2.30 (2H, m), 2.40 (3H, s), 2.51 (2H, t, J=7.5 Hz), 2.72–3.25 (3H, m), 3.37 (3H, s), 3.71 (2H, t, J=7.5 Hz), 6.76 (1H, d, J=8.5 Hz), 6.95 (1H, d, J=8.5 Hz), 7.06–7.42 (4H, m), 7.12 (2H, dd, J=9 Hz, 9 Hz), 7.58 (2H, d, J=8.5 Hz), 7.93 (2H, dd, J=9 Hz, 6 Hz)

INVENTIVE EXAMPLE 20

N-{2-[4-(4-Fluorobenzoyl)piperidino]ethyl}-4-tetrahydropyranyl-oxymethyl-N-(2-methoxyphenyl)benzenesulfonamide Using 4-tetrahydropyranyloxymethyl-N-(2-methoxyphenyl)-benzenesulfonamide (377 mg, 1.0 mmol), the procedure of Inventive Example 19 was repeated to obtain 524 mg (85.8%) of the title compound in the form of light yellow oil.

IR (neat): 2924, 1680, 1598, 1498, 1344, 1262, 1160, 1118, 1034, 976, 908, 732, 592 cm$^{-1}$ NMR (CDCl$_3$) δ: 1.40–2.33 (12H, m), 2.52 (2H, t, J=7.5 Hz), 2.70–3.20 (3H, m), 3.36 (3H, s), 3.50–4.06 (4H, m), 4.53 (1H, d, J=12.5 Hz), 4.70 (1H, br-s), 4.83 (1H, d, J=12.5 Hz), 6.60–7.35 (6H, m), 7.40 (2H, d, J=9 Hz), 7.65 (2H, d, J=9 Hz), 7.93 (2H, dd, J=9 Hz, 6 Hz)

INVENTIVE EXAMPLE 21

N-{2-[4-(4-Fluorobenzoyl)piperidino]ethyl}-N-(2-methoxyphenyl)-4-phthalimidomethylbenzamide Method A: Using N-(2-methoxyphenyl)-4-phthalimidomethylbenzamide (167 mg, 0.432 mmol), the procedure of Inventive Example 19 was repeated to obtain 56 mg (20.9%) of the title compound in a light yellow amorphous form.

Method B: Using crude N-formylmethyl-N-(2-methoxyphenyl)-4-phthalimidomethylbenzamide (300 mg, 0.70 mmol), the procedure of Inventive Example 1 was repeated to obtain 186 mg (28.8%) of the title compound.

Method C: Using 4-chloromethyl-N-{2-[4-(4-fluorobenzoyl)-piperidino]ethyl}-N-(2-methoxyphenyl)benzamide (310 mg, 0.609 mmol), the procedure of Reference Example 52 was repeated to obtain 330 mg (87.4%) of the title compound.

IR (KBr): 2944, 1716, 1680, 1642, 1596, 1502, 1392, 1306, 1278, 1238, 974, 938, 752, 716 cm$^{-1}$

NMR (CDCl$_3$) δ: 1.53–1.95 (4H, m), 1.97–2.33 (2H, m), 2.60 (2H, t, J=7.5 Hz), 2.77–3.37 (3H, m), 3.48–3.87 (1H, m), 3.65 (3H, s), 3.96–4.36 (1H, m), 4.72 (2H, s), 6.72 (1H, d, J=8 Hz), 6.80 (1H, d, J=7.5 Hz), 6.93–7.35 (8H, m), 7.55–8.13 (6H, m)

INVENTIVE EXAMPLE 22

N{2-[4-(4-Fluorobenzoyl)piperidino]ethyl}-N-(2-methoxyphenyl)-4-morpholinomethylbenzamide Using N-(2-methoxyphenyl)-4-morpholinomethylbenzamide (128 mg, 0.392 mmol), the procedure of inventive Example 19 was repeated to obtain 48.3 mg (22.0%) of the title compound in the form of colorless oil.

IR (neat): 2948, 1680, 1640, 1598, 1502, 1454, 1412, 1390, 1304, 1280, 1262, 1240, 1116, 866, 752, 732, 604 cm$^{-1}$ NMR (CDCl$_3$) δ: 1.54–1.93 (4H, m), 2.00–2.50 (2H, m), 2.63 (2H, t, J=7.5 Hz), 2.76–3.26 (3H, m), 3.36 (2H, s), 3.46–3.96 (5H, m), 3.67 (3H, s), 3.98–4.40 (1H, m), 6.72 (1H, d, J=7.5 Hz), 6.81 (1H, d, J=7.5 Hz), 6.91–7.37 (8H, m), 7.94 (2H, dd, J=9 Hz, 6 Hz)

INVENTIVE EXAMPLE 23

N-{2-[4-(4-Fluorobenzoyl)piperidino]ethyl}-N-(2-methoxyphenyl)-4-dimethylaminomethylbenzamide Using N-(2-methoxyphenyl)-4-dimethylaminomethylbenzamide (131 mg, 0.461 mmol), the procedure of Inventive Example 19 was repeated to obtain 106 mg (44.4%) of the title compound in a light yellow amorphous form.

IR (KBr): 1680, 1640, 1598, 1412, 1316, 1280, 1222 cm$^{-1}$

NMR (CDCl$_3$—CD$_3$OD) δ: 1.55–2.06 (4H, m), 2.06–2.56 (2H, m), 2.21 (6H, s), 2.73 (2H, t, J=7.5 Hz), 2.86–3.30 (3H, m), 3.43 (2H, s), 3.56–4.40 (2H, m), 3.70 (3H, s), 6.55–6.92 (2H, m), 6.94–7.43 (8H, m), 7.96 (2H, dd, J=9 Hz, 6 Hz)

INVENTIVE EXAMPLE 24

4-(N-tert-Butoxycarbonyl-N-methylamino)methyl-N-{2-[4-(4-fluorobenzoyl)piperidino]ethyl}-N-(2-methoxyphenyl)benzamide Using 4-(N-tert-butoxycarbonyl-N-methylamino)methyl-N-(2-methoxyphenyl)benzamide (493 mg, 1.33 mmol), the procedure of Inventive Example 19 was repeated to obtain 580 mg (74.0%) of the title compound in the form of colorless oil.

IR (neat): 2938, 1737, 1692, 1644, 1596, 1503, 1392, 1239, 1143 cm$^{-1}$

NMR (CDCl$_3$) δ: 1.41 (9H, s), 1.62–2.30 (6H, m), 2.52–3.26 (5H, m), 2.72 (3H, s), 3.60–3.84 (1H, m), 3.69 (3H, s), 4.00–4.20 (1H, m), 4.29 (2H, s), 6.65–7.30 (10H, m), 7.95 (2H, dd, J=9 Hz, 6 Hz)

INVENTIVE EXAMPLE 25

4-Cyano-N-{2-[4-(4-fluorobenzoyl)piperidino]ethyl}-N-(2-methoxy-phenyl)benzamide Using 4-cyano-N-(2-methoxyphenyl)benzamide (252 mg, 1.0 mmol), the procedure of Inventive Example 19 was repeated to obtain 250 mg (51.5%) of the title compound in the form of colorless flocculent crystals.

Melting point: 155°–158° C.

IR (KBr): 2932, 2228, 1678, 1642, 1594, 1502, 1406, 1392, 1306, 1274, 1226, 854 cm$^{-1}$

NMR (CDCl$_3$) δ: 1.65–1.97 (4H, m), 1.97–2.34 (2H, m), 2.42–2.74 (2H, m), 2.75–3.37 (3H, m), 3.40–3.90 (1H, m), 3.69 (3H, s), 4.00–4.43 (1H, m), 6.56–6.95 (2H, m), 6.96–7.70 (8H, m), 7.95 (2H, dd, J=9 Hz, 6 Hz)

INVENTIVE EXAMPLE 26

4-Nitro-N-{2-[4-(4-fluorobenzoyl)piperidino]ethyl}-N-(3-methoxyphenyl)benzamide

Using 4-nitro-N-(3-methoxyphenyl)benzamide (1.09 g, 4.00 mmol), the procedure of inventive Example 19 was repeated to obtain 1.19 g (53.7%) of the title compound in the form of light yellow flocculent crystals.

Melting point: 133°–135° C.

IR (KBr): 1678, 1634, 1600, 1518, 1408, 1380, 1276, 1230, 1136, 1048, 978 cm$^{-1}$

NMR (CDCl$_3$) δ: 1.60–2.33 (5H, m), 2.60 (2H, t, J=6.6 Hz), 1.97–2.34 (2H, m), 2.80–3.35 (4H, m), 3.66 (3H, s), 4.03 (2H, t, J=6.6 Hz), 6.53–6.80 (3H, m), 7.00–7.15 (1H, m), 7.10 (2H, dd, each J=9.0 Hz), 7.42 (2H, d, J=9.0 Hz), 7.98 (2H, dd, J=9.0 Hz, 6.0 Hz)

INVENTIVE EXAMPLE 27

4-Nitro-N-{2-[4-(4-fluorobenzoyl)piperidino]ethyl}-N-(4-methoxyphenyl)benzamide

Using 4-nitro-N-(4-methoxyphenyl)benzamide (857 mg, 3.14 mmol), the procedure of inventive Example 19 was repeated to obtain 973.5 mg (61.4%) of the title compound in the form of yellow powder.

Melting point: 154°–156° C.

IR (KBr): 1677, 1641, 1599, 1512, 1443, 1377, 1347, 1296, 1275, 1248, 1221, 1200, 1170, 1155, 1131, 1110, 1035, 972, 867 cm$^{-1}$

NMR (CDCl$_3$) δ: 1.67–2.00 (4H, m), 2.00–2.35 (2H, m), 2.60 (2H, t, J=6.5 Hz), 2.80–3.40 (3H, m), 3.74 (3H, s), 4.03 (2H, t, J=6.5 Hz), 6.72 (2H, d, J=9.0 Hz), 6.83–7.50 (6H, m), 7.80–8.10 (4H, m)

INVENTIVE EXAMPLE 28

4-Nitro-N-{2-[4-(4-fluorobenzoyl)piperidino]ethyl}-N-(2,5-dimethoxyphenyl)benzamide Using 4-nitro-N-(2,5-dimethoxyphenyl)benzamide (1.21 g, 4.00 mmol), the procedure of inventive Example 19 was repeated to obtain 1.48 g (69.1%) of the title compound in a yellow amorphous form.

Melting point: 154°–156° C.

IR (KBr): 2950, 1682, 1644, 1600, 1504, 1346, 1224, 1048, 976, 714 cm$^{-1}$

NMR (CDCl$_3$) δ: 1.77–2.31 (6H, m), 2.61–3.19 (5H, m), 3.64 (3H, s), 3.69 (3H, s), 4.16 (2H, t, J=7.0 Hz), 6.71 (2H, dd, J=2.0 Hz, 8.1 Hz), 7.05–7.52 (5H, m), 7.88–8.04 (4H, m)

INVENTIVE EXAMPLE 29

3-Nitro-N-{2-[4-(4-fluorobenzoyl)piperidino]ethyl}-N-(3-methoxyphenyl)benzamide

Using 3-nitro-N-(3-methoxyphenyl)benzamide (816.0 mg, 3.00 mmol), the procedure of Inventive Example 19 was repeated to obtain 823.9 mg (54.7%) of the title compound in the form of colorless powder.

Melting point: 123°–125° C.

IR (KBr): 2950, 1676, 1640, 1598, 1532, 1400, 1352, 1304, 1232, 1208, 1118, 1026 cm$^{-1}$

NMR (CDCl$_3$) δ: 1.55–2.31 (5H, m), 2.64 (2H, t, J=6.6 Hz), 2.76–3.30 (4H, m), 3.71 (3H, s), 4.07 (2H, t, J=6.6 Hz), 6.45–6.80 (3H, m), 6.90–7.38 (1H, m), 7.13 (2H, dd, each J=8.8 Hz), 7.40 (1H, d, J=7.7 Hz), 7.50–7.72 (1H, m), 7.72–8.20 (4H, m)

INVENTIVE EXAMPLE 30

4-Nitro-N-{2-[4-(4-fluorobenzoyl)piperidino]ethyl}-N-(2,4-dimethoxyphenyl)benzamide Using 4-nitro-N-(2,4-dimethoxyphenyl)benzamide (908 mg, 3.00 mmol), the procedure of Inventive Example 19 was repeated to obtain 1.46 g (91.0%) of the title compound in the form of orange powder.

Melting point: 51°–54° C.

IR (KBr): 1680, 1646, 1598, 1510, 1410, 1346, 1310, 1280, 1208, 1158, 1142, 1030, 852, 836 cm$^{-1}$

NMR (CDCl$_3$) δ: 1.25–3.73 (13H, m), 3.70 (3H, s), 3.73 (3H, s), 4.16 (2H, t, J=7.0 Hz), 6.27–6.34 (2H, m), 6.98–7.23 (3H, m), 7.41 (2H, d, J=8.6 Hz), 7.88–7.94 (2H, m), 7.99 (2H, d, J=8.6 Hz)

INVENTIVE EXAMPLE 31

4-Nitro-N-{2-[4-(4-fluorobenzoyl)piperidino]ethyl}-N-(3-methylphenyl)benzamide

Using 4-nitro-N-(3-methylphenyl)benzamide (640 mg, 2.50 mmol), the procedure of Inventive Example 19 was repeated to obtain 517 mg (42.1%) of the title compound in the form of colorless powder.

Melting point: 150°–152° C.

IR (KBr): 2935, 2830, 1677, 1641, 1599, 1515, 1410, 1344, 1299, 1281, 1227, 1134 cm$^{-1}$

NMR (CDCl$_3$) δ: 1.61–2.32 (6H, m), 2.26 (3H, s), 2.62 (2H, t, J=7.0 Hz), 2.81–3.41 (3H, m), 4.06 (2H, t, J=7.0 Hz), 6.71–7.71 (8H, m), 7.81–8.14 (4H, m)

INVENTIVE EXAMPLE 32

4-Nitro-N-{2-[4-(4-fluorobenzoyl)piperidino]ethyl}-N-(phenyl)benzamide

Using 4-nitro-N-(phenyl)benzamide (970.0 mg, 4.01 mmol), the procedure of Inventive Example 19 was repeated to obtain 1.13 g (59.5%) of the title compound in the form of colorless powder.

Melting point: 177°–181° C.

IR (KBr): 1678, 1640, 1594, 1516, 1494, 1408, 1380, 1342, 1318, 1300, 1274, 1224, 1136, 976, 870, 852, 718, 698 cm$^{-1}$

NMR (CDCl$_3$) δ: 1.66–2.32 (6H, m), 2.60 (2H, dd, J=6.6 Hz, 6.4 Hz), 2.93–3.30 (3H, m), 4.07 (2H, dd, J=6.6 Hz, 6.4 Hz), 7.03–7.18 (7H, m), 7.41 (2H, d, J=8.7 Hz), 7.88–8.04 (4H, m)

INVENTIVE EXAMPLE 33

4-Nitro-N-{2-[4-(4-fluorobenzoyl)piperidino]ethyl}-N-(3-methylthiophenyl)benzamide Using 4-nitro-N-(3-methylthiophenyl)benzamide (1.15 g, 4.00 mmol), the procedure of Inventive Example 19 was repeated to obtain 1.73 g (81.3%) of the title compound in the form of light yellow powder.

Melting point: 153°–154° C.

IR (KBr): 1680, 1644, 1602, 1580, 1522, 1434, 1372, 1344, 1308, 1298, 1226, 1138 cm$^{-1}$

NMR (CDCl$_3$) δ: 1.16–2.27 (6H, m), 2.36 (3H, s), 2.62 (2H, t, J=6.4 Hz), 2.95–3.22 (3H, m), 4.07 (2H, t, J=6.4 Hz), 6.79–6.86 (1H, m), 7.00–7.23 (5H, m), 7.43 (2H, d, J=8.6 Hz), 7.93 (2H, d, J=8.8 Hz), 8.03 (2H, d, J=8.8 Hz)

INVENTIVE EXAMPLE 34

4-Nitro-N-{2-[4-(4-fluorobenzoyl)piperidino]ethyl}-N-(2-trifluoromethylphenyl)benzamide Using 4-nitro-N-(2-trifluoromethylphenyl)benzamide (450.0 mg, 1.45 mmol), the procedure of Inventive Example 19 was repeated to obtain 299 mg (40.6%) of the title compound in the form of yellow needle crystals. Melting point: 156.6°–157.8° C.

IR (KBr): 2960, 2841, 1678, 1656, 1600, 1524, 1316, 1126, 862, 577, 614 cm$^{-1}$

NMR (CDCl$_3$) δ: 1.68–2.25 (6H, m), 2.61–2.86 (3H, m), 3.05–3.43 (2H, m), 4.57 (2H, br-s), 7.09 (2H, d, J=8.6 Hz), 7.33–7.61 (6H, m), 7.89–8.08 (4H, m)

INVENTIVE EXAMPLE 35

4-Nitro-N-{2-[4-(4-fluorobenzoyl)piperidino]ethyl}-N-(3-trifluoromethylphenyl)benzamide Using 4-nitro-N-(3-trifluoromethylphenyl)benzamide (1.55 g, 5.00 mmol), the procedure of inventive Example 19 was repeated to obtain 1.14 g (42.0%) of the title compound in the form of colorless powder.

Melting point: 123°–137.1° C.

IR (KBr): 2948, 1678, 1648, 1602, 1344, 1136, 859, 722, 601 cm$^{-1}$

NMR (CDCl$_3$) δ: 1.79–1.95 (4H, m), 2.05–2.20 (2H, m), 2.60 (2H, t, J=6.2 Hz), 2.90–3.29 (3H, m), 4.09 (2H, t, J=9.0 Hz), 7.04–7.50 (8H, m), 7.88–8.10 (4H, m)

INVENTIVE EXAMPLE 36

4-Nitro-N-{2-[4-(4-fluorobenzoyl)piperidino]ethyl}-N-(3-pyridyl)benzamide

Using 4-nitro-N-(3-pyridyl)benzamide (973 mg, 4.00 mmol), the procedure of Inventive Example 19 was repeated to obtain 178 mg (9.3%) of the title compound in the form of colorless powder.

IR (KBr): 2935, 1677, 1644, 1599, 1518, 1344, 1299, 1278, 1224, 1134, 849 cm$^{-1}$

NMR (CDCl$_3$) δ: 1.41–2.36 (6H, m), 2.62 (2H, t, J=6.0 Hz), 2.76–3.41 (3H, m), 4.08 (2H, t, J=6.0 Hz), 7.21 (2H, t, J=9.0 Hz), 6.67–7.70 (4H, m), 7.70–8.17 (4H, m), 8.17–8.53 (2H, m)

INVENTIVE EXAMPLE 37

2-Nitro-N-{2-[4-(4-fluorobenzoyl)piperidino]ethyl}-N-(3-methoxyphenyl)benzamide

Using 2-nitro-N-(3-methoxyphenyl)benzamide (816 mg, 3.00 mmol), the procedure of Inventive Example 19 was repeated to obtain 1.497 g (98.9%) of the title compound in a light yellow amorphous form.

IR (KBr): 2930, 1678, 1648, 1600, 1530, 1488, 1408, 1346, 1208, 1156, 910 cm$^{-1}$

NMR (CDCl$_3$) δ: 1.60–2.35 (6H, m), 2.67 (2H, t, J=6.0 Hz), 2.90–3.30 (4H, m), 3.63 (3H, s), 4.05 (2H, t, J=6.0 Hz), 7.10 (2H, dd, each J=9.0 Hz), 6.53–6.80 (3H, m), 6.90–7.55 (4H, m), 7.75–8.05 (1H, m), 7.95 (2H, dd, J=9.0 Hz, 6.0 Hz)

INVENTIVE EXAMPLE 38

4-Nitro-N-{2-[4-(4-fluorobenzoyl)piperidino]ethyl-N-(3-nitrophenyl)benzamide

Using 4-nitro-N-(3-nitrophenyl)benzamide (718 mg, 2.50 mmol), the procedure of Inventive Example 19 was repeated to obtain 1.11 g (53.4%) of the title compound in the form of light yellow oil.

IR (neat): 2950, 1680, 1656, 1600, 1530, 1408, 1350, 1274, 1226, 1156, 854 cm$^{-1}$ NMR (CDCl$_3$) δ: 1.40–2.40 (5H, m), 2.43 (2H, t, J=6.0 Hz), 2.77–3.40 (4H, m), 4.09 (2H, t, J=6.0 Hz), 7.13 (2H, dd, each J=9.0 Hz), 7.76–8.27 (6H, m)

INVENTIVE EXAMPLE 39

4-Nitro-N-{2-[4-(4-fluorobenzoyl)piperidino]ethyl}-N-(2-ethoxy-carbonylphenyl)benzamide Using 4-nitro-N-(2-ethoxycarbonylphenyl)benzamide (600.0 mg, 2.00 mmol), the procedure of inventive Example 19 was repeated to obtain 523 mg (49.1%) of the title compound in the form of colorless powder.

Melting point: 187°–190° C.

IR (KBr): 1678, 1656, 1600, 1314, 846, 763, 645, 610 cm$^{-1}$

NMR (CDCl$_3$) δ: 1.71–1.89 (4H, m), 2.01–2.23 (2H, m), 2.26–2.83 (2H, m), 2.91–3.17 (3H, m), 3.48–3.63 (1H, m), 3.88 (3H, s), 4.30–4.53 (1H, m), 7.03–7.46 (7H, m), 7.76–8.02 (5H, m)

INVENTIVE EXAMPLE 40

4-Cyano-N-{2-[4-(4-fluorobenzoyl)piperidino]ethyl}-N-(4-methoxyphenyl)benzamide

Using 4-cyano-N-(4-methoxyphenyl)benzamide (2.02 g, 8.00 mmol), the procedure of Inventive Example 19 was repeated to obtain 2.32 g (59.8%) of the title compound in the form of colorless powder.

Melting point: 136°–149° C.

IR (KBr): 2940, 2227, 1678, 1640, 1510, 1250, 1035, 972, 832, 601 cm$^{-1}$

NMR (CDCl$_3$) δ: 1.78–2.31 (6H, m), 2.58 (2H, t, J=6.6 Hz), 2.94–3.30 (3H, m), 3.75 (3H, s), 4.01 (2H, t, J=6.6 Hz), 6.40 (2H, d, J=9.0 Hz), 6.94–7.42 (8H, m), 7.88–8.03 (2H, m)

INVENTIVE EXAMPLE 41

3-Methyl-4-nitro-N-{2-[4-(4-fluorobenzoyl)piperidino]ethyl}-N-4-methoxyphenyl)benzamide Using 3-methyl-4-nitro-N-(4-methoxyphenyl)benzamide (1.14 g, 4.00 mmol), the procedure of Inventive Example 19 was repeated to obtain 1.06 g (51.1%) of the title compound in the form of colorless powder.

Melting point: 125.7°–126.4° C.

IR (KBr): 2930, 1678, 1640, 1510, 1346, 1250, 972, 835, 731, 602 cm$^{-1}$

NMR (CDCl$_3$) δ: 1.79–2.30 (6H, m), 2.49 (3H, s), 2.59 (2H, t, J=6.4 Hz), 2.95–3.28 (3H, m), 3.75 (3H, s), 4.01 (2H, t, J=6.4 Hz), 6.75 (2H, d, J=9.0 Hz), 6.97–7.32 (6H, m), 7.11 (1H, d, J=8.4 Hz), 7.95 (2H, dd, J=8.8 Hz, 6.5 Hz)

INVENTIVE EXAMPLE 42

3-Methoxy-4-nitro-N-{2-[4-(4-fluorobenzoyl)piperidino]ethyl}-N-(4-methoxyphenyl)benzamide Using 3-methoxy-4-nitro-N-(4-methoxyphenyl)benzamide (1.36 g, 4.50 mmol), the procedure of Inventive Example 19 was repeated to obtain 1.60 g (66.5% of the title compound in the form of light yellow powder.

Melting point: 152°–153° C.

IR (KBr): 2950, 1680, 1640, 1606 1512, 1250, 975, 837, 720 cm$^{-1}$

NMR (CDCl$_3$) δ: 1.79–2.30 (6H, m), 2.59 (2H, t, J=6.6 Hz), 2.95–3.36 (3H, m), 3.76 (3H, s), 3.81 (3H, s), 4.02 (2H, t, J=6.6 Hz), 6.77 (2H, d, J=9.0 Hz), 6.90–7.26 (6H, m), 7.60 (1H, d, J=8.4 Hz), 7.96 (2H, dd, J=8.6 Hz, 5.5 Hz)

INVENTIVE EXAMPLE 43

4-Nitro-N-{2-[4-(4-fluorobenzoyl)piperidino]ethyl}-N-(4-fluorophenyl)benzamide

Using 4-nitro-N-(4-fluorophenyl)benzamide (1.04 g, 4.00 mmol), the procedure of Inventive Example 19 was repeated to obtain 1.41 g (71.6%) of the title compound in the form of light yellow powder.

Melting point: 194°–196° C.

IR (KBr): 1680, 1642, 1600, 1516, 1504, 1376, 1342, 1306, 1276, 1240, 1222, 1136 cm$^{-1}$

NMR (CDCl$_3$) δ: 1.78–2.18 (6H, m), 2.58 (2H, dd, J=6.4 Hz, 6.2 Hz), 2.93–3.05 (3H, m), 4.03 (2H, dd, J=6.4 Hz, 6.2 Hz), 6.92–7.23 (6H, m), 7.40 (2H, dr J=8.6 Hz), 7.88–8.08 (4H, m)

INVENTIVE EXAMPLE 44

4-Nitro-N-{2-[4-(4-fluorobenzoyl)piperidino]ethyl}-N-(4-methylphenyl)benzamide

Using 4-nitro-N-(4-methylphenyl)benzamide (1.03 g, 4.01 mmol), the procedure of Inventive Example 19 was repeated to obtain 1.61 g (59.1%) of the title compound in the form of light yellow powder.

Melting point: 175°–178° C.

IR (KBr): 1678, 1640, 1600, 1516, 1376, 1342, 1296, 1376, 1222 cm$^{-1}$

NMR (CDCl$_3$) δ: 1.66–2.16 (6H, m), 2.27 (3H, s), 2.59 (2H, dd, J=6.6 Hz, 6.4 Hz), 2.95–3.10 (3H, m), 4.04 (2H, dd, J=6.6 Hz, 6.4 Hz), 6.89–7.25 (6H, m), 7.41 (2H, d, J=8.6 Hz), 7.88–8.05 (4H, m)

INVENTIVE EXAMPLE 45

4-Nitro-N-{2-[4-(4-fluorobenzoyl)piperidino]ethyl}-N-(phenyl)benzamide

Using 4-nitro-N-(phenyl)benzamide (969.0 mg, 4.00 mmol), the procedure of Inventive Example 19 was repeated to obtain 1.02 g (53.6%) of the title compound in the form of light yellow powder.

Melting point: 178°–180° C.

IR (KBr): 1680, 1640, 1596, 1530, 1492, 1394, 1352, 1308, 1278, 1226, 1208, 1160, 1126, 970, 724, 706 cm$^{-1}$

NMR (CDCl$_3$) δ: 1.66–2.32 (6H, m), 2.63 (2H, t, J=6.6 Hz), 2.94–3.27 (3H, m), 4.08 (2H, t, J=6.6 Hz), 7.03–7.64 (9H, m), 7.87–8.02 (3H, m), 8.09 (1H, s)

INVENTIVE EXAMPLE 46

3-Nitro-N-{2-[4-(4-fluorobenzoyl)piperidino]ethyl}-N-(4-methylphenyl)benzamide

Using 3-nitro-N-(4-methylphenyl)benzamide (1.03 g, 4.00 mmol), the procedure of Inventive Example 19 was repeated to obtain 1.07 g (57.0%) of the title compound in the form of light yellow powder.

Melting point: 131°–134° C.

IR (KBr): 1680, 1640, 1598, 1530, 1512, 1346 cm$^{-1}$

NMR (CDCl$_3$) δ: 1.66–2.16 (6H, m), 2.26 (3H, s), 2.60 (2H, t, J=6.4 Hz), 2.95–3.20 (3H, m), 4.04 (2H, t, J=6.4 Hz), 6.97–7.63 (8H, m), 7.86–8.02 (3H, m), 8.10 (1H, s)

INVENTIVE EXAMPLE 47

3-Nitro-N-{2-[4-(4-fluorobenzoyl)piperidino]ethyl}-N-(4-fluorophenyl)benzamide

Using 3-nitro-N-(4-fluorophenyl)benzamide (1.04 g, 4.00 mmol), the procedure of Inventive Example 19 was repeated to obtain 507.0 mg (25.7%) of the title compound in the form of light yellow powder.

Melting point: 97°–113° C.

IR (KBr): 1656, 1594, 1530, 1508, 1350, 1310, 1216, 724 cm$^{-1}$

NMR (CDCl$_3$) δ: 1.66–2.31 (6H, m), 2.60 (2H, t, J=6.6 Hz), 2.92–3.19 (3H, m), 4.03 (2H, t, J=6.6 Hz), 6.82–7.22 (6H, m), 7.34–7.62 (2H, m), 7.87–8.03 (3H, m), 8.10 (1H, s)

INVENTIVE EXAMPLE 48

3-Nitro-N-{2-[4-(4-fluorobenzoyl)piperidino]ethyl}-N-(3-methylthiophenyl)benzamide Using 3-nitro-N-(3-methylthiophenyl)benzamide (1.54 g, 4.00 mmol), the procedure of Inventive Example 19 was repeated to obtain 1.04 g (49.6%) of the title compound in the form of light yellow powder.

Melting point: 148°–149° C.

IR (KBr): 1674, 1640, 1594, 1528, 1388, 1376, 1348, 1302, 1222, 1204, 1170, 1142, 726, 692 cm$^{-1}$

NMR (CDCl$_3$) δ: 1.69–2.26 (6H, m), 2.36 (3H, s), 2.63 (2H, t, J=6.5 Hz), 2.95–3.20 (3H, m), 4.07 (2H, t, J=6.5 Hz), 6.83–7.23 (7H, m), 7.30 (1H, d, J=7.8 Hz), 7.63 (1H, d, J=7.8 Hz), 7.92 (1H, d, J=8.6 Hz), 7.98 (1H, d, J=8.6 Hz), 7.34–7.62 (2H, m), 8.13 (1H, s)

INVENTIVE EXAMPLE 49

4-Nitro-N-{2-[4-(4-fluorobenzoyl)piperidino]ethyl}-N-(3,4-methylenedioxyphenyl)benzamide Using 4-nitro-N-(3,4-methylenedioxyphenyl)benzamide (1.14 g, 4.00 mmol), the procedure of inventive Example 19 was repeated to obtain 1.49 g (72.0%) of the title compound in the form of light yellow powder.

Melting point: 197°–198° C.

IR (KBr): 1680, 1644, 1599, 1518, 1503, 1485, 1446, 1410, 1380, 1341, 1302, 1281, 1269, 1236, 1215, 1173, 1155, 1128, 1110, 1035, 972, 870, 843,717 cm$^{-1}$

NMR (CDCl$_3$) δ: 1.65–2.00 (4H, m), 2.00–2.43 (2H, m), 2.60 (2H, t, J=6.5 Hz), 2.83–3.33 (3H, m), 4.00 (2H, t, J=6.5 Hz), 5.96 (2H, s), 6.48–6.70 (3H, m), 7.00–7.29 (3H, m), 7.45 (2H, d, J=8.8 Hz), 7.80–8.20 (4H, m)

INVENTIVE EXAMPLE 50

4-Nitro-N-{2-[4-(4-fluorobenzoyl)piperidino]ethyl}-N-(4-chlorophenyl)benzamide

Using 4-nitro-N-(4-chlorophenyl)benzamide (1.11 g, 4.00 mmol), the procedure of Inventive Example 19 was repeated to obtain 1.21 g (59.2%) of the title compound in the form of light yellow powder.

Melting point: 175°–177° C.

IR (KBr): 1680, 1644, 1600, 1490, 1374, 1348, 1306, 1280, 1270, 1222, 1134, 1094 cm$^{-1}$

NMR (CDCl$_3$) δ: 1.79–2.20 (6H, m), 2.59 (2H, t, J=6.4 Hz), 2.93–3.05 (3H, m), 4.04 (2H, t, J=6.4 Hz), 7.00–7.26 (6H, m), 7.42 (2H, d, J=8.6 Hz), 7.89–8.10 (4H, m)

INVENTIVE EXAMPLE 51

4-Nitro-N-{2-[4-(4-fluorobenzoyl)piperidino]ethyl}-N-(3,4-dimethylphenyl)benzamide Using 4-nitro-N-(3,4-dimethylphenyl)benzamide (1.08 g, 4.00 mmol), the procedure of Inventive Example 19 was repeated to obtain 1.26 g (62.3%) of the title compound in the form of light yellow powder.

Melting point: 197°–199° C.

IR (KBr): 1678, 1640, 1600, 1516, 1504, 1410, 1378, 1344, 1328, 1302, 1276, 1228, 1136, 870, 856, 842, 720 cm$^{-1}$

NMR (CDCl$_3$) δ: 2.16 (6H, s), 1.59–2.33 (6H, m), 2.60 (2H, t, J=6.6 Hz), 2.95–3.28 (3H, m), 4.03 (2H, t, J=6.6 Hz), 6.23–6.71 (5H, m), 7.43 (2H, d, J=8.6 Hz), 7.89–8.05 (4H, m)

INVENTIVE EXAMPLE 52

4-Nitro-N-{2-[4-(4-fluorobenzoyl)piperidino]ethyl}-N-(3,5-dimethylphenyl)benzamide Using 4-nitro-N-(3,5-dimethylphenyl)benzamide (1.08 g, 4.00 mmol), the procedure of Inventive Example 19 was repeated to obtain 686.1 mg (34.1%) of the title compound in the form of light yellow powder.

IR (KBr): 1680, 1638, 1598, 1408, 1382, 1332, 1310, 1296, 1234, 1126, 854, 716 cm$^{-1}$

NMR (CDCl$_3$) δ: 2.19 (6H, s), 1.69–2.32 (6H, m), 2.60 (2H, t, J=6.6 Hz), 2.95–3.20 (3H, m), 4.03 (2H, t, J=6.6 Hz), 6.70 (2H, s), 6.79 (1H, s), 7.04–7.23 (2H, m), 7.43 (2H, d, J=8.6 Hz), 7.89–8.07 (4H, m)

INVENTIVE EXAMPLE 53

4-Nitro-N-{3-[4-(4-fluorobenzoyl)piperidino]propyl}-N-(3-methoxyphenyl)benzamide Using 4-nitro-N-(3-methoxyphenyl)benzamide (816.0 mg, 3.00 mmol), the procedure of inventive Example 19 was repeated to obtain 872.0 mg (56.0%) of the title compound in a light yellow amorphous form.

IR (KBr): 1680, 1644, 1600, 1524, 1490, 1408, 1392, 1348, 1314, 1282, 1234, 1200, 1156, 910, 862 cm$^{-1}$

NMR (CDCl$_3$) δ: 1.55–2.23 (7H, m), 2.43 (2H, t, J=7.2 Hz), 2.75–3.28 (3H, m), 3.70 (3H, s), 3.98 (2H, t, J=7.2 Hz), 6.41–6.78 (3H, m), 6.90–7.28 (1H, m), 7.13 (2H, dd, each J=9.0 Hz), 7.45 (2H, d, J=8.8 Hz), 7.89 (2H, d, J=8.8 Hz), 7.95 (2H, dd, J=9.0 Hz, 6.0 Hz)

INVENTIVE EXAMPLE 54

4-Nitro-N-{2-[4-(4-fluorobenzoyl)piperidino]ethyl}-N-(3-methoxyphenyl)benzamide

4-Nitro-N-(3-methoxyphenyl)benzamide (50.0 g, 183.6 mmol) was dissolved in dioxane (900 ml) to which was subsequently added potassium hydroxide (30.3 g, 85%, 459.0 mmol) at room temperature. After 1 hour of stirring at 60° C., N-1-(2-chloroethyl)-4-(4-fluorobenzoyl)piperidine hydrochloride (67.5 g, 220.0 mmol) was added to the reaction solution at room temperature. After 24 hours of additional stirring at 50° C., the reaction solution was diluted with ice water and extracted with ethyl acetate. The resulting organic layer was washed with water and saturated brine and dried on anhydrous sodium sulfate. Thereafter, the solvent was removed by evaporation, and the resulting residue was recrystallized from ethyl acetate to obtain 47.2 g (50.8%) of the title compound in the form of light yellow flocculent crystals.

Melting point: 133°–135° C.

IR (KBr): 1678, 1634, 1600, 1518, 1408, 1380, 1276, 1230, 1136, 1048, 978 cm$^{-1}$

NMR (CDCl$_3$) δ: 1.60–2.33 (5H, m), 2.60 (2H, t, J=6.6 Hz), 1.97–2.34 (2H, m), 2.80–3.35 (4H, m), 3.66 (3H, s), 4.03 (2H, t, J=6.6 Hz), 6.53–6.80 (3H, m), 7.00–7.15 (1H, m), 7.10 (2H, dd, each J=9.0 Hz), 7.42 (2H, d, J=9.0 Hz), 7.98 (2H, dd, J=9.0 Hz, 6.0 Hz)

INVENTIVE EXAMPLE 55

N-{2-[4-(4-fluorobenzoyl)piperidino]ethyl}-4-hydroxymethyl-N-(2-methoxyphenyl)benzene sulfonamide N-{2-[4-(4-Fluorobenzoyl)piperidino]ethyl}-4-tetrahydropyranyloxymethyl-N-(2-methoxyphenyl)benzene sulfonamide (101 mg, 0.165 mmol) was dissolved in methanol (5 ml) to which was subsequently added p-toluenesulfonic acid monohydrate (35 mg, 0.18 mmol) at room temperature. After 2 hour of stirring at the same temperature, methanol was removed by evaporation, and the resulting reaction solution was mixed with saturated sodium bicarbonate aqueous solution (5 ml), extracted with ethyl acetate, and washed with water and saturated brine. The water layer was extracted with ethyl acetate, and washed with water and saturated brine, and the organic layers were combined and dried on anhydrous sodium sulfate. Thereafter, the solvent was removed by evaporation, and the resulting residue was purified by a silica gel column chromatography (ethyl acetate) to obtain 87 mg (100%) of the title compound in the form of colorless oil.

IR (neat): 3520, 2944, 1680, 1598, 1496, 1342, 1280, 1262, 1238 1158, 732 cm$^{-1}$ NMR (CDCl$_3$) δ: 1.46–1.90 (4H, m), 1.90–2.15 (1H, m), 2.15–2.32 (2H, m), 2.46 (2H, t, J=7.5 Hz), 2.69–2.99 (2H, m), 3.00–3.26 (1H, m) 3.41 (3H, s), 3.70 (2H, t, J=7.5 Hz), 4.75 (2H, s), 6.77 (1H, d, J=9 Hz), 6.95 (1H, d, J=9 Hz), 7.11 (2H, dd, J=9 Hz, 9 Hz), 7.27 (2H, d, J=9 Hz), 7.40 (2H, d, J=8.5 Hz), 7.67 (2H, d, J=8.5 Hz), 7.92 (2H, dd, J=9 Hz, 6 Hz)

INVENTIVE EXAMPLE 56

N-{2-[4-(4-Fluorobenzoyl)piperidino]ethyl}-4-hydroxymethyl-N-(2-methoxyphenyl)benzamide Using N-{2-[4-(4-fluorobenzoyl)piperidino]ethyl}-4-tetrahydropyranyloxymethyl-N-(2-methoxyphenyl)benzamide (163 mg, 0.284 mmol), the procedure of Inventive Example 55 was repeated to obtain 128 mg (91.9%) of the title compound in the form of colorless solid.

Melting point: 87°–91° C.

IR (KBr): 3408, 2948, 1680, 1638, 1598, 1502, 1410, 1298, 1278, 1264, 1240, 752, 730, 602 cm$^{-1}$

NMR (CDCl$_3$) δ: 1.50–1.96 (5H, m), 2.00–2.40 (2H, m), 2.63 (2H, t, J=7.5 Hz), 2.76–3.40 (3H, m), 3.50–3.93 (1H, m), 3.68 (3H, s), 3.96–4.33 (1H, m), 4.57 (2H, s), 6.73 (1H, d, J=8 Hz), 6.84 (1H, d, J=7.5 Hz), 6.95–7.43 (8H, m), 7.95 (2H, dd, J=9 Hz, 6 Hz)

INVENTIVE EXAMPLE 57

N-{2-[4-(4-Fluorobenzoyl)piperidino]ethyl}-3-hydroxymethyl-N-(2-methoxyphenyl)benzamide Using N-{2-[4-(4-fluorobenzoyl)piperidino]ethyl}-3-tetrahydropyranyloxymethyl-N-(2-methoxyphenyl)benzamide (191 mg, 0.332 mmol), the procedure of Inventive Example 55 was repeated to obtain 148 mg (90.9%) of the title compound in the form of colorless oil.

IR (neat): 3416, 2944, 1680, 1642, 1598, 1504, 1394, 1278, 1240, 734 cm$^{-1}$

NMR (CDCl$_3$) δ: 1.45–1.90 (5H, m), 1.98–2.36 (2H, m), 2.63 (2H, t, J=7.5 Hz), 2.79–3.22 (3H, m), 3.40–3.92 (1H, m), 3.70 (3H, s), 4.04–4.35 (1H, m), 4.52 (2H, s), 6.73 (1H, d, J=8 Hz), 6.83 (1H, d, J=8 Hz), 6.94–7.39 (8H, m), 7.96 (2H, dd, J=9 Hz, 6 Hz)

INVENTIVE EXAMPLE 58

N-{2-[4-(4-Fluorobenzoyl)piperidino]ethyl}-N-(2-methoxyphenyl)-4-dimethylaminomethylbenzene sulfonamide and N-(2-methoxyphenyl)-N-{2-[4-(4-dimethylaminobenzoyl)piperidino]ethyl}-4-dimethylamino-methylbenzenesulfonamide In an atmosphere of dry air, N-{2-[4-(4-fluorobenzoyl) piperidino]ethyl}-4-hydroxymethyl-N-(2-methoxyphenyl) benzenesulfonamide (80 mg, 0.152 mmol) was dissolved in methylene chloride (2 ml) to which were subsequently added dropwise DMF (1 drop) and thionyl chloride (0.1 ml, 1.37 mmol) while cooling in an ice bath. After 2 hours of stirring at the same temperature, the solvent was removed by evaporation. The thus obtained residue was put into a 25 ml capacity eggplant type flask equipped with a cold finger, dissolved in dioxane (1 ml) and mixed with 50% dimethylamine aqueous solution (1 ml). After 2.5 hours of stirring at 80° C., dioxane was removed by evaporation, and the resulting residue was diluted with ethyl acetate (15 ml) and dried on anhydrous sodium carbonate. Thereafter, the solvent was removed by evaporation, and the resulting residue was purified by a PTLC (methylene chloride:methanol= 35:1) to obtain 33.5 mg (39.8%) of N-{2-[4-(4-fluorobenzoyl)piperidino]ethyl}-N-(2-methoxyphenyl)-4-dimethylaminomethylbenzenesulfonamide as a low polarity component in the form of colorless oil and 47.5 mg (54.0%) of N-(2-methoxyphenyl)-N-{2-[4-(4-dimethylaminobenzoyl)piperidino]ethyl}-4-dimethylaminomethylbenzenesulfonamide as a high polarity component in the form of colorless solid. Low polarity component, N-{2-[4-(4-fluorobenzoyl)piperidino]-N-(2-methoxyphenyl)-4-dimetylaminomethylbenzene sulfonamide:

IR (neat): 2944, 2816, 2776, 1680, 1598, 1496, 1458, 1342, 1280, 1262, 1160, 592 cm$^{-1}$ NMR (CDCl$_3$) δ: 1.46–1.93 (4H, m), 1.95–2.35 (2H, m), 2.23 (6H, s), 2.51 (2H, t, J=7.5 Hz), 2.70–3.20 (3H, m), 3.39 (3H, s), 3.44 (2H, s), 3.72 (2H, t, J=7.5 Hz), 6.76 (1H, d, J=8.5 Hz), 6.95 (1H, d, J=8.5 Hz), 7.11 (2H, dd, J=9 Hz, 9 Hz), 7.15–7.49 (4H, m), 7.65 (2H, d, J=8.5 Hz), 7.93 (2H, dd, J=9 Hz, 6 Hz)

High polarity component, N-(2-methoxyphenyl)-N-{2-[4-(4-dimethylaminobenzoyl)piperidino]ethyl}-4-dimethylaminomethylbenzene sulfonamide:

Melting point: 152°–155° C.

IR (KBr): 3440, 2816, 1656, 1598, 1496, 1342, 1280, 1264, 1160, 1116, 730, 592 cm$^{-1}$

NMR (CDCl$_3$) δ: 1.50–1.92 (4H, m), 1.95–2.36 (2H, m), 2.23 (6H, s), 2.52 (2H, t, J=7.5 Hz), 2.72–3.24 (3H, m), 3.02 (6H, s), 3.40 (3H, s), 3.46 (2H, s), 3.72 (2H, t, J=7.5 Hz), 6.45–7.05 (4H, m), 7.06–7.50 (4H, m), 7.65 (2H, d, J=8 Hz), 7.83 (2H, d, J=8.5 Hz)

INVENTIVE EXAMPLE 59

N-{2-[4-(4-Fluorobenzoyl)piperidino]ethyl}-4-formyl-N-(2-methoxyphenyl)benzene sulfonamide Activated manganese dioxide (870 mg, 10.0 mmol) was suspended in methylene chloride (10 ml), and N-{2-[4-(4-fluorobenzoyl)piperidino]ethyl}-4-hydroxymethyl-N-(2-methoxyphenyl)benzene sulfonamide (259 mg, 0.492 mmol) dissolved in methylene chloride (3 ml) was added to the suspension. After 30 minutes of stirring at room temperature, the reaction mixture was filtered through silica gel (1 g) which was further subjected to elution with ethyl acetate. Thereafter, the filtrate and eluate were combined, and the solvent was removed by evaporation to obtain 211 mg (81.7%) of the title compound in a colorless amorphous form.

IR (KBr): 2940, 1706, 1678, 1598, 1496, 1348, 1294, 1260, 1200, 1158, 1116, 974, 754, 716, 604, 580 cm$^{-1}$

NMR (CDCl$_3$) δ: 1.50–1.95 (4H, m), 1.95–2.32 (2H, m), 2.52 (2H, t, J=7.5 Hz), 2.70–3.47 (3H, m), 3.30 (3H, s), 3.55–4.00 (2H, m), 6.76 (1H, d, J=8 Hz), 6.90 (1H, d, J=8

Hz), 7.12 (2H, dd, J=9 Hz, 9 Hz), 7.16–7.50 (2H, m), 7.70–8.14 (6H, m), 10.1 (1H, s)

INVENTIVE EXAMPLE 60

N-{2-[4-(4-Fluorobenzoyl)piperidino]ethyl}-4-(N-hydroxyimino)-N-(2-methoxyphenyl)benzenesulfonamide N-{2-[4-(4-Fluorobenzoyl)piperidino]ethyl}-4-formyl-N-(2-methoxyphenyl)benzenesulfonamide (63 mg, 0.12 mmol) and hydroxyamine hydrochloride (9.5 mg, 0.132 mmol) were dissolved in ethanol (2 ml) to which were subsequently added anhydrous sodium carbonate (14 mg, 0.132 mmol) and water (1 ml). After 1.5 hours of stirring at room temperature, ethanol was removed by evaporation, and the resulting residue was mixed with water (10 ml) to collect crystals by filtration. The thus collected crystals were washed with water and hexane, dissolved in methylene chloride (50 ml) and then dried on anhydrous sodium carbonate. Thereafter, the solvent was removed by evaporation to obtain 65 mg (100%) of the title compound in the form of colorless powder.

Melting point: 162°–168° C.

IR (KBr): 3450, 2950, 2840, 1676, 1594, 1500, 1344, 1264, 1204, 1156, 1106, 990, 726, 604, 588 cm$^{-1}$

NMR (CDCl$_3$) δ: 1.62–1.96 (4H, m), 1.96–2.40 (2H, m), 2.60 (2H, t, J=7.5 Hz), 2.80–3.55 (3H, m), 3.31 (3H, s), 3.83 (2H, t, J=7.5 Hz), 6.75 (1H, d, J=8 Hz), 6.96 (1H, d, J=8.5 Hz), 7.12 (2H, dd, J=9 Hz, 9 Hz), 7.16–7.43 (3H, m), 7.46–7.80 (4H, m), 7.93 (2H, dd, J=9 Hz, 6 Hz), 8.11 (1H, s)

INVENTIVE EXAMPLE 61

4-Carbamoyl-N-{2-[4-(4-fluorobenzoyl)piperidino]ethyl}-N-(2-methoxyphenyl)benzenesulfonamide In an atmosphere of argon and with cooling in an ice bath, 4-{[N-[2-[4-(4-fluorobenzoyl)piperidino]ethyl}-2-methoxyanilino]-sulfonyl}benzoic acid (63 mg, 0.117 mmol) was dissolved in THF (1 ml) to which were subsequently added dropwise N-methylmorpholine (14 μl, 0.13 mmol) and isobutyl chloroformate (16.8 μl, 0.13 mmol). After 15 minutes of stirring at room temperature, 28% liquid ammonia (0.5 ml) was added to the reaction solution which was cooled in an ice bath, followed by additional 10 minutes of stirring at room temperature. The reaction mixture was extracted with methylene chloride, and the resulting organic layer was dried on anhydrous sodium carbonate. Thereafter, the solvent was removed by evaporation, and the resulting light yellow oily residue was purified by a silica gel column chromatography (ether-ethyl acetate-methylene chloride:methanol=10:1) to obtain 32 mg (50.9%) of the title compound in the form of light yellow oil.

IR (neat): 3368, 2944, 1672, 1596, 1496, 1406, 1342, 1280, 1262, 1240, 1116, 912, 732, 662, 600 cm$^{-1}$ NMR (CDCl$_3$) δ: 1.50–1.93 (4H, m), 1.95–2.30 (2H, m), 2.46 (2H, t, J=7 Hz), 2.80–3.28 (3H, m), 3.38 (3H, s), 3.56–3.93 (2H, m), 6.10 (1H, br-s), 6.78 (1H, d, J=8.5 Hz), 6.97 (1H, d, J=9 Hz), 7.13 (2H, dd, J=9 Hz, 9 Hz), 7.17–7.50 (2H, m), 7.65–8.40 (7H, m)

INVENTIVE EXAMPLE 62

N-{2-[4-(4-Fluorobenzoyl)piperidino]ethyl}-N-(2-methoxyphenyl)-4-phthalimidomethylbenzenesulfonamide Using N-{2-[4-(4-fluorobenzoyl)piperidino]ethyl}-4-hydroxymethyl-N-(2-methoxyphenyl)benzenesulfonamide (80 mg, 0.152 mmol), the procedure of Inventive Example 61 was repeated in an atmosphere off argon to obtain 78 mg (78.3%) of the title compound in a colorless amorphous form.

IR (KBr): 1716, 1678, 1598, 1496, 1392, 1346, 1280, 1260, 1158, 1092, 715 cm$^{-1}$

NMR (CDCl$_3$) δ: 1.52–1.92 (4H, m), 1.93–2.30 (2H, m), 2.50 (2H, t, J=7.5 Hz), 2.70–3.00 (2H, m), 3.00–3.40 (1H, m), 3.24 (3H, s), 3.50–3.85 2H, m), 4.89 (2H, s), 6.60–8.10 (16H, m)

INVENTIVE EXAMPLE 63

N-{2-[4-(4-Fluorobenzoyl)piperidino]ethyl}-N-(2-methoxyphenyl)-4-succinimidomethylbenzamide In an atmosphere of argon, N-{2-[4-(4-fluorobenzoyl)piperidino]ethyl}-4-hydroxymethyl-N-(2-methoxyphenyl)benzamide (54 mg, 0.11 mmol), succinimide (13 mg, 0.132 mmol) and triphenylphosphine (34.6 mg, 0.132 mmol) were dissolved in THF (1 ml) to which was subsequently added dropwise diethyl azodicarboxylate (21 μl, 0.132 mmol) while cooling in an ice bath. After 30 minutes of stirring at room temperature, the reaction solution was diluted with water (10 ml) and extracted with ethyl acetate. The resulting organic layer was washed with water and saturated brine, and dried on anhydrous sodium carbonate. Thereafter, the solvent was removed by evaporation, and the resulting residue was purified by a PTLC (chloroform:methanol= 20:1) to obtain 42 mg (66.8%) of the title compound in a light yellow amorphous form.

IR (KBr): 3472, 2944, 2800, 1704, 1683, 1644, 1401, 1305, 1164 cm$^{-1}$

NMR (CDCl$_3$) δ: 1.70–1.95 (4H, m), 2.03–2.40 (2H, m), 2.66 (4H, s), 2.60–2.80 (2H, m), 2.80–3.25 (3H, m), 3.79 (3H, s), 3.40–3.80 (1H, m), 4.00–4.28 (1H, m), 4.53 (2H, s), 6.74 (1H, d, J=8 Hz), 6.82 (1H, d, J=8 Hz), 7.00–7.30 (8H, m), 7.93 (2H, dd, J=9 Hz, 6 Hz)

INVENTIVE EXAMPLE 64

4-Aminomethyl-N-{2-[4-(4-fluorobenzoyl)piperidino]ethyl}-N-(2-methoxyphenyl)benzenesulfonamide N-{2-[4-(4-Fluorobenzoyl)piperidino]ethyl}-N-(2-methoxyphenyl)-4-phthalimidomethylbenzenesulfonamide (77 mg, 0.117 mmol) was dissolved in a methanol-THF (3:2) mixture solution (2.5 ml) to which was subsequently added hydrazine hydrate (1 ml) while cooling in an ice bath. After 15 minutes of stirring at the same temperature, the organic solvent was removed by evaporation, and the resulting residue was extracted with methylene chloride. The resulting organic layer was washed with saturated sodium bicarbonate aqueous solution and saturated brine, and dried on anhydrous sodium carbonate, followed by the removal of the solvent by evaporation. To the resulting residue was added an acetic acid-THF-water (3:1:1) mixture solution (3 ml). After 2 hours of stirring at room temperature, the solvent was removed by evaporation, and the resulting reaction solution was diluted with ethyl acetate (15 ml), mixed with saturated sodium bicarbonate aqueous solution (5 ml) and then extracted with ethyl acetate. After drying the extract on anhydrous sodium carbonate, the solvent was removed by evaporation, and the resulting light yellow oily residue was purified by a silica gel column chromatography (methylene chloride:methanol=20:1 to 9:1) to obtain 47 mg (76.4%) of the title compound in a colorless oily form.

IR (neat): 3380, 2944, 1680, 1598, 1496, 1340, 1280, 1262, 1158, 1094, 730 cm$^{-1}$ NMR (CDCl$_3$) δ: 1.40–1.93 (6H, m), 1.93–2.30 (2H, m), 2.50 (2H, t, J=7 Hz), 2.70–3.28 (3H, m), 3.40 (3H, s), 3.72 (2H, t, J=7.5 Hz), 3.94 (2H, s), 6.77 (1H, d, J=8.5 Hz), 6.95 (1H, d, J=8.5 Hz), 7.12 (2H, dd, J=9 Hz, 9 Hz), 7.15–7.50 (2H, m), 7.35 (2H, d, J=8.5 Hz), 7.66 (2H, d, J=8.5 Hz), 7.93 (2H, dd, J=9 Hz, 6 Hz)

INVENTIVE EXAMPLE 65

4-Aminomethyl-N-{2-[4-(4-fluorobenzoyl)piperidino]ethyl}-N-(2-methoxyphenyl)benzamide Using N-{2-[4-(4-fluorobenzoyl)piperidino]ethyl}-N-(2-methoxyphenyl)-4-phthalimidomethylbenzamide (56 mg, 0.0904 mmol), the procedure of Inventive Example 64 was repeated to obtain 32 mg (72.3%) of the title compound in the form of colorless oil.

IR (neat): 2944, 1678, 1638, 1598, 1500, 1440, 1410, 1390, 1310, 1278, 1240, 1158, 1140, 1024, 976, 754 cm$^{-1}$ NMR (CDCl$_3$) δ: 1.35–2.00 (6H, m), 2.00–2.36 (2H, m), 2.63 (2H, t, J=7.5 Hz), 2.80–3.36 (3H, m), 3.46–3.93 (1H, m), 3.68 (3H, s), 3.75 (2H, s), 3.93–4.35 (1H, m), 6.74 (1H, d, J=8 Hz), 6.83 (1H, d, J=7.5 Hz), 6.93–7.40 (8H, m), 7.95 (2H, dd, J=9 Hz, 6 Hz)

INVENTIVE EXAMPLE 66

4-Amino-N-{2[4-(4-fluorobenzoyl)piperidino]ethyl}-N-(2-methoxy-phenyl)benzamide

4-Nitro-N-{2-[4-(4-fluorobenzoyl)piperidino]ethyl}-N-(2-methoxyphenyl)benzamide (264.0 mg, 0.52 mmol) was dissolved in methanol (5 ml) to which were subsequently added concentrated hydrochloric acid (2.0 ml) and tin (powder, 186.0 mg, 1.57 mmol) while cooling in an ice bath. After 1 hour of stirring at room temperature, the reaction solution was poured in ice water, adjusted to pH 9 to 10 with 10% sodium hydroxide aqueous solution, mixed with chloroform and then passed through cerite to remove insoluble materials. The resulting residue was washed with chloroform, the filtrate was extracted with chloroform, and the resulting organic layer was washed with water and saturated brine, and dried on anhydrous sodium sulfate. Thereafter, the solvent was removed by evaporation, and the resulting residue was purified by a silica gel column chromatography (chloroform:methanol=10:1) to obtain 243.0 mg (97.9%) of the title compound in a colorless amorphous form.

IR (KBr): 3336, 2936, 1678, 1628, 1600, 1438, 1384, 1278 cm$^{-1}$

NMR (CDCl$_3$) δ: 1.60–1.95 (4H, m), 2.00–2.34 (2H, m), 2.45–2.76 (2H, m), 2.80–3.30 (3H, m), 3.70 (3H, s), 3.60–3.85 (1H, m), 4.02–4.34 (1H, m), 6.35 (2H, d, J=9.0 Hz), 6.83 (2H, t, J=6.0 Hz), 6.95–7.30 (6H, m), 7.93 (2H, dd, J=9.0 Hz, 6.0 Hz)

INVENTIVE EXAMPLE 67

4-Amino-N-{2-[4-(4-fluorobenzoyl)piperidino]ethyl}-N-(3-methoxyphenyl)benzamide

Using 4-nitro-N-{2-[4-(4-fluorobenzoyl)piperidino]ethyl}-N-(3-methoxyphenyl)benzamide (505.0 mg, 1.00 mmol), the procedure of inventive Example 66 was repeated to obtain 490.7 mg (quantitative) of the title compound in the form of light yellow powder.

Melting point: 126°–127.5° C.

IR (KBr): 3360, 2944, 1680, 1634, 1600, 1438, 1380, 1310 cm$^{-1}$

NMR (CDCl$_3$) δ: 1.60–2.35 (5H, m), 2.63 (2H, t, J=7.0 Hz), 2.85–3.20 (4H, m), 3.69 (3H, s), 3.60–3.86 (2H, m), 4.02 (2H, t, J=7.0 Hz), 6.40 (2H, d, J=8.6 Hz), 6.56–6.83 (1H, m), 6.69 (2H, d, J=8.6 Hz), 6.95–7.30 (3H, m), 7.11 (2H, dd, each J=9.0 Hz), 7.95 (2H, dd, J=9.0 Hz, 6.0 Hz)

INVENTIVE EXAMPLE 68

4-Amino-N-{2-[4-(4-fluorobenzoyl)piperidino]ethyl}-N-(4-methoxy-phenyl)benzamide Using 4-nitro-N-{2-[4-(4-fluorobenzoyl)piperidino]ethyl}-N-(4-methoxyphenyl)benzamide (968.6 mg, 1.92 mmol), the procedure of Inventive Example 66 was repeated to obtain 905.7 mg (99.4%) of the title compound in a light yellow amorphous form.

IR (KBr): 2944, 1677, 1626, 1602, 1509, 1440, 1380, 1287, 1245, 1221, 1170, 1155, 1137, 1107, 1029, 972, 834, 759, 603, 591 cm$^{-1}$

NMR (CDCl$_3$) δ: 1.61–1.98 (4H, m), 1.98–2.32 (2H, m), 2.62 (2H, t, J=7.1 Hz), 2.80–3.35 (3H, m), 3.76 (3H, s), 3.99 (2H, t, J=7.1 Hz), 6.40 (2H, d, J=8.6 Hz), 6.74 (2H, d, J=9.0 Hz), 6.85–7.25 (6H, m), 7.80–8.03 (2H, m)

INVENTIVE EXAMPLE 69

4-Amino-N-{2-[4-(4-fluorobenzoyl)piperidino]ethyl}-N-(2,5-dimethoxyphenyl)benzamide Using 4-nitro-N-{2-[4-(4-fluorobenzoyl)piperidino]ethyl}-N-(2,5-dimethoxyphenyl)benzamide (535.0 mg, 1.00 mmol), the procedure of Inventive Example 66 was repeated to obtain 479.0 mg (94.9%) of the title compound in a colorless amorphous form.

IR (KBr): 3370, 2950, 1678, 1630, 1602, 1504, 1222, 1041, 840, 763 cm$^{-1}$

NMR (CDCl$_3$) δ: 1.76–2.35 (6H, m), 2.63 (2H, t, J=7.0 Hz), 2.95–3.16 (3H, m), 3.61 (3H, s), 3.69 (3H, s), 3.72–3.85 (2H, m), 6.38 (2H, br-d, J=8.6 Hz), 6.69 (3H, br-s), 7.02–7.26 (4H, m), 7.87–8.03 (2H, m)

INVENTIVE EXAMPLE 70

3-Amino-N-{2-[4-(4-fluorobenzoyl)piperidino]ethyl}-N-(3-methoxyphenyl)benzamide

Using 3-nitro-N-{2-[4-(4-fluorobenzoyl)piperidino]ethyl}-N-(3-methoxyphenyl)benzamide (730.0 mg, 1.45 mmol), the procedure of Inventive Example 66 was repeated to obtain 690.0 mg (quantitative) of the title compound in the form of light yellow powder.

Melting point: 141°–142° C.

IR (KBr): 3372, 2944, 1672, 1628, 1600, 1488, 1318, 1210, 1164, 1074, 974 cm$^{-1}$

NMR (CDCl$_3$) δ: 1.50–2.33 (5H, m), 2.69 (2H, t, J=6.8 Hz), 2.84–3.30 (4H, m), 3.69 (3H, s), 4.02 (2H, t, J=6.8 Hz), 6.40–6.76 (6H, m), 6.86 (1H, d, J=7.7 Hz), 7.05 (1H, d, J=7.7 Hz), 7.12 (2H, dd, each J=8.8 Hz), 7.93 (2H, dd, J=8.8 Hz, 5.5 Hz)

INVENTIVE EXAMPLE 71

4-Amino-N-{2-[4-(4-fluorobenzoyl)piperidino]ethyl}-N-(2,4-dimethoxyphenyl)benzamide Using 4-nitro-N-{2-[4-(4-fluorobenzoyl)piperidino]ethyl}-N-(2,4-dimethoxyphenyl)benzamide (527.0 mg, 0.98 mmol), the procedure of inventive Example 66 was repeated to obtain 439.3 mg (88.3%) of the title compound in the form of light yellow powder.

Melting point: 135°–138° C.

IR (KBr): 1680, 1602, 1512, 1440, 1410, 1389, 1308, 1224, 1206, 1179, 1158, 1026, 954, 837, 765, 603 cm$^{-1}$

NMR (CDCl$_3$) δ: 1.73–3.91 (13H, m), 3.69 (3H, s), 3.76 (3H, s), 4.19 (2H, dd, J=6.6 Hz, 5.3 Hz), 6.34–6.43 (4H, m), 6.92–7.17 (5H, m), 7.87–7.95 (2H, m)

INVENTIVE EXAMPLE 72

4-Amino-N-{2-[4-(4-fluorobenzoyl)piperidino] ethyl}-N-(3-methyl-phenyl)benzamide Using 4-nitro-N-{2-[4-(4-fluorobenzoyl)piperidino] ethyl}-N-(3-methylphenyl)benzamide (517.0 mg, 1.00 mmol), the procedure of inventive Example 66 was repeated to obtain 485.0 mg (quantitative) of the title compound in a colorless amorphous form.

IR (KBr): 3300, 2935, 2780, 1677, 1626, 1599, 1440, 1377, 1299, 1227, 1155, 834 cm$^{-1}$

NMR (CDCl$_3$) δ: 1.40–2.38 (6H, m), 2.26 (3H, s), 2.64 (2H, t, J=7.0 Hz), 2.84–3.38 (3H, m), 3.51–3.86 (2H, m), 4.20 (2H, t, J=7.0 Hz), 6.39 (2H, d, J=9.0 Hz), 6.71–7.34 (8H, m), 7.94 (2H, dd, J=9.0 Hz, 6.0 Hz)

INVENTIVE EXAMPLE 73

4-Amino-N-{2-[4-(4-fluorobenzoyl)piperidino] ethyl}-N-(phenyl)benzamide

Using 4-nitro-N-{2-[4-(4-fluorobenzoyl)piperidino] ethyl}-N-(phenyl)benzamide (713.0 mg, 1.50 mmol), the procedure of Inventive Example 66 was repeated to obtain 671.9 mg quantitative) of the title compound in the form of light yellow needle crystals.

Melting point: 156°–157° C.

IR (KBr): 1680, 1626, 1596, 1494, 1376, 1296, 1278, 1222, 1204, 1172, 1156, 1138, 974, 836, 758, 698, 598 cm$^{-1}$

NMR (CDCl$_3$) δ: 1.71–2.31 (6H, m), 2.64 (2H, t, J=6.8 Hz), 2.94–3.25 (3H, m) f 3.72 (2H, br-s), 4.03 (2H, t, J=6.8 Hz), 6.39 (2H, d, J=8.1 Hz), 7.09–7.17 (9H, m), 7.92 (1H, d, J=8.1 Hz)

INVENTIVE EXAMPLE 74

4-Amino-N-{2-[4-(4-fluorobenzoyl)piperidino] ethyl}-N-(3-methylthiophenyl)benzamide Using 4-nitro-N-{2-[4-(4-fluorobenzoyl)piperidino] ethyl}-N-(3-methylthiophenyl)benzamide (793.7 mg, 1.52 mmol), the procedure of inventive Example 66 was repeated to obtain 274.4 mg (36.7%) of the title compound in a colorless amorphous form.

IR (KBr): 1676, 1628, 1600, 1438, 1374, 1296, 1262, 1224, 1204, 1172, 1156, 1140, 974, 838, 760, 698 cm$^{-1}$

NMR (CDCl$_3$) δ: 1.77–1.86 (4H, m), 2.04–2.22 (2H, m), 2.34 (3H, s), 2.62 (2H, t, J=6.8 Hz), 2.94–3.17 (3H, m), 3.74 (2H, br-s), 4.01 (2H, t, J=6.8 Hz), 6.41 (2H, d, J=8.4 Hz), 6.82–7.22 (8H, m), 7.92 (1H, d, J=8.6 Hz), 7.98 (1H, d, J=8.4 Hz)

INVENTIVE EXAMPLE 75

4-Amino-N-{2-[4-(4-fluorobenzoyl)piperidino] ethyl}-N-(2-trifluoromethylphenyl)benzamide Using 4-nitro-N-{2-[4-(4-fluorobenzoyl)piperidino] ethyl}-N-(2-trifluoromethylphenyl)benzamide (275.0 mg, 0.51 mmol), the procedure of inventive Example 66 was repeated to obtain 264.0 mg (quantitative) of the title compound in a colorless amorphous form.

IR (KBr): 3370, 2948, 1632, 1600, 1314, 1172, 1126, 977, 769, 608 cm$^{-1}$

NMR (CDCl$_3$) δ: 1.63–2.22 (6H, m), 2.45–3.54 (6H, m), 3.74 (2H, br-s), 4.32–4.63 (1H, m), 6.43 (2H, br-d, J=8.4 Hz), 7.03–7.46 (8H, m), 7.94 (2H, dd, J=8.8 Hz, 5.5 Hz)

INVENTIVE EXAMPLE 76

4-Amino-N-{2-[4-(4-fluorobenzoyl)piperidino] ethyl}-N-(3-trifluoromethylphenyl)benzamide Using 4-nitro-N-{2-[4-(4-fluorobenzoyl)piperidino] ethyl}-N-(3-trifluoromethylphenyl)benzamide (54.3.0 mg, 1.00 mmol), the procedure of Inventive Example 66 was repeated to obtain 504.0 mg (98.2%) of the title compound in a colorless amorphous form.

IR (KBr): 3371, 2950, 1680, 1632, 1600, 1332, 1274, 1172, 1126, 975, 841, 702 cm$^{-1}$

NMR (CDCl$_3$) δ: 1.60–1.89 (4H, m), 2.04–2.30 (2H, m), 2.61 (2H, t, J=6.5 Hz), 2.91–3.31 (3H, m), 3.78 (2H, br-s), 4.03 (2H, t, J=6.5 Hz), 6.42 (2H, d, J=8.6 Hz), 7.03–7.46 (8H, m), 7.94 (2H, dd, J=9.0 Hz, 5.5 Hz)

INVENTIVE EXAMPLE 77

4-Amino-N-{2-[4-(4-fluorobenzoyl)piperidino] ethyl}-N-(3-pyridyl)benzamide

Using 4-nitro-N-{2-[4-(4-fluorobenzoyl)piperidino] ethyl}-N-(3-pyridyl)benzamide (160.0 mg, 0.34 mmol), the procedure of Inventive Example 66 was repeated to obtain 150.0 mg quantitative) of the title compound in a light yellow amorphous form.

IR (KBr): 3450, 2950, 1680, 1632, 1602, 1479, 1425, 1374, 1224, 1155, 837 cm$^{-1}$

NMR (CDCl$_3$) δ: 1.38–2.34 (6H, m), 2.64 (2H, t, J=6.0 Hz), 2.82–3.39 (3H, m), 3.78 (2H, br-s), 4.07 (2H, t, J=6.0 Hz), 6.40 (2H, d, J=9.0 Hz), 6.92–7.60 (6H, m), 7.97 (2H, dd, J=9.0 Hz, 6.0 Hz), 8.24–8.44 (2H, m)

INVENTIVE EXAMPLE 78

2-Amino-N-{2-[4-(4-fluorobenzoyl)piperidino] ethyl}-N-(3-methoxyphenyl)benzamide Using 2-nitro-N-{2-[4-(4-fluorobenzoyl)piperidino] ethyl}-N-(3-methoxyphenyl)benzamide (936.4 mg, 1.85 mmol), the procedure of Inventive Example 66 was repeated to obtain 853.3 mg (97.1%) of the title compound in the form of colorless oil.

IR (KBr): 3450, 2950, 1680, 1620, 1598, 1492, 1316, 1246, 1158, 910 cm$^{-1}$

NMR (CDCl$_3$) δ: 1.60–2.33 (5H, m), 2.60 (2H, t, J=6.0 Hz), 2.76–3.30 (4H, m), 3.63 (3H, s), 4.03 (2H, t, J=6.0 Hz), 4.60 (2H, br-s), 6.13–7.00 (8H, m), 7.10 (2H, dd, each J=9.0 Hz), 7.92 (2H, dd, J=9.0 Hz, 6.0 Hz)

INVENTIVE EXAMPLE 79

4-Amino-N-{2-[4-(4-fluorobenzoyl)piperidino] ethyl}-N-(3-aminophenyl)benzamide

Using 4-nitro-N-{2-[4-(4-fluorobenzoyl)piperidino] ethyl}-N-(3-aminophenyl)benzamide (1.1 g, 2.11 mmol), the procedure of Inventive Example 66 was repeated to obtain 557.0 mg (57.0%) of the title compound in the form of light brown powder.

Melting point: 107.5°–110.5° C.

IR (KBr): 3400, 1680, 1626, 1596, 1494, 1392, 1377, 1305, 1218, 1158, 852 cm$^{-1}$

NMR (CDCl$_3$—CD$_3$OD) δ: 1.35–2.42 (7H, m), 2.63 (2H, t, J=7.0 Hz), 2.83–3.40 (3H, m), 3.40–3.85 (3H, m), 3.99 (2H, t, J=7.0 Hz), 6.23–6.60 (4H, m), 6.76–7.33 (6H, m), 7.95 (2H, dd, J=9.0 Hz, 6.0 Hz)

INVENTIVE EXAMPLE 80

4-Amino-N-{2-[4-(4-fluorobenzoyl)piperidino] ethyl}-N-(2-methoxy-carbonylphenyl)benzamide Using 4-nitro-N-{2-[4-(4-fluorobenzoyl)piperidino] ethyl}-N-(2-methoxycarbonylphenyl)benzamide (506.0 mg, 0.95 mmol), the procedure of Inventive Example 66 was repeated to obtain 307.0 mg (64.2%) of the title compound in a colorless amorphous form.

IR (KBr): 3368, 1722, 1630, 1598, 1296, 976, 821, 761, 600 cm$^{-1}$

NMR (CDCl$_3$) δ: 1.66–2.15 (6H, m), 2.66–3.15 (5H, m), 3.70 (2H, br-s), 3.81 (3H, s), 4.06–4.45 (2H, m), 6.36 (2H, d, J=8.4 Hz), 7.02–7.45 (7H, m), 7.72–8.03 (3H, m)

INVENTIVE EXAMPLE 81

3-Methyl-4-amino-N-{2-[4-(4-fluorobenzoyl) piperidino]ethyl}-N-(4-methoxyphenyl)benzamide Using 3-methyl-4-nitro-N-{2-[4-(4-fluorobenzoyl) piperidino]-ethyl}-N-( 4-methoxyphenyl)benzamide (1.02 g, 1.97 mmol), the procedure of Inventive Example 66 was repeated to obtain 955.0 mg (99.1%) of the title compound in a yellow amorphous form.

IR (KBr): 3370, 2941, 1678, 1626, 1598, 1510, 1244, 1034, 975, 838, 605 cm$^{-1}$

NMR (CDCl$_3$) δ: 1.67–2.31 (6H, m), 2.02 (3H, s), 2.61 (2H, t, J=6.8 Hz), 2.53–3.34 (3H, m), 3.75 (3H, s), 3.98 (2H, t, J=6.8 Hz), 6.35 (1H, d, J=8.1 Hz), 6.82–7.26 (8H, m), 7.95 (2H, dd, J=8.6 Hz, 5.5 Hz )

INVENTIVE EXAMPLE 82

3-Methoxy-4-amino-N-{2-[4-(4-fluorobenzoyl) piperidino]ethyl}-N-(4-methoxyphenyl)benzamide Using 3-methoxy-4-nitro-N-{2-[4-(4-fluorobenzoyl) piperidino]ethyl}-N-(4-methoxyphenyl)benzamide (1.57 g, 2.93 mmol), the procedure of Inventive Example 66 was repeated to obtain 1.24 g (83.8%) of the title compound in a light yellow amorphous form.

IR (KBr): 3342, 2930, 1675, 1620, 1510, 1234, 1028, 830, 601 cm$^{-1}$

NMR (CDCl$_3$) δ: 1.70–1.86 (4H, m), 2.04–2.31 (2H, m), 2.63 (2H, t, J=6.9 Hz), 2.95–3.33 (3H, m), 3.75 (3H, s), 3.99 (2H, t, J=6.9 Hz), 6.41 (1H, d, J=7.9 Hz), 6.70–7.26 (8H, m), 7.95 (2H, dd, J=8.8 Hz, 5.5 Hz)

INVENTIVE EXAMPLE 83

4-Amino-N-{2-[4-(4-fluorobenzoyl)piperidino] ethyl}-N-(4-fluorophenyl)benzamide

Using 4-nitro-N-{2-[4-(4-fluorobenzoyl)piperidino] ethyl}-N-(4-fluorophenyl)benzamide (707.9 mg, 1.43 mmol), the procedure of Inventive Example 66 was repeated to obtain 255.7 mg (38.6%) of the title compound in a colorless amorphous form.

IR (KBr): 3364, 1628, 1598, 1506, 1378, 1310, 1276, 1212, 1170, 1156, 1138, 836 cm$^{-1}$

NMR (CDCl$_3$) δ: 1.78–2.46 (6H, m), 2.62 (2H, t, J=6.8 Hz), 2.74–3.56 (5H, m), 4.00 (2H, t, J=6.8 Hz), 6.91–8.22 (8H, m), 7.92 (1H, d, J=8.4 Hz), 7.98 (1H, d, J=8.6 Hz)

INVENTIVE EXAMPLE 84

4-Amino-N-{2-[4-(4-fluorobenzoyl)piperidino] ethyl}-N-(4-methylphenyl)benzamide

Using 4-nitro-N-{2-[4-(4-fluorobenzoyl)piperidino] ethyl}-N-(4-methylphenyl)benzamide (744.5 mg, 1.52 mmol), the procedure of Inventive Example 66 was repeated to obtain 647.4 mg (92.7%) of the title compound in the form of colorless powder.

Melting point: 164°–165° C.

IR (KBr): 1680, 1620, 1598, 1506, 1376, 1298, 1274, 1170, 838 cm$^{-1}$

NMR (CDCl$_3$) δ: 1.71–2.16 (6H, m), 2.28 (3H, s), 2.62 (2H, dd, J=7.3 Hz, 6.6 Hz), 2.95–3.17 (3H, m), 3.66–3.71 (2H, br-s), 4.00 (2H, dd, J=7.3 Hz, 6.6 Hz), 6.40 (2H, d, J=8.6 Hz), 6.99–7.22 (8H, m), 7.92 (1H, d, J=8.6 Hz), 7.98 (1H, d, J=8.6 Hz)

INVENTIVE EXAMPLE 85

3-Amino-N-{2-[4-(4-fluorobenzoyl)piperidino] ethyl}-N-(phenyl)benzamide

Using 3-nitro-N-{2-[4-(4-fluorobenzoyl)piperidino] ethyl}-N-(phenyl)benzamide (715.5 mg, 1.50 mmol), the procedure of Inventive Example 66 was repeated to obtain 156.8 mg (23.5%) of the title compound in a colorless amorphous form.

Melting point: 228°–229° C.

IR (KBr): 1668, 1640, 1592, 1492, 1388, 1372, 1320, 1302, 1264, 1222, 1204, 1170, 746, 698, 606 cm$^{-1}$

NMR (CDCl$_3$) δ: 2.36–2.69 (6H, m), 2.62 (2H, t, J=6.6 Hz), 2.94–3.31 (3H, m), 3.43–3.69 (2H, br-s), 4.05 (2H, t, J=6.6 Hz), 6.49–7.23 (11H, m), 7.99 (1H, d, J=8.6 Hz)

INVENTIVE EXAMPLE 86

3-Amino-N-{2-[4-(4-fluorobenzoyl)piperidino] ethyl}-N-(4-methylphenyl)benzamide

Using 3-nitro-N-{2-[4-(4-fluorobenzoyl)piperidino] ethyl}-N-(4-methylphenyl)benzamide (735.0 mg, 1.50 mmol), the procedure of inventive Example 66 was repeated to obtain 355.6 mg (51.6%) of the title compound in the form of colorless powder.

Melting point: 173°–175° C.

IR (KBr): 1674, 1630, 1598, 1508, 1384, 1314, 1298, 1216, 740 cm$^{-1}$

NMR (CDCl$_3$) δ: 1.59–2.15 (6H, m), 2.26 (3H, s), 2.59 (2H, t, J=6.8 Hz), 2.93–3.27 (3H, m), 3.32–3.70 (2H, m), 4.00 (2H, t, J=6.8 Hz), 6.49–6.57 (2H, m), 6.70 (1H, s), 6.80–7.22 (7H, m), 7.91 (1H, d, J=8.6 Hz), 7.97 (1H, d, J=8.6 Hz)

INVENTIVE EXAMPLE 87

3-Amino-N-{2-[4-(4-fluorobenzoyl)piperidino] ethyl}-N-(4-fluorophenyl)benzamide

Using 3-nitro-N-{2-[4-(4-fluorobenzoyl)piperidino] ethyl}-N-(4-fluorophenyl)benzamide (491.2 mg, 1.00 mmol), the procedure of Inventive Example 66 was repeated to obtain 272.6 mg (58.8%) of the title compound in the form of colorless powder.

Melting point: 159°–162° C.

IR (KBr): 1640, 1594, 1588, 1506, 1386, 1374, 1274, 1220, 1200, 978, 844, 746, 614 cm$^{-1}$

NMR (CDCl$_3$) δ: 1.66–2.21 (6H, m), 2.58 (2H, t, J=6.6 Hz), 2.92–3.03 (3H, m), 3.59 (2H, br-s), 3.99 (2H, t, J=6.6 Hz), 6.47–6.68 (3H, m), 6.82–7.22 (7H, m), 7.93 (1H, d, J=8.6 Hz), 7.99 (1H, d, J=8.6 Hz)

INVENTIVE EXAMPLE 88

3-Amino-N-{2-[4-(4-fluorobenzoyl)piperidino]ethyl}-N-(3-methylthiophenyl)benzamide Using 3-nitro-N-{2-[4-(4-fluorobenzoyl)piperidino]ethyl}-N-(3-methylthiophenyl)benzamide (785.0 mg, 1.50 mmol), the procedure of inventive Example 66 was repeated to obtain 439.1 mg (59.5%) of the title compound in the form of colorless powder.

Melting point: 172°–174° C.

IR (KBr): 1672, 1626, 1592, 1458, 1394, 1318, 1304, 1210, 1168, 972, 862, 786, 754, 694 cm$^{-1}$

NMR (CDCl$_3$) δ: 2.33 (3H, s), 1.73–2.40 (6H, m), 2.60 (2H, dd, J=6.6 Hz, 6.4 Hz), 2.94–3.41 (3H, m), 3.42–3.71 (2H, m), 4.03 (2H, dd, J=6.6 Hz, 6.4 Hz), 6.50–7.25 (10H, m), 7.93 (1H, d, J=8.6 Hz), 7.99 (1H, d, J=8.6 Hz)

INVENTIVE EXAMPLE 89

4-Amino-N-{2-[4-(4-fluorobenzoyl)piperidino]ethyl}-N-(4-chlorophenyl)benzamide

Using 4-nitro-N-{2-[4-(4-fluorobenzoyl)piperidino]ethyl}-N-(4-chlorophenyl)benzamide (760.6 mg, 1.49 mmol), the procedure of Inventive Example 66 was repeated to obtain 517.6 mg (72.4%) of the title compound in a colorless amorphous form.

IR (KBr): 1680, 1628, 1600, 1490, 1410, 1374, 1310, 1288, 1266, 1224, 1204, 1172, 1156, 1138, 1090, 974, 834, 762, 598 cm$^{-1}$

NMR (CDCl$_3$) δ: 1.85–2.19 (6H, m), 2.60 (2H, dd, J=6.8 Hz, 6.6 Hz), 2.92–3.17 (3H, m), 3.77 (2H, br-s), 3.99 (2H, dd, J=6.8 Hz, 6.6 Hz), 6.42 (2H, d, J=7.4 Hz), 6.98–7.88 (8H, m), 7.95 (2H, dd, J=8.6 Hz, 5.5 Hz)

INVENTIVE EXAMPLE 90

4-Amino-N-{2-[4-(4-fluorobenzoyl)piperidino]ethyl}-N-(3,4-dimethylphenyl)benzamide Using 4-nitro-N-{2-[4-(4-fluorobenzoyl)piperidino]ethyl}-N-( 3,4-dimethylphenyl)benzamide (751.8 mg, 1.49 mmol), the procedure of Inventive Example 66 was repeated to obtain 567.2 mg (80.4%) of the title compound in the form of light brown powder.

Melting point: 188°–190° C.

IR (KBr): 1680, 1620, 1598, 1562, 1502, 1380, 1298, 1276, 1264, 1184, 1176, 1160, 1140, 1130, 854, 838 cm$^{-1}$

NMR (CDCl$_3$) δ: 2.17 (6H, s), 1.68–2.36 (6H, m), 2.66 (2H, dd, J=7.3 Hz, 6.8 Hz), 2.97–3.20 (3H, m), 3.72 (2H, br-s), 4.01 (2H, dd, J=7.3 Hz, 6.8 Hz), 6.40 (2H, d, J=8.6 Hz), 6.80–7.26 (7H, m), 7.95 (2H, dd, J=8.6 Hz, 5.5 Hz)

INVENTIVE EXAMPLE 91

4-Amino-N-{2-[4-(4-fluorobenzoyl)piperidino]ethyl}-N-(3,5-dimethylphenyl)benzamide Using 4-nitro-N-{2-[4-(4-fluorobenzoyl)piperidino]ethyl}-N-(3,5-dimethylphenyl)benzamide (663.2 mg, 1.32 mmol), the procedure of Inventive Example 66 was repeated to obtain 601.7 mg (96.3%) of the title compound in a light brown amorphous form.

IR (KBr): 1680, 1626, 1596, 1376, 1314, 1264, 1232, 1180, 1156, 838, 760 cm$^{-1}$

NMR (CDCl$_3$) δ: 2.20 (6H, s), 1.57–2.31 (6H, m), 2.62 (2H, dd, J=7.0 Hz, 6.8 Hz), 2.95–3.01 (3H, m), 3.71 (2H, br-s), 3.98 (2H, dd, J=7.0 Hz, 6.8 Hz), 6.40 (2H, d, J=8.6 Hz), 6.71–6.76 (3H, m), 7.03–7.26 (6H, m), 7.95 (2H, dd, J=8.6 Hz, 5.5 Hz)

INVENTIVE EXAMPLE 92

4-Amino-N-{3-[4-(4-fluorobenzoyl)piperidino]propyl}-N-(3-methoxyphenyl)benzamide Using 4-nitro-N-{3-[4-(4-fluorobenzoyl)piperidino]propyl}-N-(3-methoxyphenyl)benzamide (872.0 mg, 1.68 mmol), the procedure of Inventive Example 66 was repeated to obtain 808.8 mg (98.5%) of the title compound in a colorless amorphous form.

IR (KBr): 2948, 1680, 1628, 1600, 1488, 1452, 1380, 1310, 1230, 1198, 1180, 1158 cm$^{-1}$

NMR (CDCl$_3$) δ: 1.57–2.20 (7H, m), 2.42 (2H, d, J=7.5 Hz), 2.80–3.26 (4H, m), 3.69 (3H, s), 3.60–3.76 (2H, m), 3.92 (2H, d, J=7.5 Hz), 6.40 (2H, d, J=8.6 Hz), 6.50–6.75 (3H, m), 7.11 (2H, dd, J=8.6 Hz, 5.5 Hz), 7.15 (2H, d, J=8.6 Hz), 7.95 (2H, dd, J=8.6 Hz, 5.5 Hz)

INVENTIVE EXAMPLE 93

4-Amino-N-{2-[4-(4-fluorobenzoyl)piperidino]ethyl}-N-(3,4-methylenedioxyphenyl)benzamide Using 4-nitro-N-{2-[4-(4-fluorobenzoyl)piperidino]ethyl}-N-(3,4-methylenedioxyphenyl)benzamide (300.0 mg, 0.578 mmol), the procedure of Inventive Example 66 was repeated to obtain 245.0 mg (86.7%) of the title compound in a light yellow amorphous form.

IR (KBr): 1680, 1602, 1503, 1485, 1446, 1389, 1338, 1299, 1233, 1209, 1173, 1153, 1131, 1035, 837, 753 cm$^{-1}$

NMR (CDCl$_3$) δ: 1.70–2.00 (4H, m), 2.00–2.36 (2H, m), 2.62 (2H, t, J=6.8 Hz), 2.86–3.40 (3H, m), 3.95 (2H, t, J=6.8 Hz), 6.88–7.30 (4H, m), 7.80–8.10 (2H, m)

INVENTIVE EXAMPLE 94

4-(Acetylamino)methyl-N-{2-[4-(4-fluorobenzoyl)-piperidino]ethyl}-N-(2-methoxyphenyl)benzamide In an atmosphere of argon, 4-aminomethyl-N-{2-[4-(4-fluorobenzoyl)piperidino]ethyl}-N-(2-methoxyphenol)benzamide (60 mg, 0.123 mmol) was dissolved in methylene chloride (2 ml to which were subsequently added dropwise pyridine (23 μl, 0.284 mmol) and acetic anhydride (13 μl, 0.138 mmol) while cooling in an ice bath, followed by the addition of a catalytically effective amount of 4-dimethylaminopyridine. After 20 minutes of stirring at the same temperature and additional 12 hours of stirring at room temperature, the reaction solution was diluted with water (10 ml) and extracted with ethyl acetate. The resulting organic layer was washed with saturated brine and dried on anhydrous sodium carbonate. Thereafter, the solvent was removed by evaporation, and the resulting residue was purified by PTLC (chloroform:methanol=20:1) to obtain 58 mg (89.0%) of the title compound in a colorless amorphous form.

IR (KBr): 3304, 2944, 1674, 1641, 1596, 1503, 1413, 1392, 1380, 1278 cm$^{-1}$

NMR (CDCl₃) δ: 1.43–2.33 (6H, m), 1.98 (3H, s), 2.62 (2H, t, J=7.5 Hz), 2.82–3.30 (3H, m), 3.52–3.92 (1H, m), 3.67 (3H, s), 4.00–4.43 (1H, m), 4.31 (2H, d, J=6 Hz), 5.60 (1H, br-s), 6.73 (1H, d, J=8 Hz), 6.90 (1H, d, J=9 Hz), 6.98–7.40 (8H, m), 7.93 (2H, dd, J=9 Hz, 6 Hz)

INVENTIVE EXAMPLE 95

4-Acetylamino-N-{2-[4-(4-fluorobenzoyl) piperidino]ethyl}-N-(2-methoxyphenyl)benzamide Using 4-amino-N-{2-[4-(4-fluorobenzoyl)piperidino] ethyl}-N-(2-methoxyphenyl)benzamide (2.65 g, 5.58 mmol) and acetic anhydride (0.79 ml, 8.37 mmol), the procedure of Inventive Example 94 was repeated to obtain 2.44 g (84.3%) of the title compound in a colorless amorphous form.

IR (KBr): 3310, 2944, 1680, 1632, 1596, 1530, 1407, 1374, 1331, 1270, 1236, 750 cm⁻¹

NMR (CDCl₃) δ: 1.69–1.90 (4H, m), 2.06 (3H, s), 2.00–2.35 (2H, m), 2.63 (2H, t, J=7.0 Hz), 2.80–3.25 (3H, m), 3.65 (3H, s), 3.70–3.90 (1H, m), 3.95–4.35 (1H, m), 6.77 (2H, t, J=9.0 Hz), 6.96–7.30 (8H, m), 7.50 (1H, br-s), 7.95 (2H, dd, J=9.0 Hz, 6.0 Hz)

INVENTIVE EXAMPLE 96

4-Acetylamino-N-{2-[4-(4-fluorobenzoyl) piperidino]ethyl}-N-(3-methoxyphenyl)benzamide Using 4-amino-N-{2-[4-(4-fluorobenzoyl)piperidino] ethyl}-N-(3-methoxyphenyl)benzamide (1.00 g, 2.10 mmol) and acetic anhydride (0.24 ml, 2.54 mmol), the procedure of Inventive Example 94 was repeated to obtain 851.0 mg (78.3%) of the title compound in the form of colorless powder.

Melting point: 145.5°–151.5° C.

IR (KBr): 1680, 1632, 1600, 1530, 1488, 1400, 1314, 1282, 1158 cm⁻¹

NMR (CDCl₃) δ: 1.60–2.43 (5H, m), 2.10 (3H, s), 2.68 (2H, t, J=7.0 Hz), 2.83–3.40 (4H, m), 3.69 (3H, s), 4.05 (2H, t, J=7.0 Hz), 6.52–6.73 (3H, m), 6.78 (2H, s), 6.52–7.50 (5H, m), 7.13 (2H, dd, J=8.8 Hz, 5.5 Hz), 7.96 (2H, dd, J=8.8 Hz, 5.5 Hz)

INVENTIVE EXAMPLE 97

4-Acetylamino-N-{2-[4-(4-fluorobenzoyl) piperidino]ethyl}-N-(4-methoxyphenyl)benzamide Using 4-amino-N-{2-[4-(4-fluorobenzoyl)piperidino] ethyl}-N-(4-methoxyphenyl)benzamide (556.9 mg, 1.17 mmol) and acetic anhydride (0.13 ml, 1.41 mmol), the procedure of Inventive Example 94 was repeated to obtain 476.8 mg (78.7%) of the title compound in the form of colorless powder.

Melting point: 171°–173° C.

IR (KBr): 3316, 1671, 1632, 1599, 1527, 1512, 1437, 1404, 1377, 1314, 1296, 1245, 1203, 1173, 1153, 1113, 1029, 972, 852, 837, 762 cm⁻¹

NMR (CDCl₃—CD₃OD) δ: 1.67–2.00 (4H, m), 2.00–2.40 (2H, m), 2.12 (3H, s), 2.63 (2H, t, J=6.9 Hz), 2.85–3.40 (3H, m), 3.75 (3H, s), 4.01 (2H, t, J=6.9 Hz), 6.72 (2H, d, J=9.0 Hz), 6.87–7.40 (8H, m), 6.78 (2H, s), 7.80–8.06 (2H, m)

INVENTIVE EXAMPLE 98

4-Acetylamino-N-{2-[4-(4-fluorobenzoyl) piperidino]ethyl}-N-(2,5-dimethoxyphenyl) benzamide Using 4-amino-N-{2-[4-(4-fluorobenzoyl)piperidino] ethyl}-N-(2,5-dimethoxyphenyl)benzamide (170.0 mg, 0.34 mmol) and acetic anhydride (0.16 ml, 1.70 mmol), the procedure of Inventive Example 94 was repeated to obtain 132.0 mg (71.5%) of the title compound in a colorless amorphous form.

IR (KBr): 3352, 2973, 1678, 1600, 1508, 1314, 1262, 1222 cm⁻¹

NMR (CDCl₃) δ: 1.76–2.38 (6H, m), 2.11 (3H, s), 2.62 (2H, br-t, J=7.3 Hz), 2.85–3.40 (3H, m), 3.68 (3H, s), 3.78 (3H, s), 4.01–4.08 (2H, m), 6.58–6.78 (2H, m), 7.03–7.62 (7H, m), 7.87–8.03 (2H, m)

INVENTIVE EXAMPLE 99

3-Acetylamino-N-{2-[4-(4-fluorobenzoyl) piperidino]ethyl}-N-(3-methoxyphenyl)benzamide Using 3-amino-N-{2-[4-(4-fluorobenzoyl)piperidino] ethyl}-N-(3-methoxyphenyl)benzamide (216.0 mg, 0.45 mmol) and acetic anhydride (0.051 ml, 0.54 mmol), the procedure of Inventive Example 97 was repeated to obtain 197.5 mg (84.9%) of the title compound in a colorless amorphous form.

IR (KBr): 3300, 2948, 1680, 1640, 1598, 1434, 1376, 1282, 1046 cm⁻¹

NMR (CDCl₃) δ: 1.60–2.33 (5H, m), 2.08 (3H, s), 2.60 (2H, t, J=6.6 Hz), 2.83–3.30 (4H, m), 3.66 (3H, s), 4.05 (2H, t, J=6.6 Hz), 6.53–6.75 (2H, m), 6.75–7.28 (6H, m), 7.40 (1H, br-s), 7.46–7.70 (1H, m), 7.93 (2H, dd, J=8.8 Hz, 5.5 Hz)

INVENTIVE EXAMPLE 100

4-Acetylamino-N-{2-[4-(4-fluorobenzoyl) piperidino]ethyl}-N-(2,4-dimethoxyphenyl) benzamide Using 4-amino-N-{2-[4-(4-fluorobenzoyl)piperidino] ethyl}-N-(2,4-dimethoxyphenyl)benzamide (203.4 mg, 0.40 mmol) and acetic anhydride (0.046 ml, 0.49 mmol), the procedure of Inventive Example 94 was repeated to obtain 161.2 mg (73.6%) of the title compound in a colorless amorphous form.

IR (KBr): 1680, 1630, 1598, 1530, 1510, 1408, 1312, 1282, 1260, 1208, 1158, 850 cm⁻¹

NMR (CDCl₃) δ: 1.68–4.27 (14H, m), 3.67 (3H, s), 3.73 (3H, s), 6.20–6.38 (2H, m), 6.93–7.20 (7H, m), 7.87–7.95 (2H, m)

INVENTIVE EXAMPLE 101

4-Acetylamino-N-{2-[4-(4-fluorobenzoyl) piperidino]ethyl}-N-(3-methylphenyl)benzamide Using 4-amino-N-{2-[4-(4-fluorobenzoyl)piperidino] ethyl}-N-(3-methylphenyl)benzamide (285.0 mg, 0.62 mmol) and acetic anhydride (0.071 ml, 0.74 mmol), the procedure of Inventive Example 94 was repeated to obtain 311.8 mg (99.9%) of the title compound in a colorless amorphous form.

IR (KBr): 3310, 2940, 2790, 1680, 1629, 1602, 1527, 1446, 1374, 1227, 1155, 849 cm⁻¹

NMR (CDCl₃—CD₃OD) δ: 1.42–2.35 (6H, m), 2.09 (3H, s), 2.24 (3H, s), 2.62 (2H, t, J=7.0 Hz), 2.78–3.38 (3H, m), 4.02 (2H, t, J=7.0 Hz), 6.60–7.46 (11H, m), 7.95 (2H, dd, J=9.0 Hz, 6.0 Hz)

INVENTIVE EXAMPLE 102

4-Acetylamino-N-{2-[4-(4-fluorobenzoyl) piperidino]ethyl}-N-(phenyl)benzamide

Using 4-amino-N-{2-[4-(4-fluorobenzoyl)piperidino] ethyl}-N-(phenyl)benzamide (503.8 mg, 1.13 mmol) and acetic anhydride (0.128 ml, 1.36 mmol), the procedure of Inventive Example 94 was repeated to obtain 309.9 mg (71.0%) of the title compound in a light brown amorphous form.

IR (KBr): 1680, 1632, 1599, 1530, 1407, 1374, 1314, 1260 cm$^{-1}$

NMR (CDCl$_3$) δ: 1.77–1.99 (5H, m), 2.11 (3H, s), 2.26–2.31 (2H, m), 2.63 (2H, t, J=6.8 Hz), 2.93–3.17 (3H, m), 4.04 (2H, t, J=6.8 Hz), 6.99–7.40 (11H, m), 7.92 (2H, d, J=7.9 Hz), 7.98 (1H, d, J=7.9 Hz)

INVENTIVE EXAMPLE 103

4-Acetylamino-N-{2-[4-(4-fluorobenzoyl) piperidino]ethyl}-N-(3-thiomethylphenyl)benzamide Using 4-amino-N-{2-[4-(4-fluorobenzoyl)piperidino] ethyl}-N-(3-thiomethylphenyl)benzamide (220.6 mg, 0.45 mmol) and acetic anhydride (0.051 ml, 0.54 mmol), the procedure of Inventive Example 94 was repeated to obtain 231.2 mg (91.8%) of the title compound in a colorless amorphous form.

IR (KBr): 1680, 1630, 1598, 1530, 1476, 1438, 1406, 1372, 1312, 1260, 1226, 1204, 1156, 850, 760 cm$^{-1}$

NMR (CDCl$_3$) δ: 1.77–1.96 (4H, m), 2.04–2.19 (2H, m), 2.12 (3H, s), 2.45 (4H, s), 2.61 (2H, t, J=6.6 Hz), 2.94–3.18 (3H, m), 4.03 (2H, t, J=6.6 Hz), 6.80–7.38 (10H, m), 7.92 (2H, d, J=8.6 Hz), 7.98 (1H, d, J=8.6 Hz)

INVENTIVE EXAMPLE 104

4-Acetylamino-N-{2-[4-(4-fluorobenzoyl) piperidino]ethyl}-N-(2-trifluoromethylphenyl) benzamide Using 4-amino-N-{2-[4-(4-fluorobenzoyl)piperidino] ethyl}-N-(2-trifluoromethylphenyl)benzamide (243.0 mg, 0.474 mmol) and acetic anhydride (0.13 ml, 1.40 mmol), the procedure of Inventive Example 94 was repeated to obtain 265.0 mg quantitative) of the title compound in a colorless amorphous form.

IR (KBr): 3348, 2942, 1680, 1636, 1600, 1316, 1262, 1172, 842, 760, 608 cm$^{-1}$

NMR (CDCl$_3$) δ: 1.66–1.83 (4H, m), 2.04–2.19 (2H, m), 2.09 (3H, s), 2.52–3.52 (6H, m), 4.45 (1H, br-s), 7.03–7.87 (10H, m), 7.92 (2H, dd, J=8.8 Hz, 5.5 Hz)

INVENTIVE EXAMPLE 105

4-Acetylamino-N-{2-[4-(4-fluorobenzoyl) piperidino]ethyl}-N-(3-trifluoromethylphenyl) benzamide Using 4-amino-N-{2-[4-(4-fluorobenzoyl)piperidino] ethyl}-N-(3-trifluoromethylphenyl)benzamide (256.0 mg, 0.474 mmol) and acetic anhydride (0.13 ml, 1.40 mmol), the procedure of Inventive Example 94 was repeated to obtain 267.0 mg (96.2%) of the title compound in a colorless amorphous form.

IR (KBr): 3335, 2949, 1680, 1598, 1408, 1330, 1262, 1128, 843, 697 cm$^{-1}$

NMR (CDCl$_3$) δ: 1.69–1.87 (4H, m), 2.04–2.32 (2H, m), 2.12 (3H, s), 2.61 (2H, t, J=6.2 Hz), 2.89–3.20 (3H, m), 4.05 (2H, t, J=6.2 Hz), 7.03–7.44 (10H, m), 7.95 (2H, dd, J=8.8 Hz, 5.5 Hz)

INVENTIVE EXAMPLE 106

4-Acetylamino-N-{2-[4-(4-fluorobenzoyl) piperidino]ethyl}-N-(3-pyridyl)benzamide Using 4-amino-N-{2-[4-(4-fluorobenzoyl)piperidino] ethyl}-N-(3-pyridyl)benzamide (150.0 mg, 0.335 mmol) and acetic anhydride (0.038 ml, 0.40 mmol), the procedure of Inventive Example 94 was repeated to obtain 151.0 mg (95.6%) of the title compound in a colorless amorphous form.

IR (KBr): 3290, 2920, 1680, 1641, 1599, 1530, 1428, 1407, 1374, 1227, 1158, 849 cm$^{-1}$

NMR (CDCl$_3$) δ: 1.50–2.35 (6H, m), 2.12 (3H, s), 2.64 (2H, t, 7.0 Hz), 2.79–3.32 (3H, m), 4.50 (2H, t, J=7.0 Hz), 6.92–7.62 (9H, m), 7.94 (2H, dd, J=9.0 Hz, 6.0 Hz)

INVENTIVE EXAMPLE 107

2-Acetylamino-N-{2-[4-(4-fluorobenzoyl) piperidino]ethyl}-N-(3-methoxyphenyl)benzamide Using 2-amino-N-{2-[4-(4-fluorobenzoyl)piperidino] ethyl}-N-(3-methoxyphenyl)benzamide (238.0 mg, 0.50 mmol) and acetic anhydride (0.057 ml, 0.60 mmol), the procedure of Inventive Example 94 was repeated to obtain 170.4 mg (65.9%) of the title compound in a colorless amorphous form.

IR (KBr): 3459, 2940, 1680, 1635, 1595, 1505, 1440, 1370, 1290, 1160, 1035, 960 cm$^{-1}$

NMR (CDCl$_3$) δ: 1.43–2.35 (5H, m), 2.20 (3H, s), 2.60 (2H, t, J=6.0 Hz), 2.80–3.30 (4H, m), 3.63 (3H, s), 4.05 (2H, t, J=6.0 Hz), 6.45–7.00 (5H, m), 7.08 (2H, t, J=8.8 Hz), 7.10 (2H, dd, each J=9.0 Hz), 7.93 (2H, dd, J=9.0 Hz, 6.0 Hz), 8.20 (1H, d, J=9.0 Hz), 9.15–9.33 (1H, m)

INVENTIVE EXAMPLE 108

4-Acetylamino-N-{2-[4-(4-fluorobenzoyl) piperidino]ethyl}-N-(3-acetylaminophenyl) benzamide Using 2-amino-N-{2-[4-(4-fluorobenzoyl)piperidino] ethyl}-N-(3-acetylaminophenyl)benzamide (230.0 mg, 0.50 mmol) and acetic anhydride (0.113 ml, 0.60 mmol), the procedure of inventive Example 94 was repeated to obtain 248.0 mg (91.2%) of the title compound in a light yellow amorphous form.

IR (KBr): 3290, 2930, 1677, 1602, 1533, 1488, 1443, 1374, 1230, 849 cm$^{-1}$

NMR (CDCl$_3$) δ: 1.50–2.36 (6H, m), 2.06 (6H, s), 2.64 (2H, t, J=7.0 Hz), 2.80–3.34 (3H, m), 4.01 (2H, t, J=7.0 Hz), 6.65–7.63 (10H, m), 7.74–8.31 (4H, m)

INVENTIVE EXAMPLE 109

4-Acetylamino-N-{2-[4-(4-fluorobenzoyl) piperidino]ethyl}-N-(2-methoxycarbonylphenyl) benzamide Using 4-amino-N-{2-[4-(4-fluorobenzoyl)piperidino] ethyl}-N-(2-methoxycarbonylphenyl)benzamide (291.0 mg, 0.58 mmol) and acetic anhydride (0.11 ml, 1.16 mmol), the procedure of Inventive Example 94 was repeated to obtain 303.0 mg (96.0%) of the title compound in a colorless amorphous form.

IR (KBr): 3351, 2948, 1724, 1678, 1598, 1312, 1260, 972, 848, 758, 602 cm$^{-1}$

NMR (CDCl$_3$) δ: 1.71–2.23 (6H, m), 2.09 (6H, s), 2.66–3.22 (5H, m), 3.60–3.75 (1H, m), 3.82 (3H, s), 4.16–4.45 (1H, m), 7.02–7.72 (10H, m), 7.93 (2H, dd, J=8.8 Hz, 5.5 Hz)

INVENTIVE EXAMPLE 110

3-Methyl-4-acetylamino-N-{2-[4-(4-fluorobenzoyl) piperidino]ethyl}-N-(3-methoxyphenyl)benzamide Using 4-amino-3-methyl-N-{2-[4-(4-fluorobenzoyl) piperidino]-ethyl}-N-(3-methoxyphenyl)benzamide (489.0 mg, 1.00 mmol) and acetic anhydride (0.19 ml, 2.00 mmol), the procedure of Inventive Example 94 was repeated to obtain 474.0 mg (89.3%) of the title compound in a colorless amorphous form.

IR (KBr): 3298, 2949, 1678, 1512, 1246, 972, 835, 601 cm⁻¹

NMR (CDCl₃) δ: 1.71–2.32 (6H, m), 2.13 (6H, s), 2.60 (2H, t, J=6.8 Hz), 3.32 (2H, t, J=6.8 Hz), 2.95–3.32 (3H, m), 3.75 (3H, s), 3.99 (2H, t, J=6.8 Hz), 6.74 (2H, d, J=8.8 Hz), 6.96–7.25 (6H, m), 7.74 (1H, br-s), 7.95 (2H, dd, J=8.6 Hz, 5.5 Hz)

INVENTIVE EXAMPLE 111

3-Methoxy-4-acetylamino-N-{2-[4-(4-fluorobenzoyl)piperidino]-ethyl}-N-(3-methoxyphenyl)benzamide Using 4-amino-3-methoxy-N-{2-[4-(4-fluorobenzoyl)piperidino]ethyl}-N-(3-methoxyphenyl)benzamide (253.0 mg, 0.50 mmol) and acetic anhydride (0.095 ml, 1.00 mmol), the procedure of inventive Example 94 was repeated to obtain 213.0 mg (77.9%) of the title compound in a yellow amorphous form.

IR (KBr): 3435, 2945, 1680, 1636, 1596, 1510, 1246, 1031, 829, 600 cm⁻¹

NMR (CDCl₃) δ: 1.71–1.86 (4H, m), 2.04–2.33 (2H, m), 2.15 (3H, s), 2.62 (2H, t, J=6.8 Hz), 2.95–3.33 (3H, m), 3.75 (6H, s), 4.01 (2H, t, J=6.8 Hz), 6.74 (2H, d, J=8.6 Hz), 6.87–7.26 (5H, m), 7.74 (1H, brs), 7.88–8.17 (3H, m)

INVENTIVE EXAMPLE 112

4-Acetylamino-N-{2-[4-(4-fluorobenzoyl)piperidino]ethyl}-N-(4-fluorophenyl)benzamide Using 4-amino-N-{2-[4-(4-fluorobenzoyl)piperidino]ethyl}-N-(4-fluorophenyl)benzamide (227.3 mg, 0.49 mmol) and acetic anhydride (0.083 ml, 0.88 mmol), the procedure of Inventive Example 94 was repeated to obtain 202.1 mg (81.6%) of the title compound in a light brown amorphous form.

IR (KBr): 1680, 1628, 1598, 1532, 1506, 1405, 1372, 1312, 1262, 1214, 850 cm⁻¹

NMR (CDCl₃) δ: 1.85–2.32 (6H, m), 2.11 (3H, s), 2.60 (2H, t, J=6.6 Hz), 2.82–3.19 (4H, m), 4.01 (2H, t, J=6.6 Hz), 6.90–7.62 (9H, m), 7.88–8.04 (3H, m)

INVENTIVE EXAMPLE 113

4-Acetylamino-N-{2-[4-(4-fluorobenzoyl)piperidino]ethyl}-N-(4-methylphenyl)benzamide Using 4-amino-N-{2-[4-(4-fluorobenzoyl)piperidino]ethyl}-N-(4-methylphenyl)benzamide (452.7 mg, 0.99 mmol) and acetic anhydride (0.122 ml, 1.19 mmol), the procedure of Inventive Example 94 was repeated to obtain 473.6 mg (95.4%) of the title compound in a light brown amorphous form.

IR (KBr): 1680, 1628, 1598, 1532, 1512, 1444, 1406, 1374, 1314, 1278, 1260, 1226, 1206, 1156, 1140, 974, 850, 602 cm⁻¹

NMR (CDCl₃) δ: 1.68–2.04 (7H, m), 2.11 (3H, s), 2.27 (3H, s), 2.61 (2H, dd, J=7.0 Hz, 6.4 Hz), 2.94–3.10 (3H, m), 4.01 (2H, dd, J=7.0 Hz, 6.4 Hz), 6.98–7.26 (10H, m), 7.92 (1H, d, J=8.2 Hz), 7.98 (1H, d, J=8.2 Hz)

INVENTIVE EXAMPLE 114

3-Acetylamino-N-{2-[4-(4-fluorobenzoyl)piperidino]ethyl}-N-(phenyl)benzamide

Using 3-amino-N-{2-[4-(4-fluorobenzoyl)piperidino]ethyl}-N-(phenyl)benzamide (126.4 mg, 0.28 mmol) and acetic anhydride (0.03 ml, 0.32 mmol), the procedure of Inventive Example 94 was repeated to obtain 101.1 mg (73.1%) of the title compound in a colorless powder form.

Melting point: 198°–201° C.

IR (KBr): 1676, 1666, 1648, 1594, 1428, 1382, 1304, 1292, 1266, 1228, 1208, 746 cm⁻¹

NMR (CDCl₃) δ: 1.69–2.19 (7H, m), 2.13 (3H, s), 2.60 (2H, t, J=6.6 Hz), 2.94–3.09 (3H, m), 4.05 (2H, t, J=6.6 Hz), 6.92–7.53 (11H, m), 7.92 (1H, d, J=8.6 Hz), 7.99 (1H, d, J=8.6 Hz)

INVENTIVE EXAMPLE 115

3-Acetylamino-N-{2-[4-(4-fluorobenzoyl)piperidino]ethyl}-N-(4-methylphenyl)benzamide Using 3-amino-N-{2-[4-(4-fluorobenzoyl)piperidino]ethyl}-N-(4-methylphenyl)benzamide (230.1 mg, 0.50 mmol) and acetic anhydride (0.057 ml, 0.60 mmol), the procedure of Inventive Example 94 was repeated to obtain 245.2 mg (97.8%) of the title compound in a light yellow amorphous form.

IR (KBr): 1680, 1630, 1512, 750 cm⁻¹

NMR (CDCl₃) δ: 1.71–2.66 (7H, m), 2.13 (3H, s), 2.25 (3H, s, 2.58 (2H, dd, J=6.8 Hz, 6.6 Hz), 2.94–3.19 (3H, m), 4.01 (2H, dd, J=6.8 Hz, 6.6 Hz), 6.82–7.69 (10H, m), 7.93 (1H, d, J=8.8 Hz), 7.99 (1H, d, J=8.8 Hz)

INVENTIVE EXAMPLE 116

3-Acetylamino-N-{2-[4-(4-fluorobenzoyl)piperidino]ethyl}-N-(4-fluorophenyl)benzamide Using 3-amino-N-{2-[4-(4-fluorobenzoyl)piperidino]ethyl}-N-(4-fluorophenyl)benzamide (223.2 mg, 0.48 mmol) and acetic anhydride (0.055 ml, 0.58 mmol), the procedure of inventive Example 94 was repeated to obtain 238.6 mg (98.3%) of the title compound in a light yellow amorphous form.

IR (KBr): 1680, 1642, 1598, 1552, 1508, 1428, 1374, 1310, 1214, 748 cm⁻¹

NMR (CDCl₃) δ: 1.67–2.31 (7H, m), 2.14 (3H, s), 2.58 (2H, t, J=6.4 Hz), 2.93–3.25 (3H, m), 4.01 (2H, t, J=6.4 Hz), 6.80–7.56 (10H, m), 7.93 (1H, d, J=8.6 Hz), 7.99 (1H, d, J=8.6 Hz)

INVENTIVE EXAMPLE 117

3-Acetylamino-N-{2-[4-(4-fluorobenzoyl)piperidino]ethyl}-N-(3-methylthiophenyl)benzamide Using 3-amino-N-{2-[4-(4-fluorobenzoyl)piperidino]ethyl}-N-(3-methylthiophenyl)benzamide (196.7 mg, 0.40 mmol) and acetic anhydride (0.046 ml, 0.48 mmol), the procedure of Inventive Example 94 was repeated to obtain 172.2 mg (80.7%) of the title compound in a light brown amorphous form.

IR (KBr): 1678, 1636, 1586, 1552, 1434, 1372, 1310, 1224, 748 cm⁻¹

NMR (CDCl₃) δ: 1.73–2.40 (7H, m), 2.13 (3H, s), 2.33 (3H, 2.59 (2H, dd, J=6.6 Hz, 6.4 Hz), 2.94–3.21 (3H, m), 4.03 (2H, dd, J=6.6 Hz, 6.4 Hz), 6.85–7.63 (10H, m), 7.93 (1H, d, J=8.6 Hz), 7.99 (1H, d, J=8.6 Hz)

INVENTIVE EXAMPLE 118

4-Acetylamino-N-{2-[4-(4-fluorobenzoyl)piperidino]ethyl}-N-(4-chlorophenyl)benzamide Using 4-amino-N-{2-[4-(4-fluorobenzoyl)piperidino]ethyl}-N-(3-chlorophenyl)benzamide (328.6 mg, 0.68 mmol) and acetic anhydride (0.078 ml, 0.83 mmol), the procedure of Inventive Example 94 was repeated to obtain 345.4 mg (97.3%) of the title compound in a light yellow amorphous form.

IR (KBr): 1680, 1630, 1598, 1530, 1492, 1408, 1372, 1312, 1260, 1224, 850, 758 cm$^{-1}$

NMR (CDCl$_3$) δ: 1.69–2.19 (7H, m), 2.13 (3H, s), 2.59 (2H, t, J=6.6 Hz), 2.92–3.09 (3H, m), 4.00 (2H, t, J=6.6 Hz), 6.97–7.39 (10H, m), 7.95 (2H, dd, J=8.6 Hz, 5.5 Hz)

INVENTIVE EXAMPLE 119

4-Acetylamino-N-{2-[4-(4-fluorobenzoyl)piperidino]ethyl}-N-(3,4-dimethylphenyl)benzamide Using 4-amino-N-{2-[4-(4-fluorobenzoyl)piperidino]ethyl}-N-(3,4-dimethylphenyl)benzamide (333.1 mg, 0.70 mmol) and acetic anhydride (0.080 ml, 0.85 mmol), the procedure of Inventive Example 94 was repeated to obtain 359.9 mg (99.7%) of the title compound in a light brown amorphous form.

IR (KBr): 2944, 1680, 1628, 1598, 1530, 1504, 1446, 1408, 1372, 1312, 1260, 1228, 1206, 1178, 1156, 1140, 850, 760 cm$^{-1}$

NMR (CDCl$_3$) δ: 1.68–1.86 (4H, m), 2.16 (3H, s), 2.16 (6H, s), 2.05–2.31 (3H, m), 2.61 (2H, t, J=6.8 Hz), 2.94–3.18 (3H, m), 4.00 (2H, t, J=6.8 Hz), 6.79–7.27 (9H, m), 7.95 (2H, dd, J=8.6 Hz, 5.5 Hz)

INVENTIVE EXAMPLE 120

4-Acetylamino-N-{2-[4-(4-fluorobenzoyl)piperidino]ethyl}-N-(3,5-dimethylphenyl)benzamide Using 4-amino-N-{2-[4-(4-fluorobenzoyl)piperidino]ethyl}-N-(3,5-dimethylphenyl)benzamide (382.8 mg, 0.81 mmol) and acetic anhydride (0.092 ml, 0.99 mmol), the procedure of Inventive Example 94 was repeated to obtain 360.9 mg (86.4%) of the title compound in a light brown amorphous form.

IR (KBr): 3252, 2948, 1686, 1616, 1598, 1518, 1506, 1474, 1436, 1408, 1396, 1374, 1334, 1312, 1296, 1236, 1210, 1138, 1128, 974 cm$^{-1}$

NMR (CDCl$_3$) δ: 1.67–1.86 (4H, m), 2.12 (3H, s), 2.19 (6H, s), 2.04–2.32 (3H, m), 2.61 (2H, t, J=6.8 Hz), 2.94–3.11 (3H, m), 4.00 (2H, t, J=6.8 Hz), 6.70–6.76 (3H, m), 7.03–7.33 (6H, m), 7.95 (2H, dd, J=8.6 Hz, 5.5 Hz )

INVENTIVE EXAMPLE 121

4-Acetylamino-N-{2-[4-(4-fluorobenzoyl)piperidino]ethyl}-N-(3,4-methylenedioxyphenyl)benzamide Using 4-amino-N-{2-[4-(4-fluorobenzoyl)piperidino]ethyl}-N-(3,4-methylenedioxyphenyl)benzamide (245.0 mg, 0.501 mmol) and acetic anhydride (0.057 ml, 0.60 mmol), the procedure of Inventive Example 94 was repeated to obtain 210.3 mg (79.0%) of the title compound in a colorless amorphous form.

IR (KBr): 1671, 1638, 1623, 1599, 1533, 1506, 1485, 1433, 1407, 1377, 1314, 1299, 1260, 1236, 1215 1173, 1155, 1134, 1035 cm$^{-1}$

NMR (CDCl$_3$) δ: 1.62–1.97 (4H, m), 2.12 3H, s), 2.00–2.40 (2H, m), 2.64 (2H, t, J=6.9 Hz), 2.90–3.47 (3H, m), 3.99 (2H, t, J=6.9 Hz), 5.95 (2H, s), 6.40–6.70 (3H, m), 6.93–7.43 (6H, m), 7.80–8.03 (2H, m)

INVENTIVE EXAMPLE 122

4-Acetylamino-N-{3-[4-(4-fluorobenzoyl)piperidino]propyl}-N-(3-methoxyphenyl)benzamide Using 4-amino-N-{3-[4-(4-fluorobenzoyl)piperidino]propyl}-N-(3-methoxyphenyl)benzamide (300.0 mg, 0.61 mmol) and acetic anhydride (0.069 ml, 0.73 mmol), the procedure of inventive Example 94 was repeated to obtain 312.6 mg (96.5%) of the title compound in a light yellow amorphous form.

IR (KBr): 1680, 1628, 1600, 1530, 1490, 1408, 1374, 1314, 1282, 1262, 1234, 1156, 910, 760 cm$^{-1}$

NMR (CDCl$_3$) δ: 1.60–2.25 (7H, m), 2.10 (3H, s), 2.44 (2H, t, J=6.8 Hz), 2.75–3.30 (4H, m), 3.69 (3H, s), 3.92 (2H, t, J=6.8 Hz), 6.46–6.75 (3H, m), 7.12 (2H, dd, each J=8.4 Hz), 7.15–7.40 (4H, m), 7.40–7.56 (1H, m), 7.95 (2H, dd, J=8.4 Hz, 4.3 Hz)

INVENTIVE EXAMPLE 123

4-Isobutyrylamino-N-{2-[4-(4-fluorobenzoyl)piperidino]ethyl}-N-(2-methoxyphenyl)benzamide Using 4-amino-N-{2-[4-(4-fluorobenzoyl)piperidino]ethyl}-N-(2-methoxyphenyl)benzamide (200.0 mg, 0.42 mmol) and isobutylyl chloride (0.053 ml, 0.51 mmol), the procedure of inventive Example 94 was repeated to obtain 222.7 mg (97.0%) of the title compound in a colorless amorphous form.

IR (KBr): 1680, 1630, 1598, 1528, 1502, 1408, 1306, 1278, 1242, 848, 752 cm$^{-1}$

NMR (CDCl$_3$) δ: 1.20 (6H, d, J=6.8 Hz), 1.58–2.78 (9H, m), 2.80–3.30 (3H, m), 3.55–3.90 (1H, m), 3.69 (3H, s), 3.90–4.30 (1H, m), 6.60–7.40 (10H, m), 7.78–8.07 (2H, m)

INVENTIVE EXAMPLE 124

4-Butyrylamino-N-{2-[4-(4-fluorobenzoyl)piperidino]ethyl}-N-(2-methoxyphenyl)benzamide Using 4-amino-N-{2-[4-(4-fluorobenzoyl)piperidino]ethyl}-N-(2-methoxyphenyl)benzamide (200.0 mg, 0.42 mmol) and butylyl chloride (0.053 ml, 0.51 mmol), the procedure of Inventive Example 94 was repeated to obtain 196.3 mg (85.5%) of the title compound in a colorless amorphous form.

IR (KBr): 2956, 1680, 1632, 1599, 1527, 1503, 1443, 1410, 1308, 1278, 1239, 1179, 1158, 1140, 1116, 1023, 975, 849 cm$^{-1}$

NMR (CDCl$_3$) δ: 0.93 (3H, t, J=7.0 Hz), 1.50–2.00 (6H, m), 2.00–2.40 (4H, m), 2.47–2.75 (2H, m), 2.80–3.30 3H, m), 3.60–3.93 (1H, m), 3.68 (3H, s), 3.97–4.30 (1H, m) 6.63–7.30 (10H, m), 7.80–8.03 (2H, m)

INVENTIVE EXAMPLE 125

4-Butyrylamino-N-{2-[4-(4-fluorobenzoyl)piperidino]ethyl}-N-(3-methoxyphenyl)benzamide Using 4-amino-N-{2-[4-(4-fluorobenzoyl)piperidino]ethyl}-N-(3-methoxyphenyl)benzamide (238.0 mg, 0.50 mmol and butylyl chloride (0.10 ml, 0.10 mmol), the procedure of Inventive Example 94 was repeated to obtain 145.0 mg (53.2%) of the title compound in a colorless amorphous form.

IR (KBr): 2980, 1680, 1600, 1200, 970, 848, 699 cm$^{-1}$

NMR (CDCl$_3$) δ: 0.87 (3H, t, J=7.2 Hz), 1.47–2.16 (8H, m), 2.41 (2H, t, J=7.2 Hz), 2.63 (2H, t, J=6.7 Hz), 2.95–3.26 (3H, m), 3.69 (3H, s), 4.06 (2H, t, J=6.7 Hz), 6.64–6.72 (3H, m), 6.87–7.44 (7H, m), 7.91 (2H, dd, J=8.8 Hz, 5.4 Hz)

INVENTIVE EXAMPLE 126

4-Propionylamino-N-{2-[4-(4-fluorobenzoyl)piperidino]ethyl}-N-(3-methoxyphenyl)benzamide Using 4-amino-N-{2-[4-(4-fluorobenzoyl)piperidino]ethyl}-N-(3-methoxyphenyl)benzamide (238.0 mg, 0.50 mmol) and propionyl chloride (0.077 ml, 0.60 mmol), the procedure of Inventive Example 94 was repeated to obtain 240.0 mg (90.4%) of the title compound in a yellow amorphous form.

IR (KBr): 3320, 2940, 1680, 1600, 1306, 971, 850, 699 cm$^{-1}$

NMR (CDCl$_3$) δ: 1.20 (3H, t, J=7.5 Hz), 1.78–2.34 (8H, m), 2.38 (2H, t, J=7.5 Hz), 2.63 (2H, t, J=5.8 Hz), 2.95–3.26 (3H, m), 3.69 (3H, s), 4.03 (2H, t, J=6.8 Hz), 6.63–6.71 (3H, m), 7.02–7.29 (7H, m), 7.95 (2H, dd, J=8.8 Hz, 5.4 Hz)

INVENTIVE EXAMPLE 127

4-Valerylamino-N-{2-[4-(4-fluorobenzoyl)piperidino]ethyl}-N-(3-methoxyphenyl)benzamide Using 4-amino-N-{2-[4-(4-fluorobenzoyl)piperidino]ethyl}-N-(3-methoxyphenyl)benzamide (238.0 mg, 0.50 mmol) and valeryl chloride (0.071 ml, 0.60 mmol), the procedure of Inventive Example 94 was repeated to obtain 232.0 mg (83.0%) of the title compound in a yellow amorphous form.

IR (KBr): 3305, 2596, 1680, 1600, 1308, 972, 850, 799 cm$^{-1}$

NMR (CDCl$_3$) δ: 0.92 (3H, t, J=6.4 Hz), 1.32–2.49 (10H, m), 2.63 (2H, t, J=6.8 Hz), 2.96–3.28 (3H, m), 3.70 (3H, s), 4.04 (2H, t, J=6.8 Hz), 6.63–6.71 (3H, m), 7.02–7.29 (7H, m), 7.96 (2H, dd, J=8.8 Hz, 5.4 Hz)

INVENTIVE EXAMPLE 128

4-Pivaloylamino-N-{2-[4-(4-fluorobenzoyl)piperidino]ethyl}-N-(2-methoxyphenyl)benzamide Using 4-amino-N-{2-[4-(4-fluorobenzoyl)piperidino]ethyl}-N-(2-methoxyphenyl)benzamide (200.0 mg, 0.42 mmol) and pivaloyl chloride (0.062 ml, 0.51 mmol), the procedure of Inventive Example 94 was repeated to obtain 214.6 mg (91.2%) of the title compound in a colorless amorphous form.

IR (KBr): 2956, 1680, 1630, 1599, 1503, 1461, 1443, 1404, 1314, 1278, 1242, 1176, 1158, 1140, 1116, 1044, 1026, 975, 915, 852 cm$^{-1}$

NMR (CDCl$_3$) δ: 1.26 (9H, s), 1.50–1.93 (4H, m), 2.00–2.37 (2H, m), 2.65 (2H, t, J=7.0 Hz), 2.80–3.38 (3H, m), 3.53–3.93 (1H, m), 3.69 (3H, s), 3.93–4.30 (1H, m), 6.67–6.92 (2H, m), 6.97–7.33 (6H, m), 7.80–8.07 (2H, m)

INVENTIVE EXAMPLE 129

4-(Trifluoroacetylamino)methyl-N-{2-[4-(4-fluorobenzoyl)piperidino]ethyl}-N-(2-methoxyphenyl)benzamide Using 4-aminomethyl-N-{2-[4-(4-fluorobenzoyl)piperidino]ethyl}-N-(2-methoxyphenyl)benzamide (60 mg, 0.123 mmol) and trifluoroacetic anhydride (19 µl, 0.135 mmol), the procedure of Inventive Example 94 was repeated to obtain 48 mg (67.0%) of the title compound in a colorless amorphous form.

IR (KBr): 3406, 3064, 2944, 1719, 1680, 1641, 1599, 1503, 1221, 1179, 1158 cm$^{-1}$

NMR (CDCl$_3$) δ: 1.46–1.98 (4H, m), 1.98–2.35 (2H, m), 2.62 (2H, t, J=7.5 Hz), 2.79–3.36 (3H, m), 3.50–3.95 (1H, m), 3.69 (3H, s), 4.00–4.54 (1H, m), 4.40 (2H, d, J=6 Hz), 6.61–6.83 (2H, m), 6.90 (1H, d, J=7.5 Hz), 6.96–7.40 (8H, m), 7.93 (2H, dd, J=9 Hz, 6 Hz)

INVENTIVE EXAMPLE 130

4-Trifluoroacetylamino-N-{2-[4-(4-fluorobenzoyl)piperidino]ethyl}-N-(2-methoxyphenyl)benzamide Using 4-amino-N-{2-[4-(4-fluorobenzoyl)piperidino]ethyl}-N-(2-methoxyphenyl)benzamide (200.0 mg, 0.42 mmol) and trifluoroacetic anhydride (0.18 ml, 1.26 mmol), the procedure of Inventive Example 94 was repeated to obtain 253.3 mg (quantitative) of the title compound in a colorless amorphous form.

IR (KBr): 2948, 1720, 1678, 1628, 1544, 1500, 1440, 1284, 1200, 1158, 1026, 976 cm$^{-1}$

NMR (CDCl$_3$) δ: 1.53–2.30 (5H, m), 2.57 (2H, t, J=6.0 Hz), 3.46–3 85 (2H, m), 3.65 (3H, s), 3.90–4.30 (2H, m), 6.50–6.89 (1H, m), 6.76 (2H, t, J=9.0 Hz), 6.90–7.40 (7H, m), 7.92 (2H, dd, J=9.0 Hz, 6.0 Hz), 8.43–8.85 (1H, m)

INVENTIVE EXAMPLE 131

N-{2-[4-(4-fluorobenzoyl)piperidino]ethyl}-4-(methanesulfonylamino)methyl-N-(2-methoxyphenyl)benzamide Using 4-aminomethyl-N-{2-[4-(4-fluorobenzoyl)piperidino]-ethyl}-N-(2-methoxyphenyl)benzamide (60 mg, 0.123 mmol) and methanesulfonyl chloride (11 µl, 0.142 mmol), the procedure of Inventive Example 94 was repeated to obtain 40 mg (57.5%) of the title compound in a colorless amorphous form.

IR (KBr): 2926, 1677, 1638, 1596, 1503, 1410, 1323, 1278, 1146 cm$^{-1}$

NMR (CDCl$_3$) δ: 1.50–2.00 (4H, m), 2.00–2.37 (2H, m), 2.46–2.78 (2H, m), 2.70 (3H, s), 2.81–3.29 (3H, m), 3.40–3.88 (1H, m), 3.70 (3H, s), 4.00–4.41 (1H, m), 4.18 (2H, d, J=6 Hz), 4.69 (1H, br-s), 6.71 (1H, d, J=8 Hz), 6.80 (1H, d, J=8 Hz), 6.90–7.35 (8H, m), 7.93 (2H, dd, J=9 Hz, 6 Hz)

INVENTIVE EXAMPLE 132

N-{2-[4-(4-fluorobenzoyl)piperidino]ethyl}-4-methanesulfonylamino-N-(2-methoxyphenyl)benzamide Using 4-amino-N-{2-[4-(4-fluorobenzoyl)piperidino]ethyl}-N-(2-methoxyphenyl)benzamide (50.0 mg, 0.11 mmol) and methanesulfonyl chloride (0.025 ml, 0.316 mmol), the procedure of Inventive Example 94 was repeated to obtain 29.5 mg (50.7%) of the title compound in a colorless amorphous form.

IR (KBr): 3310, 2944, 1680, 1629, 1599, 1503, 1464, 1395, 1335, 1278, 1236, 1155, 1116, 972 cm$^{-1}$

NMR (CDCl$_3$) δ: 1.50–1.93 (4H, m), 2.00–2.40 (2H, m), 2.64 (2H, t, J=7.0 Hz), 2.90 (3H, s, 2.78–3.20 (3H, m), 3.50–3.90 (1H, m), 3.70 (3H, s), 3.95–4.37 (1H, m), 6.77 (2H, t, J=9.0 Hz), 6.93–7.40 (8H, m) 7.94 (2H, dd, J=9.0 Hz, 6.0 Hz)

INVENTIVE EXAMPLE 133

N-{2-[4-(4-fluorobenzoyl)piperidino]ethyl}-4-methanesulfonylamino-N-(3-methoxyphenyl)benzamide Using 4-amino-N-{2-[4-(4-fluorobenzoyl)piperidino]ethyl}-N-(3-methoxyphenyl)benzamide (475.0mg, 1.00 mmol) and methanesulfonyl chloride (0.12 ml, 1.50 mmol), the procedure of inventive Example 94 was repeated to obtain 527.8 mg (95.4%) of the title compound in a colorless amorphous form.

IR (KBr): 1678, 1640, 1598, 1508, 1490, 1454, 1390, 1332, 1284, 1218, 1154, 970 cm$^{-1}$

NMR (CDCl$_3$) δ: 1.50–2.73 (7H, m), 2.93 (3H, s), 2.73–3.55 (4H, m), 3.69 (3H, s), 4.20–4.50 (2H, m), 6.66 (2H, br-d, J=7.5 Hz), 6.85–7.40 (5H, m), 7.94 (2H, dd, J=9.0 Hz, 6.0 Hz)

INVENTIVE EXAMPLE 134

4-(Ethoxycarbonylamino)methyl-N-{2-[4-(4-fluorobenzoyl)piperidino]ethyl}-N-(2-methoxyphenyl)benzamide Using 4-aminomethyl-N-{2-[4-(4-fluorobenzoyl)piperidino]ethyl}-N-(2-methoxyphenyl)benzamide (60 mg, 0.123 mmol) and ethyl chloroformate (13 μl, 0.136 mmol), the procedure of Inventive Example 94 was repeated to obtain 50 mg (72.7%) of the title compound in a colorless amorphous form.

IR (KBr): 3340, 2938, 2806, 1716, 1680, 1641, 1599, 1503, 1413, 1239, 1137 cm$^{-1}$

NMR (CDCl$_3$) δ: 1.22 (3H, t, J=7.5 Hz), 1.69–1.90 (4H, m), 2.10–2.34 (2H, m), 2.60 (2H, t, J=7 Hz), 2.80–3.27 (3H, m), 3.65–3.85 (1H, m), 3.67 (3H, s), 4.00–4.30 (1H, m), 4.11 (2H, q, J=7.5 Hz), 4.24 (2H, d, J=6 Hz), 4.88 (1H, br-s), 6.73 (1H, d, J=8 Hz), 6.80–7.30 (9H, m), 7.93 (2H, dd, J=9 Hz, 6 Hz)

INVENTIVE EXAMPLE 135

4-Ethoxycarbonylamino-N-{2-[4-(4-fluorobenzoyl)piperidino]ethyl}-N-(2-methoxyphenyl)benzamide Using 4-amino-N-{2-[4-(4-fluorobenzoyl)piperidino]ethyl}-N-(2-methoxyphenyl)benzamide (185.0 mg, 0.39 mmol) and ethyl chloroformate (0.11 ml, 1.17 mmol), the procedure of Inventive Example 94 was repeated to obtain 80.0 mg (37.5%) of the title compound in a colorless oily form.

IR (neat): 3288, 2948, 1720, 1680, 1630, 1528, 1440, 1316, 1120, 1026, 976 cm$^{-1}$ NMR (CDCl$_3$) δ: 1.36 (3H, t, J=7.2 Hz), 1.46–2.35 (5H, m), 2.63 (2H, t, J=6.0 Hz), 2.76–3.30 (4H, m), 3.66 (3H, s), 4.10 (2H, t, J=6.0 Hz), 4.15 (2H, q, J=7.2 Hz), 6.53–6.73 (1H, m), 6.85 (2H, t, J=8.4 Hz), 6.90–7.33 (8H, m), 7.95 (2H, dd, J=9.0 Hz, 6.0 Hz)

INVENTIVE EXAMPLE 136

4-[(S)-2-(tert-Butoxycarbonylamino)propionyl]aminomethyl-N-{2-[4-(4-fluorobenzoyl)piperidino]ethyl}-N-(2-methoxyethyl)benzamide 4-Aminomethyl-N-{2-[4-(4-fluorobenzoyl)piperidino]ethyl}-N-(2-methoxyethyl)benzamide (120 mg, 0.245 mmol) was dissolved in methylene chloride (5 ml) to which were subsequently added Boc-L-alanine (46.4 mg, 0.245 mmol) and EDC hydrochloride (52 mg, 0.270 mmol) while cooling in an ice bath. After 4 hours of stirring at the same temperature, the reaction solution was mixed with water (10 ml), adjusted to pH 8 with saturated sodium bicarbonate aqueous solution and then extracted with methylene chloride. Thereafter, the resulting organic layer was dried on anhydrous sodium carbonate, the solvent was removed by evaporation, and the resulting residue was purified by a silica gel column chromatography (ethyl acetate) to obtain 109 mg (68.9%) of the title compound in a colorless amorphous form.

IR (KBr): 3328, 2938, 1713, 1677, 1641, 1599, 1503, 1392, 1242, 1161 cm$^{-1}$

NMR (CDCl$_3$) δ: 1.33 (3H, d, J=7 Hz), 1.40 (9H, s), 1.66–1.90 (4H, m) 2.00–2.32 (2H, m), 2.62 (2H, t, J=8 Hz), 2.80–3.26 (3H, m), 3.60–3.80 (1H, m), 3.69 (3H, s), 4.00–4.25 (2H, m) 4.33 (2H, d, J=6 Hz), 4.88 (1H, br-s), 6.40 (1H, br-s), 6.73 (1H, d, J=8 Hz), 6.89 (1H, d, J=8 Hz), 6.96–7.30 (8H, m), 7.94 (2H, dd, J=9 Hz, 6 Hz)

INVENTIVE EXAMPLE 137

N-{2-[4-(4-Fluorobenzoyl)piperidino]ethyl}-N-(2-methoxyphenyl)-4-(methylamino)methylbenzamide 4-(N-tert-Butoxycarbonyl-N-methylamino)methyl-N-{2-[4-(4-fluorobenzoyl)piperidino]ethyl}-N-(2-methoxyphenyl)benzamide (144 mg, 0.239 mmol) was dissolved in methylene chloride (4 ml) to which was subsequently added dropwise trifluoroacetic acid (0.4 ml) while cooling in an ice bath. After 2 hours of stirring at the same temperature, the solvent was removed by evaporation, and the resulting residue was diluted with methylene chloride (10 ml), washed with saturated sodium bicarbonate aqueous solution and saturated brine, and then dried on anhydrous sodium carbonate. Thereafter, the solvent was removed by evaporation to obtain 119 mg (98.9%) of the title compound in a colorless amorphous form.

IR (KBr): 2944, 2794, 1680, 1641, 1596, 1503, 1278, 1236, 750 cm$^{-1}$

NMR (CDCl$_3$) δ: 1.62–1.97 (5H, m), 2.00–2.30 (2H, m), 2.36 (3H, s), 2.63 (2H, t, J=7.5 Hz), 2.80–3.26 (3H, m), 3.64 (2H, s), 3.68 (3H, s), 3.60–3.85 (1H, m), 4.00–4.26 (1H, m), 6.73 (1H, d, J=8 Hz), 6.82 (1H, d, J=8 Hz), 7.00–7.31 (8H, m), 7.94 (2H, dd, J=9 Hz, 6 Hz)

INVENTIVE EXAMPLE 138

4-[(S)-2-(tert-Aminopropionyl]aminomethyl-N-{2-[4-(4-fluorobenzoyl)piperidino]ethyl}-N-(2-methoxyethyl)benzamide 4-[(S)-2-tert-Butoxycarbonylamino)propionyl]aminomethyl-N-{2-[4-(4-fluorobenzoyl)piperidino]ethyl}-N-(2-methoxyethyl)benzamide (100 mg, 0.156 mmol) was treated in the same manner as described in Inventive Example 137 to obtain 84.7 mg (100%) of the title compound in a colorless amorphous form.

IR (KBr): 3370, 2926, 1677, 1641, 1599, 1503, 1413, 1278, 1239, 1158, 1122 cm$^{-1}$

NMR (CDCl$_3$) δ: 1.10–1.45 (3H, m), 1.70–2.58 (8H, m), 2.76 (2H, t, J=7 Hz), 2.92–3.35 (4H, m), 3.68 (3H, s), 3.65–3.92 (1H, m), 4.05–4.40 (3H, m), 6.51–6.70 (1H, m), 6.73 (1H, d, J=8 Hz), 6.82–7.30 (9H, m), 7.93 (2H, dd, J=9 Hz, 6 Hz )

INVENTIVE EXAMPLE 139

4-Amidino-N-{2-[4-(4-fluorobenzoyl)piperidino]ethyl}-N-(2-methoxyphenyl)benzamide In an atmosphere of dry air, 4-cyano-N-{2-[4-(4-fluorobenzoyl)piperidino]ethyl}-N-(2-methoxyphenyl)benzamide (100 mg, 0.206 mmol) was dissolved in ethanol (2 ml) to which was subsequently introduced hydrogen chloride gas at −10° C. for 15 minutes. After 5.5 hours of stirring at the same temperature and additional stirring at room temperature for 1 hour, ethanol was removed by evaporation, and 10% ammonia-methanol solution (1 ml) was added to the resulting residue at room temperature. After 16 hours of stirring at the same temperature, the solvent was removed by evaporation, and the resulting residue was purified by a silica gel column chromatography (ether:methanol=10:1-methylene chloride:methanol=6:1). Thereafter, a methylene chloride-methanol (10:1) mixture solution (5 ml) was added to the thus purified product, insoluble materials were removed by filtration, and then the solvent was removed by evaporation to obtain 92 mg (88.9%) of the title compound in a colorless amorphous form.

IR (KBr): 3250, 3064, 1678, 1642, 1598, 1502, 1440, 1410, 1280, 1224, 1158, 854 cm⁻¹

NMR (CDCl₃—CD₃OD) δ: 1.80–2.40 (4H, m), 2.40–4.10 (8H, m), 3.74 (3H, s), 4.13–4.59 (1H, m), 6.60–6.93 (2H, m), 6.98–7.37 (2H, m), 7.16 (2H, dd, J=9 Hz, 9 Hz), 7.43 (2H, d, J=8 Hz), 7.58 (2H, d, J=8 Hz), 7.99 (2H, dd, J=9 Hz, 6 Hz)

MS (FAB, m/z): 120, 157, 220, 234, 296, 357, 503 (M⁺+H)

INVENTIVE EXAMPLE 140

4-Amidino-N-{2-[4-(4-fluorobenzoyl)piperidino]ethyl}-N-(4-methoxyphenyl)benzamide Using 4-cyano-N-{2-[4-(4-fluorobenzoyl)piperidino]ethyl}-N-(4-methoxyphenyl)benzamide (728.0 mg, 1.50 mmol), the procedure of Inventive Example 139 was repeated to obtain 635.0 mg (84.3%) of the title compound in a colorless powder form.

IR (KBr): 3270, 3075, 1678, 1626, 1598, 1510, 1246, 971, 853, 730, 600 cm⁻¹

NMR (CDCl₃) δ: 1.82–1.91 (4H, m), 2.12–2.36 (2H, m), 2.62 (2H, t, J=6.4 Hz), 2.97–3.41 (6H, m), 3.72 (3H, s), 4.03 (2H, t, J=6.4 Hz), 6.74 (2H, d, J=8.8 Hz), 7.08 (2H, d, J=8.8 Hz), 7.05–7.32 (2H, m), 7.40 (2H, d, J=8.4 Hz), 7.57 (2H, d, J=8.4 Hz), 7.96 (2H, dd, J=8.8 Hz, 5.5 Hz)

INVENTIVE EXAMPLE 141

4-(N-acetylamidino)-N-{2-[4-(4-fluorobenzoyl)piperidino]ethyl}-N-(2-methoxyphenyl)benzamide Using 4-amidino-N-{2-[4-(4-fluorobenzoyl)piperidino]ethyl}-N-(2-methoxyphenyl)benzamide (100 mg, 0.20 mmol), the procedure of Inventive Example 94 was repeated to obtain 81 mg (74.4%) of the title compound in a light yellow amorphous form.

IR (KBr): 3264, 2944, 1730, 1680, 1642, 1596, 1502, 1408, 1298, 1262 cm⁻¹

NMR (CDCl₃) δ: 1.56–1.98 (4H, m), 1.98–2.45 (2H, m), 2.16 (3H, s), 2.46–2.80 (2H, m), 2.80–3.36 (3H, m), 3.54–3.93 (1H, m), 3.70 (3H, s), 4.00–4.40 (1H, m), 6.62–6.97 (3H, m), 7.00–7.75 (9H, m), 8.01 (2H, dd, J=9 Hz, 6 Hz)

INVENTIVE EXAMPLE 142

N-{2-[4-(4-fluorobenzoyl)piperidino]ethyl}-4-(N-methanesulfonyl-amidino)-N-(2-methoxyphenyl)benzamide Using 4-amidino-N-{2-[4-(4-fluorobenzoyl)piperidino]ethyl}-N-(2-methoxyphenyl)benzamide (120 mg, 0.239 mmol), the procedure of Inventive Example 94 was repeated to obtain 81 mg (73.6%) of the title compound in a colorless amorphous form.

IR (KBr): 3406, 2944, 1680, 1641, 1596, 1533, 1503, 1410, 1278, 1155, 1113, 1020, 972, 852, 750, 603, 528 cm⁻¹

NMR (CDCl₃) δ: 1.46–2.00 (4H, m), 2.02–2.38 (2H, m), 2.46–2.76 (2H, m), 2.80–3.37 (3H, m), 3.04 (3H, s), 3.50–3.90 (1H, m), 3.70 (3H, s), 4.00–4.43 (1H, m), 6.50–6.91 (3H, m), 6.96–7.38 (7H, m), 7.55 (2H, d, J=8 Hz), 7.95 (2H, dd, J=9 Hz, 6 Hz)

INVENTIVE EXAMPLE 143

4-(N-Ethoxycarbonylamidino)-N-{2-[4-(4-fluorobenzoyl)piperidino]ethyl}-N-(2-methoxyphenyl)benzamide Using 4-amidino-N-{2-[4-(4-fluorobenzoyl)piperidino]ethyl}-N-(2-methoxyphenyl)benzamide (120 mg, 0.239 mmol), the procedure of Inventive Example 94 was repeated to obtain 108 mg (78.7%) of the title compound in a colorless amorphous form.

IR (KBr): 3376, 2944, 1680, 1620, 1596, 1503, 1299, 1263, 1134 cm⁻¹

NMR (CDCl₃) δ: 1.32 (3H, t, J=7 Hz), 1.50–1.97 (4H, m), 2.02–2.38 (2H, m), 2.47–2.66 (2H, m), 2.80–3.38 (3H, m), 3.50–3.90 (1H, m), 3.67 (3H, s), 4.00–4.40 (1H, m), 4.18 (2H, q, J=7 Hz), 6.50–6.90 (3H, m), 6.93–7.42 (7H, m), 7.63 (2H, d, J=8 Hz), 7.94 (2H, dd, J=9 Hz, 6 Hz)

INVENTIVE EXAMPLE 144

4-(Ethylthioureido)-N-{2-[4-(4-fluorobenzoyl)piperidino]ethyl}-N-(2-methoxyphenyl)benzamide 4-Amino-N-{2-[4-(4-fluorobenzoyl)piperidino]ethyl}-N-(2-methoxyphenyl)benzamide (80.0 mg, 0.168 mmol) was dissolved in ethanol (2.0 ml), and the solution was mixed with ethylthio isocyanate (0.035 ml, 0.404 mmol) at room temperature and then heated under reflux for 14 hours. After cooling, the solvent was distilled off under a reduced pressure. Thereafter, the resulting residue was purified by a silica gel column chromatography (chloroform:methanol=20:1) to obtain 95.5 mg (quantitative) of the title compound in a colorless oily form.

IR (neat): 2944, 1680, 1629, 1599, 1536, 1503, 1443, 1410, 1314, 1278, 1260, 1239, 1158, 1140, 1116, 975, 912, 854, 729, 645 cm⁻¹

NMR (CDCl₃) δ: 1.14 (3H, t, J=7.3 Hz), 1.50–1.88 (4H, m), 1.96–2.30 (2H, m), 2.40–2.70 (2H, m), 2.73–3.27 (3H, m), 3.40–3.90 (3H, m), 3.72 (3H, s), 3.90–4.40 (1H, m), 6.60–7.38 (10H, m), 7.70–8.03 (2H, m)

INVENTIVE EXAMPLE 145

4-(tert-Butylureido)-N-{2-[4-(4-fluorobenzoyl)-piperidino]ethyl}-N-(2-methoxyphenyl)benzamide Using 4-amino-N-{2-[4-(4-fluorobenzoyl)piperidino]ethyl}-N-(2-methoxyphenyl)benzamide (77.7 mg, 0.164 mmol) and tertbutyl isocyanate (0.022 ml, 0.196 mmol), the procedure of inventive Example 144 was repeated to obtain 72.9 mg (77.6%) of the title compound in a colorless oily form.

IR (neat): 3370, 2956, 1680, 1617, 1599, 1536, 1503, 1452, 1410, 1392, 1314, 1278, 1251, 1206, 1179, 1158, 909, 729, 645, 603 cm⁻¹

NMR (CDCl₃) δ: 1.33 (9H, s), 1.58–1.94 (4H, m), 1.98–2.32 (2H, m), 2.49–2.75 (2H, m), 2.80–3.30 (3H, m), 3.50–3.92 (1H, m), 3.68 (3H, s), 3.92–4.30 (1H, m), 6.60–7.30 (10H, m), 7.80–8.07 (2H, m)

INVENTIVE EXAMPLE 146

4-Ureido-N-{2-[4-(4-fluorobenzoyl)piperidino]ethyl}-N-(3-methoxyphenyl)benzamide 4-Amino-N-{2-[4-(4-fluorobenzoyl)piperidino]ethyl}-N-(3-methoxyphenyl)benzamide (237.2 mg, 0.50 mmol) was dissolved in acetic acid-water (1:2, 1.8 ml) to which was subsequently added dropwise an aqueous solution (0.5 ml) of potassium cyanate (81.1 mg, 0.90 mmol) After 3 hours of stirring at room temperature, the reaction solution was mixed with saturated sodium bicarbonate aqueous solution, alkanized with 10% sodium hydroxide aqueous solution and then extracted with ethyl acetate. The resulting organic layer was washed with water and saturated brine, and dried on anhydrous sodium sulfate. Thereafter, the solvent was removed by evaporation, and the resulting residue was purified by a silica gel column chromatography (chloroform:methanol=10:1) and recrystallized from ethyl acetate-ether to obtain 125.6 mg (48.4%) of the title compound in a colorless powder form.

Melting point: 123°–128° C.

IR (KBr): 3476, 3352, 1680, 1598, 1526, 1490, 1438, 1410, 1396, 1310, 1264, 1238, 1214, 1182, 1158, 1140, 852, 840 cm$^{-1}$

NMR (CDCl$_3$) δ: 1.77–2.22 (6H, m), 2.60 (2H, t, J=6.4 Hz), 2.92–3.18 (3H, m), 3.69 (3H, s), 4.02 (2H, t, J=6.4 Hz), 4.80 (2H, br-s), 6.64–6.71 (3H, m), 6.98–7.25 (8H, m), 7.95 (2H, dd, J=8.6 Hz, 5.5 Hz)

INVENTIVE EXAMPLE 147

4-(N-Methylacetylamino)-N-{2-[4-(4-fluorobenzoyl) piperidino]ethyl}-N-(4-methoxyphenyl)benzamide 4-Acetylamino-N-{2-[4-(4-fluorobenzoyl)piperidino] ethyl}-N-(4-methoxyphenyl)benzamide (155.0 mg, 0.30 mmol) was dissolved in THF (3.0 ml) to which were subsequently added 60% sodium hydride (28.0 mg, 0.70 mmol) and methyl iodide (0.060 ml, 1.00 mmol) at room temperature, followed by 2 hours of stirring. The reaction solution was mixed with saturated ammonium chloride aqueous solution and extracted with ethyl acetate. The resulting organic layer was washed with water and saturated brine, and dried on anhydrous sodium sulfate. Thereafter, the solvent was removed by evaporation, and the resulting residue was recrystallized from methanol-ether to obtain 128.0 mg (80.4%) of the title compound in a colorless powder form.

IR (KBr): 2931, 1680, 1666, 1636, 1598, 1510, 1242, 1029, 960, 601 cm$^{-1}$

NMR (CDCl$_3$) δ: 1.78 (3H, s), 1.78–1.95 (4H, m), 2.04–2.31 (2H, m), 2.61 (2H, t, J=6.6 Hz), 2.95–3.30 (3H, m), 3.18 (3H, s), 3.74 (3H, s), 4.02 (2H, t, J=6.6 Hz), 6.74 (2H, d, J=8.8 Hz), 6.93–7.36 (8H, m), 7.96 (2H, dd, J=8.8 Hz, 5.3 Hz)

INVENTIVE EXAMPLE 148

4-(N-Methylacetylamino)-N-{2-[4-(4-fluorobenzoyl) piperidino]ethyl}-N-(3-methoxyphenyl)benzamide Using 4-Acetylamino-N-{2-[4-(4-fluorobenzoyl) piperidino]ethyl}-N-( 3-methoxyphenyl)benzamide (310.0 mg, 0.60 mmol), the procedure of inventive Example 147 was repeated to obtain 89.2 mg (28.0%) of the title compound in a colorless amorphous form.

IR (neat): 2940, 1654, 1600, 1376, 1138, 970, 749, 699 cm$^{-1}$

NMR (CDCl$_3$) δ: 1.71–1.87 (4H, m), 1.78 (3H, s), 2.06–2.43 (2H, m), 2.63 (2H, t, J=6.6 Hz), 2.96–3.25 (3H, m), 3.69 (3H, s), 4.06 (2H, t, J=6.6 Hz), 6.64–6.72 (4H, m), 6.63–6.78 (4H, m), 6.94–7.40 (6H, m), 7.97 (2H, dd, J=8.7 Hz, 5.6 Hz)

INVENTIVE EXAMPLE 149

4-(Pyrrole-1-yl)-N-{2-[4-(4-fluorobenzoyl) piperidino]ethyl}-N-(4-methoxyphenyl)benzamide 4-Amino-N-{2-[4-(4-fluorobenzoyl)piperidino]ethyl}-N-(4-methoxyphenyl)benzamide (237.0 mg, 0.50 mmol) was dissolved in acetic acid (5.0 ml), and the solution was mixed with 2,5-dimethoxytetrahydrofuran (0.065 ml, 0.50 mmol) and heated for 1 hour under reflux. After cooling, acetic acid was distilled off under a reduced pressure, the residue was dissolved in ethyl acetate, and the organic layer was washed with water and saturated brine, and dried on anhydrous sodium sulfate. Thereafter, the solvent was distilled off under a reduced pressure, and the resulting residue was purified by a silica gel column chromatography (hexane:ethyl acetate=1:4) to obtain 217.0 mg (82.7%) of the title compound in a colorless amorphous form.

IR (KBr): 2943, 1678, 1638, 1510, 1330, 1246, 815, 724, 602 cm$^{-1}$

NMR (CDCl$_3$) δ: 1.80–2.33 (6H, m), 2.62 (2H, t, J=6.8 Hz), 2.96–3.33 (3H, m), 3.75 (3H, s), 4.02 (2H, t, J=6.8 Hz), 6.30 (2H, t, J=9.0 Hz), 6.72 (2H, dd, J=6.8, 2.2 Hz), 6.99–7.40 (10H, m), 7.96 (2H, dd, J=8.8 Hz, 5.6 Hz)

INVENTIVE EXAMPLE 150

4-(Pyrrole-1-yl)-N-{2-[4-(4-fluorobenzoyl) piperidino]ethyl}-N-(3-methoxyphenyl)benzamide Using 4-amino-N-{2-[4-(4-fluorobenzoyl)piperidino] ethyl}-N-(3-methoxyphenyl)benzamide (238.1 mg, 0.50 mmol) and 2,5-dimethoxytetrahydrofuran (0.066 ml, 0.50 mmol), the procedure of Inventive Example 149 was repeated to obtain 205.0 mg (78.0%) of the title compound in a light brown amorphous form.

IR (KBr): 1674, 1638, 1600, 1488, 1400, 1392, 1326, 1310, 1280, 1266, 1228, 1140, 842, 728 cm$^{-1}$

NMR (CDCl$_3$) δ: 1.69–2.25 (6H, m), 2.64 (2H, t, J=6.6 Hz), 2.97–3.19 (3H, m), 3.70 (3H, s), 4.06 (2H, t, J=6.6 Hz), 6.31 (2H, s), 6.66 (2H, s), 6.73 (1H, s), 7.03–7.43 (9H, m), 7.96 (2H, dd, J=8.4 Hz, 5.5 Hz)

INVENTIVE EXAMPLE 151

4-N-Dimethylamino-N-{2-[4-(4-fluorobenzoyl) piperidino]ethyl}-N-(4-methoxyphenyl)benzamide 4-Amino-N-{2-[4-(4-fluorobenzoyl)piperidino]ethyl}-N-(4-methoxyphenyl)benzamide (143.0 mg, 0.30 mmol) was dissolved in methanol (5.0 ml) to which were subsequently added 37% formaldehyde aqueous solution (1.0 ml) and sodium cyanoborohydride (38.0 mg, 0.60 mmol). The resulting mixture was stirred for 24 hours while adjusting the pH to 5 to 6 with trifluoroacetic acid. The reaction solution was mixed with ethyl acetate, and the organic layer was washed with water and saturated brine, and dried on anhydrous sodium sulfate. Thereafter, the solvent was distilled off under a reduced pressure, and the resulting residue was purified by a silica gel column chromatography (ethyl acetate) to obtain 87.0 mg (61.1%) of the title compound in a colorless amorphous form.

IR (KBr): 2944, 1678, 1600, 1510, 1444, 1246, 974, 836, 602 cm$^{-1}$

NMR (CDCl$_3$) δ: 1.66–2.38 (6H, m), 2.66 (2H, t, J=6.8 Hz), 2.91 (6H, s), 2.97–3.36 (3H, m), 3.77 (3H, s), 4.00 (2H, t, J=6.8 Hz), 6.42 (2H, d, J=9.0 Hz), 6.76 (2H, d, J=9.0 Hz), 7.00–7.22 (6H, m), 7.96 (2H, dd, J=8.8 Hz, 5.5 Hz)

INVENTIVE EXAMPLE 152

4-N-Dimethylamino-N-{2-[4-(4-fluorobenzoyl) piperidino]ethyl}-N-(3-methoxyphenyl)benzamide Using 4-amino-N-{2-[4-(4-fluorobenzoyl)piperidino] ethyl}-N-(3-methoxyphenyl)benzamide (238.9 mg, 0.50 mmol), the procedure of Inventive Example 151 was repeated to obtain 92.3 mg (36.7%) of the title compound in a light yellow amorphous form.

IR (KBr): 1680, 1634, 1600, 1524, 1486, 1448, 1364, 1310, 1280, 1230, 1198, 1158, 1136, 1040, 974, 824, 760, 700 cm$^{-1}$

NMR (CDCl$_3$) δ: 1.78–2.17 (6H, m), 2.65 (2H, t, J=6.8 Hz), 2.89 (6H, s), 2.89–3.08 (3H, m), 3.70 (3H, s), 4.02 (2H, t, J=6.8 Hz), 6.40 (2H, d, J=8.8 Hz), 6.71 (3H, br-s), 7.11–7.30 (5H, m), 7.96 (2H, dd, J=8.6 Hz, 5.7 Hz)

INVENTIVE EXAMPLE 153

4-Acetylamino-N-{2-[4-(4-fluorobenzoyl) piperidino]ethyl}-N-(3-hydroxyphenyl)benzamide 4-Acetylamino-N-{2-[4-(4-fluorobenzoyl)piperidino] ethyl}-N-(3-methoxyphenyl)benzamide (50.0 mg, 0.10 mmol) was dissolved in methylene chloride (3.0 ml) to which was subsequently added a methylene chloride solution (1 ml) of boron tribromide (0.018 ml, 0.19 mmol) at 0° C. After 12 hours of stirring at 0° C. to room temperature, the reaction solution was mixed with saturated sodium bicarbonate aqueous solution and extracted with ethyl acetate. The resulting organic layer was washed with saturated sodium bicarbonate aqueous solution and saturated brine, and dried on anhydrous sodium sulfate. Thereafter, the solvent was distilled off under a reduced pressure, and the resulting residue was purified by a silica gel column chromatography (ethyl acetate-chloroform:methanol=10:1) to obtain 37.3 mg (76.7%) of the title compound in a light yellow amorphous form.

IR (KBr): 3310, 3124, 2944, 1680, 1602, 1533, 1488, 1446, 1410, 1377, 1314, 1263, 1236, 1209, 1158, 909, 852, 729, 699, 648 cm$^{-1}$

NMR (CDCl$_3$) δ: 1.60–2.00 (4H, m), 2.00–2.40 (2H, m), 2.07 (3H, s), 2.63 (2H, t, J=6.0 Hz), 2.83–3.40 (3H, m), 4.01 (2H, t, J=6.0 Hz), 6.40–6.70 (3H, m), 6.85–7.40 (7H, m), 7.80–8.03 (2H, m)

INVENTIVE EXAMPLE 154

4-Acetylamino-N-{2-[4-(4-fluorobenzoyl) piperidino]ethyl}-N-(4-hydroxyphenyl)benzamide Using 4-acetylamino-N-{2-[4-(4-fluorobenzoyl) piperidino]ethyl}-N-(4-methoxyphenyl)benzamide (280.7 mg, 0.54 mmol), the procedure of Inventive Example 153 was repeated to obtain 215.0 mg (78.7%) of the title compound in a colorless powder form.

Melting point: 133°–137° C.

IR (KBr): 3328, 3010, 1689, 1617, 1593, 1515, 1479, 1452, 1413, 1371, 1314, 1278, 1248, 1236, 1206, 1185, 1161, 1101, 969, 852, 840, 828, 759, 669, 600 cm$^{-1}$

NMR (CDCl$_3$) δ: 1.56–1.93 (4H, m), 1.97–2.40 (2H, m), 2.10 (3H, s), 2.63 (2H, t, J=7.0 Hz), 2.75–3.40 (3H, m), 3.99 (2H, t, J=7.0 Hz), 6.65 (2H, d, J=8.8 Hz), 6.90 (2H, d, J=8.8 Hz), 6.97–7.40 (4H, m), 7.80–8.03 (2H, m)

INVENTIVE EXAMPLE 155

4-Formylamino-N-{2-[4-(4-fluorobenzoyl) piperidino]ethyl}-N-(3-pyridyl)benzamide Formic acid (0.37 ml, 9.61 mmol) was mixed with acetic anhydride (0.74ml, 7.84 mmol) at 0° C. After 2 hours of stirring at 60° C., the reaction solution was cooled to room temperature to which was subsequently added THF (3.0 ml), followed by the addition of 4-amino-N-{2-[4-(4-fluorobenzoly) piperidino]ethyl}-N-(3-pyridyl)benzamide (1.34 g, 3.00 mmol) at 0° C. The resulting reaction mixture was stirred for 1 hour at the same temperature, added saturated sodium bicarbonate aqueous solution and extracted with chloroform. The resulting organic layer was washed with saturated sodium chloride aqueous solution and water in that order, and dried on anhydrous magnesium sulfate. Thereafter, the solvent was removed by evaporation, and the resulting residue was purified by a silica gel column chromatography (chloroform:methanol=20:1) to obtain 1.40 g (98.6%) of the title compound in a colorless powder form.

Melting point: 147°–148° C.

IR (KBr): 1680, 1642, 1598, 1528, 1480, 1426, 1408, 1376, 1306, 1262, 1224, 1204, 1178, 1156, 1140, 848, 754, 712 cm$^{-1}$

NMR (CDCl$_3$) δ: 1.68–1.94 (4H, m), 2.03–2.26 (2H, m), 2.62 (2H, t, J=6.4 Hz), 2.90–3.18 (3H, m), 4.05 (2H, t, J=6.4 Hz), 6.81–7.54 (8H, m), 7.95 (2H, dd, J=8.6 Hz, 5.5 Hz), 8.33–8.40 (3H, m)

INVENTIVE EXAMPLE 156

4-Valerylamino-N-{2-[4-(4-fluorobenzoyl) piperidino]ethyl}-N-(3-pyridyl)benzamide 4-Amino-N-{2-[4-(4-fluorobenzoly)piperidino]ethyl}-N-(3-pyridyl)benzamide (177.2 mg, 0.40 mmol) was dissolved in dichloromethane (3.0 ml) to which were subsequently added valeryl chloride (0.06 ml, 0.48 mmol) and pyridine (0.04 ml, 0.49 mmol) at 0° C. After 2 days of stirring at room temperature, the reaction solution was mixed with 4-DMAP (a catalytically effective amount), followed by additional one day of stirring at room temperature, and then mixed with saturated sodium bicarbonate aqueous solution and extracted with dichloromethane. The resulting organic layer was washed with saturated sodium chloride aqueous solution and water in that order, and dried on anhydrous sodium sulfate. Thereafter, the solvent was removed by evaporation, and the resulting residue was purified by a silica gel column chromatography (chloroform:methanol=20:1) to obtain 178.8 mg (84.2%) of the title compound in a light brown amorphous powder form.

IR (KBr): 2956, 1728, 1696, 1666, 1650, 1598, 1382, 1306, 1286, 1226, 1186, 1170, 1136, 1112, 1096, 714 cm$^{-1}$

NMR (CDCl$_3$) δ: 0.78–0.98 (3H, m), 1.07–1.63 (4H, m), 1.77–1.92 (4H, m), 2.03–2.50 (6H, m), 2.62 (2H, t, J=6.2 Hz), 2.90–3.02 (3H, m), 4.07 (2H, t, J=6.2 Hz), 6.95 (2H, d, J=8.4 Hz), 7.03–7.40 (6H, m), 7.95 (2H, dd, J=8.6 Hz, 5.5 Hz), 8.35–8.45 (2H, m)

INVENTIVE EXAMPLE 157

4-Methylamino-N-{2-[4-(4-fluorobenzoyl) piperidino]ethyl}-N-(3-pyridyl)benzamide 4-Formylamino-N-{2-[4-(4-fluorobenzoly)piperidino] ethyl}-N-(3-pyridyl)benzamide (304.7 mg, 0.64 mmol) was dissolved in DMF (4.0 ml) to which was subsequently added sodium hydride (30.1 mg, 0.75 mmol) at 0° C. After 1 hour of stirring at same temperature, the reaction solution was mixed with methyl iodide (44.0 μl, 0.71 mmol), followed by additional 2 hour of stirring at 0° C., and then diluted in water and extracted with ethyl acetate. The resulting organic layer was washed with saturated sodium chloride aqueous solution and water in that order, and dried on anhydrous magnesium sulfate. Thereafter, the solvent was removed by evaporation, and the resulting residue was purified by a silica gel column chromatography (chloroform:methanol= 20:1) to obtain 248.5 mg (79.5%) of 4-(N-formylmethylamino)-N-{2-[4-(4-fluorobenzoly)piperidino] ethyl}-N-(3-pyridyl)benzamide in a light yellow amorphous powder form.

IR (KBr): 1680, 1642, 1600, 1508, 1480, 1424, 1410, 1376, 1336, 1306, 1264, 1226, 1204, 1156, 1140, 1112, 974, 850, 760, 710 cm$^{-1}$

NMR (CDCl$_3$) δ: 1.77–1.86 (4H, m), 2.04–2.20 (2H, m), 2.63 (2H, t, J=6.4 Hz), 2.90–3.07 (3H, m), 3.24 (3H, s), 4.07 (2H, t, J=6.4 Hz), 6.98 (2H, d, J=8.6 Hz), 7.13–7.36 (5H, m), 7.44 (1H, d, J=8.1 Hz), 7.95 (2H, dd, J=8.6 Hz, 5.5 Hz), 8.34–8.46 (3H, m)

4-(N-formylmethylamino)-N-{2-[4-(4-fluorobenzoly) piperidino]ethyl}-N-(3-pyridyl)benzamide (241.9 mg, 0.50 mmol) was dissolved in 5% hydrochloric acid methanol solution (10 ml) at 0° C. After 4 hours of stirring at room temperature, the reaction solution was mixed with saturated sodium bicarbonate aqueous solution and extracted with chloroform. The resulting organic layer was washed with saturated sodium chloride aqueous solution and water in that order, and dried on anhydrous sodium sulfate. Thereafter, the solvent was removed by evaporation, and the resulting residue was purified by a silica gel column chromatography (chloroform:methanol=20:1) to obtain 220.1 mg (95.6%) of the title compound in a light yellow amorphous powder form.

IR (KBr): 1678, 1636, 1606, 1372, 1334, 1300, 1226, 1204, 1182, 1172, 1156, 1140, 974, 830, 760 cm$^{-1}$

NMR (CDCl$_3$) δ: 1.66–1.86 (4H, m), 2.03–2.26 (2H, m), 2.64 (2H, t, J=6.6 Hz), 2.77 (3H, s), 2.91–3.16 (3H, m), 3.96 (1H, br-s), 4.03 (2H, t, J=6.6 Hz), 6.32 (2H, d, J=8.6 Hz), 7.03–7.26 (5H, m), 7.49 (1H, d, J=8.1 Hz), 7.95 (2H, dd, J=8.8 Hz, 5.5 Hz), 8.33–8.41 (2H, m)

INVENTIVE EXAMPLE 158

4-Dimethylamino-N-{2-[4-(4-fluorobenzoyl) piperidino]ethyl}-N-(3-pyridyl)benzamide 4-Amino-N-{2-[4-(4-fluorobenzoly)piperidino]ethyl}-N-(3-pyridyl)benzamide (360.7 mg, 0.81 mmol) was dissolved in methanol (7.0 ml) to which was subsequently added 37% formaldehyde aqueous solution/3.2 ml), and roughly adjusted to pH 5 with trifluoroacetic acid while stirring at room temperature, and then added sodium cyanoborohydride (107.0 mg, 1.62 mmol). After 15 hours of stirring at room temperature, the reaction solution was mixed with 10% sodium hydroxide aqueous solution and extracted with ethyl acetate. The resulting organic layer was washed with saturated sodium chloride aqueous solution and water in that order, and dried on anhydrous magnesium sulfate. Thereafter, the solvent was removed by evaporation, and the resulting residue was purified by a silica gel column chromatography (chloroform:methanol=20:1) and recrystallization (ethyl acetate -ether) to obtain 233.8 mg (60.8%) of the title compound in a colorless powder form.

Melting point: 147°–152° C.

IR (KBr): 1666, 1638, 1620, 1600, 1580, 1478, 1426, 1372, 1326, 1302, 1232, 1200, 1168, 1142, 1114, 976, 812, 758 cm$^{-1}$

NMR (CDCl$_3$) δ: 1.66–1.85 (4H, m), 2.04–2.31 (2H, m), 2.65 (2H, t, J=6.6 Hz), 2.91 (6H, s), 3.00–3.97 (3H, m), 4.11 (2H, t, J=6.6 Hz), 6.42 (2H, d, J=9.0 Hz), 7.02–7.22 (5H, m), 7.48 (1H, d, J=8.1 Hz), 7.95 (2H, dd, J=8.8 Hz, 5.5 Hz), 8.33–8.39 (2H, m)

INVENTIVE EXAMPLE 159

4-Methanesulfonylamino-N-{2-[4-(4-fluorobenzoyl) piperidino]ethyl}-N-(3-pyridyl)benzamide 4-Amino-N-{2-[4-(4-fluorobenzoly)piperidino]ethyl}-N-(3-pyridyl)benzamide (197.8 mg, 0.44 mmol) was dissolved in dichloromethane (3.0 ml) to which were subsequently added methanesulfonic acid chloride (41.5 μl, 0.53 mmol), pyridine (42.0 μl, 0.53 mmol) and 4-DMAP (a catalytically effective amount) in that order at 0° C. After 1 hour of stirring at 0° C. and additional 14 hours of stirring at room temperature, the reaction solution was mixed with saturated sodium bicarbonate aqueous solution and extracted with chloroform. The resulting organic layer was washed with saturated sodium chloride aqueous solution and water in that order, and dried on anhydrous sodium sulfate. Thereafter, the solvent was removed by evaporation, and the resulting residue was purified by a silica gel column chromatography (chloroform:methanol=20:1) to obtain 232.0 mg (100%) of the title compound in a light yellow amorphous powder form.

IR (KBr): 2944, 1680, 1644, 1598, 1510, 1480, 1446, 1426, 1378, 1336, 1304, 1264, 1226, 1206, 1154, 974, 850, 758, 516 cm$^{-1}$

NMR (CDCl$_3$) δ: 1.54–1.94 (4H, m), 2.04–2.26 (2H, m), 2.63 (2H, t, J=6.2 Hz), 2.95 (3H, s), 3.02–3.18 (3H, m), 4.06 (2H, t, J=6.2 Hz), 6.94–7.29 (7H, m), 7.54 (1H, d, J=8.1 Hz), 7.95 (2H, dd, J=8.6 Hz, 5.5 Hz), 8.31–8.42 (2H, m)

INVENTIVE EXAMPLE 160

4-Ethylamino-N-{2-[4-(4-fluorobenzoyl)piperidino] ethyl}-N-(3-pyridyl)benzamide

Using 4-formylamino-N-{2-[4-(4-fluorobenzoly) piperidino]ethyl}-N-(3-pyridyl)benzamide (310.2 mg, 0.65 mmol), ethyl iodide (0.13 ml, 1.51 mmol) and sodium hydride (32.7 mg, 0.82 mmol), the procedure of Inventive Example 157 was repeated and purified by recrystallization (ethyl acetate-ether) to obtain 301.0 mg (92.1%) of 4-(N-formyllethylamino)-N-{2-[4-(4-fluorobenzoly)piperidino] ethyl}-N-(3-pyridyl)benzamide in colorless powder form.

Melting point: 140°–143° C.

IR (KBr): 1676, 1648, 1598, 1478, 1424, 1378, 1350, 1318, 1300, 1288, 1254, 1224, 1208, 1142, 1114, 854 cm$^{-1}$

NMR (CDCl$_3$) δ: 1.10 (3H, t, J=7.0 Hz), 1.76–1.96 (4H, m), 2.04–2.25 (2H, m), 2.63 (2H, t, J=6.2 Hz), 2.91–3.12 (3H, m), 3.80 (2H, q, J=7.0 Hz), 4.07 (2H, t, J=6.2 Hz), 6.98 (2H, d, J=8.8 Hz), 7.13–7.37 (5H, m), 7.47–7.51 (1H, m), 7.95 (2H, dd, J=8.6 Hz, 5.5 Hz), 8.38–8.43 (3H, m)

Using 4-(N-formylethylamino)-N-{2-[4-(4-fluorobenzoly)piperidino]ethyl}-N-(3-pyridyl)benzamide (284.8 mg, 0.57 mmol), the procedure of inventive Example 157 was repeated to obtain 222.1 mg (82.1%) of the title compound in light yellow amorphous powder form.

IR (KBr): 1674, 1642, 1602, 1528, 1480, 1422, 1362, 1328, 1298, 1266, 1228, 1202, 1182, 1170, 1156, 1112, 974, 606 cm$^{-1}$

NMR (CDCl$_3$) δ: 1.20 (3H, t, J=7.0 Hz), 1.74–1.93 (4H, m), 2.03–2.26 (2H, m), 2.64 (2H, t, J=6.6 Hz), 2.91–3.21 (5H, m), 4.03 (2H, t, J=6.6 Hz), 6.31 (2H, d, J=8.6 Hz), 7.03–7.26 (5H, m), 7.47 (1H, d, J=8.1 Hz), 7.94 (2H, dd, J=8.6 Hz, 5.5 Hz), 8.37–8.38 (2H, m)

INVENTIVE EXAMPLE 161

4-Ethoxycarbonylamino-N-{2-[4-(4-fluorobenzoyl) piperidino]ethyl}-N-(3-pyridyl)benzamide 4-Amino-N-{2-[4-(4-fluorobenzoly)piperidino]ethyl}-N-(3-pyridyl)benzamide (164.2 mg, 0.37 mmol) was dissolved in dichloromethane (2.0 ml) to which were subsequently added triethylamine (0.31 ml, 2.20 mmol) and ethyl chlorocarbonate (0.11 ml, 1.12 mmol) in that order at 0° C. After 28 hours of stirring at 0° C. to room temperature, the reaction solution was mixed with saturated sodium bicarbonate aqueous solution and extracted with dichloromethane. The resulting organic layer was washed with saturated sodium chloride aqueous solution and water in that order, and dried on anhydrous sodium sulfate. Thereafter, the solvent was removed by evaporation, and the resulting residue was purified by a silica gel column chromatography (chloroform:methanol=20:1) to obtain 123.9 mg (64.6%) of the title compound in a yellow amorphous powder form.

IR (KBr): 1730, 1680, 1642, 1598, 1530, 1480, 1426, 1410, 1376, 1310, 1262, 1224, 1180, 1156, 1140, 1062, 848, 762 cm$^{-1}$

NMR (CDCl$_3$) δ: 1.28 (3H, t, J=7.3 Hz), 1.62–1.85 (4H, m), 2.03–2.26 (2H, m), 2.63 (2H, t, J=6.4 Hz), 2.90–3.17 (3H, m), 4.05 (2H, t, J=6.4 Hz), 4.19 (2H, q, J=7.3 Hz), 6.56 (1H, br-s), 7.08 (2H, d, J=8.6 Hz), 7.21–7.26 (5H, m), 7.48 (1H, d, J=8.8 Hz), 7.95 (2H, dd, J=8.6 Hz, 5.5 Hz), 8.34–8.37 (2H, m)

INVENTIVE EXAMPLE 162

4-Nitro-N-[2-(4-benzoyl-1-piperidinyl)ethyl]-N-(3-pyridyl)benzamide

In an atmosphere of argon, 4-nitro-N-(3-pyridyl)benzamide (973 mg, 4.00 mmol) was dissolved in DMF (10 ml) to which was subsequently added sodium hydride (176 mg, 60%, 4.40 mmol) at room temperature, stirred for 1 hour at 60° C., and added dropwise 1-(2-chloroethyl)-4-benzoylpiperidine (1.38 g, 5.49 mmol) and a catalytically effective amount of a DMF solution (12 ml) of sodium iodide. After 4 hours of stirring at 60° C., the reaction solution was mixed with saturated sodium chloride aqueous solution and extracted with ethyl acetate. The resulting organic layer was washed with saturated sodium chloride aqueous solution and water in that order, and dried on anhydrous sodium sulfate. Thereafter, the solvent was removed by evaporation, and the resulting residue was purified by recrystallization (ethyl acetate-ether) to obtain 439.6 mg (24.0%) of the title compound in a light yellow powder form.

Melting point: 134°–136° C.

IR (KBr): 1680, 1646, 1600, 1520, 1478, 1446, 1376, 1344, 1304, 1176, 1114, 976 cm$^{-1}$

NMR (CDCl$_3$) δ: 1.73–2.03 (4H, m), 2.03–2.39 (2H, m), 2.62 (2H, t, J=6.2 Hz), 2.83–3.15 (2H, m), 3.15–3.50 (1H, m), 4.08 (2H, t, J=6.2 Hz), 7.10–7.73 (7H, m), 7.80–8.17 (2H, m), 8.06 (2H, d, J=8.8 Hz), 8.20–8.50 (2H, m)

INVENTIVE EXAMPLE 163

4-Trifluoroacetylamino-N-{2-[4-(4-fluorobenzoyl)piperidino]ethyl}-N-(3-pyridyl)benzamide 4-Amino-N-{2-[4-(4-fluorobenzoyl)piperidino]ethyl}-N-(3-pyridyl)benzamide (229.3 mg, 0.51 mmol) was dissolved in methylene chloride (2.0 ml) to which were subsequently added pyridine (0.05 ml, 0.62 mmol) and anhydrous trifluoroacetic acid (0.09 ml, 0.64 mmol) at 0° C. After 3 hours of stirring at 0° C. to room temperature, the reaction solution was mixed with saturated sodium bicarbonate aqueous solution and extracted with chloroform. The resulting organic layer was washed with saturated sodium chloride aqueous solution and water in that order, and dried on anhydrous sodium sulfate. Thereafter, the solvent was removed by evaporation, and the resulting residue was purified by silica gel column chromatography (chloroform:methanol=20:1) to obtain 224.8 mg (81.2%) of the title compound in a light yellow powder form.

Melting point: 181°–183° C.

IR (KBr): 1740, 1676, 1658, 1608, 1596, 1412, 1360, 1324, 1288, 1256, 1230, 1204, 1192, 1156, 1142, 1114, 1078, 976 cm$^{-1}$

NMR (CDCl$_3$) δ: 1.76–1.82 (4H, m), 2.04–2.30 (2H, m), 2.62 (2H, t, J=6.4 Hz), 2.89–3.18 (3H, m), 4.06 (2H, t, J=6.4 Hz), 7.08 (2H, d, J=8.8 Hz), 7.22–7.56 (6H, m), 7.95 (2H, dd, J=8.6 Hz, 5.5 Hz), 8.18 (1H, br-s), 8.32–8.41 (2H, m)

INVENTIVE EXAMPLE 164

4-Ureido-N-{2-[4-(4-fluorobenzoyl)piperidino]ethyl}-N-(3-pyridyl)benzamide

4-Amino-N-{2-[4-(4-fluorobenzoly)piperidino]ethyl}-N-(3-pyridyl)benzamide (334.9 mg, 0.75 mmol) was dissolved in acetic acid-water (1:2) mixture solution (2.7 ml) to which was subsequently added dropwise the aqueous solution (1.0 ml) of potassium cyanate (162.2 mg, 1.80 mmol). After 1 day of stirring at room temperature, the reaction solution was mixed with 10% sodium hydroxide aqueous solution and extracted with ethyl acetate. The resulting organic layer was washed with saturated sodium chloride aqueous solution and water in that order, and dried on anhydrous sodium sulfate. Thereafter, the solvent was removed by evaporation, and the resulting residue was purified by recrystallization (methanol-ethyl acetate) to obtain 183.7 mg (50.0%) of the title compound in a colorless powder form.

Melting point: 191°–195° C. (decomposition)

IR (KBr): 3440, 1702, 1682, 1632, 1610, 1596, 1530, 1480, 1444, 1410, 1378, 1334, 1312, 1260, 1230, 1204, 854 cm$^{-1}$

NMR (CDCl$_3$) δ: 1.26–1.90 (4H, m), 2.04–2.30 (2H, m), 2.63 (2H, t, J=6.4 Hz), 2.89–3.19 (3H, m), 4.04 (2H, t, J=6.4 Hz), 7.04–7.23 (7H, m), 7.53 (1H, d, J=8.1 Hz), 7.95 (2H, dd, J=8.6 Hz, 5.5 Hz), 8.32–8.37 (2H, m)

INVENTIVE EXAMPLE 165

4-Benzoylamino-N-{2-[4-(4-fluorobenzoyl)piperidino]ethyl}-N-(3-pyridyl)benzamide 4-Amino-N-{2-[4-(4-fluorobenzoyl)piperidino]ethyl}-N-(3-pyridyl)benzamide (225.3 mg, 0.50 mmol) was dissolved in methylene chloride (2.0 ml) to which were subsequently added pyridine (0.05 ml, 0.62 mmol) and benzoyl chloride (0.09 ml, 0.77 mmol). After 14 hours of stirring at room temperature, the reaction solution was mixed with saturated sodium bicarbonate aqueous solution and extracted with chloroform. The resulting organic layer was washed with saturated sodium chloride aqueous solution and water in that order, and dried on anhydrous sodium sulfate. Thereafter, the solvent was removed by evaporation, and the resulting residue was purified by silica gel column chromatography (chloroform:methanol=20:1) and recrystallization (ethyl acetate-ether) to obtain 196.3 mg (70.6%) of the title compound in a light brown powder form.

Melting point: 162°–166° C.

IR (KBr): 1672, 1634, 1598, 1478, 1402, 1378, 1306, 1244, 1228, 1206, 976, 840, 702 cm$^{-1}$

NMR (CDCl$_3$) δ: 1.66–1.83 (4H, m), 2.04–2.18 (2H, m), 2.64 (2H, t, J=6.2 Hz), 2.91–3.02 (3H, m), 4.06 (2H, t, J=6.2

Hz), 7.03–7.33 (4H, m), 7.46–7.87 (3H, m), 7.95 (2H, dd, J=8.6 Hz, 5.5 Hz), 8.36–8.39 2H, m)

INVENTIVE EXAMPLE 166

4-Benzoylamino-N-[2-(4-benzoylpiperidino)ethyl]-N-(3-pyridyl)benzamide

Using 4-amino-N-[2-(4-benzoylpiperidino)ethyl]-N-(3-pyridyl)benzamide (210.7 mg, 0.49 mmol), benzoyl chloride (0.07 ml, 0.60 mmol) and pyridine (0.05 ml, 0.62 mmol), the procedure of Inventive Example 165 was repeated to obtain 224.3 mg (85.9%) of the title compound in a colorless powder form.

Melting point: 172°–173° C.

IR (KBr): 1672, 1640, 1594, 1580, 1522, 1430, 1402, 1378, 1320, 1302, 1264, 1246, 1190, 976, 700 cm$^{-1}$

NMR (CDCl$_3$) δ: 1.77–1.86 (4H, m), 2.04–2.31 (2H, m), 2.63 (2H, t, J=6.4 Hz), 2.90–3.22 (3H, m), 4.06 (2H, t, J=6.4 Hz), 7.25–7.32 (3H, m), 7.46–7.51 (8H, m), 7.77–7.95 (5H, m), 8.36–8.39 (2H, m)

INVENTIVE EXAMPLE 167

N-{2-[4-{4-Fluorobenzoyl)piperidino]ethyl}-4-(N-hydroxyimino)-N-(2-methoxyphenyl)benzenesulfonamide hydrochloride N-{2-[4-(4-fluorobenzoyl)piperidino]ethyl}-4-(N-hydroxyimino)-N-(2-methoxyphenyl)benzenesulfonamide (65 mg, 0.12 mmol) was dissolved in methylene chloride (2 ml) to which was subsequently added saturated hydrogen chloride/ether solution (1 ml). After 5 minutes of stirring, the solvent was removed by evaporation, and the resulting residue was solidified in ether (5 ml) and collected by filtration to obtain 69 mg (99.8%) of the title compound in a colorless amorphous powder form.

IR (KBr): 3200, 2950, 1678, 1598, 1496, 1348, 1282, 1220, 1158, 974, 760, 728, 602 cm$^{-1}$

NMR (CDCl$_3$—CD$_3$OD) δ: 1.85–2.40 (4H, m), 3.00–3.90 (7H, m), 3.36 (3H, s), 3.96–4.35 (2H, m), 6.80 (1H, d, J=8.5 Hz), 6.90–7.45 (5H, m), 7.60 (4H, s), 7.96 (2H, dd, J=9 Hz, 6 Hz), 8.11 (1H, s)

INVENTIVE EXAMPLE 168

4-Methanesulfonylamino-N-(2-[4-(4-fluorobenzoyl)-piperidino]ethyl}-N-(3-methoxymhenyl)benzamide hydrochloride Using 4-methanesulfonylamino-N-{2-[4-(4-fluorobenzoyl)piperidino]ethyl}-N-(3-methoxyphenyl)benzamide (164.0 mg, 0.30 mmol), the procedure of Inventive Example 167 was repeated to obtain 157.1 mg (88.9%) of the title compound in a colorless powder form.

Melting point: 125°–127° C.

IR (KBr): 1680, 1640, 1598, 1490, 1456, 1440, 1392, 1332, 1284, 1218, 1152, 970 cm$^{-1}$

NMR (CDCl$_3$—CD$_3$OD) δ: 1.90–2.70 (7H, m), 2.93 (3H, s), 3.00–3.90 (4H, m), 3.71 (3H, s), 4.23–4.53 (2H, m), 6.53–6.80 (3H, m), 6.90–7.40 (7H, m), 7.96 (2H, dd, J=9.0 Hz, 6.0 Hz)

INVENTIVE EXAMPLE 169

4-(Pyrrole-1-yl)-N-{2-[4-(4-fluorobenzoyl)piperidino]ethyl}-N-(3-methoxyphenyl)benzamide hydrochloride Using 4-(pyrrole-1-yl)-N-{2-[4-(4-fluorobenzoyl)piperidino]ethyl}-N-(3-methoxyphenyl)benzamide (170.2 mg, 0.32 mmol), the procedure of Inventive Example 167 was repeated to obtain 170.4 mg (94.7%) of the title compound in a brown powder form.

Melting point: 131°–134° C.

IR (KBr): 3416, 1678, 1634, 1598, 1520, 1488, 1476, 1438, 1412, 1390, 1330, 1282, 1234, 1214, 1158, 1068, 844, 698 cm$^{-1}$

NMR (CDCl$_3$—CD$_3$OD) δ: 2.54–2.71 (3H, m), 3.73 (3H, s), 3.17–3.81 (9H, m), 4.45 (4H, t, J=6.6 Hz), 6.73 (1H, s), 6.68–6.77 (3H, m), 7.09–7.48 (10H, m), 7.97 (2H, dd, J=8.6 Hz, 5.3 Hz)

INVENTIVE EXAMPLE 170

4-Ureido-N-{2-[4-(4-fluorobenzoyl)piperidino]ethyl}-N-(3-methoxyphenyl)benzamide hydrochloride Using 4-ureido-N-{2-[4-(4-fluorobenzoyl)piperidino]ethyl}-N-(3-methoxyphenyl)benzamide (107.2 mg, 0.21 mmol), the procedure of Inventive Example 167 was repeated to obtain 119.5 mg (quantitative) of the title compound in a light brown powder form.

Melting point: 146°–149° C.

IR (KBr): 3348, 1680, 1598, 1532, 1488, 1438, 1412, 1318, 1256, 1216, 1180, 1156, 948, 840, 760, 698 cm$^{-1}$

NMR (CDCl$_3$—CD$_3$OD) δ: 2.04–2.41 (6H, m), 3.82 (3H, s), 3.11–3.88 (5H, m), 4.31–4.37 (2H, m), 6.64–6.72 (4H, m), 7.08–7.30 (9H, m), 7.95 (2H, dd, J=8.4 Hz, 5.3 Hz)

INVENTIVE EXAMPLE 171

4-Acetylamino-N-{2-[4-(4-fluorobenzoyl)piperidino]ethyl}-N-(3-methoxyphenyl)benzamide hydrochloride Using 4-acetylamino-N-{2-[4-(4-fluorobenzoyl)piperidino]ethyl}-N-(3-methoxyphenyl)benzamide (360.0 mg, 0.70 mmol), the procedure of Inventive Example 167 was repeated to obtain 342.0 mg (88.5%) of the title compound in a colorless powder form.

Melting point: 138°–145° C.

IR (KBr): 3445, 1676, 1640, 1600, 1316, 1218, 851, 762 cm$^{-1}$

NMR (CDCl$_3$—CD$_3$OD) δ: 2.15 (3H, s), 2.04–3.79 (11H, m), 3.70 (3H, s), 4.22 (2H, t, J=6.8 Hz), 6.65–6.74 (3H, m), 7.03–7.49 (7H, m), 7.94 (2H, dd, J=8.8 Hz, 5.5 Hz)

INVENTIVE EXAMPLE 172

4-Amino-N-{2-[4-(4-fluorobenzoyl)piperidino]ethyl}-N-(3-methoxyphenyl)benzamide hydrochloride Using 4-amino-N-{2-[4-(4-fluorobenzoyl)piperidino]ethyl}-N-(3-methoxyphenyl)benzamide (142.0 mg, 0.30 mmol), the procedure of Inventive Example 167 was repeated to obtain 100.0 mg (60.8%) of the title compound in a colorless powder form.

Melting point: 145°–155° C.

IR (KBr): 3440, 1678, 1600, 1490, 1210, 1158, 844 cm$^{-1}$

NMR (CDCl$_3$—CD$_3$OD) δ: 2.08–3.82 (11H, m), 3.71 (3H, s), 4.31–4.39 (2H, m), 6.70–6.82 (3H, m), 7.08–7.44 (7H, m), 7.95–8.02 (2H, m)

INVENTIVE EXAMPLE 173

4-Dimethylamino-N-{2-[4-(4-fluorobenzoyl)piperidino]ethyl}-N-(3-methoxyphenyl)benzamide hydrochloride Using 4-dimethylamino-N-{2-[4-(4-fluorobenzoyl)piperidino]ethyl}-N-(3-methoxyphenyl)benzamide (83.5 mg, 0.17 mmol), the procedure of Inventive Example 167 was repeated to obtain 87.5 mg (95.3%) of the title compound in a orange powder form.

Melting point: 119°–121° C.

IR (KBr): 3428, 2632, 2552, 2448, 1678, 1642, 1598, 1506, 1490, 1452, 1410, 1320, 1284, 1216, 1180, 1158, 1130, 952, 852, 700 cm$^{-1}$

NMR (CDCl$_3$—CD$_3$OD) δ: 2.51–2.68 (2H, m), 3.11 (6H, s), 3.19–3.42 (6H, m), 3.74 (3H, s), 3.49–3.93 (3H, m), 4.39 (2H, t, J=6.6 Hz), 6.73–6.87 (3H, m), 7.14 (2H, d, J=8.2 Hz), 7.27–7.32 (2H, m), 7.54–7.56 (3H, m), 7.99 (2H, dd, J=8.6 Hz, 5.5 Hz)

INVENTIVE EXAMPLE 174

N-{2-[4-(4-Fluorobenzoyl)piperidino]ethyl}-3-methoxy-N-(2-methoxyphenyl)benzamide oxalate N-{2-[4-(4-fluorobenzoyl)piperidino]ethyl}-3-methoxy-N-(2-methoxyphenyl)benzamide (107 mg, 0.218 mmol) was dissolved in methanol (10 ml) to which was subsequently added oxalic acid (19.7 mg, 0.218 mmol). After 5 minutes of stirring at room temperature, methanol was removed by evaporation, and the resulting residue was solidified in ether (5 ml) and collected by filtration to obtain 100 mg (79.2%) of the title compound in a colorless powder form.

Melting point: 170.5°–174° C.

IR (KBr): 3450, 1680, 1644, 1598, 1504, 1452, 1388, 1226 cm$^{-1}$

NMR (CDCl$_3$) δ: 1.86–2.50 (4H, m), 3.10–3.83 (7H, m), 3.62, 3.71 (each 3H, s), 3.85–4.40 (2H, m), 6.60–7.35 (10H, m), 7.67–8.15 (2H, m)

INVENTIVE EXAMPLE 175

N-{2-[4-(4-Fluorobenzoyl)piperidino]ethyl}-4-methoxy-N-(2-methoxyphenyl)benzenesulfonamide oxalate Using N-{2-[4-(4-fluorobenzoyl)piperidino]ethyl}-4-methoxy-N-(2-methoxyphenyl)benzenesulfonamide (56.7 mg, 0.108 mmol), the procedure of inventive Example 174 was repeated to obtain 59.8 mg (89.9%) of the title compound in a colorless amorphous powder form.

IR (KBr): 3440, 1680, 1596, 1498, 1344, 1260, 1222, 1156, 588, 562 cm$^{-1}$

NMR (CDCl$_3$—CD$_3$OD) δ: 1.90–2.50 (4H, m), 3.10–3.77 (2H, m), 3.40 (3H, s), 3.77–4.10 (2H, m), 3.86 (3H, s), 6.68–7.38 (8H, m), 7.53 (2H, d, J=9 Hz), 7.95 (2H, dd, J=9 Hz, 6 Hz)

INVENTIVE EXAMPLE 176

4-Fluoro-N-(2-[4-(4-fluorobenzoyl)piperidino]ethyl}-N-(2-methoxyphenyl)benzenesulfonamide oxalate Using 4-fluoro-N-(2-[4-(4-fluorobenzoyl)piperidino]ethyl}-N-(2-methoxyphenyl)benzenesulfonamide (81 mg, 0.157 mmol), the procedure of Inventive Example 174 was repeated to obtain 82.3 mg (86.7%) of the title compound in a beige powder form.

Melting point: 155°–165° C.

IR (KBr): 3450, 1682, 1598, 1496, 1460, 1344, 1292, 1224, 1168, 1156, 1118, 836, 586, 556 cm$^{-1}$

NMR (CDCl$_3$—CD$_3$OD) δ: 1.90–2.37 (4H, m), 2.80–3.70 (7H, m), 3.35 (3H, s), 3.75–4.20 (2H, m), 6.66–7.45 (8H, m), 7.60, 7.93 (each 2H, dd, J=9 Hz, 6 Hz)

INVENTIVE EXAMPLE 177

N-{2-[4-(4-Fluorobenzoyl)piperidino]ethyl}-4-methoxymethyl-N-(2-methoxyphenyl)benzamide oxalate Using N-{2-[4-(4-fluorobenzoyl)piperidino]ethyl}-4-methoxymethyl-N-(2-methoxyphenyl)benzamide (128 mg, 0.254 mmol), the procedure of Inventive Example 174 was repeated to obtain 128 mg (84.7%) of the title compound in a colorless powder form.

Melting point: 151°–155° C.

IR (KBr): 1680, 1640, 1598, 1502, 1412, 1388, 1306, 1224, 1158, 752 cm$^{-1}$

NMR (CDCl$_3$) δ: 1.90–2.56 (4H, m), 3.06–3.83 (7H, m), 3.30 (3H, s), 3.70 (3H, s), 3.97–4.45 (2H, m), 4.35 (2H, s), 4.85 (2H, br-s), 6.77 (1H, d, J=8.5 Hz), 6.86 (1H, d, J=6.5 Hz), 6.91–7.40 (8H, m), 7.95 (2H, dd, J=9 Hz, 6 Hz)

INVENTIVE EXAMPLE 178

N-{2-[4-{4-Fluorobenzoyl)piperidino]ethyl}-3-methoxy-N-(2-pyridyl)benzamide oxalate Using N-{2-[4-(4-fluorobenzoyl)piperidino]ethyl}-3-methoxy-N-(2-pyridyl)benzamide (19 mg, 0.0412 mmol), the procedure of Inventive Example 174 was repeated to obtain 22.2 mg (97.7%) of the title compound in a beige amorphous powder form.

IR (KBr): 3450, 1682, 1634, 1596, 1546, 1504, 1454, 1226 cm$^{-1}$

NMR (CDCl$_3$—CD$_3$OD) δ: 1.75–2.32 (4H, m), 2.95–4.00 (7H, m), 3.83 (3H, s), 4.60–5.00 (2H, m), 6.56–7.45 (6H, m), 7.53–8.30 (6H, m)

INVENTIVE EXAMPLE 179

N-{2-[4-(4-Fluorobenzoyl)piperidino]ethyl}-N-(2-methoxyphenyl)-3-nitrobenzenesulfonamide oxalate Using N-(2-[4-(4-fluorobenzoyl)piperidino]ethyl}-N-(2-methoxyphenyl)-3-nitrobenzenesulfonamide (70 mg, 0.129 mmol), the procedure of Inventive Example 174 was repeated to obtain 73.6 mg (90.3%) of the title compound in a colorless amorphous powder form.

IR (KBr): 3450, 1680, 1598, 1532, 1496, 1354, 1220, 1172 cm$^{-1}$

NMR (CDCl$_3$—CD$_3$OD) δ: 1.85–2.60 (4H, m), 2.80–3.75 (7H, m), 3.35 (3H, s), 3.82–4.35 (2H, m), 6.67–7.50 (6H, m), 7.54–8.13 (4H, m), 8.27–8.60 (2H, m)

INVENTIVE EXAMPLE 180

N-{2-[4-(4-Fluorobenzoyl)piperidino]ethyl]-4-methoxy-N-(3-methoxyphenyl)benzenesulfonamide oxalate Using N-{2-[4-(4-fluorobenzoyl)piperidino]ethyl]-4-methoxy-N-(3-methoxyphenyl)benzenesulfonamide (87 mg, 0.165 mmol), the procedure of Inventive Example 174 was repeated to obtain 98.3 mg (96.6%) of the title compound in a colorless powder form.

Melting point: 163.5°–167° C.

IR (KBr): 1676, 1598, 1496, 1346, 1308, 1262, 1214, 1158, 1094, 694 cm$^{-1}$

NMR (CDCl$_3$—CD$_3$OD) δ: 1.80–2.35 (4H, m), 2.95–3.50 (5H, m), 3.50–4.17 (4H, m), 3.74, 3.88 (each 3H, s), 6.52–6.73 (2H, m), 6.83–7.40 (6H, m), 7.52 (2H, d, J=9 Hz), 8.04 (2H, dd, J=9 Hz, 6 Hz)

INVENTIVE EXAMPLE 181

N-(2-Cyanophenyl)-N-{2-[4-(4-fluorobenzoyl) piperidino]ethyl]-4-methoxybenzenesulfonamide oxalate Using N-(2-cyanophenyl)-N-{2-[4-(4-fluorobenzoyl) piperidino]ethyl]-4-methoxybenzenesulfonamide (107 mg, 0.205 mmol), the procedure of Inventive Example 174 was repeated to obtain 96 mg (76.6%) of the title compound in a colorless powder form.

Melting point: 167°–173° C.

IR {KBr}: 1678, 1638, 1596, 1496, 1356, 1262, 1218, 1158, 704, 578, 552 cm$^{-1}$

NMR (CD$_3$OD—CDCl$_3$) δ: 1.85–2.30 (4H, m), 2.95–3.75 (8H, m), 3.76–4.14 (1H, m), 3.90 (3H, s), 6.90–7.30 (5H, m), 7.37–7.96 (5H, m), 8.00 (2H, dd, J=9 Hz, 6 Hz)

INVENTIVE EXAMPLE 182

N-{2-[4-(4-Fluorobenzoyl)piperidino]ethyl}-N-(2-trifluoromethyl-phenyl)-4-methoxybenzenesulfonamide oxalate Using N-{2-[4-(4-fluorobenzoyl)piperidino]ethyl}-N-(2-trifluoromethylphenyl)-4-methoxybenzenesulfonamide (46.7 mg, 0.0827 mmol), the procedure of inventive Example 174 was repeated to obtain 49 mg (90.5%) of the title compound in a colorless powder form.

Melting point: 174°–180° C.

IR (KBr): 1680, 1596, 1498, 1356, 1316, 1264, 1224, 1160, 1036 722, 576, 558 cm$^{-1}$

NMR CD$_3$OD—CDCl$_3$) δ: 1.91–2.30 (4H, m), 2.90–3.80 (8H, m), 3.80–4.32 (1H, m), 3.90 (3H, s), 6.79–7.30 (5H, m), 7.40–8.07 (7H, m)

INVENTIVE EXAMPLE 183

N-{2-[4-(4-Fluorobenzoyl)piperidino]ethyl}-N-(2-methoxyphenyl}-3-pyridinesulfonamide oxalate Using N-{2-[4-(4-fluorobenzoyl)piperidino]ethyl}-N-(2-methoxyphenyl)-3-pyridinesulfonamide (55 mg, 0.1105 mmol), the procedure of Inventive Example 174 was repeated to obtain 53.6 mg (82.5%) of the title compound in a creamy-colored powder form.

Melting point: 178°–182° C.

IR (KBr): 1684, 1598, 1498, 1466, 1416, 1338, 1224, 1168, 1118, 956, 782, 698, 594 cm$^{-1}$

NMR (CDCl$_3$—CD$_3$OD) δ: 1.90–2.40 (4H, m), 3.10–3.75 (7H, m), 3.30 (3H, s), 3.83–4.20 (2H, m), 6.65–7.56 (7H, m), 7.78–8.10 (2H, m), 8.60–8.86 (2H, m)

INVENTIVE EXAMPLE 184

3-{[N-[2-[4-(4-Fluorobenzoyl)piperidino]ethyl]-2-methoxyanilino]-sulfonyl}pyridine N-oxide oxalate Using 3-{[N-[2-[4-(4-fluorobenzoyl)piperidino]ethyl]-2-methoxyanilino]sulfonyl}pyridine N-oxide (101 mg, 0.197 mmol, the procedure of Inventive Example 174 was repeated to obtain 114 mg (95.9%) of the title compound in a light orange amorphous powder form.

IR (KBr): 3450, 2940, 2820, 1664, 1628, 1596, 1464, 1428, 1290, 1280, 1212, 1170, 1112, 1048, 1014, 978 cm$^{-1}$

NMR (CDCl$_3$) δ: 1.43–2.30 (7H, m), 2.36–3.39 (5H, m), 3.32 (3H, s), 3.39–3.90 (6H, m), 4.71 (2H, s), 7.12 (2H, dd, J=9 Hz, 9 Hz), 7.38 (4H, s), 7.94 (2H, dd, J=9 Hz, 6 Hz)

INVENTIVE EXAMPLE 185

N-{2-[4-(4-Fluorobenzoyl)piperidino]ethyl}-N-(2-methoxyphenyl)-p-toluenesulfonamide oxalate Using N-(2-[4-(4-fluorobenzoyl)piperidino]ethyl}-N-(2-methoxyphenyl)-p-toluenesulfonamide (41 mg, 0.0803 mmol), the procedure of inventive Example 174 was repeated to obtain 40.5 mg (84.0%) of the title compound in a colorless powder form.

Melting point: 160°–163° C.

IR (KBr): 1682, 1598, 1496, 1336, 1224, 1158, 1118, 954, 658, 558 cm$^{-1}$

NMR (CDCl$_3$) δ: 2.00–2.55 (4H, m), 2.40 (3H, s), 3.00–3.73 (7H, m), 3.32 (3H, s), 3.80–4.20 (2H, m), 6.76 (1H, d, J=8.5 Hz), 6.88–7.56 (7H, m), 7.47 (2H, d, J=8 Hz), 7.93 (2H, dd, J=9 Hz, 6 Hz)

INVENTIVE EXAMPLE 185

N-{2-[4-(4-Fluorobenzoyl)piperidino]ethyl}-N-(2-methoxyphenyl)-4-morpholinomethylbenzamide oxalate Using N-{2-[4-(4-fluorobenzoyl)piperidino]ethyl}-N-(2-methoxyphenyl)-4-morpholinobenzamide (48.3 mg, 0.0863 mmol), the procedure of Inventive Example 174 was repeated to obtain 52 mg (92.7%) of the title compound in a beige amorphous powder form.

IR (KBr): 1678, 1638, 1598, 1502, 1454, 1390, 1280, 1224, 1158, 1116, 864, 756 cm$^{-1}$

NMR (CDCl$_3$—CD$_3$OD) δ: 1.86–2.35 (4H, m), 2.74–4.35 (17H, m), 3.52 (2H, s), 3.70 (3H, s), 5.53–7.40 (10H, m), 7.95 (2H, dd, J=9 Hz, 6 Hz)

INVENTIVE EXAMPLE 187

N-{2-[4-(4-Fluorobenzoyl)piperidino]ethyl}-N-(2-methoxyphenyl)-4-dimethylaminomethylbenzamide oxalate Using N-{2-[4-(4-fluorobenzoyl)piperidino]ethyl}-N-(2-methoxyphenyl)-4-dimethylaminomethylbenzamide (105 mg, 0.203 mmol), the procedure of Inventive Example 174 was repeated to obtain 117 mg (94.8%) of the title compound in a light beige amorphous powder form.

IR (KBr): 1680, 1640, 1598, 1500, 1412, 1316, 1280, 1222 cm$^{-1}$

NMR (CDCl$_3$— DMSO-d$_6$) δ: 1.60–2.16 (4H, m), 2.20–3.11 (6H, m), 2.55 (6H, s), 3.15–4.60 (5H, m), 3.72 (3H, s), 6.55–6.94 (2H, m), 7.00–7.46 (8H, m), 8.00 (2H, dd, J=9 Hz, 6 Hz)

INVENTIVE EXAMPLE 188

N-(2-[4-(4-Fluorobenzoyl)piperidino]ethyl}-4-hydroxymethyl-N-(2-methoxyphenyl) benzenesulfonamide oxalate Using N-{2-[4-(4-fluorobenzoyl)piperidino]ethyl}-4-hydroxymethyl-N-(2-methoxyphenyl)benzenesulfonamide (87 mg, 0.165 mmol), the procedure of Inventive Example 174 was repeated to obtain 90.5 mg (88.9%) of the title compound in a beige amorphous powder form.

IR (KBr): 3350, 2920, 1680, 1638, 1596, 1496, 1344, 1220, 1150 cm$^{-1}$

NMR (CDCl$_3$—CD$_3$OD) δ: 1.85–2.40 (4H, m), 2.90–3.70 (7H, m), 3.37 (3H, s), 3.76–4.14 (2H, m), 4.71

(2H, s), 6.80 (1H, d, J=8.5 Hz), 6.99 (1H, d, J=8.5 Hz), 7.17 (2H, dd, J=9 Hz, 9 Hz), 7.29 (2H, d, J=6 Hz), 7.42 (2H, d, J=8.5 Hz), 7.60 (2H, d, J=8.5 Hz), 7.95 (2H, dd, J=9 Hz, 6 Hz)

INVENTIVE EXAMPLE 189

N-{2-[4-(4-Fluorobenzoyl)piperidino]ethyl}-4-hydroxymethyl-N-(2-methoxyphenyl)benzamide oxalate Using N-{2-[4-(4-fluorobenzoyl)piperidino]ethyl}-4-hydroxymethyl-N-(2-methoxyphenyl)benzamide (128 mg, 0.261 mmol), the procedure of Inventive Example 174 was repeated to obtain 145 mg (95.7%) of the title compound in a light beige amorphous powder form.

IR (KBr): 3400, 1680, 1640, 1598, 1502, 1440, 1412, 1280, 1222, 1158, 1020, 954 cm$^{-1}$

NMR (CDCl$_3$—CD$_3$OD) δ: 1.95–2.35 (4H, m), 3.08–3.83 (7H, m), 3.70 (3H, s), 3.95–4.33 (2H, m), 4.56 (2H, s), 6.77 (1H, d, J=8 Hz), 6.85 (1H, d, J=7 Hz), 6.93–7.40 (8H, m), 7.95 (2H, dd, J=9 Hz, 6 Hz)

INVENTIVE EXAMPLE 190

N-{2-[4-(4-Fluorobenzoyl)piperidino]ethyl}-3-hydroxymethyl-N-(2-methoxyphenyl)benzamide oxalate Using N-{2-[4-(4-fluorobenzoyl)piperidino]ethyl}-3-hydroxymethyl-N-(2-methoxyphenyl)benzamide (148 mg, 0.302 mmol), the procedure of Inventive Example 174 was repeated to obtain 164 mg (93.5%) of the title compound in a light beige amorphous powder form.

IR (KBr): 3390, 2948, 1680, 1638, 1598, 1502, 1440, 1392, 1280, 1220, 1158, 1022 cm$^{-1}$

NMR (CDCl$_3$) δ: 1.90–2.40 (4H, m), 3.00–3.85 (7H, m), 3.70 (3H, s), 3.95–4.30 (2H, m), 4.50 (2H, s), 6.26 (3H, br-s), 6.75 (1H, d, J=8 Hz), 6.83 (1H, d, J=6.5 Hz), 6.90–7.56 (8H, m), 7.93 (2H, dd, J=9 Hz, 6 Hz)

INVENTIVE EXAMPLE 191

N-{2-[4-(4-Fluorobenzoyl)piperidino]ethyl}-N-(2-methoxyphenyl)-4-dimethylaminomethylbenzenesulfonamide oxalate Using N-{2-[4-(4-fluorobenzoyl)piperidino]ethyl}-N-(2-methoxyphenyl)-4-dimethylaminomethylbenzenesulfonamide (33.5 mg, 0.0605 mmol), the procedure of Inventive Example 174 was repeated to obtain 35 mg (89.9%) of the title compound in a colorless amorphous powder form.

IR (KBr): 1680, 1599, 1497, 1341, 1220, 1158, 759, 591 cm$^{-1}$

NMR (CDCl$_3$—CD$_3$OD) δ: 1.63–2.35 (4H, m), 2.20 (6H, s), 2.40–3.59 (8H, m), 3.43 (3H, s), 3.65–4.15 (3H, m), 6.70–7.43 (7H, m), 7.45–7.80 3H, m), 7.95 (2H, dd, J=9 Hz, 6 Hz)

INVENTIVE EXAMPLE 192

N-(2-Methoxyphenyl)-N-{2-[4-(4-dimethylaminobenzoyl)piperidino]ethyl}-4-dimethylaminomethylbenzenesulfonamide oxalate Using N-(2-methoxyphenyl)-N-{2-[4-(4-dimethylaminobenzoyl)piperidino]ethyl}-4-dimethylaminomethylbenzenesulfonamide (47.5 mg, 0.0812 mmol), the procedure of Inventive Example 174 was repeated to obtain 51 mg (92.9%) of the title compound in a creamy-colored amorphous powder form.

IR (KBr): 1596, 1494, 1342, 1158, 944, 754, 588 cm$^{-1}$

NMR (CDCl$_3$—CD$_3$OD) δ: 1.70–2.15 (4H, m), 2.27 (6H, m), 2.52 (4H, s), 2.70–3.57 (4H, m), 3.05 (6H, s), 3.42 (3H, s), 3.70–4.10 (3H, m), 6.65 (2H, d, J=9 Hz), 6.80 (1H, d, J=8 Hz), 6.96 (1H, d, J=8 Hz), 7.10–7.36 (2H, m), 7.36–8.00 (4H, m), 7.81 (2H, d, J=9 Hz)

INVENTIVE EXAMPLE 193

4-Carbamoyl-N-{2-[4-(4-fluorobenzoyl)piperidino]ethyl}-N-(2-methoxyphenyl)benzenesulfonamide oxalate Using 4-carbamoyl-N-{2-[4-(4-fluorobenzoyl)piperidino]ethyl}-N-(2-methoxyphenyl)benzenesulfonamide (32 mg, 0.0593 mmol), the procedure of inventive Example 174 was repeated to obtain 33 mg (88.4%) of the title compound in a beige amorphous powder form.

IR (KBr): 3460, 1678, 1598, 1496, 1408, 1348, 1282, 1220, 1166, 1118, 708, 600 cm$^{-1}$

NMR (CDCl$_3$—CD$_3$OD) δ: 1.90–2.40 (4H, m), 2.90–3.75 (10H, m), 3.80–4.20 (2H, m), 6.84 (2H, d, J=9 Hz), 6.99–7.48 (4H, m), 7.55–7.77 (2H, m), 7.79–8.20 (4H, m)

INVENTIVE EXAMPLE 194

N-{2-[4-(4-Fluorobenzoyl)piperidino]ethyl}-N-(2-methoxyphenyl)-4-succinimidomethylbenzamide oxalate Using N-{2-[4-(4-fluorobenzoyl)piperidino]ethyl}-N-(2-methoxyphenyl)-4-succinimidomethylbenzamide (42 mg, 0.0735 mmol), the procedure of inventive Example 174 was repeated to obtain 33 mg (67.9%) of the title compound in a beige amorphous powder form.

IR (KBr): 3472, 2944, 1704, 1644, 1599, 1503, 1401, 1227, 1164 cm$^{-1}$

NMR (CDCl$_3$—CD$_3$OD) δ: 2.00–2.46 (6H, m), 2.66 (4H, s), 3.20–3.60 (5H, m), 3.68 (3H, s), 4.00–4.23 (2H, m), 4.52 (2H, s), 6.76 (1H, d, J=8 Hz), 6.88 (1H, d, J=7 Hz), 7.00–7.31 (8H, m), 7.92 (2H, dd, J=9 Hz, 6 Hz)

INVENTIVE EXAMPLE 195

4-Aminomethyl-N-{2-[4-(4-fluorobenzoyl)piperidino]ethyl}-N-(2-methoxyphenyl)benzenesulfonamide oxalate Using 4-aminomethyl-N-{2-[4-(4-fluorobenzoyl)piperidino]ethyl}-N-(2-methoxyphenyl)benzenesulfonamide (47 mg, 0.0894 mmol), the procedure of Inventive Example 174 was repeated to obtain 52 mg (94.5%) of the title compound in a colorless amorphous powder form.

IR (KBr): 2940, 1678, 1598, 1496, 1342, 1282, 1218, 1158, 760, 586 cm$^{-1}$

NMR (CDCl$_3$) δ: 1.40–2.25 (4H, m), 2.25–2.89 (4H, m), 2.90–3.55 (2H, m), 3.29 (3H, s), 3.56–5.40 (9H, m), 6.53–6.92 (2H, m), 6.92–7.34 (4H, m), 7.36–7.71 (4H, m), 7.73–8.10 (2H, m)

INVENTIVE EXAMPLE 196

4-Aminomethyl-N-{2-[4-(4-fluorobenzoyl)piperidino]ethyl}-N-(2-methoxyphenyl)benzamide oxalate Using 4-aminomethyl-N-{2-[4-(4-fluorobenzoyl)piperidino]-ethyl}-N-(2-methoxyphenyl)benzamide (32 mg, 0.0654 mmol), the procedure of Inventive Example 174 was repeated to obtain 33 mg (87.1%) of the title compound in a beige amorphous powder form.

IR (KBr): 3420, 2948, 1598, 1502, 1412, 1310, 1224, 1158, 758 cm$^{-1}$

NMR (CDCl$_3$) δ: 1.50–2.13 (4H, m), 2.13–4.50 (11H, m), 3.56 (3H, s), 6.40–6.82 (2H, m), 6.82–7.70 (8H, m), 7.72–8.20 (2H, m)

INVENTIVE EXAMPLE 197

4-(Acetylamino)methyl-N-{2-[4-(4-fluorobenzoyl)-piperidino]ethyl}-N-(2-methoxyphenyl)benzamide oxalate Using 4-(acetylamino)methyl-N-{2-[4-(4-fluorobenzoyl)piperidino]ethyl}-N-(2-methoxyphenyl)benzamide (58 mg, 0.109 mmol), the procedure of inventive Example 174 was repeated to obtain 40 mg (59.0%) of the title compound in a colorless powder form.

Melting point: 159°–161° C.

IR (KBr): 3400, 1728, 1680, 1626, 1599, 1563, 1503, 1413, 1278, 1224 cm$^{-1}$

NMR (CDCl$_3$—CD$_3$OD) δ: 1.83–2.46 (4H, m), 1.99 (3H, s), 2.52–2.75 (1H, m), 3.15–4.80 (6H, m), 3.71 (3H, s), 3.90–4.40 (2H, m), 4.30 (2H, s), 6.62–7.38 (10H, m), 7.83–8.05 (2H, m)

INVENTIVE EXAMPLE 198

4-(Trifluoroacetylamino)methyl-N-{2-[4-(4-fluorobenzoyl)piperidino]ethyl}-N-(2-methoxyphenyl)benzamide oxalate Using 4-(trifluoroacetylamino)methyl-N-(2-[4-(4-fluorobenzoyl)piperidino]ethyl}-N-(2-methoxyphenyl)benzamide (48 mg, 0.0820 mmol), the procedure of Inventive Example 174 was repeated to obtain 37 mg (66.8%) of the title compound in a colorless powder form.

Melting point: 107°–109° C.

IR (KBr): 3406, 3064, 2944, 1719, 1680, 1641, 1599, 1503, 1221, 1179, 1158 cm$^{-1}$

NMR (CDCl$_3$) δ: 1.90–2.40 (4H, m), 3.10–3.80 (7H, m), 3.70 (3H, s), 3.95–4.28 (2H, m), 4.42 (2H, d, J=6 Hz), 6.45–7.60 (13H, m), 7.91 (2H, dd, J=9 Hz, 6 Hz)

INVENTIVE EXAMPLE 199

N-{2-[4-(4-Fluorobenzoyl)piperidino]ethyl}-4-(methanesulfonylamino)methyl-N-(2-methoxyphenyl)benzamide oxalate Using N-{2-[4-(4-fluorobenzoyl)piperidino]ethyl}-4-(methanesulfonylamino)methyl-N-(2-methoxyphenyl)benzamide (40 mg, 0.0705 mmol), the procedure of Inventive Example 174 was repeated to obtain 40 mg (86.3%) of the title compound in a colorless powder form.

Melting point: 89°–92° C.

IR (KBr): 2926, 1722, 1677, 1641, 1599, 1503, 1440, 1410, 1320, 1278, 1221 cm$^{-1}$

NMR (CDCl$_3$—CD$_3$OD) δ: 1.80–2.55 (5H, m), 2.75 (3H, s), 3.10–3.85 (6H, m), 3.72 (3H, s), 3.97–4.40 (2H, m), 4.18 (2H, s), 6.76 (1H, d, J=8 Hz), 6.92 (1H, d, J=8 Hz), 7.00–7.42 (8H, m), 7.94 (2H, dd, J=9 Hz, 6 Hz)

INVENTIVE EXAMPLE 200

4-(Ethoxycarbonylamino)methyl-N-{2-[4-(4-fluorobenzoyl)piperidino]ethyl}-N-(2-methoxyphenyl)benzamide oxalate Using 4-(ethoxycarbonylamino)methyl-N-{2-[4-(4-fluorobenzoyl)piperidino]ethyl}-N-(2-methoxyphenyl) benzamide (50 mg, 0.0890 mmol), the procedure of Inventive Example 174 was repeated to obtain 47 mg (81.0%) of the title compound in a colorless powder form.

Melting point: 118°–120° C.

IR (KBr): 2940, 1710, 1682, 1640, 1598, 1502, 1414, 1278, 1226 cm$^{-1}$

NMR (CDCl$_3$) δ: 1.22 (3H, t, J=8 Hz), 1.70–2.50 (8H, m), 3.20–3.75 (4H, m), 3.70 (3H, s), 4.11 (2H, q, J=8 Hz), 4.00–4.30 (1H, m), 4.25 (2H, d, J=6 Hz), 6.70–7.31 (10H, m), 7.91 (2H, dd, J=9 Hz, 6 Hz)

INVENTIVE EXAMPLE 201

N-{2-[4-(4-Fluorobenzoyl)piperidino]ethyl}-N-(2-methoxyphenyl)-4-(methylamino)methylbenzamide oxalate Using N-{2-[4-(4-fluorobenzoyl)piperidino]ethyl}-N-(2-methoxyphenyl)-4-(methylamino)methylbenzamide (119 mg, 0.236 mmol), the procedure of Inventive Example 174 was repeated to obtain 108 mg (77.0%) of the title compound in a colorless powder form.

Melting point: 174°–176° C.

IR (KBr): 3454, 3010, 2944, 2806, 1674, 1644, 1596, 1503, 1299, 1278 cm$^{-1}$

NMR (CDCl$_3$—CD$_3$OD) δ: 1.70–1.95 (4H, m), 2.16–2.80 (4H, m), 2.40 (3H, s), 2.85–3.42 (3H, m), 3.70 (3H, s), 3.83 (2H, s), 3.80–4.38 (2H, m), 6.65–6.89 (2H, m), 6.94–7.36 (8H, m), 7.93 (2H, dd, J=9 Hz, 6 Hz)

INVENTIVE EXAMPLE 202

4-Amidino-N-{2-[4-(4-fluorobenzoyl)piperidino]ethyl}-N-(2-methoxyphenyl)benzamide oxalate Using 4-amidino-N-{2-[4-(4-fluorobenzoyl)piperidino]ethyl}-N-(2-methoxyphenyl)benzamide (89 mg, 0.177 mmol), the procedure of Inventive Example 174 was repeated to obtain 91 mg (86.8%) of the title compound in a colorless amorphous powder form.

IR (KBr): 3360, 3064, 1678, 1642, 1598, 1502, 1440, 1410, 1280, 1224, 1158, 720 cm$^{-1}$

NMR (CDCl$_3$—DMSO-d$_6$) δ: 1.90–2.70 (4H, m), 3.00–5.00 (9H, m), 3.76 (3H, s), 6.58–7.00 (2H, m), 7.00–7.84 (9H, m), 7.85–8.25 (2H, m), 9.11 (2H, br-s), 9.53 (2H, br-s)

MS (FAB, m/z): 120, 157, 220, 234, 296, 357, 503 (M$^+$+H)

INVENTIVE EXAMPLE 203

4-(N-Acetylamidino)-N-{2-[4-(4-fluorobenzoyl)piperidino]ethyl}-N-(2-methoxyphenyl)benzamide oxalate Using 4-(N-acetylamidino)-N-{2-[4-(4-fluorobenzoyl)piperidino]ethyl}-N-(2-methoxyphenyl)benzamide (80 mg, 0.147 mmol), the procedure of Inventive Example 174 was repeated to obtain 84 mg (90.0%) of the title compound in a light yellow amorphous powder form.

IR (KBr): 3262, 2938, 1644, 1599, 1503, 1443, 1410, 1278, 1224, 1158, 1119, 1086, 1044, 1020, 954, 852, 756, 720 cm$^{-1}$

NMR (CDCl$_3$) δ: 2.08–2.38 (4H, m), 2.54 (3H, s), 3.05–3.60 (7H, m), 3.70 (3H, s), 4.00–4.33 (2H, m), 6.55–6.93 (2H, m), 6.94–7.29 (5H, m), 7.37 (2H, d, J=7.5 Hz), 7.64 (2H, d, J=7.5 Hz), 7.93 (2H, dd, J=9 Hz, 6 Hz), 8.73 (1H, br-s)

INVENTIVE EXAMPLE 204

N-{2-[4-(4-Fluorobenzoyl)piperidino]ethyl}-4-(N-methanesulfonylamidino)-N-(2-methoxyphenyl) benzamide oxalate Using N-{2-[4-(4-fluorobenzoyl)piperidino]ethyl}-4-(N-methanesulfonylamidino)-N-(2-methoxyphenyl)benzamide (101 mg, 0.174 mmol), the procedure of Inventive Example 174 was repeated to obtain 100 mg (85.7%) of the title compound in a light yellow amorphous powder form.

IR (KBr): 3406, 1641, 1596, 1533, 1503, 1410, 1278, 1224, 1155, 1116, 957, 852, 756, 528 $cm^{-1}$

NMR ($CDCl_3$—$CD_3OD$) δ: 1.80–2.80 (4H, m), 3.03 (3H, s), 3.14–3.90 (7H, m), 3.69 (3H, s), 3.95–4.38 (2H, m), 6.74 (1H, d, J=8 Hz), 6.84 (1H, d, J=7.5 Hz), 6.95–7.45 (6H, m), 7.62 (2H, d, J=8.5 Hz), 7.94 (2H, dd, J=9 Hz, 6 Hz)

INVENTIVE EXAMPLE 205

4-(N-Ethoxycarbonylamidino)-N-{2-[4-(4-fluorobenzoyl)piperidino]-ethyl}-N-(2-methoxyphenyl)benzamide oxalate Using 4-(N-ethoxycarbonylamidino)-N-{2-[4-(4-fluorobenzoyl)-piperidino]ethyl}-N-(2-methoxyphenyl)benzamide (107 mg, 0.186 mmol), the procedure of Inventive Example 174 was repeated to obtain 113 mg (91.4%) of the title compound in a light yellow amorphous powder form.

IR (KBr): 3388, 1623, 1599, 1503, 1461, 1407, 1368, 1299, 1263, 1224, 1158, 1140, 1119, 1020, 954, 855, 756, 720 $cm^{-1}$

NMR ($CDCl_3$—$CD_3OD$) δ: 1.31 (3H, t, J=7 Hz), 1.85–2.34 (4H, m), 2.95–3.90 (7H, m), 3.70 (3H, s), 3.93–4.33 (2H, m), 4.17 (2H, q, J=7 Hz), 6.75 (1H, d, J=8 Hz), 6.84 (1H, d, J=7.5 Hz), 6.96–7.45 (6H, m), 7.66 (2H, d, J=8 Hz), 7.96 (2H, dd, J=9 Hz, 6 Hz)

INVENTIVE EXAMPLE 206

4-Nitro-N-{2-[4-(4-fluorobenzoyl)piperidino]ethyl}-N-(2-methoxyphenyl)benzamide oxalate Using 4-nitro-N-{2-[4-(4-fluorobenzoyl)piperidino]ethyl}-N-(2 -methoxyphenyl)benzamide (120 mg, 0.24 mmol), the procedure of Inventive Example 174 was repeated to obtain 106 mg (75.0%) of the title compound in a light yellow powder form.

Melting point: 201°–203° C.

IR (KBr): 2944, 2608, 1686, 1656, 1599, 1524, 1503, 1410, 1347, 1278, 1227, 1155 $cm^{-1}$

NMR ($CDCl_3$—$CD_3OD$) δ: 1.90–2.24 (4H, m), 3.10–3.65 (7H, m), 3.73 (3H, s), 4.04 (2H, m), 6.70–6.96 (2H, m), 7.00–7.33 (4H, m), 7.45 (2H, d, J=9.0 Hz), 7.84–8.06 (4H, m)

INVENTIVE EXAMPLE 207

4-{[N-[2-[4-(4-Fluorobenzoyl)piperidino]ethyl]-2-methoxyanilino]-carbonyl}pyridine oxalate Using 4-{[N-[2-[4-(4-fluorobenzoyl)piperidino]ethyl}-2-methoxyanilino]carbonyl}pyridine (200 mg, 0.43 mmol), the procedure of inventive Example 174 was repeated to obtain 221 mg (92.5%) of the title compound in a colorless powder form.

Melting point: 98°–100° C.

IR (KBr): 1678, 1654, 1620, 1598, 1502, 1434, 1412, 1396, 1224 $cm^{-1}$

NMR ($CDCl_3$—$CD_3OD$) δ: 1.85–2.54 (6H, m), 2.86–3.64 (6H, m), 3.70 (3H, s), 3.90–4.22 (1H, m), 6.66–6.94 (2H, m), 7.01–7.22 (6H, m), 7.81–8.04 (2H, m), 8.37 (2H, d, J=6.0 Hz)

INVENTIVE EXAMPLE 208

4-[(S)-2-Aminopropionyl]aminomethyl-N-{2-[4-(4-fluorobenzoyl)piperidino]ethyl}-N-(2-methoxyphenyl)benzamide dioxalate 4-[(S)-2-Aminopropionyl]aminomethyl-N-{2-[4-(4-fluorobenzoyl)piperidino]ethyl}-N-(2-methoxyphenyl) benzamide (84.7 mg, 0.155 mmol) was dissolved in methanol (5 ml) and mixed with oxalic acid (28 mg, 0.311 mmol). After 5 minutes of stirring at room temperature, methanol was removed by evaporation, and the resulting amorphous residue was washed with acetone (5 ml) and collected by filtration to obtain 84 mg (85.1%) of the title compound in a colorless amorphous powder form.

IR (KBr): 3076, 1718, 1682, 1636, 1598, 1502, 1440, 1412, 1278, 1224 $cm^{-1}$

NMR ($CDCl_3$—$CD_3OD$) δ: 1.25–1.55 (3H, m), 2.03–2.30 (4H, m), 3.25–3.90 (9H, m), 3.74 (3H, s), 4.00–4.42 (4H, m), 6.78–7.41 (10H, m), 7.92–8.15 (2H, m)

MS (FAB, m/z): 220, 354, 561 ($M^+$+1)

INVENTIVE EXAMPLE 209

4-Acetylamino-N-{2-[4-(4-fluorobenzoyl) piperidino]ethyl}-N-(2-methoxyphenyl)benzamide oxalate Using 4-acetylamino-N-{2-[4-(4-fluorobenzoyl) piperidino]ethyl}-N-(2-methoxyphenyl)benzamide (135.0 mg, 0.26 mmol), the procedure of Inventive Example 174 was repeated to obtain 108.0 mg (68.2%) of the title compound in a colorless powder form.

Melting point: 190°–192° C.

IR (KBr): 3364, 2926, 2854, 1731, 1680, 1644, 1598, 1530, 1407, 1377, 1311, 1278, 1227, 1182, 1020 $cm^{-1}$

NMR ($CDCl_3$—$CD_3OD$) δ: 2.07 (3H, s), 2.10–2.30 (4H, m), 3.10–3.64 (8H, m), 3.70 (3H, s), 4.00–4.26 (2H, m), 6.70–6.93 (2H, m), 6.96–7.45 (8H, m), 7.98 (2H, dd, J=9.0 Hz, 6.0 Hz)

INVENTIVE EXAMPLE 210

4-Methanesulfonylamino-N-{2-[4-(4-fluorobenzoyl) piperidino]-ethyl}-N-(2-methoxyphenyl)benzamide oxalate Using 4-methanesulfonylamino-N-{2-[4-(4-fluorobenzoyl)piperidino]ethyl}-N-(2-methoxyphenyl) benzamide (29.5 mg, 0.05 mmol), the procedure of Inventive Example 174 was repeated to obtain 20.7 mg (60.3%) of the title compound in a colorless powder form.

Melting point: 75°–76° C.

IR (KBr): 3364, 2930, 1680, 1641, 1599, 1503, 1443, 1395, 1332, 1302, 1281, 1152 $cm^{-1}$

NMR ($CDCl_3$—$CD_3OD$) δ: 1.90–2.33 (4H, m), 2.90 (3H, s), 3.10–3.80 (8H, m), 3.72 (3H, s), 3.90–4.30 (2H, m), 6.60–7.40 (10H, m), 7.96 (2H, dd, J=9.0 Hz, 6.0 Hz)

INVENTIVE EXAMPLE 211

4-Acetylamino-N-{2-[4-(4-fluorobenzoyl) piperidino]ethyl}-N-(3-methoxyphenyl)benzamide fumarate 4-Acetylamino-N-{2-[4-(4-fluorobenzoyl)piperidino] ethyl}-N-(3-methoxyphenyl)benzamide (282.4 mg, 0.55 mmol) was dissolved in methanol (1.5 ml) and mixed with a methanol solution (3.0 ml) of fumaric acid (63.8 mg, 0.55 mmol) at 0° C. Thereafter, the thus precipitated crystals were collected by filtration and washed with ether to obtain 278.3 mg (80.0%) of the title compound in a colorless powder form.

Melting point: 215°–222° C. (decomposition)

IR (KBr): 3450, 1680, 1644, 1600, 1528, 1408, 1316, 1218, 1160, 852 cm$^{-1}$

NMR (CDCl$_3$—CD$_3$OD) δ: 1.60–2.43 (5H, m), 2.10 (3H, s), 2.68 (2H, t, J=7.0 Hz), 2.83–3.40 (4H, m), 3.69 (3H, s), 4.05 (2H, t, J=7.0 Hz), 6.52–6.73 (3H, m), 6.78 (2H, s), 6.52–7.50 (5H, m), 7.13 (2H, dd, each J=8.8 Hz), 7.98 (2H, dd, J=8.8 Hz, 5.5 Hz)

INVENTIVE EXAMPLE 212

4-Ethoxycarbonylamino-N-{2-[4-(4-fluorobenzoyl) piperidino]ethyl}-N-(2-methoxyphenyl)benzamide fumarate Using 4-ethoxycarbonylamino-N-{2-[4-(4-fluorobenzoyl)piperidino]ethyl}-N-(2-methoxyphenyl) benzamide (80.0 mg, 0.15 mmol), the procedure of Inventive Example 211 was repeated to obtain 74.6 mg (77.0%) of the title compound in a light brown powder form.

Melting point: 142°–146° C.

IR (KBr): 2950, 1724, 1578, 1638, 1598, 1500, 1410, 1314, 1226, 1190 cm$^{-1}$

NMR (CDCl$_3$—CD$_3$OD) δ: 1.27 (3H, t, J=7.3 Hz), 1.80–2.20 (5H, m), 2.40–3.43 (4H, m), 3.68 (3H, s), 3.93–4.30 (2H, m), 4.17 (2H, q, J=7.3 Hz), 6.73 (2H, s), 6.85 (2H, t, J=7.5), 6.90–7.33 (9H, m), 7.94 (2H, dd, J=8.8 Hz, 5.5 Hz)

INVENTIVE EXAMPLE 213

4-Trifluoroacetylamino-N-{2-[4-(4-fluorobenzoyl) piperidino]ethyl}-N-(2-methoxyphenyl)benzamide fumarate Using 4-trifluoroacetylamino-N-(2-[4-(4-fluorobenzoyl) piperidino]ethyl}-N-(2-methoxyphenyl)benzamide (253.3 mg, 0.42 mmol), the procedure of Inventive Example 211 was repeated obtain 167.7 mg (61.0%) of the title compound in a colorless powder form.

Melting point: 213°–215° C. (decomposition)

IR (KBr): 2950, 1720, 1680, 1640, 1598, 1500, 1410, 1385, 1240, 1200, 1150, 950 cm$^{-1}$

NMR (CDCl$_3$—CD$_3$OD) δ: 1.70–2.06 (5H, m), 2.20–3.46 (6H, m), 3.70 (3H, s), 3.76–4.26 (2H, m), 6.73 (2H, s), 6.81 (2H, t, J=6.8 Hz), 6.93–7.51 (9H, m), 7.95 (2H, dd, J=8.8 Hz, 5.5 Hz)

INVENTIVE EXAMPLE 214

4-(3-Ethylthioureido)-N-{2-[4-(4-fluorobenzoyl) piperidino]ethyl}-N-(2-methoxyphenyl)benzamide fumarate Using 4-(3-ethylthioureido)-N-(2-[4-(4-fluorobenzoyl) piperidino]ethyl}-N-(2-methoxyphenyl)benzamide (95.5 mg, 0.17 mmol), the procedure of Inventive Example 211 was repeated to obtain 87.9 mg (76.3%) of the title compound in a colorless powder form.

Melting point: 154°–156° C.

IR (KBr): 1678, 1640, 1598, 1544, 1502, 1420, 1382, 1314, 1278, 1226 cm$^{-1}$

NMR (CDCl$_3$—CD$_3$OD) δ: 1.16 (3H, t, J=7.1 Hz), 1.70–2.12 (4H, m), 2.20–3.46 (11H, m), 3.72 (3H, s), 6.78 (2H, s), 6.60–7.40 (10H, m), 7.80–8.10 (2H, m)

INVENTIVE EXAMPLE 215

4-(tert-Butylureido)-N-{2-[4-(4-fluorobenzoyl) piperidino]ethyl}-N-(2-methoxyphenyl)benzamide fumarate Using 4-(tert-butylureido)-N-{2-[4-(4-fluorobenzoyl) piperidino]ethyl}-N-(2-methoxyphenyl)benzamide (72.9 mg, 0.13 mmol), the procedure of Inventive Example 211 was repeated to obtain 84.2 mg (96.1%) of the title compound in a light yellow powder form.

Melting point: 110°–114° C.

IR (KBr): 2968, 1683, 1638, 1599, 1536, 1503, 1452, 1410, 1392, 1312, 1278, 1251, 1209, 1179, 1158, 1119, 975, 954, 846, 753 cm$^{-1}$

NMR (CDCl$_3$—CD$_3$OD) δ: 1.32 (9H, s), 1.77–2.20 (4H, m), 2.20–3.55 (8H, m), 3.69 (3H, s), 3.83–4.20 (1H, m), 6.66–7.32 (10H, m), 6.78 (2H, s), 7.80–8.03 (2H, m)

INVENTIVE EXAMPLE 216

4-Amino-N-{2-[4-(4-fluorobenzoyl)piperidino] ethyl}-N-(2-methoxyphenyl)benzamide fumarate Using 4-amino-N-{2-[4-(4-fluorobenzoyl)piperidino] ethyl}-N-(2-methoxyphenyl)benzamide (150.0 mg, 0.32 mmol), the procedure of Inventive Example 211 was repeated to obtain 151.6 mg (81.2%) of the title compound in a light yellow powder form.

Melting point: 152°–158° C.

IR (KBr): 1678, 1632, 1600, 1500, 1388, 1224, 1182, 1160, 756 cm$^{-1}$

NMR (CDCl$_3$—CD$_3$OD) δ: 1.76–2.03 (4H, m), 2.30–2.60 (2H, m), 2.70–3.00 (2H, m), 3.00–3.47 (3H, m), 3.69 (3H, s), 3.80–4.22 (2H, m), 6.37 2H, d, J=8.0 Hz), 6.70–6.90 (4H, m), 6.98–7.30 (6H, m) 7.80–8.07 (2H, m)

INVENTIVE EXAMPLE 217

4-Isobutylylamino-N-{2-[4-(4-fluorobenzoylpiperidino]ethyl}-N-(2-methoxyphenyl)benzamide fumarate Using 4-isobutylylamino-N-{2-[4-(4-fluorobenzoyl) piperidino]ethyl}-N-(2-methoxyphenyl)benzamide (222.7 mg, 0.41 mmol), the procedure of Inventive Example 211 was repeated to obtain 268.0 mg (99.2%) of the title compound in a light pink powder form.

Melting point: 154°–157° C.

IR (KBr): 2968, 1683, 1641, 1599, 1530, 1503, 1455, 1410, 1386, 1305, 1278, 1251, 1224, 1179, 1155, 1116, 1020, 975, 957, 849, 753 cm$^{-1}$

NMR (CDCl$_3$—CD$_3$OD) δ: 1.18 (6H, d, J=5.3 Hz), 1.75–2.00 (4H, m), 2.20–3.50 (8H, m), 3.69 (3H, s), 3.80–4.20 (2H, m), 6.67–6.93 (4H, m), 7.00–7.40 (8H, m), 7.83–8.03 (2H, m)

INVENTIVE EXAMPLE 218

4-Butyrylamino-N-{2-[4-(4-fluorobenzoyl) piperidino]ethyl}-N-(2-methoxyphenyl)benzamide fumarate Using 4-butyrylamino-N-{2-[4-(4-fluorobenzoyl) piperidino]-ethyl}-N-(2-methoxyphenyl)benzamide (196.3 mg, 0.36 mmol), the procedure of inventive Example 211 was repeated to obtain 227.8 mg (95.7%) of the title compound in a light orange powder form.

Melting point: 155°–160° C.

IR (KBr): 1683, 1638, 1599, 1530, 1503, 1455, 1407, 1386, 1308, 1251, 1224, 1203, 1179, 1155, 957, 852, 750 cm$^{-1}$

NMR (CDCl$_3$—CD$_3$OD) δ: 0.98 (3H, t, J=8.0 Hz), 1.47–2.07 (6H, m), 2.10–3.48 (9H, m), 3.69 (3H, s), 3.85–4.30 (2H, m), 6.67–6.93 (4H, m), 7.00–7.40 (8H, m), 7.80–8.10 (2H, m)

INVENTIVE EXAMPLE 219

4-Amino-N-{2-[4-(4-fluorobenzoyl)piperidino] ethyl}-N-(4-methoxyphenyl)benzamide fumarate Using 4-amino-N-{2-[4-(4-fluorobenzoyl)piperidino] ethyl}-N-(4-methoxyphenyl)benzamide (132.9 mg, 0.28 mmol), the procedure of Inventive Example 211 was repeated to obtain 136.3 mg (82.4%) of the title compound in a light yellow amorphous form.

IR (KBr): 1680, 1600, 1510, 1440, 1386, 1292, 1248, 1226, 1182, 1158, 838 cm$^{-1}$

NMR (CDCl$_3$—CD$_3$OD) δ: 1.72–2.10 (4H, m), 2.30–2.70 (2H, m), 2.70–3.23 (2H, m), 3.23–3.58 3H, m), 3.77 (3H, s), 4.08 (2H, t, J=7.0 Hz), 6.42 (2H, d, J=9.0 Hz), 6.60–7.33 (8H, m), 6.77 (2H, s), 7.80–8.10 (2H, m)

INVENTIVE EXAMPLE 220

4-Acetylamino-N-{2-[4-(4-fluorobenzoyl) piperidino]ethyl}-N-(4-methoxyphenyl)benzamide fumarate Using 4-acetylamino-N-{2-[4-(4-fluorobenzoyl) piperidino]ethyl}-N-(4-methoxyphenyl)benzamide (476.8 mg, 0.92 mmol), the procedure of Inventive Example 211 was repeated to obtain 515.6 mg (88.3%) of the title compound in a colorless powder form.

Melting point: 202°–208° C.

IR (KBr): 1683, 1641, 1596, 1512, 1443, 1410, 1386, 1317, 1293, 1257, 1227, 1179, 1158 cm$^{-1}$

NMR (CDCl$_3$—CD$_5$OD) δ: 1.70–2.03 (4H, m), 2.13 (3H, s), 2.20–2.92 (4H, m), 2.92–3.30 (3H, m), 3.78 (3H, s, 4.08 (2H, t, J=8.0 Hz), 6.60–7.47 (10H, m), 6.82 (2H, s, 7.80–8.10 (2H, m)

INVENTIVE EXAMPLE 221

4-Pivaloylamino-N-{2-[4-(4-fluorobenzoyl) piperidino]ethyl}-N-(2-methoxymhenyl)benzamide fumarate Using 4-pivaloylamino-N-{2-[4-(4-fluorobenzoyl) piperidino|-ethyl}-N-(2-methoxyphenyl)benzamide (214.6 mg, 0.38 mmol), the procedure of Inventive Example 211 was repeated to obtain 263.9 mg (quantitative) of the title compound in a light yellow amorphous form.

IR (KBr): 1680, 1641, 1599, 1503, 1443, 1404, 1314, 1278, 1245, 1224, 1158, 975, 849, 753 cm$^{-1}$

NMR (CDCl$_3$—CD$_3$OD) δ: 1.26 (9H, s), 1.70–2.03 (4H, m), 2.40–3.40 (7H, m), 3.69 (3H, s), 3.80–4.20 (2H, m), 6.60–6.90 (2H, m), 6.75 (2H, s), 6.90–7.40 (8H, m), 7.80–8.04 (2H, m)

INVENTIVE EXAMPLE 222

4-Amino-N-{2-[4-(4-fluorobenzoyl)piperidino] ethyl}-N-(2,5-dimethoxyphenyl)benzamide fumarate Using 4-amino-N-{2-[4-(4-fluorobenzoyl)piperidino] ethyl}-N-( 2,5-dimethoxyphenyl)benzamide (152.0 mg, 0.30 mmol), the procedure of Inventive Example 211 was repeated to obtain 175.0 mg (80.4%) of the title compound in a yellow powder form.

Melting point: 199.5°–200.8° C.

IR (KBr): 3470, 3380, 2951, 1683, 1641, 1617, 1514, 1223, 850, 652 cm$^{-1}$

NMR (CDCl$_3$—CD$_3$OD) δ: 1.95–2.16 (5H, m), 2.18–3.80 (6H, m), 3.61 (3H, s), 3.69 (3H, s), 3.80–4.20 (2H, m), 6.35 (2H, d, J=7.8 Hz), 6.72 (5H, s), 7.08–7.26 (4H, m), 7.91–8.06 (2H, m)

INVENTIVE EXAMPLE 223

4-Acetylamino-N-{2-[4-(4-fluorobenzoyl) piperidino]ethyl}-N-(2,5-dimethoxyphenyl) benzamide fumarate Using 4-acetylamino-N-{2-[4-(4-fluorobenzoyl) piperidino]ethyl}-N-(2,5-dimethoxyphenyl)benzamide (109.0 mg, 0.20 mmol), the procedure of Inventive Example 211 was repeated to obtain 111.0 mg (84.3%) of the title compound in a colorless powder form.

Melting point: 207°–208° C.

IR (KBr): 3460, 1945, 1679, 1640, 1598, 1506, 1316, 1223, 855 cm$^{-1}$

NMR (CDCl$_3$—CD$_3$OD) δ: 1.94–2.15 (4H, m), 2.09 (3H, s), 2.61–3.53 (7H, m), 3.61 (3H, s), 3.69 (3H, s), 4.01 (2H, br-s), 6.71 (2H, d, J=4.8 Hz), 7.05–7.41 (7H, m), 7.89–8.04 (2H, m)

INVENTIVE EXAMPLE 224

4-Amino-N-{2-[4-(4-fluorobenzoyl)piperidino] ethyl}-N-(3-methoxyphenyl)benzamide fumarate Using 4-amino-N-{2-[4-(4-fluorobenzoyl)piperidino] ethyl}-N-(3-methoxyphenyl)benzamide (185.1 mg, 0.39 mmol), the procedure of Inventive Example 211 was repeated to obtain 215.8 mg (93.8%) of the title compound in a colorless powder form.

Melting point: 155°–157° C.

IR (KBr): 3444, 3360, 1680, 1628, 1600, 1516, 1440, 1384, 1314, 1214, 1180, 1042 cm$^{-1}$

NMR (CDCl$_3$—CD$_3$OD) δ: 1.80–2.23 (5H, m), 2.56–3.60 (8H, m), 3.70 (3H, s), 4.18 (2H, t, J=7.5 Hz), 6.42 (2H, d, J=8.6 Hz), 6.53–6.72 (2H, m), 6.75 (2H, s), 7.00–7.30 (6H, m), 6.75 (2H, s), 7.95 (2H, dd, J=8.8 Hz, 5.5 Hz)

INVENTIVE EXAMPLE 225

3-Amino-N-{2-[4-(4-fluorobenzoyl)piperidino] ethyl}-N-(3-methoxyphenyl)benzamide fumarate Using 3-amino-N-{2-[4-(4-fluorobenzoyl)piperidino] ethyl}-N-(3-methoxyphenyl)benzamide (153.7 mg, 0.32 mmol), the procedure of Inventive Example 211 was repeated to obtain 176.9 mg (93.5%) of the title compound in a light yellow amorphous form.

IR (KBr): 3460, 3364, 1680, 1638, 1598, 1456, 1318, 1234, 1158, 1080, 980 cm$^{-1}$

NMR (CDCl$_3$—CD$_3$OD) δ: 1.80–2.16 (5H, m), 2.56–3.50 (8H, m), 3.68 (3H, s), 4.11 (2H, t, J=5.7 Hz), 6.40–7.33 (10H, m), 6.75 (2H, s), 7.96 (2H, dd, J=8.8 Hz, 5.5 Hz)

INVENTIVE EXAMPLE 226

3-Acetylamino-N-{2-[4-(4-fluorobenzoyl) piperidino]ethyl}-N-(3-methoxyphenyl)benzamide fumarate Using 3-acetylamino-N-{2-[4-(4-fluorobenzoyl) piperidino]ethyl}-N-(3-methoxyphenyl)benzamide (197.5 mg, 0.38 mmol), the procedure of inventive Example 211 was repeated to obtain 176.6 mg (73.6%) of the title compound in a light red powder form.

Melting point: 122°–125° C.

IR (KBr): 3300, 2930, 1676, 1640, 1598, 1456, 1318, 1234, 1158, 1080, 980 cm$^{-1}$

NMR (CDCl$_3$—CD$_3$OD) δ: 1.73–2.20 5H, m), 2.12 (3H, s), 2.33–2.75 (2H, m), 2.83 (2H, t, J=7.5 Hz), 2.95–3.46 (2H, m), 3.68 (3H, s), 4.12 (2H, t, J=7.5 Hz), 6.53–6.90 (3H, m), 6.76 (2H, s), 6.93–7.43 (6H, m), 7.73 (1H, d, J=7.5 Hz), 7.96 (2H, dd, J=9.0 Hz, 6.0 Hz)

INVENTIVE EXAMPLE 227

4-Amino-N-{2-[4-(4-fluorobenzoyl)piperidino]ethyl}-N-(2,4-dimethoxyphenyl)benzamide fumarate Using 4-amino-N-{2-[4-(4-fluorobenzoyl)piperidino]ethyl}-N-(2,4-dimethoxyphenyl)benzamide (102.3 mg, 0.20 mmol), the procedure of inventive Example 211 was repeated to obtain 92.4 mg (74.3%) of the title compound in a colorless amorphous form.

Melting point: 105°–106° C.

IR (KBr): 1710, 1680, 1600, 1510, 1438, 1410, 1308, 1278, 1224, 1208, 1182, 1158 cm$^{-1}$

NMR (CDCl$_3$—CD$_3$OD) δ: 2.17–2.20 (4H, m), 2.25–3.91 (15H, m) 3.69 (3H, s), 3.77 (3H, s), 6.38–6.51 (3H, m), 6.81 (2H, s) 7.00–7.34 (5H, m), 7.99–8.09 (2H, m)

INVENTIVE EXAMPLE 228

4-Acetylamino-N-{2-[4-(4-fluorobenzoyl)piperidino]ethyl}-N-(2,4-dimethoxyphenyl)benzamide fumarate Using 4-acetylamino-N-{2-[4-(4-fluorobenzoyl)piperidino]ethyl}-N-(2,4-dimethoxyphenyl)benzamide (102.1 mg, 0.19 mmol), the procedure of Inventive Example 211 was repeated to obtain 80.0 mg (64.7%) of the title compound in a colorless amorphous form.

Melting point: 109°–110° C.

IR (KBr): 1681, 1636, 1597, 1529, 1510, 1439, 1406, 1312, 1258, 1223, 1208, 1181, 1158, 1027, 851 cm$^{-1}$

NMR (CDCl$_3$—CD$_3$OD) δ: 1.93–2.06 (4H, m), 2.27 (3H, s), 2.35–3.25 (2H, m), 3.27–4.84 (8H, m), 3.69 (3H, s), 3.77 (3H, s), 6.38–6.51 (3H, m), 6.81 (2H, s), 7.00–7.34 (5H, m), 7.00–7.34 (5H, m), 7.99–8.09 (2H, m)

INVENTIVE EXAMPLE 229

4-Amino-N-{2-[4-(4-fluorobenzoyl)piperidino]ethyl}-N-(3-methylphenyl)benzamide fumarate Using 4-amino-N-{2-[4-(4-fluorobenzoyl)piperidino]ethyl}-N-(3-methylphenyl)benzamide (184.5 mg, 0.40 mmol), the procedure of Inventive Example 211 was repeated to obtain 72.0 mg (31.2%) of the title compound in a light yellow amorphous form.

IR (KBr): 3330, 2935, 2450, 1680, 1629, 1599, 1440, 1380, 1302, 1230, 1155, 843 cm$^{-1}$

NMR (CDCl$_3$—CD$_3$OD) δ: 1.15–2.10 (6H, m), 2.26 (3H, s), 2.34–3.50 (7H, m), 4.10 (2H, t, J=7.0 Hz), 6.40 (2H, d, J=9.0 Hz), 6.77 (2H, s), 6.61–7.31 (8H, m), 7.94 (2H, dd, J=9.0 Hz, 6.0 Hz )

INVENTIVE EXAMPLE 230

4-Acetylamino-N-{2-[4-(4-fluorobenzoyl)piperidino]ethyl}-N-(3-methylphenyl)benzamide fumarate Using 4-acetylamino-N-{2-[4-(4-fluorobenzoyl)piperidino]ethyl}-N-(3-methylphenyl)benzamide (236.0 mg, 0.47 mmol), the procedure of Inventive Example 211 was repeated to obtain 246.0 mg (84.8%) of the title compound in a colorless powder form.

Melting point: 196°–202° C.

IR (KBr): 3250, 2400, 1683, 1644, 1599, 1530, 1407, 1380, 1230, 1161, 849 cm$^{-1}$

NMR (CDCl$_3$—CD$_3$OD) δ: 2.11 (3H, s), 2.26 (3H, s), 1.50–2.60 (6H, m), 2.76 (2H, t, J=7.0 Hz), 2.93–3.53 (3H, m), 4.09 (2H, t, J=7.0 Hz), 6.80 (2H, s), 6.70–7.43 (11H, m), 7.95 (2H, dd, J=9.0 Hz, 6.0 Hz)

INVENTIVE EXAMPLE 231

4-Acetylamino-N-{2-[4-(4-fluorobenzoyl)piperidino]ethyl}-N-(phenyl)benzamide fumarate Using 4-acetylamino-N-{2-[4-(4-fluorobenzoyl)piperidino]ethyl}-N-(phenyl)benzamide (314.3 mg, 0.64 mmol), the procedure of Inventive Example 211 was repeated to obtain 349.8 mg (90.5%) of the title compound in a colorless powder form.

Melting point: 210°–214° C.

IR (KBr): 1686, 1641, 1599, 1527, 1497, 1452, 1410, 1389, 1314, 1260, 1227, 1185, 1158, 852, 759 cm$^{-1}$

NMR (CDCl$_3$—CD$_3$OD) δ: 1.86–1.97 (6H, m), 2.09 (3H, s), 2.28–2.55 (4H, m), 2.66–2.94 (4H, m), 3.04–3.08 (2H, m), 4.11 (2H, dd, J=7.0 Hz, 6.6 Hz), 6.78 (2H, s), 7.06–7.42 (9H, m), 7.93 (2H, dd, J=9.0 Hz, 6.0 Hz)

INVENTIVE EXAMPLE 232

4-Amino-N-{2-[4-(4-fluorobenzoyl)piperidino]ethyl}-N-(3-methylthiophenyl)benzamide fumarate Using 4-amino-N-{2-[4-(4-fluorobenzoyl)piperidino]ethyl}-N-(3-methylthiophenyl)benzamide (148.2 mg, 0.30 mmol), the procedure of Inventive Example 211 was repeated to obtain 488.0 mg (80.3%) of the title compound in a colorless powder form.

Melting point: 224°–227° C.

IR (KBr): 1710, 1680, 1600, 1512, 1312, 1204, 1192, 836 cm$^{-1}$

NMR (CDCl$_3$—CD$_3$OD) δ: 2.17–2.20 (4H, m), 2.43 (3H, s), 3.29–4.09 (15H, m), 6.38–6.98 (5H, m), 7.00–7.33 (5H, m), 7.98–8.01 (2H, m)

INVENTIVE EXAMPLE 233

4-Amino-N-{2-[4-(4-fluorobenzoyl)piperidino]ethyl}-N-(2-trifluoromethylphenyl)benzamide fumarate Using 4-amino-N-{2-[4-(4-fluorobenzoyl)piperidino]ethyl}-N-(2-trifluoromethylphenyl)benzamide (102.6 mg, 0.20 mmol), the procedure of Inventive Example 211 was repeated to obtain 112.0 mg (89.0%) of the title compound in a colorless powder form.

Melting point: 175°–176° C.

IR (KBr): 3480, 3380, 1676, 1640, 1602, 1314, 1226, 1174, 1128, 646 cm$^{-1}$

NMR (CDCl$_3$—CD$_3$OD) δ: 1.81–1.91 (4H, m), 2.19–2.44 (2H, m), 2.66–4.51 (7H, m), 6.46 (4H, br-d, J=8.6 Hz), 6.79 (2H, s), 7.05–7.61 (8H, m), 7.88–8.04 (2H, m)

INVENTIVE EXAMPLE 234

4-Acetylamino-N-{2-[4-(4-fluorobenzoyl)piperidino]ethyl}-N-(2-trifluoromethylphenyl)benzamide fumarate Using 4-acetylamino-N-{2-[4-(4-fluorobenzoyl)piperidino]ethyl}-N-(2-trifluoromethylphenyl)benzamide (139.0 mg, 0.25 mmol), the procedure of Inventive Example 211 was repeated to obtain 143.0 mg (85.1%) of the title compound in a colorless powder form.

Melting point: 188°–190° C.

IR (KBr): 3380, 1680, 1600, 1532, 1318, 1262, 1166, 1076, 705, 646 cm$^{-1}$

NMR (CDCl$_3$—CD$_3$OD) δ: 1.88–1.99 (4H, m), 2.09 (3H, s), 2.36–2.65 (2H, m), 2.82 (2H, t, J=6.9 Hz), 3.06–3.23 (3H, m), 4.15 (2H, t, J=6.9 Hz), 6.77 (2H, s), 7.06–7.45 (10H, m), 7.96 (2H, dd, J=8.8 Hz, 5.5 Hz)

INVENTIVE EXAMPLE 235

4-Amino-N-{2-[4-(4-fluorobenzoyl)piperidino]ethyl}-N-(3-trifluoromethylphenyl)benzamide fumarate Using 4-amino-N-{2-[4-(4-fluorobenzoyl)piperidino]ethyl}-N-(3-trifluoromethylphenyl)benzamide (140.0 mg, 0.27 mmol), the procedure of Inventive Example 211 was repeated to obtain 110.1 mg (64.1%) of the title compound in a light brown powder form.

Melting point: 149°–150° C.

IR (KBr): 3476, 2952, 1680, 1600, 1336, 1130, 840, 701 cm$^{-1}$

NMR (CDCl$_3$—CD$_3$OD) δ: 1.75–1.94 (4H, m), 2.20–2.40 (4H, m), 2.65–3.41 (5H, m), 4.08 (2H, t, J=6.8 Hz), 6.43 (2H, t, J=8.4 Hz), 6.78 (2H, s), 7.03–7.42 (8H, m), 7.95 (2H, dd, J=8.6 Hz, 5.5 Hz)

INVENTIVE EXAMPLE 236

4-Acetylamino-N-{2-[4-(4-fluorobenzoyl)piperidino]ethyl}-N-(3-trifluoromethylphenyl)benzamide fumarate Using 4-acetylamino-N-{2-[4-(4-fluorobenzoyl)piperidino]ethyl}-N-(3-trifluoromethylphenyl)benzamide (139.0 mg, 0.25 mmol), the procedure of Inventive Example 211 was repeated to obtain 157.0 mg (94.0%) of the title compound in a colorless powder form.

Melting point: 205°–206° C.

IR (KBr): 3343, 1680, 1600, 1314, 1264, 1174, 1130, 850, 763, 609 cm$^{-1}$

NMR (CDCl$_3$—CD$_3$OD) δ: 1.82–1.98 (4H, m), 2.09 (3H, s), 2.33–2.60 (2H, m), 2.80 (2H, t, J=6.6 Hz), 3.05–3.30 (2H, m), 4.13 (2H, t, J=6.6 Hz), 6.78 (2H, s), 7.05–7.46 (10H, m), 7.96 (2H, dd, J=8.8 Hz, 5.5 Hz)

INVENTIVE EXAMPLE 237

4-Acetylamino-N-{2-[4-(4-fluorobenzoyl)piperidino]ethyl}-N-(3-pyridyl)benzamide fumarate Using 4-acetylamino-N-{2-[4-(4-fluorobenzoyl)piperidino]ethyl}-N-(3-pyridyl)benzamide (151.0 mg, 0.31 mmol), the procedure of inventive Example 211 was repeated to obtain 145.0 mg (77.6%) of the title compound in a colorless powder form.

Melting point: 200–208° C.

IR (KBr): 3245, 1683, 1644, 1599, 1527, 1428, 1410, 1314, 1230, 1182, 849 cm$^{-1}$

NMR (CDCl$_3$—CD$_3$OD) δ: 2.12 (3H, s), 1.60–2.44 (6H, m), 2.68 (2H, t, J=7.0 Hz), 2.97–3.72 (3H, m), 4.09 (2H, t, J=7.0 Hz), 6.80 (2H, s), 6.97–7.60 (8H, m), 7.95 (2H, dd, J=9.0 Hz, 6.0 Hz), 8.24–8.70 (3H, m)

INVENTIVE EXAMPLE 238

4-Acetylamino-N-{2-[4-(4-fluorobenzoyl)piperidino]ethyl}-N-(3-methylthiophenyl)benzamide fumarate Using 4-acetylamino-N-{2-[4-(4-fluorobenzoyl)piperidino]ethyl}-N-(3-methylthiophenyl)benzamide (167.2 mg, 0.31 mmol), the procedure of Inventive Example 211 was repeated to obtain 177.7 mg (88.2%) of the title compound in a colorless powder form.

Melting point: 128°–133° C.

IR (KBr): 1680, 1640, 1598, 1532, 1476, 1440, 1408, 1372, 1314 1260, 1226, 1180, 1158, 972, 954, 852, 760 cm$^{-1}$

NMR CDCl$_3$—CD$_3$OD) δ: 2.11 (3H, s), 1.89–2.52 (10H, m), 2.50 (3H, s), 2.74–2.77 (2H, m), 3.04–3.45 (4H, m), 4.09 (2H, dd, J=6.6 Hz, 6.4 Hz), 6.77–7.40 (10H, m), 7.95 (2H, dd, J=8.6 Hz, 6.0 Hz)

INVENTIVE EXAMPLE 239

2-Acetylamino-N-{2-[4-(4-fluorobenzoyl)piperidino]ethyl}-N-(3-methoxyphenyl)benzamide fumarate Using 2-acetylamino-N-{2-[4-(4-fluorobenzoyl)piperidino]ethyl}-N-3-methoxyphenyl)benzamide (170.4 mg, 0.33 mmol), the procedure of Inventive Example 211 was repeated to obtain 146.2 mg 70.0%) of the title compound in a colorless powder form.

Melting point: 105°–107° C.

IR (KBr): 3450, 1678, 1598, 1492, 1386, 1284, 1158 cm$^{-1}$

NMR (CDCl$_3$—CD$_3$OD) δ: 2.23 (3H, s), 1.63–2.50 (5H, m), 2.68 (2H, t, J=6.6 Hz), 2.85–3.46 (2H, m), 3.67 (3H, s), 4.10 (2H, t, J=6.6 Hz), 6.40–6.92 (4H, m), 6.80 (2H, s), 6.92–7.35 (5H, m), 7.95 (2H, dd, J=9.0 Hz, 6.0 Hz), 8.17 (1H, d, J=8.4 Hz), 9.30 (1H, br-s)

INVENTIVE EXAMPLE 240

4-Amino-N-{2-[4-(4-fluorobenzoyl)piperidino]ethyl}-N-(3-aminophenyl)benzamide fumarate Using 4-amino-N-{2-[4-(4-fluorobenzoyl)piperidino]ethyl}-N-(3-aminophenyl)benzamide (123.0 mg, 0.27 mmol), the procedure of Inventive Example 211 was repeated to obtain 107.8 mg/70.1%) of the title compound in a light yellow amorphous form.

IR (KBr): 3350, 1680, 1599, 1494, 1440, 1218, 1158, 840 cm$^{-1}$

NMR (CDCl$_3$—CD$_3$OD) δ: 1.80–2.30 (4H, m), 2.70–3.77 (11H, m), 4.17 (2H, t, J=7.0 Hz), 6.18–6.57 (5H, m), 6.73 (2H, s), 6.80–7.32 (5H, m), 7.95 (2H, dd, J=9.0 Hz, 6.0 Hz)

INVENTIVE EXAMPLE 241

4-Acetylamino-N-{2-[4-(4-fluorobenzoyl)piperidino]ethyl}-N-(3-acetylaminophenyl)benzamide fumarate Using 4-acetylamino-N-{2-[4-(4-fluorobenzoyl)piperidino]ethyl}-N-(3-acetylaminophenyl)benzamide (231.0 mg, 0.424 mmol), the procedure of Inventive Example 211 was repeated to obtain 201.0 mg (75.6%) of the title compound in a colorless powder form.

Melting point: 214.5°–222.5° C.

IR (KBr): 3260, 3060, 1689, 1326, 1596, 1530, 1446, 1389, 1248, 1155, 855 cm$^{-1}$

NMR (CDCl$_3$—DMSO-d$_6$) δ: 1.52–3.29 (11H, m), 2.10 (6H, s), 2.51–3.36 (6H, m), 4.13 (2H, t, J=7.0 Hz), 6.80 (2H, s), 6.92–7.55 (10H, m), 7.97 (2H, dd, J=9.0 Hz, 6.0 Hz), 8.49–8.78 (2H, m)

INVENTIVE EXAMPLE 242

4-Acetylamino-N-{2-[4-(4-fluorobenzoyl)piperidino]ethyl}-N-(2-methoxycarbonylphenyl)benzamide fumarate Using 4-acetylamino-N-{2-[4-(4-fluorobenzoyl)piperidino]ethyl}-N-(2-methoxycarbonylphenyl)benzamide (164.0 mg, 0.30 mmol), the procedure of Inventive Example 211 was repeated to obtain 150.4 mg (75.6%) of the title compound in a colorless powder form.

Melting point: 176°–186° C.

IR (KBr): 3342, 1714, 1680, 1598, 1314, 1264, 843, 759, 675, 600 cm$^{-1}$

NMR (CDCl$_3$—CD$_3$OD) δ: 1.83–2.01 (4H, m), 2.08 (3H, s), 2.51–3.36 (6H, m), 3.80 (3H, s), 4.17–4.41 (1H, m), 6.73 (2H, s), 7.06–7.70 (10H, m), 7.96 (2H, dd, J=8.6 Hz, 5.5 Hz)

INVENTIVE EXAMPLE 243

4-Amidino-N-{2-[4-(4-fluorobenzoyl)piperidino]ethyl}-N-methoxyphenyl)benzamide fumarate Using 4-amidino-N-{2-[4-(4-fluorobenzoyl)piperidino]ethyl}-N-(4-methoxyphenyl)benzamide (150.0 mg, 0.30 mmol), the procedure of Inventive Example 211 was repeated to obtain 185.0 mg (quantitative) of the title compound in a colorless amorphous form.

Melting point: 137°–164° C.

IR (KBr): 3370, 3045, 1678, 1638, 1510, 848, 652, 603 cm$^{-1}$

NMR (CDCl$_3$—CD$_3$OD) δ: 2.05–2.27 (4H, m), 2.73–3.43 (7H, m), 3.72 (3H, s), 4.09–4.29 (2H, m), 6.74 (2H, s), 6.75 (2H, d, J=8.8 Hz), 7.07–7.63 (8H, m), 7.94 (2H, dd, J=8.6 Hz, 5.3 Hz)

INVENTIVE EXAMPLE 244

4-Acetylamino-3-methyl-N-{2-[4-(4-fluorobenzoyl)piperidino]ethyl}-N-(4-methoxyphenyl)benzamide fumarate Using 4-acetylamino-3-methyl-N-{2-[4-(4-fluorobenzoyl)piperidino]ethyl}-N-(4-methoxyphenyl)benzamide (159.0 mg, 0.30 mmol), the procedure of Inventive Example 211 was repeated to obtain 176.4 mg (90.7%) of the title compound in a colorless powder form.

Melting point: 171°–172° C.

IR (KBr): 3440, 2951, 1682, 1644, 1598, 1512, 1304, 1032, 847, 637 cm$^{-1}$

NMR (CDCl$_3$—CD$_3$OD) δ: 1.71–2.04 (4H, m), 2.14 (6H, s), 2.42–2.66 (2H, m), 2.85 (2H, t, J=7.5 Hz), 3.11–3.39 (3H, m), 3.75 (3H, s), 4.09 (2H, t, J=7.5 Hz), 6.69–6.79 (4H, m), 6.95–7.32 (6H, m), 7.53–7.62 (1H, m), 7.96 (2H, dd, J=8.8 Hz, 5.5 Hz)

INVENTIVE EXAMPLE 245

4-Acetylamino-3-methoxy-N-{2-[4-(4-fluorobenzoyl)-piperidino]ethyl}-N-(4-methoxyphenyl)benzamide fumarate Using 4-acetylamino-3-methoxy-N-{2-[4-(4-fluorobenzoyl)piperidino]ethyl}-N-(4-methoxyphenyl)benzamide (137.0 mg, 0.25 mmol), the procedure of inventive Example 211 was repeated to obtain 160.0 mg (96.4%) of the title compound in a colorless needle crystal form.

Melting point: 189°–193° C.

IR (KBr): 3440, 2945, 1680, 1638, 1598, 1510, 1301, 759, 643 cm$^{-1}$

NMR (CDCl$_3$—CD$_3$OD) δ: 1.89–2.04 (4H, m), 2.16 (3H, s), 2.35–3.31 (7H, m), 3.73 (3H, s), 3.76 (3H, s), 4.08 (2H, t, J=7.3 Hz), 6.78 (2H, s), 6.70–7.32 (8H, m), 7.88–8.14 (3H, m)

INVENTIVE EXAMPLE 246

4-Acetylamino-N-{2-[4-(4-fluorobenzoyl)piperidino]ethyl}-N-(4-methylphenyl)benzamide fumarate Using 4-acetylamino-N-{2-[4-(4-fluorobenzoyl)piperidino]ethyl}-N-(4-methylphenyl)benzamide (307.9 mg, 0.61 mmol), the procedure of Inventive Example 211 was repeated to obtain 335.3 mg (89.0%) of the title compound in a colorless powder form.

Melting point: 217°–221° C. (decomposition)

IR (KBr): 1682, 1638, 1594, 1530, 1510, 1452, 1414, 1390, 1316, 1262, 1228, 1184, 1158, 1136, 1110, 974, 852, 764, 636 cm$^{-1}$

NMR (CDCl$_3$—CD$_3$OD) δ: 1.79–1.84 (4H, m), 2.08 (3H, s), 2.27 (3H, s), 2.56–2.70 (4H, m), 2.95–3.23 (3H, m), 3.94–4.08 (3H, m), 6.74–7.56 (10H, m), 7.95 (2H, dd, J=8.8 Hz, 5.5 Hz)

INVENTIVE EXAMPLE 247

4-Acetylamino-N-{2-[4-(4-fluorobenzoylpiperidino]ethyl}-N-(4-fluorophenyl)benzamide fumarate Using 4-acetylamino-N-{2-[4-(4-fluorobenzoyl)piperidino]ethyl}-N-(4-fluorophenyl)benzamide (158.8 mg, 0.31 mmol), the procedure of inventive Example 211 was repeated to obtain 131.9 mg (68.4%) of the title compound in a colorless amorphous form.

Melting point: 210°–214° C. (decomposition)

IR (KBr): 1684, 1632, 1594, 1530, 1510, 1410, 1386, 1332, 1316, 1264, 1224 cm$^{-1}$

NMR (CDCl$_3$—CD$_3$OD) δ: 1.77–1.83 (4H, m), 2.08 (3H, s), 2.09–2.29 (2H, m), 2.59–2.67 (4H, m), 2.88–3.04 (4H, m), 3.14–3.78 (2H, m), 4.00 (2H, dd, J=6.4 Hz, 6.2 Hz), 6.96 (2H, J=8.6 Hz), 7.03–7.22 (5H, m), 7.44 (2H, d, J=8.6 Hz), 7.58 (1H, br-s), 7.89–8.04 (2H, m)

INVENTIVE EXAMPLE 248

4-(Pyrrole-1-yl)-N-{2-[4-(4-fluorobenzoyl)piperidino]ethyl}-N-(4-methoxyphenyl)benzamide fumarate Using 4-(pyrrole-1-yl)-N-{2-[4-(4-fluorobenzoyl)piperidino]ethyl}-N-(4-methoxyphenyl)benzamide (131.0 mg, 0.25 mmol), the procedure of Inventive Example 211 was repeated to obtain 144.0 mg (90.0%) of the title compound in a colorless needle crystal form.

Melting point: 167°–169° C.

IR (KBr): 3446, 2951, 1680, 1610, 1512, 1330, 836, 710 cm$^{-1}$

NMR (CDCl$_3$—CD$_3$OD) δ: 1.94–2.04 (4H, m), 2.07–2.88 (4H, m), 3.12–3.34 (3H, m), 3.75 (3H, s), 4.13 (2H, d, J=6.3 Hz), 6.31 (2H, t, J=2.2 Hz), 6.76 (2H, s), 6.77 (2H, d, J=8.8 Hz), 6.96–7.40 (10H, m), 7.96 (2H, dd, J=8.8 Hz, 5.3 Hz)

INVENTIVE EXAMPLE 249

4-Acetylamino-N-{2-[4-(4-fluorobenzoyl)piperidino]ethyl}-N-(3-hydroxyphenyl)benzamide fumarate Using 4-acetylamino-N-{2-[4-(4-fluorobenzoyl)piperidino]ethyl}-N-(3-hydroxyphenyl)benzamide (154.3 mg, 0.31 mmol), the procedure of Inventive Example 211 was repeated to obtain 167.6 mg (88.3%) of the title compound in a light yellow amorphous form.

IR (KBr): 2974, 1683, 1641, 1599, 1530, 1485, 1443, 1410, 1380, 1314, 1257, 1182, 1152, 972, 954, 849, 759 cm$^{-1}$

NMR (CDCl$_3$—CD$_3$OD) δ: 1.80–2.05 (4H, m), 2.10 (3H, s), 2.37–3.67 (7H, m), 4.13 (2H, t, J=7.0 Hz), 6.77 (2H, s), 6.30–7.40 (10H, m), 7.80–8.05 (2H, m)

INVENTIVE EXAMPLE 250

4-(N-Methyl-acetylamino)-N-{2-[4-(4-fluorobenzoyl)piperidino]ethyl}-N-(4-methoxyphenyl)benzamide fumarate Using 4-(N-methyl-acetylamino)-N-{2-[4-(4-fluorobenzoyl)piperidino]ethyl}-N-(3-methoxyphenyl)benzamide (115.0 mg, 0.22 mmol), the procedure of Inventive Example 211 was repeated to obtain 141.0 mg (quantitative) of the title compound in a colorless needle crystal form.

Melting point: 143°–145° C.

IR (KBr): 3450, 1680, 1652, 1600, 1512, 1250, 857, 651 cm$^{-1}$

NMR (CDCl$_3$—CD$_3$OD) δ: 1.78 (3H, s), 1.78–2.03 (4H, m), 2.29–2.60 (2H, m), 2.81 (2H, t, J=7.0 Hz), 3.08–3 40 (3H, m), 3.17 (3H, s), 3.75 (3H, s), 4.10 (2H, t, J=7.0 Hz), 6.74 (2H, d, J=8.8 Hz), 6.78 (2H, s), 6.96–7.37 (8H, m), 7.96 (2H, dd, J=8.8 Hz, 5.5 Hz)

INVENTIVE EXAMPLE 251

4-(N-Dimethylamino)-N-{2-[4-(4-fluorobenzoyl)piperidino]ethyl}-N-(4-methoxyphenyl)benzamide fumarate Using 4-(N-dimethylamino)-N-{2-[4-(4-fluorobenzoyl)piperidino]ethyl}-N-(4-methoxyphenyl)benzamide (110.0 mg, 0.22 mmol), the procedure of Inventive Example 211 was repeated to obtain 114.0 mg (61.1%) of the title compound in a colorless needle crystal form.

Melting point: 226°–228° C. (decomposition)

IR (KBr): 3440, 2940, 1600, 1510, 1370, 1032, 832, 644 cm$^{-1}$

NMR (CDCl$_3$—CD$_3$OD) δ: 1.95–2.06 (4H, m), 2.62–3.45 (7H, m), 2.92 (6H, s), 3.77 (3H, s), 4.11 (2H, t, J=7.0 Hz), 6.43 (2H, d, J=9.0 Hz), 6.77 (2H, s), 6.78 (2H, d, J=9.0 Hz), 6.97–7.30 (6H, m), 7.97 (2H, dd, J=8.8 Hz, 5.5 Hz)

INVENTIVE EXAMPLE 252

3-Acetylamino-N-{2-[4-(4-fluorobenzoylpiperidino]ethyl}-N-(phenyl)benzamide fumarate Using 3-acetylamino-N-{2-[4-(4-fluorobenzoyl)piperidino]ethyl}-N-(phenyl)benzamide (91.1 mg, 0.19 mmol), the procedure of inventive Example 211 was repeated to obtain 74.3 mg (65.9%) of the title compound in a light yellow powder form.

Melting point: 137°–138° C.

IR (KBr): 1676, 1648, 1596, 1560, 1494, 1430, 1382, 1306, 1290, 1264, 1228, 1158, 976, 748, 698 cm$^{-1}$

NMR (CDCl$_3$—CD$_3$OD) δ: 1.77–1.93 (4H, m), 2.13 (3H, s), 2.27–2.43 (2H, m), 2.67 (2H, t, J=6.6 Hz), 2.97–3.84 (8H, m), 4.07 (2H, t, J=6.6 Hz), 6.79–6.84 (2H, m), 7.14–7.34 (9H, m), 7.93 (1H, d, J=8.6 Hz), 7.99 (1H, d, J=8.6 Hz)

INVENTIVE EXAMPLE 253

3-Acetylamino-N-{2-[4-(4-fluorobenzoyl)piperidino]ethyl}-N-(4-methylthiophenyl)benzamide fumarate Using 4-acetylamino-N-{2-[4-(4-fluorobenzoyl)piperidino]ethyl}-N-(4-methylthiophenyl)benzamide (127.2 mg, 0.24 mmol), the procedure of inventive Example 211 was repeated to obtain 88.1 mg (56.9%) of the title compound in a light yellow powder form.

Melting point: 95°–97° C.

IR (KBr): 1680, 1640, 1588, 1552, 1374, 1314, 1226 cm$^{-1}$

NMR (CDCl$_3$—CD$_3$OD) δ: 1.80–2.12 (4H, m), 2.13 (3H, s), 2.35 (3H, s), 2.31–2.54 (4H, m), 2.77 (2H, t, J=6.6 Hz), 3.06–3.31 (6H, m), 4.12 (2H, t, J=6.6 Hz), 6.81–7.39 (10H, m), 7.93 (1H, d, J=8.4 Hz), 7.99 (1H, d, J=8.4 Hz)

INVENTIVE EXAMPLE 254

3-Acetylamino-N-{2-[4-(4-fluorobenzoylpiperidino]ethyl}-N-(4-methylphenyl)benzamide fumarate Using 4-acetylamino-N-{2-[4-(4-fluorobenzoyl)piperidino]ethyl}-N-(4-methylphenyl)benzamide (199.4 mg, 0.40 mmol), the procedure of Inventive Example 211 was repeated to obtain 230.2 mg (93.2%) of the title compound in a light brown amorphous form.

Melting point: 93°–95° C.

IR (KBr): 1680, 1598 cm$^{-1}$

NMR (CDCl$_3$—CD$_3$OD) δ: 1.87–2.43 (6H, m), 2.13 (3H, s), 2.28 (3H, s), 2.70 (2H, t, J=6.6 Hz), 2.98–3.62 (4H, m), 4.07 (2H, t, J=6.6 Hz), 6.82–7.28 (9H, m), 7.69–7.72 (1H, m), 7.93 (1H, d, J=8.8 Hz), 7.99 (1H, d, J=8.8 Hz)

INVENTIVE EXAMPLE 255

3-Acetylamino-N-{2-[4-(4-fluorobenzoyl)piperidino]ethyl}-N-(4-fluorophenyl)benzamide fumarate Using 3-acetylamino-N-{2-[4-(4-fluorobenzoyl)piperidino]ethyl}-N-(4-fluorophenyl)benzamide (182.5 mg, 0.36 mmol), the procedure of Inventive Example 211 was repeated to obtain 184.2 mg (82.3%) of the title compound in a light brown amorphous form.

Melting point: 93°–95° C.

IR (KBr): 1682, 1640, 1598, 1554, 1508, 1378, 1320, 1220, 1156

NMR (CDCl$_3$—CD$_3$OD) δ: 1.84–1.96 (4H, m), 2.12 (3H, s), 2.20–2.45 (3H, m), 2.61–3.42 (9H, m), 4.04 (2H, t, J=6.4 Hz), 6.69–7.70 (10H, m), 7.93 (1H, d, J=8.6 Hz), 7.99 (1H, d, J=8.8 Hz)

INVENTIVE EXAMPLE 256

4-Acetylamino-N-{2-[4-(4-fluorobenzoyl)piperidino]ethyl}-N-(4-hydroxyphenyl)benzamide fumarate Using 4-acetylamino-N-{2-[4-(4-fluorobenzoyl)piperidino]ethyl}-N-(4-hydroxyphenyl)benzamide (215.0 mg, 0.43 mmol), the procedure of inventive Example 211 was repeated to obtain 254.0 mg (96.0%) of the title compound in a light yellow powder form.

Melting point: 72°–74° C.

IR (KBr): 3044, 1680, 1598, 1512, 1448, 1408, 1378, 1316, 1264, 1228, 1182, 1158, 976, 952,842, 760 cm$^{-1}$

NMR (CDCl$_3$—CD$_3$OD) δ: 1.70–2.13 (6H, m), 2.08 (3H, s), 2.30–2.73 (5H, m), 3.88–4.20 (2H, m), 6.53–6.99 (4H, m), 6.75 (2H, s), 7.00–7.40 (6H, m), 7.80–8.05 (2H, m)

INVENTIVE EXAMPLE 257

4-Propionylamino-N-{2-[4-(4-fluorobenzoyl)piperidino]ethyl}-N-(3-methoxyphenyl)benzamide fumarate Using 4-propionylamino-N-{2-[4-(4-fluorobenzoyl)piperidino]ethyl}-N-(3-methoxyphenyl)benzamide (106.0 mg, 0.20 mmol), the procedure of Inventive Example 211 was repeated to obtain 110.0 mg (85.3%) of the title compound in a colorless powder form.

Melting point: 214°–218° C.

IR (KBr): 3445, 1680, 1600, 1296, 1216, 853, 638 cm$^{-1}$

NMR (CDCl$_3$—CD$_3$OD) δ: 1.70 (3H, t, J=7.4 Hz), 1.83–2.00 (4H, m), 2.22–3.86 (9H, m), 3.70 (3H, s), 3.88–4.20 (2H, m), 6.61–6.77 (5H, m), 7.05–7.45 (7H, m), 7.89–8.04 (2H, m)

INVENTIVE EXAMPLE 258

4-Valerylamino-N-{2-[4-(4-fluorobenzoylpiperidino]ethyl}-N-(3-methoxyphenyl)benzamide fumarate Using 4-valerylamino-N-{2-[4-(4-fluorobenzoyl)piperidino]ethyl}-N-(3-methoxyphenyl)benzamide (142.0 mg, 0.25 mmol), the procedure of Inventive Example 211 was repeated to obtain 152.0 mg (85.9%) of the title compound in a colorless powder form.

Melting point: 229°–230° C. (decomposition)

IR (KBr): 3450, 2951, 1678, 1600, 1296, 1180, 857, 646 cm$^{-1}$

NMR (CDCl$_3$—CD$_3$OD) δ: 0.92 (3H, t, J=6.4 Hz), 1.00–4.37 (22H, m), 3.71 (3H, s), 6.64–6.77 (5H, m), 7.06–7.45 (7H, m), 7.96 (2H, dd, J=8.6 Hz, 5.5 Hz)

INVENTIVE EXAMPLE 259

4-Acetylamino-N-{2-[4-(4-fluorobenzoyl)piperidino]ethyl}-N-(3,4-methylenedioxyphenyl)benzamide fumarate Using 4-acetylamino-N-{2-[4-(4-fluorobenzoyl)piperidino]ethyl}-N-(3,4-methylenedioxyphenyl)benzamide (210.3 mg, 0.40 mmol), the procedure of Inventive Example 211 was repeated to obtain 195.9 mg (76.5%) of the title compound in a colorless powder form.

Melting point: 223°–224° C.

IR (KBr): 1710, 1680, 1644, 1596, 1530, 1506, 1485, 1452, 1410, 1389, 1317, 1257, 1218, 1182, 1161, 1041, 849 cm$^{-1}$

NMR (CDCl$_3$—CD$_3$OD) δ: 1.70–2.00 (4H, m), 2.11 (3H, s), 2.20–2.57 (2H, m), 2.74 (2H, t, J=6.9 Hz), 2.87–3.47 (3H, m), 4.03 (2H, t, J=6.9 Hz), 5.95 (2H, s), 6.37–6.70 (3H, m), 6.79 (2H, s), 6.90–7.50 (6H, m), 7.80–8.05 (2H, m)

INVENTIVE EXAMPLE 260

4-Acetylamino-N-{2-[4-(4-fluorobenzoyl)piperidino]ethyl}-N-(3,4-dimethylphenyl)benzamide fumarate Using 4-acetylamino-N-{2-[4-(4-fluorobenzoyl)piperidino]ethyl}-N-(3,4-dimethylphenyl)benzamide (218.2 mg, 0.42 mmol), the procedure of Inventive Example 211 was repeated to obtain 223.6 mg (84.3%) of the title compound in a colorless powder form.

Melting point: 210°–212° C. (decomposition)

IR (KBr): 1710, 1682, 1656, 1642, 1534, 1504, 1408, 1382, 1316, 1262, 1234, 1218, 1182, 1160, 848, 762, 636 cm$^{-1}$

NMR (CDCl$_3$—CD$_3$OD) δ: 2.09 (3H, s), 2.19 (6H, br-s), 1.96–2.92 (10H, m), 3.01 (2H, t, J=7.0 Hz), 3.20–3.54 (3H, m), 4.16 (2H, t, J=6.8 Hz), 6.73 (2H, s), 6.87–7.47 (7H, m), 8.05 (2H, dd, J=8.6 Hz, 5.5 Hz)

INVENTIVE EXAMPLE 261

4-Acetylamino-N-{2-[4-(4-fluorobenzoyl)piperidino]ethyl}-N-(4-chlorophenyl)benzamide fearate Using 4-acetylamino-N-{2-[4-(4-fluorobenzoyl)piperidino]ethyl}-N-(4-chlorophenyl)benzamide (159.0 mg, 0.30 mmol), the procedure of Inventive Example 211 was repeated to obtain 140.8 mg (73.6%) of the title compound in a colorless powder form.

Melting point: 218°–220° C. (decomposition)

IR (KBr): 1682, 1636, 1596, 1530, 1492, 1414, 1384, 1318, 1262, 1228, 1186 cm$^{-1}$

NMR (CDCl$_3$—CD$_3$OD) δ: 1.78–1.84 (4H, m), 2.10 (3H, s), 2.10–2.31 (2H, m), 2.61–2.68 (3H, m), 2.93–3.83 (7H, m), 4.01 (2H, t, J=6.8 Hz), 6.75 (2H, s), 7.00–7.23 (4H, m), 7.40–7.53 (4H, m), 7.96 (2H, dd, J=8.6 Hz, 5.5 Hz)

INVENTIVE EXAMPLE 262

4-Acetylamino-N-{3-[4-(4-fluorobenzoyl)piperidino]propyl}-N-(3-methoxyphenyl)benzamide fumarate Using 4-acetylamino-N-{3-[4-(4-fluorobenzoyl)piperidino]propyl}-N-(3-methoxyphenyl)benzamide (312.6 mg, 0.59 mmol), the procedure of inventive Example 211 was repeated to obtain 308.7 mg (80.9%) of the title compound in a colorless powder form.

Melting point: 190°–193° C.

IR (KBr): 1682, 1634, 1600, 1528, 1490, 1408, 1314, 1258, 1182, 1050, 844 cm$^{-1}$

NMR (CDCl$_3$—CD$_3$OD) δ: 1.76–2.25 (6H, m), 2.09 (3H, s), 2.56–3.00 (4H, m), 3.69 (3H, s), 3.94 (2H, dd, J=7.0 Hz, 6.5 Hz), 6.50–6.80 (3H, m), 6.74 (2H, s), 6.95–7.50 (7H, m), 7.96 (2H, dd, J=8.5 Hz, 5.3 Hz)

INVENTIVE EXAMPLE 263

4-Amino-N-{3-[4-(4-fluorobenzoyl)piperidino]propyl}-N-(3-methoxyphenyl)benzamide fumarate Using 4-amino-N-{3-[4-(4-fluorobenzoyl)piperidino]propyl}-N-(3-methoxyphenyl)benzamide (300.0 mg, 0.61 mmol), the procedure of Inventive Example 211 was repeated to obtain 321.3 mg (81.1%) of the title compound in a colorless powder form.

Melting point: 170°–172° C.

IR (KBr): 1680, 1598, 1562, 1488, 1452, 1394, 1306, 1282, 1230, 1180, 1158 cm$^{-1}$

NMR (CDCl$_3$—CD$_3$OD) δ: 1.70–2.23 (6H, m), 2.50–2.95 (4H, m), 3.00–3.53 (5H, m), 3.70 (3H, s), 3.92 (2H, t, J=7.0 Hz), 6.41 (2H, d, J=8.4 Hz), 6.50–6.85 (2H, m), 6.74 (2H, s), 6.95–7.36 (6H, m), 7.95 (2H, dd, J=8.6 Hz, 5.5 Hz)

INVENTIVE EXAMPLE 264

4-(N-Methyl-acetylamino)-N-{2-[4-(4-fluorobenzoyl)piperidino]-ethyl}-N-(3-methoxyphenyl)benzamide fumarate Using 4-(N-methyl-acetylamino)-N-{2-[4-(4-fluorobenzoyl)piperidino]ethyl}-N-(3-methoxyphenyl)benzamide (81.8 mg, 0.154 mmol), the procedure of Inventive Example 211 was repeated to obtain 69.7 mg (69.8%) of the title compound in a colorless powder form.

Melting point: 161°–167° C.

IR (KBr): 3440, 1648, 1600, 1382, 1304, 1158, 854, 700 cm$^{-1}$

NMR (CDCl$_3$—CD$_3$OD) δ: 1.78 (3H, s), 1.84–2.01 (4H, m), 2.22–2.64 (2H, m), 2.82 (2H, t, J=6.7 Hz), 3.18 (3H, s), 3.09–3.40 (3H, m), 3.70 (3H, s), 4.14 (2H, t, J=6.7 Hz), 6.63–6.78 (4H, m), 6.96–7.41 (6H, m), 7.95 (2H, dd, J=8.6 Hz, 5.5 Hz)

INVENTIVE EXAMPLE 265

4-Trifluoroacetylamino-N-{2-[4-(4-fluorobenzoyl)piperidino]ethyl}-N-(3-pyridyl)benzamide fumarate Using 4-trifluoroacetylamino-N-{2-[4-(4-fluorobenzoyl)piperidino]ethyl}-N-(3-pyridyl)benzamide (206.2 mg, 0.38 mmol), the procedure of Inventive Example 211 was repeated to obtain 119.7 mg (47.8%) of the title compound in a light brown powder form.

Melting point: 173°–176° C. (decomposition)

IR (KBr): 1716, 1680, 1644, 1600, 1546, 1510, 1452, 1430, 1412, 1382, 1364, 1306, 1246, 1208, 1184, 1158, 848, 766 cm$^{-1}$

NMR (CDCl$_3$—CD$_3$OD) δ: 1.69–1.90 (4H, m), 2.14–2.40 (2H, m), 2.72 (2H, t, J=6.6 Hz), 2.97–3.40 (3H, m), 4.10 (2H, t, J=6.6 Hz), 6.80 (2H, s) 7.04–7.28 (5H, m), 7.44–7.52 (3H, m), 7.95 (2H, dd, J=8.4 Hz, 5.5 Hz), 8.29–8.39 (2H, m)

INVENTIVE EXAMPLE 266

4-Benzoylamino-N-{2-[4-(4-fluorobenzoyl)piperidino]ethyl}-N-(3-pyridyl)benzamide fumarate Using 4-benzoylamino-N-{2-[4-(4-fluorobenzoyl)piperidino]-ethyl}-N-(3-pyridyl)benzamide (168.2 mg, 0.31 mmol), the procedure of Inventive Example 211 was repeated to obtain 194.3 mg (94.0%) of the title compound in a colorless powder form.

Melting point: 212°–217° C. (decomposition)

IR (KBr): 1678, 1668, 1642, 1600, 1530, 1452, 1428, 1408, 1380, 1364, 1324, 1266, 1228, 1156, 852, 762, 702 cm$^{-1}$

NMR (CDCl$_3$—CD$_3$OD) δ: 1.82–1.92 (4H, m), 2.19–2.23 (2H, m), 2.73 (2H, t, J=6.4 Hz), 2.98–3.10 (3H, m), 4.10 (2H, t, J=6.4 Hz), 6.80 (1H, s), 7.04–7.31 (5H, m), 7.51–7.61 (6H, m), 7.80–8.04 (4H, m), 8.34–8.38 (2H, m)

INVENTIVE EXAMPLE 267

4-Benzoylamino-N-[2-(4-benzoylpiperidino)ethyl]-N-(3-pyridyl)benzamide fumarate

Using 4-benzoylamino-N-[2-(4-benzoylpiperidino)ethyl]-N-(3-pyridyl)benzamide (212.5 mg, 0.40 mmol), the procedure of Inventive Example 211 was repeated to obtain 181.9 mg (77.0%) of the title compound in a colorless powder form.

Melting point: 207°–211° C. (decomposition)

IR (KBr): 1712, 1672, 1642, 1596, 1530, 1478, 1448, 1430, 1406, 1378, 1366, 1312, 1270, 1224, 1186, 954, 764, 700, 644 cm$^{-1}$

NMR (CDCl$_3$—CD$_3$OD) δ: 1.76–1.95 (4H, m), 2.25–2.52 (2H, m), 2.77 (2H, t, J=6.6 Hz), 3.00–3.41 (3H, m), 4.12 (2H, t, J=6.6 Hz), 6.80 (1H, s), 7.22–7.31 (3H, m), 7.40–7.61 (9H, m), 7.80–7.97 (4H, m), 8.30–8.38 (2H, m)

INVENTIVE EXAMPLE 268

4-Acetylamino-N-{2-[4-(4-fluorobenzoyl)piperidino]ethyl}-N-(3-methoxyphenyl)benzamide tartarate Using 4-acetylamino-N-{2-[4-(4-fluorobenzoyl)piperidino]ethyl}-N-(3-methoxyphenyl)benzamide (155.0 mg, 0.30 mmol) and tartaric acid (35.0 mg, 0.30 mmol), the procedure of Inventive Example 211 was repeated to obtain 143.0 mg (75.3%) of the title compound in a colorless powder form.

Melting point: 152°–175° C.

IR (KBr): 3440, 3325, 1686, 1600, 1312, 1216, 851 cm$^{-1}$

NMR (CDCl$_3$—CD$_3$OD) δ: 2.10 (3H, s), 1.99–4.44 (12H, m), 3.70 (3H, s), 6.62–6.77 (3H, m), 7.07–7.45 (7H, m), 7.91–8.06 (2H, m)

INVENTIVE EXAMPLE 269

4-Acetylamino-N-{2-[4-(4-fluorobenzoyl)piperidino]ethyl}-N-(3-methoxyphenyl)benzamide maleate Using 4-acetylamino-N-{2-[4-(4-fluorobenzoyl)piperidino]ethyl}-N-(3-methoxyphenyl)benzamide (155.0 mg, 0.30 mmol) and maleic acid (45.0 mg, 0.30 mmol), the procedure of Inventive Example 211 was repeated to obtain 164.0 mg (82.0%) of the title compound in a colorless powder form.

Melting point: 212.0°–213° C.

IR (KBr): 3447, 1686, 1640, 1598, 1320, 1214, 856 cm$^{-1}$

NMR (CDCl$_3$—CD$_3$OD) δ: 2.11 (3H, s), 2.16–3.75 (11H, m), 3.70 (3H, s), 4.27 (2H, t, J=7.0 Hz), 6.23 (2H, s), 6.58–6.77 (3H, m), 7.08–7.45 (7H, m), 7.98 (2H, dd, J=8.7 Hz, 5.4 Hz)

INVENTIVE EXAMPLE 270

4-Amino-N-[2-(4-benzoylpiperidino)ethyl]-N-(3-pyridyl)benzamide maleate

4-Amino-N-[2-(4-benzoylpiperidino)ethyl]-N-(3-pyridyl)benzamide (3.00 g, 7.00 mmol) was dissolved in ethanol (10.0 ml) to which was subsequently added a ethanol solution (20.0 ml) of maleic acid (812.0 mg, 7.00 mmol) at room temperature, and then stirred. After the solvent was removed by evaporation, the thus precipitated crystals were collected by filtration and washed with ether, and then purified by recrystallization from ethanol-water mixed solution to obtain 2.476 g (65%) of the title compound in a colorless powder form.

Melting point: 174°–175° C.

IR (KBr): 1680, 1634, 1606, 1580, 1518, 1480, 1448, 1384, 1360, 1314, 1232, 1186, 864 cm$^{-1}$

NMR (CDCl$_3$—DMSO-d$_6$) δ: 1.90–2.35 (4H, m), 2.92–3.80 (9H, m), 4.27 (2H, t, J=6.8 Hz), 6.24 (2H, s), 6.41 (2H, d, J=8.8 Hz), 7.07 (2H, d, J=8.8 Hz), 7.15–7.66 (5H, m), 7.75–8.03 (2H, m), 8.16–8.45 (2H, m)

INVENTIVE EXAMPLE 271

4-Amino-N-{2-[4-(4-fluorobenzoyl)piperidino]ethyl}-N-(3-methoxyphenyl)benzamide hemifumarate 4-Amino-N-{2-[4-(4-fluorobenzoyl)piperidino]ethyl}-N-(3-methoxyphenyl)benzamide (475.0 mg, 1.00 mmol) was dissolved in methanol (4.0 ml) and mixed with a methanol solution (3.0 ml) of fumaric acid (58.0 mg, 0.50 mmol) at 0° C. Thereafter, the thus precipitated crystals were collected by filtration and recrystallized from an ethanol-water mixture solution to obtain 481.0 mg (90.0%) of the title compound in a colorless powder form.

Melting point: 176°–179° C.

IR (KBr): 3450, 3340, 1672, 1632, 1602, 1510, 1490, 1362, 1318, 1284, 1202, 1122, 960, 840 cm$^{-1}$

NMR (CDCl$_3$—DMSO-d$_6$) δ: 1.50–2.00 (5H, m), 2.13–2.49 (2H, m), 2.72 (2H, t, J=7.5 Hz), 2.90–3.25 (4H, m), 3.69 (3H, s), 4.05 (2H, t, J=7.5 Hz), 6.40 (2H, d, J=8.5 Hz), 6.50–6.80 (2H, m), 6.75 (1H, s), 6.93–7.26 (6H, m), 7.95 (2H, dd, J=8.8 Hz, 5.5 Hz)

INVENTIVE EXAMPLE 272

4-Formylamino-N-{2-[4-(4-fluorobenzoyl)piperidino]ethyl}-N-(3-pyridyl)benzamide hemifumarate Using 4-formylamino-N-{2-[4-(4-fluorobenzoyl)piperidino]ethyl}-N-(3-pyridyl)benzamide (208.8 mg, 0.44 mmol) and fumaric acid (25.8 mg, 0.22 mmol), the procedure of Inventive Example 271 was repeated to obtain 122.2 mg (52.1%) of the title compound in a colorless powder form.

Melting point: 182°–187° C. (decomposition)

IR (KBr): 1692, 1642, 1596, 1528, 1480, 1426, 1408, 1382, 1314, 1254, 1230, 1182, 1160, 1132, 848 cm$^{-1}$

NMR (CDCl$_3$—CD$_3$OD) δ: 1.72–1.91 (4H, m), 2.27–3.43 (2H, m), 2.70 (2H, t, J=6.6 Hz), 2.96–3.41 (3H, m), 4.09 (2H, t, J=6.6 Hz), 6.81 (1H, s), 6.94–7.47 (7H, m), 7.92 (2H, dd, J=8.8 Hz, 5.5 Hz), 8.28–8.39 (2H, m)

INVENTIVE EXAMPLE 273

4-Valerylamino-N-{2-[4-(4-fluorobenzoyl)piperidino]ethyl}-N-(3-pyridyl)benzamide hemifumarate Using 4-valerylamino-N-{2-[4-(4-fluorobenzoyl)piperidino]-ethyl}-N-(3-pyridyl)benzamide (139.4 mg, 0.26 mmol) and fumaric acid (15.4 mg, 0.13 mmol), the procedure of inventive Example 271 was repeated to obtain 128.5 mg (84.0%) of the title compound in a light brown amorphous powder form.

IR (KBr): 1710, 1682, 1652, 1598, 1410, 1380, 1312, 1278, 1178, 1156, 1092, 974, 710 cm$^{-1}$

NMR (CDCl$_3$—CD$_3$OD) δ: 0.79–0.93 (3H, m), 1.07–1.74 (6H, m), 1.82–1.91 (2H, m), 2.28–2.50 (4H, m), 2.69 (2H, t, J=6.4 Hz), 2.95–3.41 (3H, m), 4.11 (2H, t, J=6.4 Hz), 6.81 (1H, s), 6.97 (2H, d, J=8.4 Hz), 7.09 (2H, d, J=8.8 Hz), 7.18–7.53 (4H, m), 7.95 (2H, dd, J=8.6 Hz, 5.5 Hz), 8.36–8.40 (2H, m)

INVENTIVE EXAMPLE 274

4-Methylamino-N-{2-[4-(4-fluorobenzoyl)piperidino]ethyl}-N-(3-pyridyl)benzamide hemifumarate Using 4-methylamino-N-{2-[4-(4-fluorobenzoyl)piperidino]ethyl}-N-(3-pyridyl)benzamide (209.5 mg, 0.45 mmol) and fumaric acid (26.7 mg, 0.23 mmol), the procedure of Inventive Example 271 was repeated to obtain 184.9 mg (79.2%) of the title compound in a light brown powder form.

Melting point: 90°–96° C.

IR (KBr): 1680, 1638, 1598, 1530, 1478, 1426, 1374, 1334, 1300, 1226, 1182, 1156, 976, 832, 762 cm$^{-1}$

NMR (CDCl$_3$—CD$_3$OD) δ: 1.82–1.89 (4H, m), 2.21–2.34 (2H, m), 2.68–2.83 (2H, m), 2.76 (3 h, s), 2.99–3.24 (4H, m), 4.08 (2H, t, J=6.6 Hz), 6.32 (2H, d, J=8.6 Hz), 6.79 (1H, s), 7.04–7.28 (5H, m), 7.51 (1H, dd, J=8.1 Hz, 1.8 Hz), 7.95 (2H, dd, J=8.8 Hz, 5.5 Hz), 8.31–8.36 (2H, m)

INVENTIVE EXAMPLE 275

4-Dimethylamino-N-{2-[4-(4-fluorobenzoylpiperidino]ethyl}-N-(3-pyridyl)benzamide hemifumarate Using 4-dimethylamino-N-{2-[4-(4-fluorobenzoyl)piperidino]-ethyl}-N-(3-pyridyl)benzamide (221.4 mg, 0.47 mmol) and fumaric acid (27.4 mg, 0.23 mmol), the procedure of Inventive Example 271 was repeated to obtain 155.3 mg (62.0%) of the title compound in a colorless powder form.

Melting point: 154°–162° C.

IR (KBr): 1677, 1641, 1608, 1530, 1482, 1449, 1428, 1374, 1305, 1230, 1197, 1158, 975, 954, 822, 759, 711 cm$^{-1}$

NMR (CDCl$_3$—CD$_3$OD) δ: 1.72–1.87 (4H, m), 2.29–2.53 (2H, m), 2.79 (2H, t, J=6.6 Hz), 2.92 (6H, s, 3.08–3.45 (3H, m), 4.10 (2H, t, J=6.6 Hz), 6.42 (2H, d, J=8.8 Hz), 6.78 (1H, s), 7.04–7.29 (5H, m), 7.54 (1H, d, J=7.9 Hz), 7.95 (2H, dd, J=8.4 Hz, 5.5 Hz), 8.31–8.36 2H, m)

INVENTIVE EXAMPLE 276

4-Methanesulfonylamino-N-{2-[4-(4-fluorobenzoyl)piperidino]ethyl}-N-(3-pyridyl)benzamide hemifumarate Using 4-methanesulfonylamino-N-{2-[4-(4-fluorobenzoyl)piperidino]ethyl}-N-(3-pyridyl)benzamide (216.8 mg, 0.41 mmol) and fumaric acid (24.3 mg, 0.21 mmol), the procedure of Inventive Example 271 was repeated to obtain 103.4 mg (43.3%) of the title compound in a light brown powder form.

Melting point: 196°–200° C. (decomposition)

IR (KBr): 1674, 1644, 1598, 1478, 1426, 1386, 1364, 1326, 1308, 1232, 1222, 1206, 1156, 1114, 974, 848, 606, 532 cm$^{-1}$

NMR (CDCl$_3$—CD$_3$OD) δ: 1.76–1.86 (4H, m), 2.05–2.22 (2H, m), 2.62 (2H, t, J=6.4 Hz), 2.93 (3H, s), 2.99–3.40 (3H, m), 4.05 (2H, t, J=6.4 Hz), 6.97–7.29 (8H, m), 7.55 (1H, d, J=8.1 Hz), 7.95 (2H, dd, J=8.6 Hz, 5.5 Hz), 8.28–8.39 (2H, m)

INVENTIVE EXAMPLE 277

4-Ethylamino-N-{2-[47(4-fluorobenzoyl)piperidino]ethyl}-N-(3-pyridyl)benzamide hemifumarate Using 4-ethylamino-N-{2-[4-(4-fluorobenzoyl)piperidino]ethyl}-N-(3-pyridyl)benzamide (194.9 mg, 0.41 mmol) and fumaric acid (24.1 mg, 0.21 mmol), the procedure of Inventive Example 271 was repeated to obtain 177.6 mg 81.3%) of the title compound in a light brown powder form.

Melting point: 100°–108° C.

IR (KBr): 1680, 1638, 1604, 1528, 1506, 1480 1448, 1424, 1410, 1374, 1334, 1300, 1228, 1182, 1156, 1110, 974, 832, 762 cm$^{-1}$

NMR (CDCl$_3$—CD$_3$OD) δ: 1.20 (3H, t, J=7.0 Hz), 1.71–1.93 (4H, m), 2.22–3.50 (2H, m), 2.76 (2H, t, J=6.8 Hz), 2.97–3.52 (5H, m), 4.08 (2H, t, J=6.8 Hz), 6.32 (2H, d, J=8.8 Hz), 6.79 (1H, s), 7.06–7.56 (5H, m), 7.95 (2H, dd, J=8.6 Hz, 5.3 Hz), 8.31–8.36 (2H, m)

INVENTIVE EXAMPLE 278

4-Ethoxycarbonylamino-N-{2-[4-(4-fluorobenzoyl)piperidino]ethyl}-N-(3-pyridyl)benzamide hemifumarate Using 4-ethoxycarbonylamino-N-{2-[4-(4-fluorobenzoyl)piperidino]ethyl}-N-(3-pyridyl)benzamide (121.9 mg, 0.24 mmol) and fumaric acid (14.0 mg, 0.12 mmol), the procedure of Inventive Example 271 was repeated to obtain 103.8 mg (75.0%) of the title compound in a light yellow amorphous powder form.

IR (KBr): 1730, 1680, 1644, 1598, 1532, 1480, 1446, 1410, 1376, 1314, 1226, 1180, 1156, 1104, 1062, 974, 848, 762, 710, 602 cm$^{-1}$

NMR (CDCl$_3$—CD$_3$OD) δ: 1.20 (3H, t, J=7.0 Hz), 1.58–1.96 (4H, m), 2.15–2.60 (2H, m), 2.70 (2H, t, J=6.6 Hz), 2.95–3.52 (4H, m), 4.01–4.31 (4H, m), 6.80 (1H, s), 7.08 (2H, d, J=8.8 Hz), 7.22–7.40 (5H, m), 7.52 (2H, dd, J=8.1 Hz, 1.3 Hz), 7.95 (2H, dd, J=8.6 Hz, 5.5 Hz), 8.30–8.58 (2H, m)

INVENTIVE EXAMPLE 279

4-Ureido-N-{2-[4-(4-fluorobenzoyl)piperidino]ethyl}-N-(3-pyridyl)benzamide hemifumarate Using 4-ureido-N-{2-[4-(4-fluorobenzoyl)piperidino]ethyl}-N-(3-pyridyl)benzamide (174.1 mg, 0.36 mmol) and fumaric acid (20.8 mg, 0.18 mmol), the procedure of Inventive Example 271 was repeated to obtain 111.3 mg (56.3%) of the title compound in a colorless powder form.

Melting point: 198°–202° C. (decomposition)

IR (KBr): 1702, 1674, 1640, 1590, 1530, 1412, 1384, 1338, 1306, 1260, 1230, 1184, 972, 848, 764 cm$^{-1}$

NMR (CDCl$_3$—CD$_3$OD) δ: 1.63–1.83 (4H, m), 2.08–2.26 (2H, m), 2.63 (2H, t, J=6.4 Hz), 2.88–3.32 (5H, m), 4.00 (2H, t, J=6.4 Hz), 6.73 (1H, s), 6.97–7.23 (7H, m), 7.42–7.50 (1H, m), 7.88 (2H, dd, J=8.6 Hz, 5.5 Hz), 8.21–8.29 (2H, m)

While the invention has been described in detail and with reference to specific embodiments thereof, it will be apparent to one skilled in the art that various changes and modifications can be made therein without departing from the spirit and scope thereof.

What is claimed is:

1. A substituted cyclic amine compound represented by the following general formula (1)

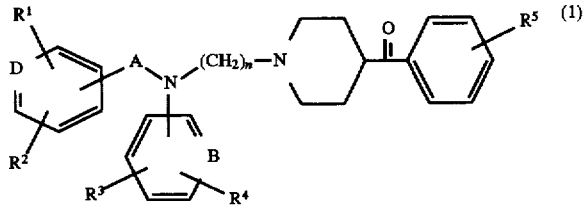

wherein R$^1$ and R$^2$ may be the same or different from each other and each represents a hydrogen atom, a halogen atom, lower straight or branched-chain alkyl group which may be substituted with halogen atom(s), a hydroxy group, a lower alkoxy group, a five- or six-membered cycloalkyl group selected from the group consisting of piperazinyl, succinimide, and phthalimide, an amino group, a lower mono or dialkylamino group, a five- or six-membered cyclic amine group selected from the group consisting of pyrrolidine, piperidine and morpholine, a lower acylamino group, a substituted or unsubstituted benzyloxymethylcarbonylamino group or a phthalimide group, a lower alkoxy group, a cyano group, a formyl group, an oxyme group, a carboxyl group, a lower alkoxycarbonyl group, a carbamoyl group, a nitro group, an amino group which may be substituted with a lower mono or dialkyl group, a lower acyl group, a lower halogenated acyl group, a lower aminoacyl group, a lower alkoxycarbonyl group or a lower alkylsulfonyl group, an amidino group which may be substituted with a lower acyl group, a lower alkoxycarbonyl group or a lower alkylsulfonyl group, a ureido group which may be substituted with a lower alkyl group, and a thioureido group which may be substituted with a lower alkyl group or pyrrole ring, R$^3$ and R$^4$ may be the same or different from each other and each represents a hydrogen atom, a halogen atom, a lower alkyl group, a lower halogenated alkyl group, a hydroxy group, a lower alkoxy group, a lower alkylthio group, a cyano group, a lower alkoxycarbonyl group, a nitro group or an amino group which may be substituted with a lower acyl group, or R$^3$ and R$^4$ taken together form a methylenedioxy group, R$^5$ represents a hydrogen atom, a halogen atom or an amino group which may be substituted with a lower mono or dialkyl group, A represents a carbonyl group or a sulfonyl group, B represents a methine moiety or a nitrogen atom, D represents a methine moiety, a nitrogen atom or =N(→O) —, and n is the integer 2 or 3; or a pharmaceutically acceptable salt thereof.

2. A substituted cyclic amine compound as claimed in claim 1 wherein A represents a carbonyl group, B represents a methine moiety or a nitrogen atom, D represents a methine moiety, a nitrogen atom or =N(→O)—, and n is the integer 2 or 3; or a pharmaceutically acceptable salt thereof.

3. A substituted cyclic amine compound as claimed in claim 1 wherein R$^1$ and R$^2$ may be the same or different from each other and each represents a hydrogen atom, a halogen atom, lower straight or branched-chain alkyl group which may be substituted with a halogen atom, a hydroxy group, a lower alkoxy group, an amino group, a lower mono or dialkylamino group, a five- or six-membered cyclic amine group selected from the group consisting of pyrrolidine, piperidine and morpholine, or a lower acylamino group, a lower alkoxy group or an amino group which may be substituted with a lower alkoxy group or an amino group which may be substituted with a lower mono dialkyl group, a lower acyl group, a lower a halogenated acyl group, a lower alkoxycarbonyl group or a lower alkylsulfonyl group, a lower alkylthio group or an amino group which may be substituted with a lower acyl group, or R$^3$ and R$^4$ taken together form a methylenedioxy group, R$^5$ represents a hydrogen atom or a halogen atom, A represents a carbonyl group, B represents a nitrogen atom, D represents a methine moiety, and n is the integer 2 or 3; or a pharmaceutically acceptable salt thereof.

4. A process for producing a substituted cyclic amine compound of claim 1 or a pharmaceutically acceptable salt thereof, wherein a compound represented by the following general formula (2)

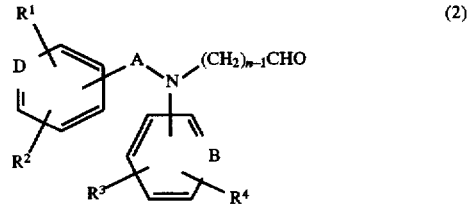

wherein R$^1$ and R$^2$ may be the same or different from each other and each represents a hydrogen atom, a halogen atom, lower straight or branched-chain alkyl group which may be substituted with halogen atom(s), a hydroxy group, a lower alkoxy group, a five- or six-membered cycloalkyl group selected from the group consisting of piperazinyl, succinimide, and phthalimide, an amino group, a lower mono or dialkylamino group, a five- or six-membered cyclic amine group selected from the group consisting of pyrrolidine, piperidine and morpholine, a lower acylamino group, a substituted or unsubstituted benzyloxymethylcarbonylamino group or a phthalimide group, a lower alkoxy group, a cyano group, a formyl group, and oxyme group, a carboxyl group, a lower alkoxycarbonyl group, a carbamoyl group, a nitro group, an amino group which may be substituted with a lower mono or dialkyl group, a lower acyl group, a lower halogenated acyl group, a lower aminoacyl group, a lower alkoxycarbonyl group or a lower alkylsulfonyl group, an amidino group which may be substituted with a lower acyl group, a lower alkoxycarbonyl group or a lower alkylsulfonyl group, an ureido group which may be substituted with a lower alkyl group, a thioureido group which may substituted with a lower alkyl group or pyrrole ring, $R^3$ and $R^4$ may be the same or different from each other and each represents a hydrogen atom, a halogen atom, a lower alkyl group, a lower halogenated alkyl group, a hydroxy group, a lower alkoxy group, a lower alkylthio group, a cyano group, a lower alkoxycarbonyl group, a nitro group or an amino group which may be substituted with a lower acyl group, or $R^3$ and $R^4$ taken together form a methylenedioxy group, A represents a carbonyl group or a sulfonyl group, B represents a methine moiety or a nitrogen atom, D represents a methine moiety, a nitrogen atom or =N(→O)—, and n is the integer 2 or 3, is reduced by allowing it to react with a compound represented by the following general formula (3)

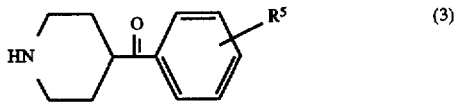

wherein $R^5$ represents a hydrogen atom, a halogen atom or an amino group which may be substituted with a lower mono or dialkyl group.

5. The process for producing a substituted cyclic amine compound (1) or a pharmaceutically acceptable salt thereof according to claim 4, wherein a compound represented by the following general formula (4)

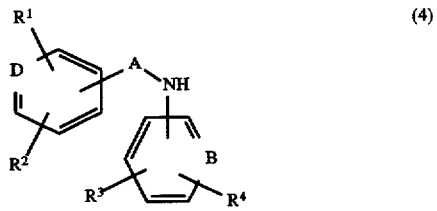

wherein $R^1$ and $R^2$ may be the same or different from each other and each represents a hydrogen atom, a halogen atom, lower straight or branched-chain alkyl group which may be substituted with halogen atom(s), a hydroxy group, a lower alkoxy group, a five- or six-membered cycloalkyl group selected from the group consisting of piperazinyl, succinimide, and phthalimide, an amino group, a lower mono or dialkylamino group, a five- or six-membered cyclic amine group selected from the group consisting of pyrrolidine, piperidine and morpholine, a lower acylamino group, a substituted or unsubstituted benzyloxymethylcarbonylamino group or a phthalimide group, a lower alkoxy group, a cyano group, a formyl group, and oxyme group, a carboxyl group, a lower alkoxycarbonyl group, a carbamoyl group, a nitro group, an amino group which may be substituted with a lower mono or dialkyl group, a lower acyl group, a lower halogenated acyl group, a lower aminoacyl group, a lower alkoxycarbonyl group or a lower alkylsulfonyl group, an amidino group which may be substituted with a lower acyl group, a lower alkoxycarbonyl group or a lower alkylsulfonyl group, an ureido group which may be substituted with a lower alkyl group, a thioureido group which may substituted with a lower alkyl group or pyrrole ring, $R^3$ and $R^4$ may be the same or different from each other and each represents a hydrogen atom, a halogen atom, a lower alkyl group, a lower halogenated alkyl group, a hydroxy group, a lower alkoxy group, a lower alkylthio group, a cyano group, a lower alkoxycarbonyl group, a nitro group or an amino group which may be substituted with a lower acyl group, or $R^3$ and $R^4$ taken together form a methylenedioxy group, A represents a carbonyl group or a sulfonyl group, B represents a methine moiety or a nitrogen atom, D represents a methine moiety, a nitrogen atom or =N(→O)—, is allowed to react with a compound represented by the following general formula (5)

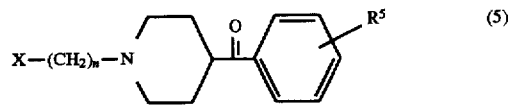

wherein $R^5$ represents a hydrogen atom, a halogen atom or an amino group which may be substituted with a lower mono or dialkyl group, X represents a halogen atom, a p-toluenesulfonyloxy group, a methanesulfonyloxy group or a trifluoromethanesulfonyloxy group, and n is the integer 2 or 3.

6. A process for producing a substituted cyclic amine compound (1) or a pharmaceutically acceptable salt thereof according to claim 2, wherein a compound represented by the following general formula (6)

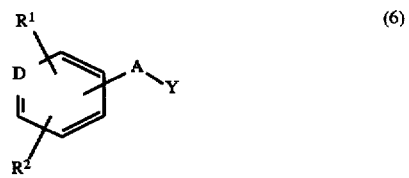

wherein $R^1$ and $R^2$ may be the same or different from each other and each represents a hydrogen atom, a halogen atom, lower straight or branched-chain alkyl group which may be substituted with halogen atom(s), a hydroxy group, a lower alkoxy group, a five- or six-membered cycloalkyl group selected from the group consisting of piperazinyl, succinimide, and phthalimide, an amino group, a lower mono or dialkylamino group, a five- or six-membered cyclic amine group selected from the group consisting of pyrrolidine, piperidine and morpholine, a lower acylamino group, a substituted or unsubstituted benzyloxymethylcarbonylamino group or a phthalimide group, a lower alkoxy group, a cyano group, a formyl group, an oxyme group, a carboxyl group, a lower alkoxycarbonyl group, a carbamoyl group, a nitro group, an amino group which may be substituted with a lower mono or dialkyl group, a lower acyl group, a lower halogenated acyl group, a lower aminoacyl group, a lower alkoxycarbonyl group or a lower alkylsulfonyl group, an amidino group which may be substituted with a lower acyl group, a lower alkoxycarbonyl group or a lower alkylsulfonyl group, an ureido group which may be substituted with a lower alkyl group, a thioureido group which may be substituted with a lower alkyl group or pyrrole ring, $R^3$ and $R^4$ may be the same or different from each other and each represents a hydrogen atom, a halogen atom, a lower alkyl group, a lower halogenated alkyl group, a hydroxy group, a lower alkoxy group, a lower alkylthio group, a group, a nitro group alkoxycarbonyl group, a nitro group or an amino group which may be substituted with a lower acyl group, or $R^3$ and $R^4$ taken together form a methylenedioxy group, $R^5$ represents a hydrogen atom, a halogen atom or an amino group which may be substituted with a lower mono or dialkyl group, A represents a carbonyl group or a sulfonyl group, and Y represents a halogen atom, is allowed to react with a compound represented by the following general formula (7)

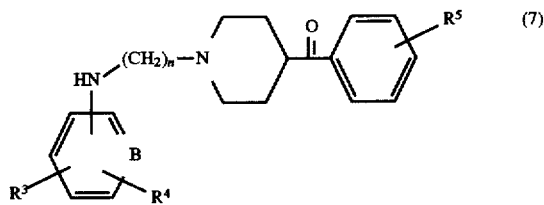

wherein $R^3$ and $R^4$ may be the same or different from each other and each represents a hydrogen atom, a halogen atom, a lower alkyl group, a lower halogenated alkyl group, a hydroxy group, a lower alkyl group, a lower alkylthio group, a cyano group, a lower alkoxycarbonyl group, a nitro group or an amino group which may be substituted with a lower acyl group, or $R^3$ and $R^4$ taken together form a methylenedioxy group, $R^5$ represents a hydrogen atom, a halogen atom or an amino group which may be substituted with a lower mono or dialkyl group, B represents a methine moiety or a nitrogen atom, and n is the integer 2 or 3.

7. A pharmaceutical composition for circulatory organ use comprising a substituted cyclic amine compound of the formula (1) or a pharmaceutically acceptable salt as disclosed in claim 1, together with a pharmaceutically acceptable carrier.

* * * * *